United States Patent
Park et al.

(10) Patent No.: US 11,133,473 B2
(45) Date of Patent: Sep. 28, 2021

(54) CONDENSED CYCLIC COMPOUND AND ORGANIC LIGHT-EMITTING DEVICE INCLUDING THE SAME

(71) Applicant: SAMSUNG DISPLAY CO., LTD., Yongin-si (KR)

(72) Inventors: Junha Park, Yongin-si (KR); Munki Sim, Yongin-si (KR); Hyoyoung Lee, Yongin-si (KR); Youngkook Kim, Yongin-si (KR); Seokhwan Hwang, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 259 days.

(21) Appl. No.: 15/867,855

(22) Filed: Jan. 11, 2018

(65) Prior Publication Data

US 2018/0342682 A1    Nov. 29, 2018

(30) Foreign Application Priority Data

May 23, 2017   (KR) .................. 10-2017-0063520

(51) Int. Cl.
    *H01L 51/50*    (2006.01)
    *H01L 51/00*    (2006.01)
    (Continued)

(52) U.S. Cl.
    CPC ........ *H01L 51/0067* (2013.01); *C07D 221/18* (2013.01); *C07D 401/10* (2013.01);
    (Continued)

(58) Field of Classification Search
    None
    See application file for complete search history.

(56) References Cited

U.S. PATENT DOCUMENTS

| 5,645,948 A    | 7/1997 | Shi et al. |
| 2004/0053069 A1 | 3/2004 | Sotoyama et al. |

(Continued)

FOREIGN PATENT DOCUMENTS

| JP | 10-017860 A | 1/1998 |
| JP | 11-87067 A  | 3/1999 |

(Continued)

OTHER PUBLICATIONS

Glinka Jadwiga, Oxidation photocyclization of 3, 4-diphenylquinoline to dibenzo[i,k]phenanthridine, Chem, vol. 51, 3, p. 577(1977), Doc. No. 87:102140.

(Continued)

*Primary Examiner* — Gregory D Clark
(74) *Attorney, Agent, or Firm* — Lewis Roca Rothgerber Christie LLP

(57) ABSTRACT

A condensed cyclic compound and an organic light-emitting device are provided, the condensed cyclic compound being represented by Formula 1.

(Continued)

in which $R_1$ may be selected from a $C_6$-$C_{60}$ aryl group, a $C_1$-$C_{60}$ heteroaryl group, a monovalent non-aromatic condensed polycyclic group, and a monovalent non-aromatic condensed heteropolycyclic group, each substituted with at least one selected from —F, —Cl, —Br, —I, a cyano group, and a nitro group, and at least one selected from $R_2$ to $R_{13}$ may be a group represented by Formula 2

$$*\text{-}(L_{11})_{a11}\text{-}(Ar_{11})_{b11}, \quad \text{<Formula 2>}$$

Formulae 1 and 2 being fully described in the specification.

17 Claims, 4 Drawing Sheets

(51) Int. Cl.

| | | |
|---|---|---|
| *C07D 401/14* | (2006.01) | |
| *C07F 9/53* | (2006.01) | |
| *C07D 221/18* | (2006.01) | |
| *C07D 401/10* | (2006.01) | |
| *C07F 5/02* | (2006.01) | |
| *C07D 403/04* | (2006.01) | |
| *C07D 471/04* | (2006.01) | |
| *C07D 403/10* | (2006.01) | |

(52) U.S. Cl.
CPC ......... *C07D 401/14* (2013.01); *C07D 403/04* (2013.01); *C07D 403/10* (2013.01); *C07D 471/04* (2013.01); *C07F 5/025* (2013.01); *C07F 5/027* (2013.01); *C07F 9/5325* (2013.01); *H01L 51/0052* (2013.01); *H01L 51/0072* (2013.01); *H01L 51/5004* (2013.01); *H01L 51/504* (2013.01); *H01L 51/5056* (2013.01); *H01L 51/5072* (2013.01); *H01L 51/5088* (2013.01); *H01L 51/5092* (2013.01); *H01L 51/5096* (2013.01)

(56) References Cited

U.S. PATENT DOCUMENTS

| | | |
|---|---|---|
| 2015/0243895 A1 | 8/2015 | Lim et al. |
| 2015/0349275 A1* | 12/2015 | Jeong .................. H01L 51/0072 257/40 |
| 2016/0204357 A1 | 7/2016 | Jang et al. |

FOREIGN PATENT DOCUMENTS

| | | |
|---|---|---|
| JP | 4060669 B2 | 12/2007 |
| KR | 10-0525408 B1 | 10/2005 |
| KR | 10-1558495 B1 | 10/2015 |
| KR | 10-2015-0132809 A | 11/2015 |
| KR | 10-2015-0139125 A | 12/2015 |
| KR | 10-2016-0001713 A | 1/2016 |

OTHER PUBLICATIONS

Tang, et al., Organic electroluminescent diodes, Appl. Phys. Lett., 51, 913-915 (1987).
Adachi, et al., Confinement of charge carriers and molecular excitons within 5-nm-thick emitter layer in organic electroiuminescent devices with a double heterostructure, Appl. Phys. Lett., 57, 531-533 (1990).
Johansson, et al., Solid-State Amplified Spontaneous Emission in Some Spiro-Type Molecules: A New Concept for the Design of Solid-State Lasing Molecules, Adv. Mater. 10 (1998) 1136-1141.
Sakamoto, et al. Synthesis, Characterization, and Electron-Transport Property of Perfluorinated Phenylene Dendrimers, J. Am. Chem. Soc., 2000, 122 (8), p. 1832-1833.
Tao, et al., Sharp green electroluminescence from 1 *H*-pyrazolo[3,4-*b*]quinoline-based light-emitting diodes, Appl. Phys. Lett. 77 (2000) 1575-1577.
Yamaguchi, et al., Diphenylamino-Substituted 2,5-Diarylsiloles for Single-Layer Organic Electroluminescent Devices, Chem. Lett., 98-99 (2001).
Tobisu, et al., Modular Synthesis of Phenanthridine Derivatives by Oxidative Cyclization of 2-Isocyanobiphenyls with Organoboron Reagents, Angewandte. Chem. Int. Ed. 2012, 51, 11363-11366.

* cited by examiner

| 190 |
|-----|
| 150 |
| 110 |

| 190 |
|---|
| 150 |
| 110 |
| 210 |

| 220 |
|---|
| 190 |
| 150 |
| 110 |

| 220 |
|---|
| 190 |
| 150 |
| 110 |
| 210 |

CONDENSED CYCLIC COMPOUND AND ORGANIC LIGHT-EMITTING DEVICE INCLUDING THE SAME

CROSS-REFERENCE TO RELATED APPLICATION

Korean Patent Application No. 10-2017-0063520, filed on May 23, 2017, in the Korean Intellectual Property Office, and entitled: "Condensed Cyclic Compound and Organic Light-Emitting Device Including the Same," is incorporated by reference herein in its entirety.

BACKGROUND

1. Field

One or more embodiments relate to a condensed cyclic compound for an organic light-emitting device and an organic light-emitting device including the same.

2. Description of the Related Art

Organic light-emitting devices are self-emission devices and have wide viewing angles, high contrast ratios, short response times, and excellent characteristics in terms of brightness, driving voltage, and response speed, compared to devices in the art.

An example of such organic light-emitting devices may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transit from an excited state to a ground state, thereby generating light.

SUMMARY

Embodiments are directed to a condensed cyclic compound represented by Formula 1.

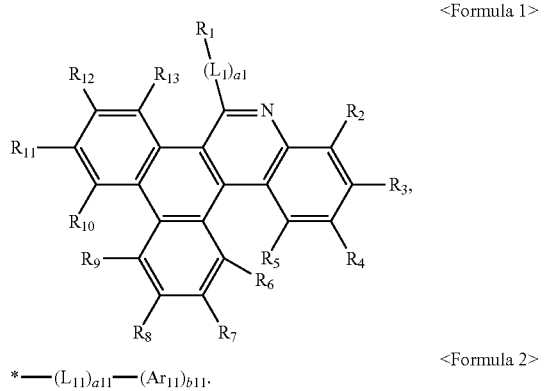

<Formula 1>

\*—$(L_{11})_{a11}$—$(Ar_{11})_{b11}$.

<Formula 2>

In Formulae 1 and 2, $L_1$ and $L_{11}$ may each independently be a substituted or unsubstituted $C_3$-$C_{60}$ carbocyclic group or a substituted or unsubstituted $C_1$-$C_{60}$ heterocyclic group, a1 and a11 may each independently be an integer from 0 to 3, $Ar_{11}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group(substituted or unsubstituted monovalent non-aromatic condensed polycyclic group), a substituted or unsubstituted monovalent non-aromatic condensed heteropolycyclic group(substituted or unsubstituted monovalent non-aromatic condensed heteropolycyclic group), —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), b11 may be an integer from 1 to 4, $R_2$ to $R_{13}$ may each independently be selected from a group represented by Formula 2, hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, and a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —S(=O)$_2$($Q_1$), and —P(=O)($Q_1$)($Q_2$), at least one selected from $R_2$ to $R_{13}$ may be a group represented by Formula 2, at least one substituent of the substituted $C_3$-$C_{60}$ carbocyclic group, substituted $C_1$-$C_{60}$ heterocyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_2$-$C_{60}$ heteroaryl group, substituted monovalent non-aromatic condensed polycyclic group, and substituted monovalent non-aromatic condensed heteropolycyclic group, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$) and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$) and —P(=O)($Q_{31}$)($Q_{32}$);

$Q_1$ to $Q_3$, $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_1$-$C_{60}$ heteroaryl group, a monovalent non-aromatic condensed polycyclic group, a monovalent non-aromatic condensed heteropolycyclic group, a biphenyl group, and a terphenyl group; and a $C_6$-$C_{60}$ aryl group substituted with at least one selected from —F, —Cl, —Br, —I, and a cyano group, and

* is a binding site to a neighboring atom.

Embodiments are also directed to an organic light-emitting device, including a first electrode; a second electrode facing the first electrode; and an organic layer between the first electrode and the second electrode, the organic layer including an emission layer, wherein the organic layer includes at least one of the condensed cyclic compound.

BRIEF DESCRIPTION OF THE DRAWINGS

Features will become apparent to those of skill in the art by describing in detail example embodiments with reference to the attached drawings in which:

FIG. 1 illustrates a schematic view of an organic light-emitting device according to an embodiment;

FIG. 2 illustrates a schematic view of an organic light-emitting device according to an embodiment;

FIG. 3 illustrates a schematic view of an organic light-emitting device according to an embodiment; and FIG. 4 illustrates a schematic view of an organic light-emitting device according to an embodiment.

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey example implementations to those skilled in the art. Like reference numerals refer to like elements throughout.

As used herein, the term "and/or" includes any and all combinations of one or more of the associated listed items. Expressions such as "at least one of" when preceding a list of elements, modify the entire list of elements and do not modify the individual elements of the list.

According to an example embodiment, a condensed cyclic compound is represented by Formula 1:

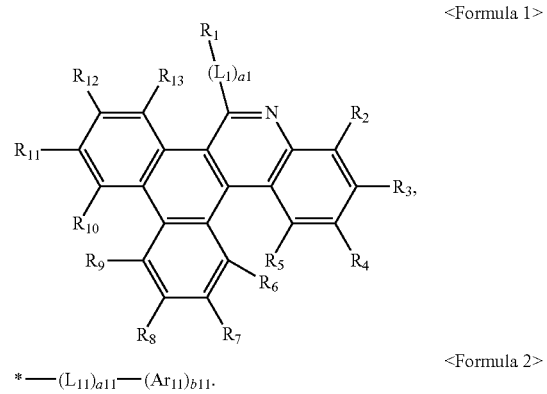

<Formula 1>

<Formula 2>

*—($L_{11}$)$_{a11}$—(Ar$_{11}$)$_{b11}$.

In Formulae 1 and 2, $L_1$ and $L_{11}$ may each independently be a substituted or unsubstituted $C_3$-$C_{60}$ carbocyclic group or a substituted or unsubstituted $C_1$-$C_{60}$ heterocyclic group.

In one embodiment, $L_1$ and $L_{11}$ may each independently selected from:

a benzene group, a pentalene group, an indene group, a naphthalene group, an azulene group, a heptalene group, an indacene group, an acenaphthalene group, a fluorene group, a spiro-bifluorene group, a spiro-benzofluorene-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pyrrole group, a thiophene group, a furan group, a silole group, an imidazole group, a pyrazole group, a thiazole group, an isothiazole group, an oxazole group, an isoxazole group, a pyridine group, a pyrazine group, a pyrimidine group, a pyridazine group, a triazine group, a benzofuran group, a benzothiophene group, a benzosilole group, a dibenzofuran group, a dibenzothiophene group, a dibenzosilole group, a carbazole group, a quinoline group, an isoquinoline group, a benzocarbazole group, a dibenzocarbazole group, a benzimidazole group, an imidazopyridine group, and an imidazopyrimidine group; and a benzene group, a pentalene group, an indene group, a naphthalene group, an azulene group, a heptalene group, an indacene group, an acenaphthalene group, a fluorene group, a spiro-bifluorene group, a spiro-benzofluorene-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pyrrole group, a thiophene group, a furan group, a silole group, an imidazole group, a pyrazole group, a thiazole group, an isothiazole group, an oxazole group, an isoxazole group, a pyridine group, a pyrazine group, a pyrimidine group, a pyridazine group, a triazine group, a benzofuran group, a benzothiophene group, a benzosilole group, a dibenzofuran group, a dibenzothiophene group, a dibenzosilole group, a carbazole group, a quinoline group, an isoquinoline group, a benzocarbazole group, a dibenzocarbazole group, a benzimidazole group, an imidazopyridine group, and an imidazopyrimidine group, each substituted with at least one selected from deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, a carbazolyl group, a pyridinyl group, a pyrazinyl group, a pyrimidinyl group, a pyridazinyl group, a quinolinyl group, an isoquinolinyl group, a benzofuranyl group, a benzothiophenyl group, a dibenzofuranyl group, a dibenzothiophenyl group, a benzocarbazolyl group, a dibenzocarbazolyl group, —Si($Q_{31}$)($Q_{32}$)($Q_{33}$), —N($Q_{31}$)($Q_{32}$), and —B($Q_{31}$)($Q_{32}$);

wherein $Q_{31}$ to $Q_{33}$ may each independently be selected from a $C_1$-$C_{20}$ alkyl group, a $C_1$-$C_{20}$ alkoxy group, a phenyl group, a biphenyl group, a terphenyl group, a naphthyl group, and a pyridinyl group.

For example, $L_1$ and $L_{11}$ may each independently be selected from:

a benzene group, a naphthalene group, an anthracene group, a fluorene group, a spiro-bifluorene group, a pyridine group, a pyrimidine group, a triazine group, a carbazole group, a quinoline group, and an isoquinoline group; and a benzene group, a naphthalene group, an anthracene group, a fluorene group, a spiro-bifluorene group, a pyridine group, a pyrimidine group, a triazine group, a carbazole group, a quinoline group, and an isoquinoline group, each substituted with at least one selected from —F, —Cl, —Br, —I, a cyano group, a $C_1$-$C_{20}$ alkyl group, a phenyl group, a biphenyl group, a pyridinyl group, and a fluorenyl group, but embodiments are not limited thereto.

For example, $L_1$ and $L_{11}$ may each independently be selected from:

groups represented by Formulae 3-1 to Formula 3-33, but embodiments are not limited thereto:

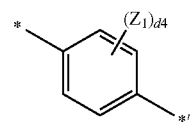

3-1

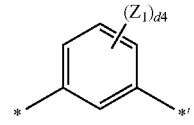

3-2

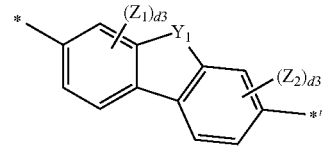

3-3

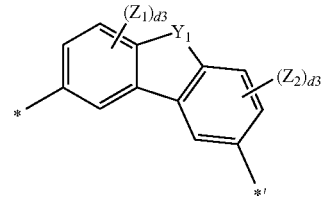

3-4

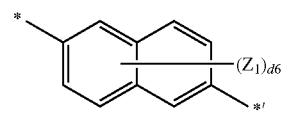

3-5

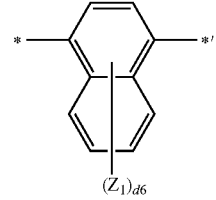

3-6

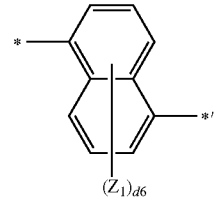

3-7

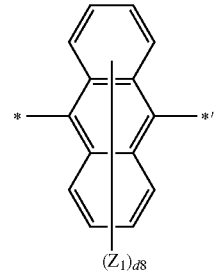

3-8

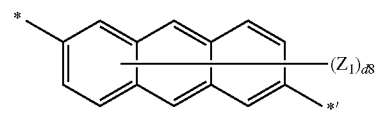

3-9

3-10
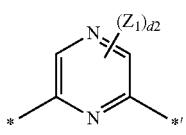
3-21
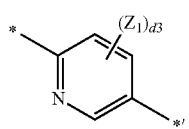
3-11
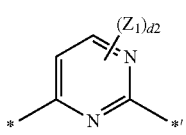
3-22
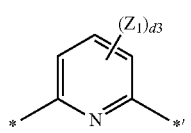
3-12
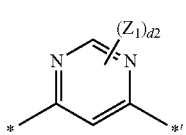
3-23
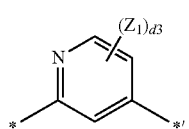
3-13
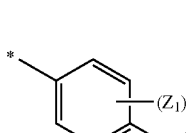
3-24
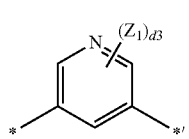
3-14
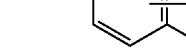
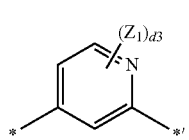
3-15
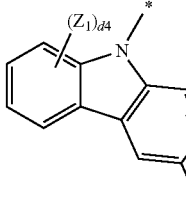
3-25
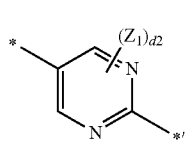
3-16
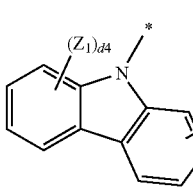
3-26
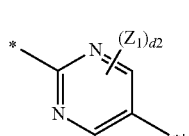
3-17
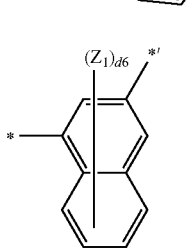
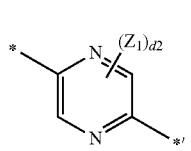
3-18
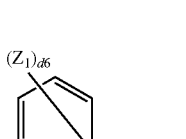
3-27
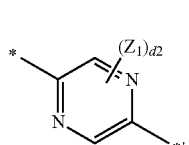
3-19
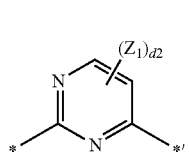
3-20
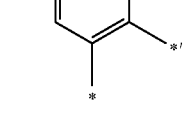
3-28

-continued 3-29
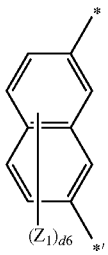

3-30
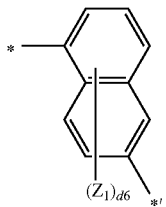

3-31
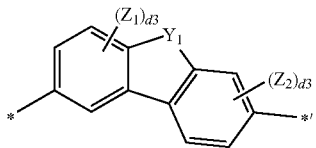

3-32
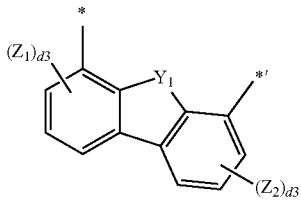

3-33
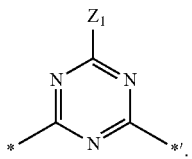

In Formulae 3-1 to 3-33, $Y_1$ may be O, S, $C(Z_3)(Z_4)$, $N(Z_5)$, or $Si(Z_6)(Z_7)$, $Z_1$ to $Z_7$ may each independently be selected from hydrogen, deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a benzofuranyl group, a benzothiophenyl group, a benzosilolyl group, a dibenzofuranyl group, a dibenzothiophenyl group, a dibenzosilolyl group, a carbazolyl group, a benzocarbazolyl group, a dibenzocarbazolyl group, and —$Si(Q_{31})(Q_{32})(Q_{33})$; and a phenyl group substituted with at least one selected from —F, —Cl, —Br, —I, and a cyano group, $Q_{31}$ to $Q_{33}$ may each independently be selected from a $C_1$-$C_{20}$ alkyl group, a $C_1$-$C_{20}$ alkoxy group, a phenyl group, a biphenyl group, a terphenyl group, a naphthyl group, and a pyridinyl group, d2 may be an integer from 0 to 2,
d3 may be an integer from 0 to 3,
d4 may be an integer from 0 to 4,
d6 may be an integer from 0 to 6,
d8 may be an integer from 0 to 8, and
* and *' are each a binding site to a neighboring atom.

In Formulae 1 and 2, a1 and a11 may each independently be an integer from 0 to 3, wherein, when a1 is 0, *-$(L_1)_{a1}$-*' may be a single bond, and when a1 is two or more, two or more of $L_1$(s) may be identical to or different from each other, when a11 is 0, *-$(L_{11})_{a11}$-*' may be a single bond, and when a11 is two or more, two or more of $L_{11}$(s) may be identical to or different from each other.

In one embodiment, in Formulae 1 and 2, a1 is 0 or 1, and a11 is an integer from 0 to 2.

$Ar_{11}$ in Formula 2 may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group(substituted or unsubstituted monovalent non-aromatic condensed polycyclic group), a substituted or unsubstituted monovalent non-aromatic condensed heteropolycyclic group(substituted or unsubstituted monovalent non-aromatic condensed heteropolycyclic group), —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, and —$P(=O)(Q_1)(Q_2)$, $Q_1$ to $Q_3$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_1$-$C_{60}$ heteroaryl group, a monovalent non-aromatic condensed polycyclic group, a monovalent non-aromatic condensed heteropolycyclic group, a biphenyl group, and a terphenyl group; and a $C_6$-$C_{60}$ aryl group substituted with at least one selected from —F, —Cl, —Br, —I, and a cyano group.

In one embodiment, $Ar_{11}$ may be selected from a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyridinyl group, a pyrazinyl group, a pyrimidinyl group, a pyridazinyl group, a triazinyl group, a thiophenyl group, a furanyl group, a quinolinyl group, an isoquinolinyl group, a carbazolyl group, a benzofuranyl group, a benzothiophenyl group, a dibenzofuranyl group, a dibenzothiophenyl group, a benzonaphthofuranyl group, a dinaphthofuranyl group, a benzocarbazolyl group, a dibenzocarbazolyl group, a dibenzosilolyl group, a benzonaphtho silolyl group, a dinaphtho silolyl group, a benzimidazolyl group, a phenanthrolinyl group, and an imidazopyridinyl group;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyridinyl group, a pyrazinyl group, a pyrimidinyl group, a pyridazinyl group, a triazinyl group, a thiophenyl group, a furanyl group, a quinolinyl group, an isoquinolinyl group, a carbazolyl group, a benzofuranyl group, a benzothiophenyl group, a dibenzofuranyl group, a dibenzothiophenyl group, a benzonaphthofuranyl group, a dinaphthofuranyl group, a benzocarbazolyl group, a dibenzocarbazolyl group, a dibenzosilolyl group, a benzonaphtho silolyl group, a dinaphtho silolyl group, a benzimidazolyl group, a phenanthrolinyl group, and an imidazopyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyridinyl group, a pyrazinyl group, a pyrimidinyl group, a pyridazinyl group, a triazinyl group, a thiophenyl group, a furanyl group, a quinolinyl group, an isoquinolinyl group, a carbazolyl group, a benzofuranyl group, a benzothiophenyl group, a dibenzofuranyl group, a dibenzothiophenyl group, a benzocarbazolyl group, a dibenzocarbazolyl group, and a dibenzosilolyl group, —N($Q_{31}$)($Q_{32}$), and —Si($Q_{31}$)($Q_{32}$)($Q_{33}$) and
—N($Q_1$)($Q_2$), —B($Q_1$)($Q_2$), —S(=O)$_2$($Q_1$), and —P(=O)($Q_1$)($Q_2$);

$Q_1$, $Q_2$ and $Q_{31}$ to $Q_{33}$ may each independently be selected from a $C_1$-$C_{20}$ alkyl group, a $C_1$-$C_{20}$ alkoxy group, a phenyl group, a biphenyl group, a terphenyl group, a naphthyl group, and a pyridinyl group; and a phenyl group substituted with at least one selected from —F, —Cl, —Br, —I, a cyano group, and a $C_1$-$C_{20}$ alkyl group.

For example, $Ar_{11}$ may be selected from a phenyl group, a biphenyl group, a naphthyl group, a fluorenyl group, a pyridinyl group, a pyrimidinyl group, a triazinyl group, a quinolinyl group, a carbazolyl group, and a phenanthrolinyl group;

a phenyl group, a biphenyl group, a naphthyl group, a fluorenyl group, a pyridinyl group, a pyrimidinyl group, a triazinyl group, a quinolinyl group, a carbazolyl group, and a phenanthrolinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a naphthyl group, a fluorenyl group, a pyridinyl group, a pyrimidinyl group, a triazinyl group, a quinolinyl group, a carbazolyl group, a phenanthrolinyl group, —N($Q_{31}$)($Q_{32}$), and —Si($Q_{31}$)($Q_{32}$)($Q_{33}$); and
—N($Q_1$)($Q_2$), —B($Q_1$)($Q_2$), —S(=O)$_2$($Q_1$), and —P(=O)($Q_1$)($Q_2$);

$Q_1$, $Q_2$, and $Q_{31}$ to $Q_{33}$ may each independently be selected from a $C_1$-$C_{20}$ alkyl group, a $C_1$-$C_{20}$ alkoxy group, a phenyl group, a biphenyl group, a terphenyl group, a naphthyl group, and a pyridinyl group, and a phenyl group substituted with at least one selected from —F, —Cl, —Br, —I, a cyano group, and a $C_1$-$C_{20}$ alkyl group.

For example, $Ar_{11}$ may be selected from a group represented by one of Formulae 5-1 to 5-47, —N($Q_1$)($Q_2$), —B($Q_1$)($Q_2$), —S(=O)$_2$($Q_1$), and —P(=O)($Q_1$)($Q_2$):

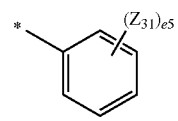

5-1

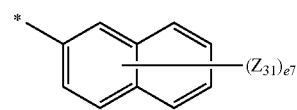

5-2

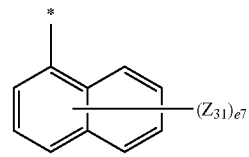

5-3

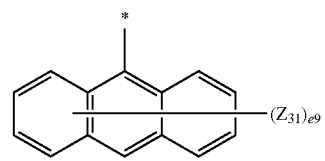

5-4

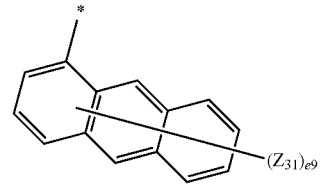

5-5

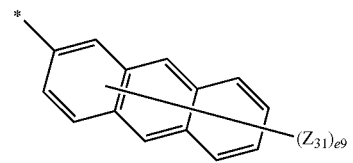

5-6

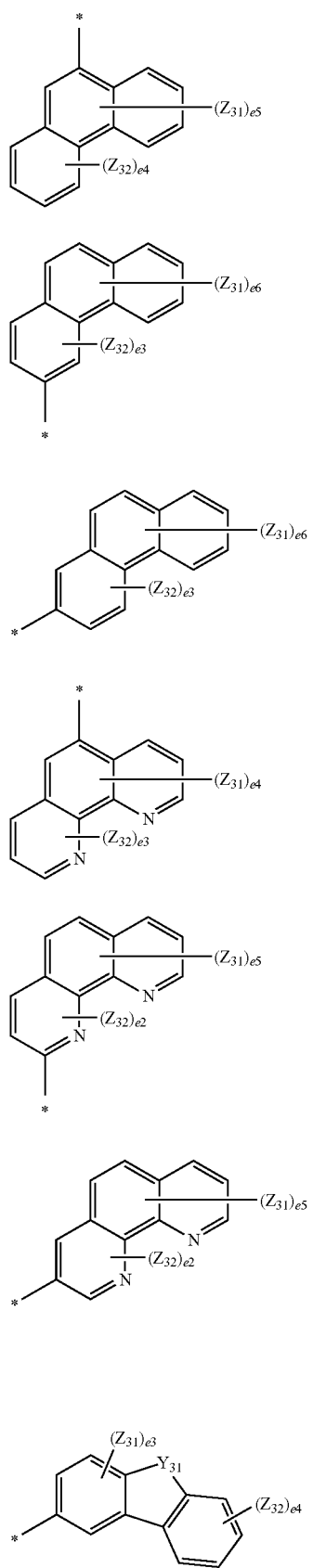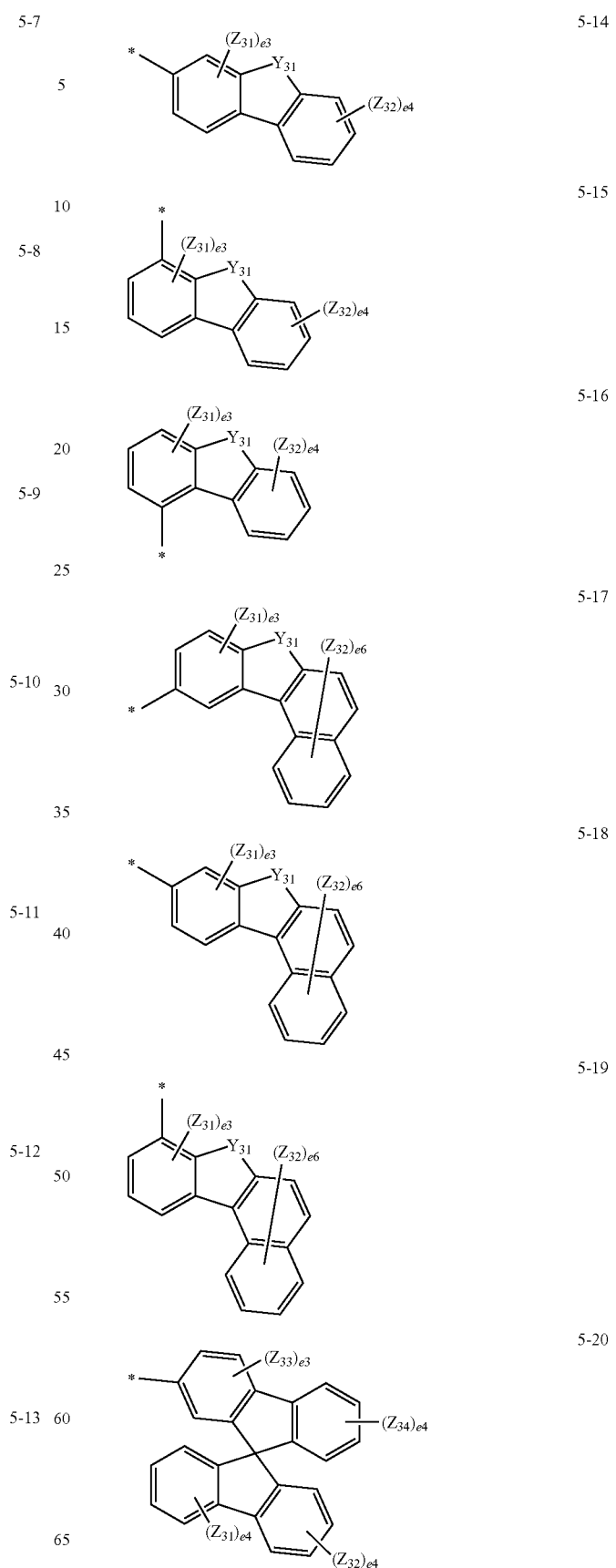

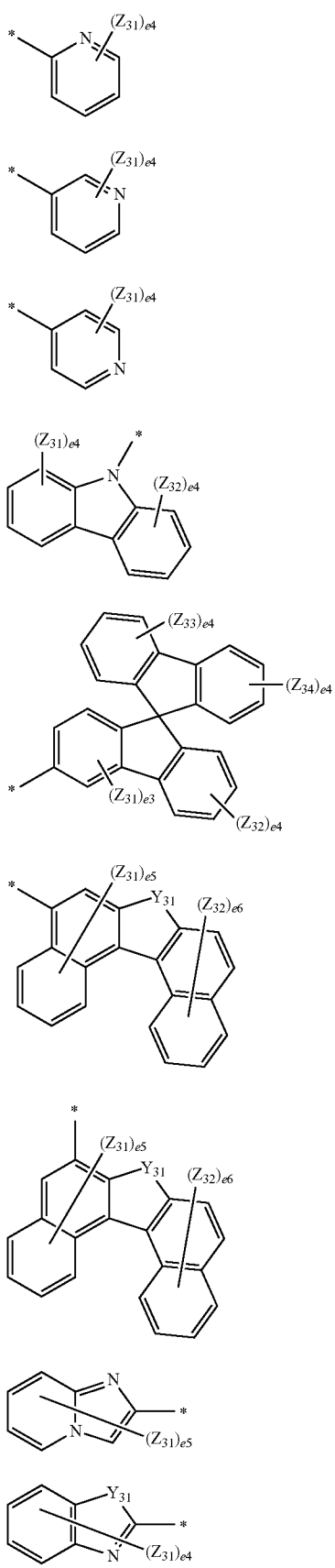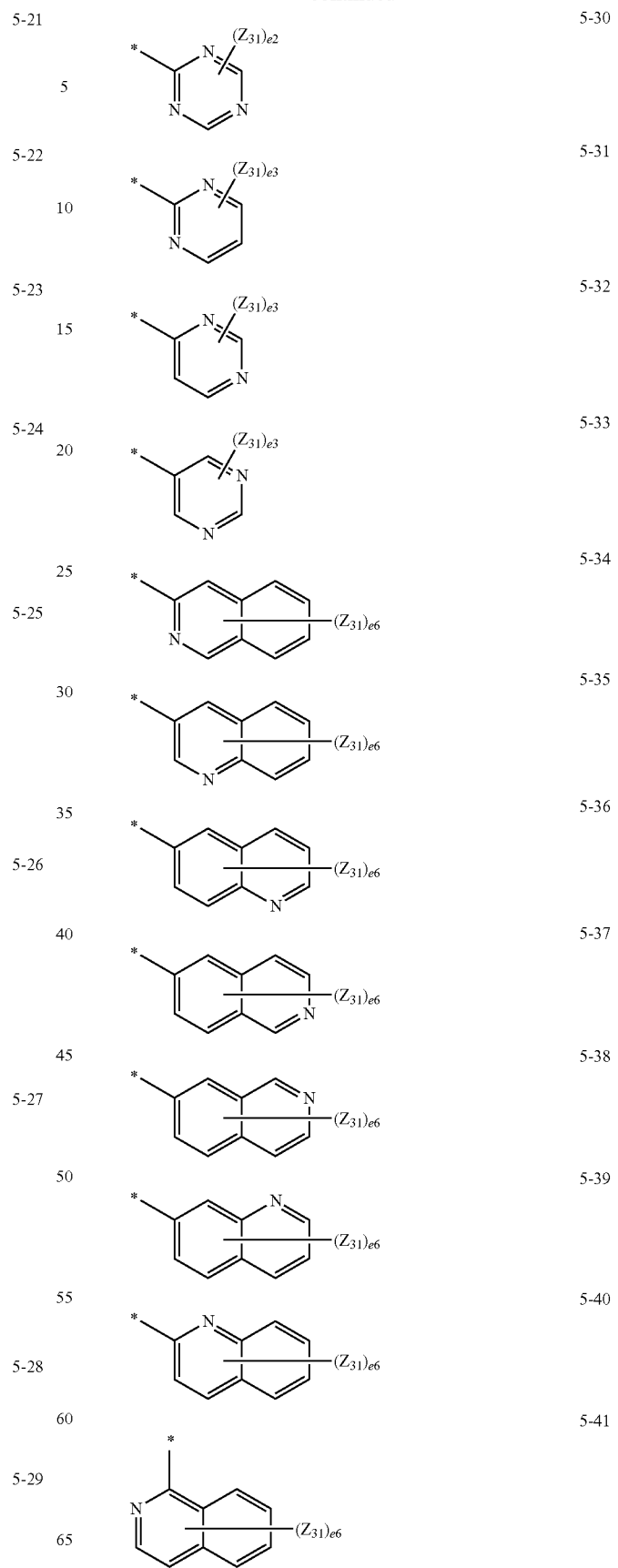

-continued 5-42
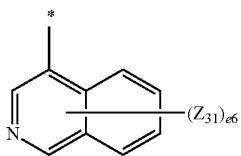

5-43
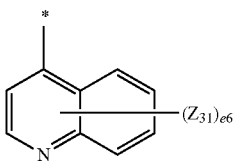

5-44
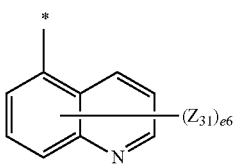

5-45
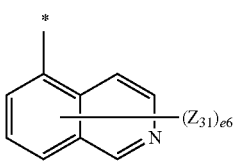

5-46
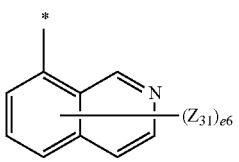

5-47
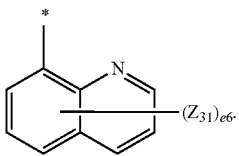

In Formulae 5-1 to 5-47, $Y_{31}$ may be O, S, $C(Z_{33})(Z_{34})$, $N(Z_{35})$, or $Si(Z_{36})(Z_{37})$, $Z_{31}$ to $Z_{37}$ may each independently be selected from hydrogen, deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, a silolyl group, a pyridinyl group, an indolyl group, an isoindolyl group, a benzofuranyl group, a benzothiophenyl group, a benzosilolyl group, a dibenzofuranyl group, a dibenzothiophenyl group, a dibenzosilolyl group, a carbazolyl group, a benzocarbazolyl group, a dibenzocarbazolyl group, and —Si($Q_{31}$)($Q_{32}$)($Q_{33}$); and a phenyl group substituted with at least one selected from —F, —Cl, —Br, —I, and a cyano group, $Q_1$, $Q_2$, and $Q_{31}$ to $Q_{33}$ may each independently selected from a $C_1$-$C_{20}$ alkyl group, a $C_1$-$C_{20}$ alkoxy group, a phenyl group, a biphenyl group, a terphenyl group, a naphthyl group, and a pyridinyl group, and a phenyl group substituted with at least one selected from —F, —Cl, —Br, —I, a cyano group, and a $C_1$-$C_{20}$ alkyl group, e2 may be an integer from 0 to 2,
e3 may be an integer from 0 to 3,
e4 may be an integer from 0 to 4,
e5 may be an integer from 0 to 5,
e6 may be an integer from 0 to 6,
e7 may be an integer from 0 to 7,
e9 may be an integer from 0 to 9, and
* indicates a binding site to a neighboring atom.

In one or more embodiments, $Ar_{11}$ may be selected from a group represented by one of Formulae 6-1 to 6-62 and a group represented by one of Formulae 10-1 to 10-20, but embodiments are not limited thereto:

6-1

6-2

6-3
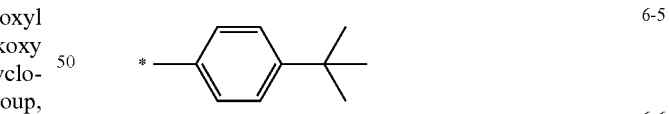

6-4

6-5

6-6
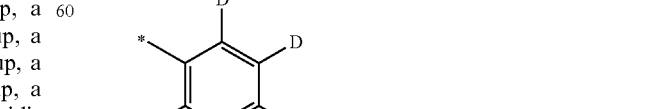

6-7
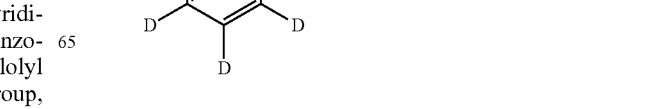

-continued

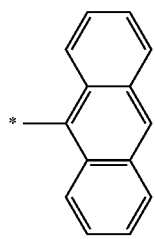
6-24
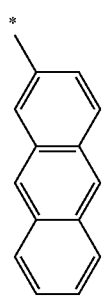
6-25
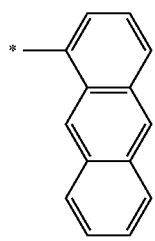
6-26
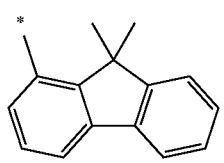
6-27
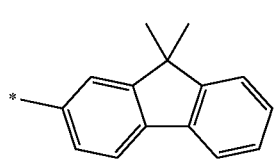
6-28
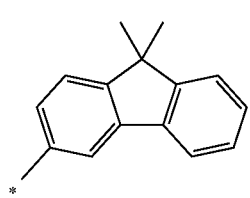
6-29
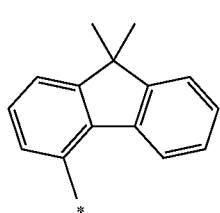
6-30
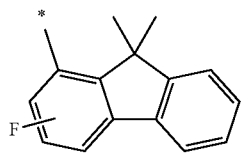
6-31
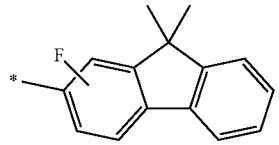
6-32
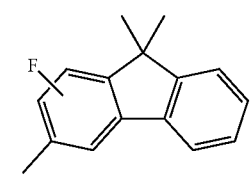
6-33
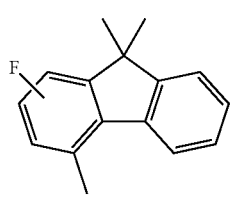
6-34
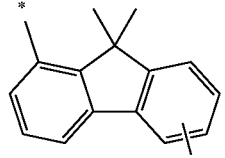
6-35
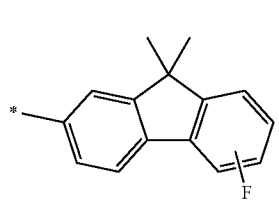
6-36
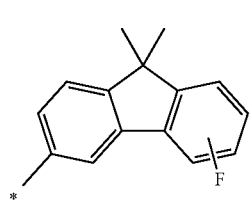
6-37
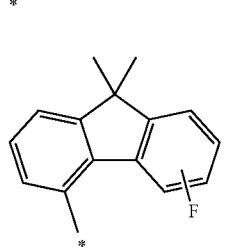
6-38

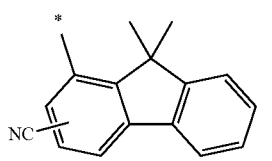
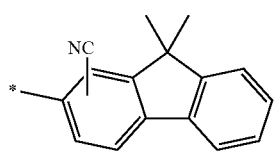
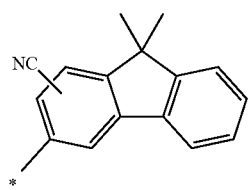
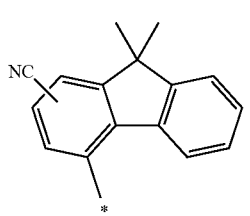
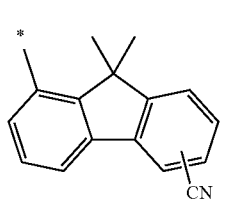
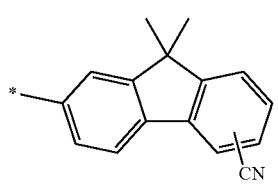
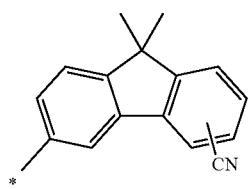
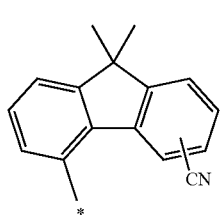
6-39
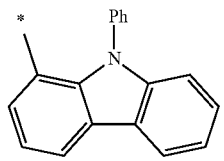
6-40
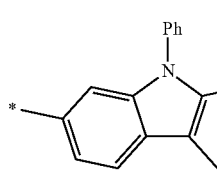
6-41
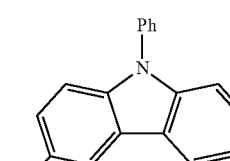
6-42
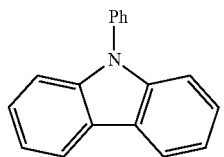
6-43
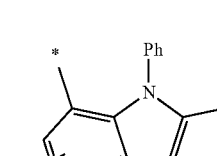
6-44
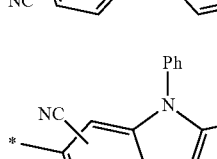
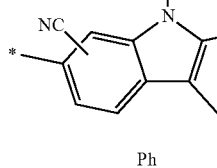
6-45
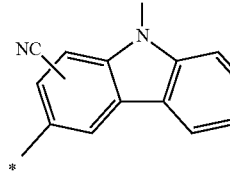
6-46
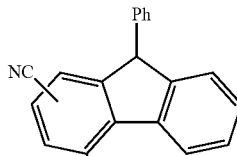
6-47
6-48
6-49
6-50
6-51
6-52
6-53
6-54

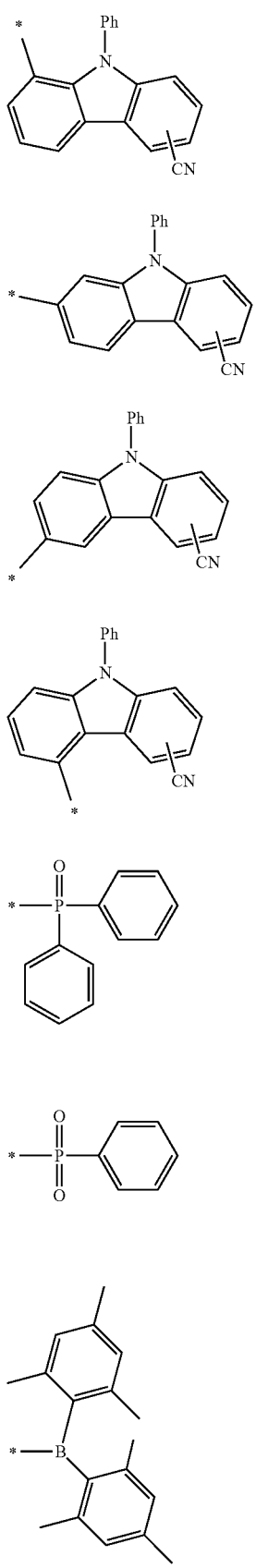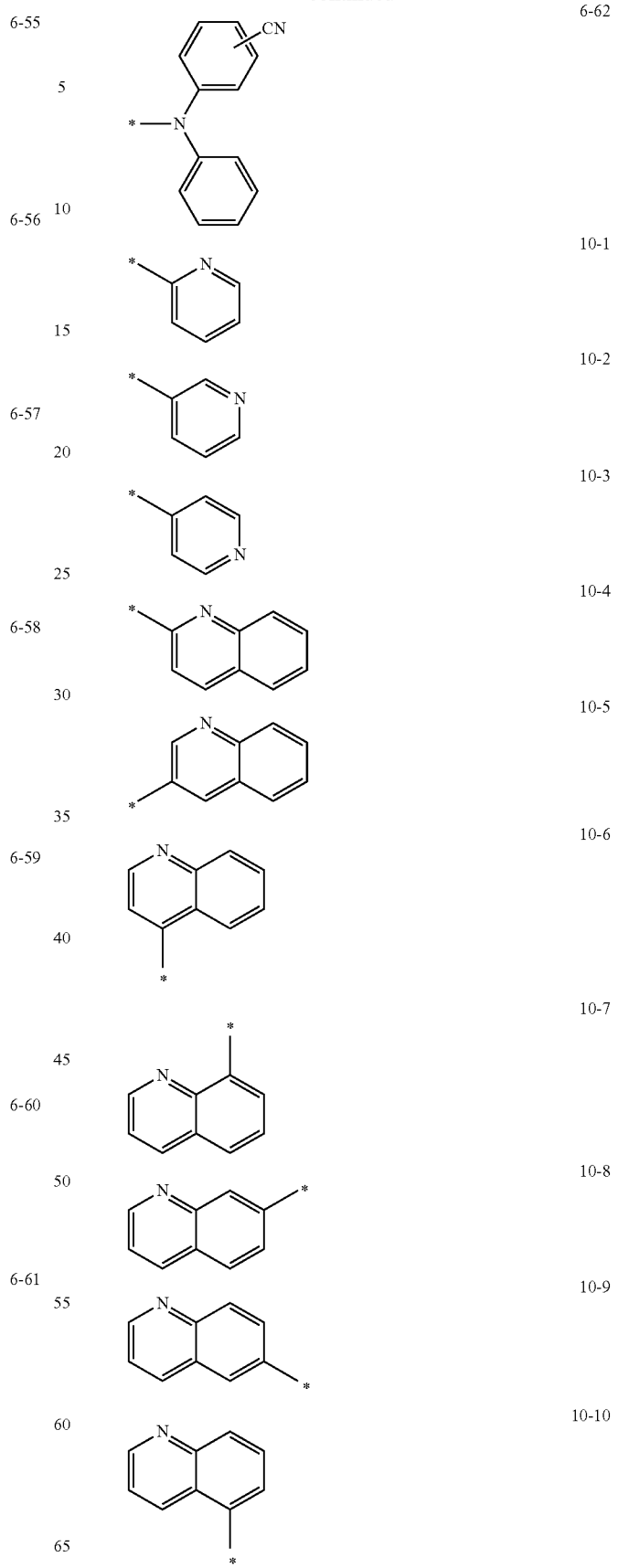

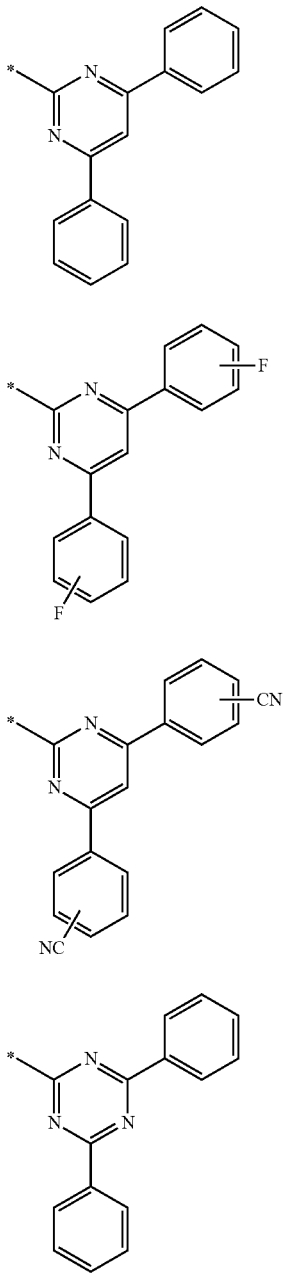

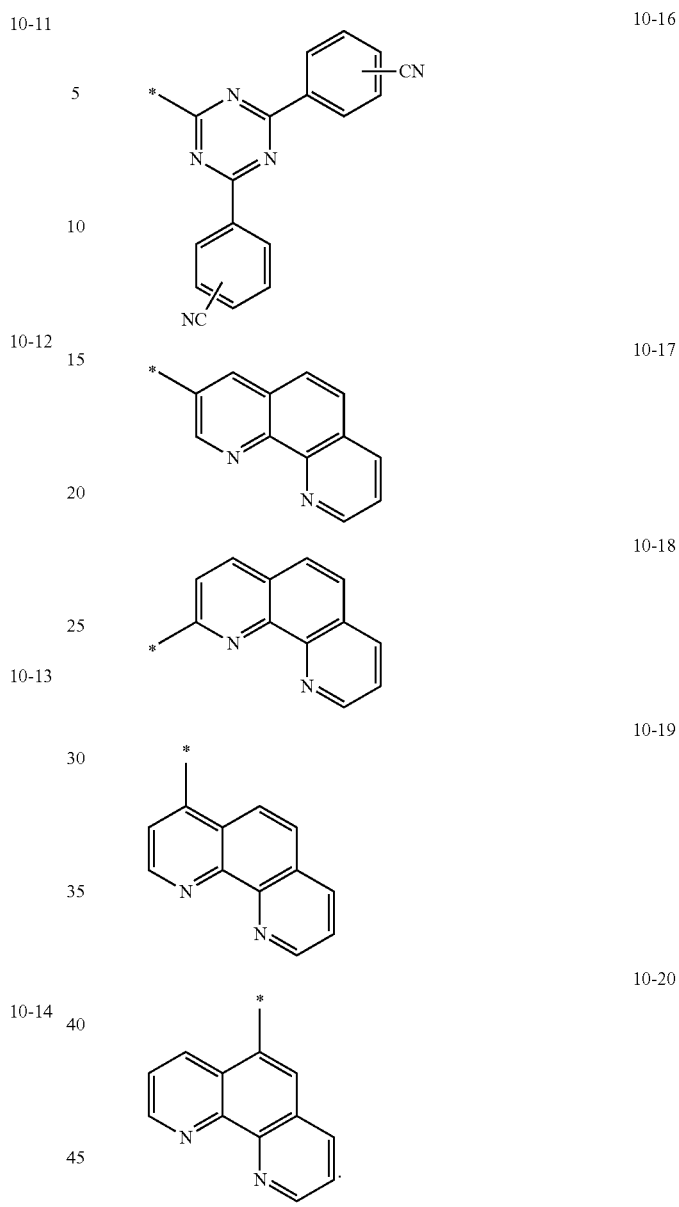

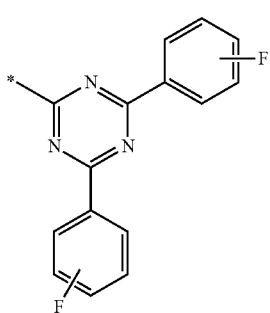

In Formulae 6-1 to 6-62 and 10-1 to 10-20, Ph refers to a phenyl group, and * indicates a binding site to a neighboring atom.

For example, $Ar_1$ may be selected from a group represented by one of Formulae 6-1 to 6-3, 6-11, 6-14, 6-23, 6-35 to 6-38, 6-43 to 6-46, and 6-55 to 6-62 and a group represented by one of Formulae 10-1 to 10-12, 10-14, 10-15, and 10-17 to 10-20, but embodiments are not limited thereto.

In one embodiment, $R_1$ in Formula 1 may be selected from a $C_6$-$C_{60}$ aryl group, a $C_1$-$C_{60}$ heteroaryl group, a monovalent non-aromatic condensed polycyclic group, and a monovalent non-aromatic condensed heteropolycyclic group, each substituted with at least one selected from —F, —Cl, —Br, —I, and a nitro group.

In one or more embodiments, $R_1$ may be a group represented by one of Formulae 4-1 to 4-23, but embodiments are not limited thereto:

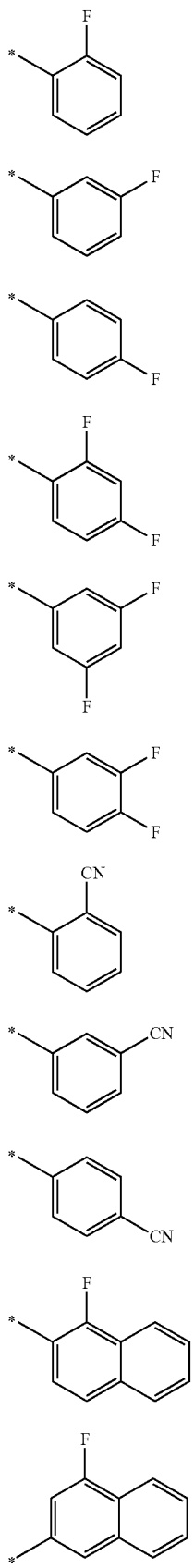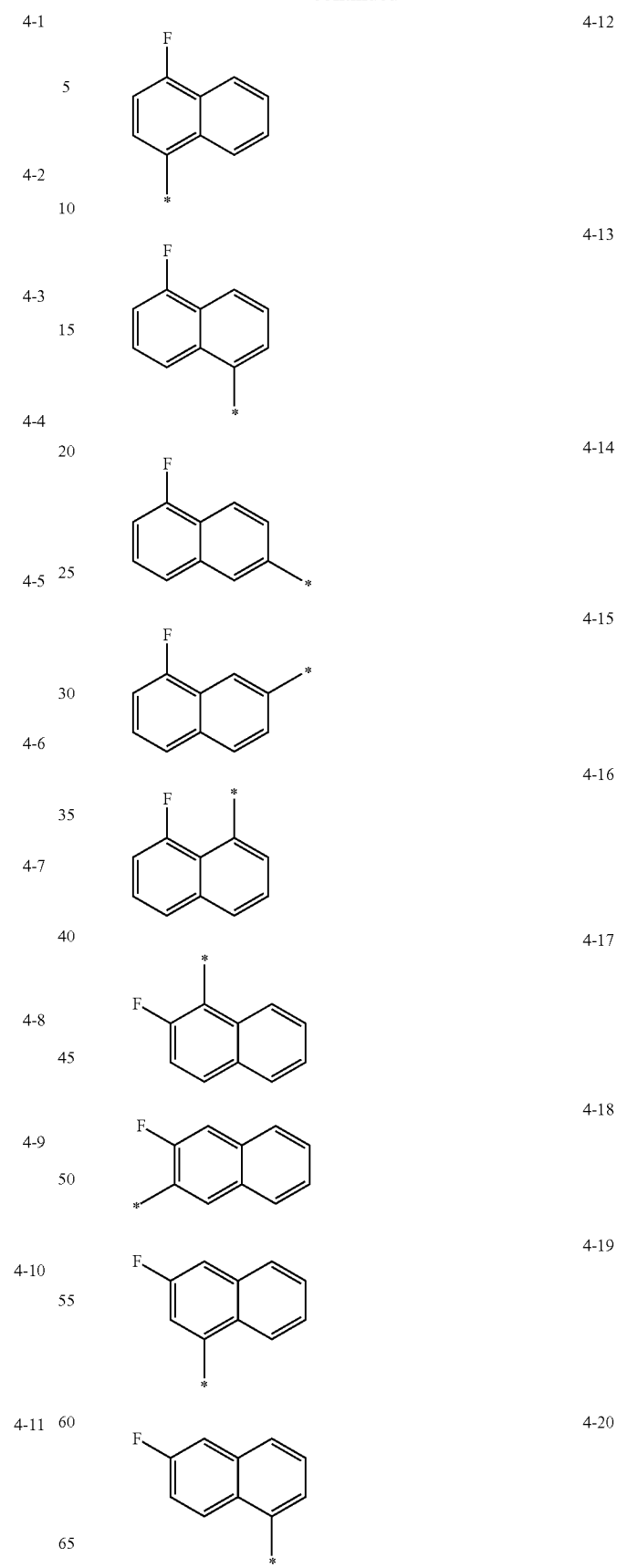

4-21

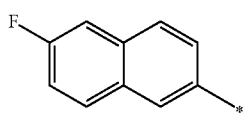

4-22

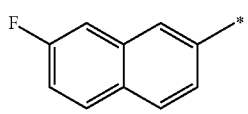

4-23

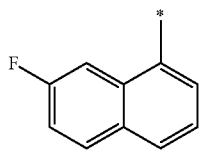

* in Formulae 4-1 to 4-23 indicates a binding site to a neighboring atom.

For example, $R_1$ may be a group represented by one of Formulae 4-1 to 4-6 and 4-10 to 4-23.

At least one selected from $R_2$ to $R_{13}$ in Formula 1 may be a group represented by Formula 2.

In one or more embodiments, at least one selected from $R_2$ to $R_5$ may be a group represented by Formula 2.

In one or more embodiments, $R_6$ to $R_{13}$ may each be hydrogen.

For example, in Formula 1, i) $R_2$ may be a group represented by Formula 2, and $R_3$ to $R_{13}$ may each be hydrogen; or ii) $R_3$ may be a group represented by Formula 2, and $R_2$, and $R_4$ to $R_{13}$ may each be hydrogen; or iii) $R_4$ may be a group represented by Formula 2, and $R_2$, $R_3$, $R_5$ to $R_{13}$ may each be hydrogen, but embodiments are not limited thereto.

In one embodiment, the condensed cyclic compound may be selected from Compounds 1 to 77:

1

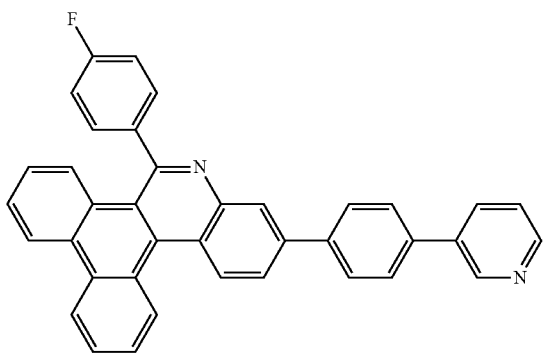

2

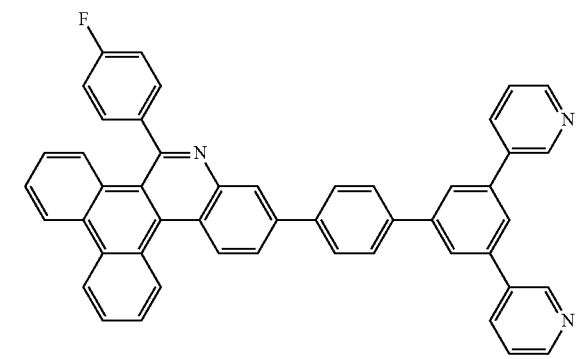

3

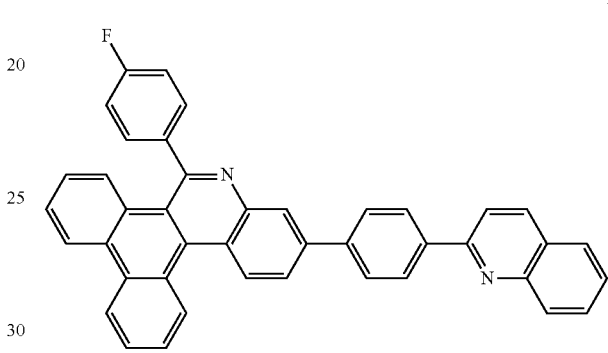

4

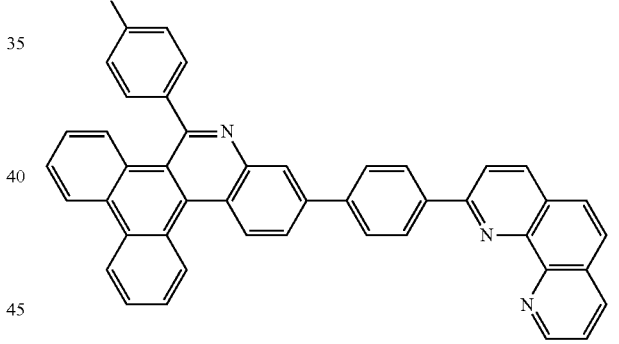

5

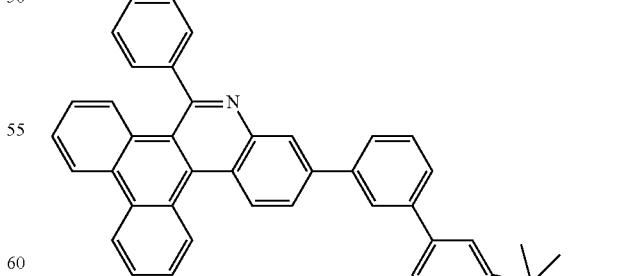

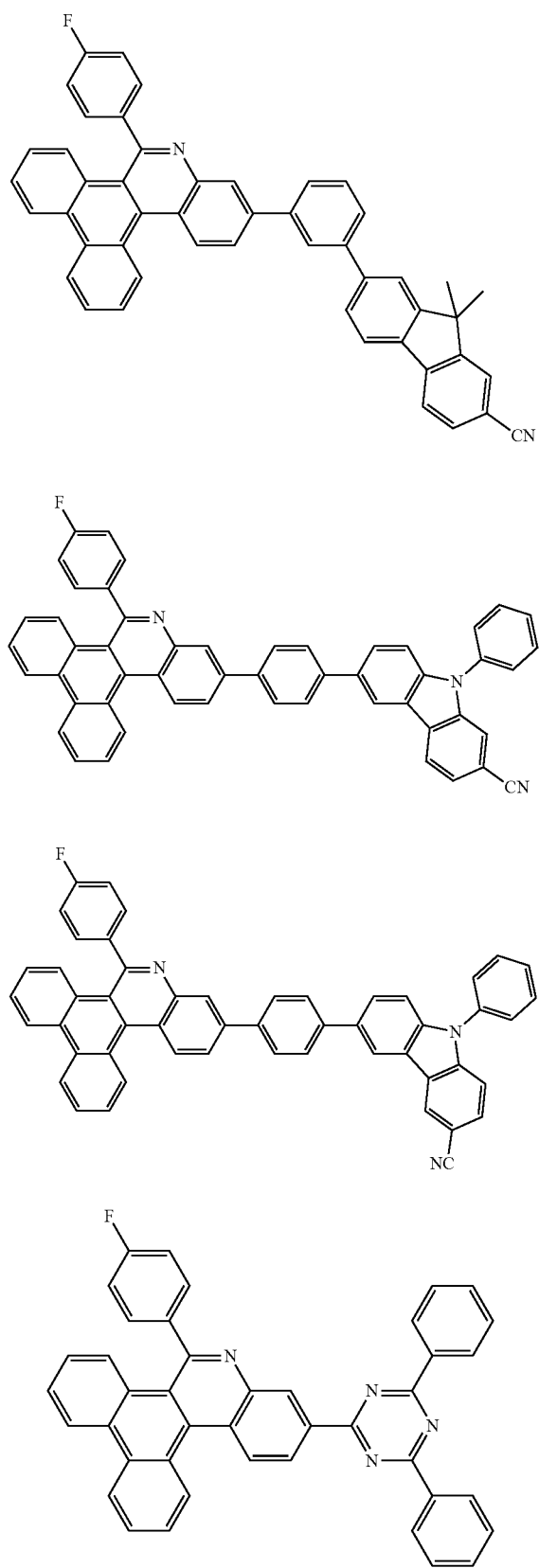
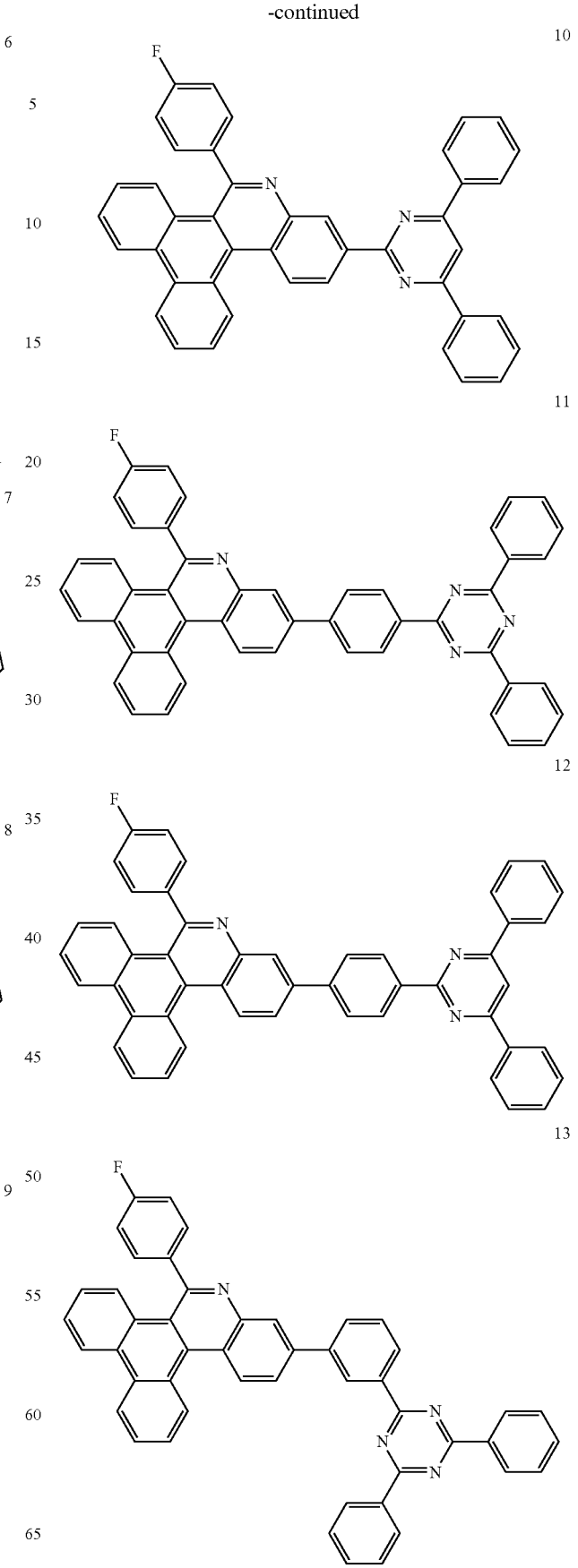

14
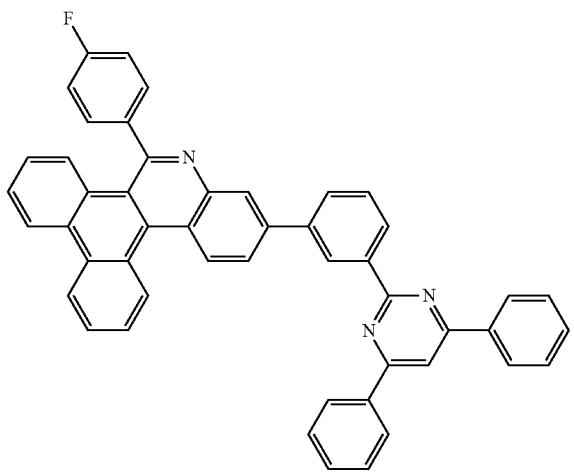
15
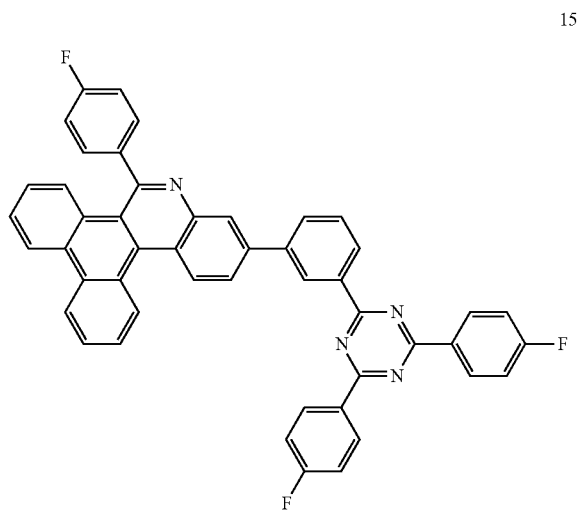
16
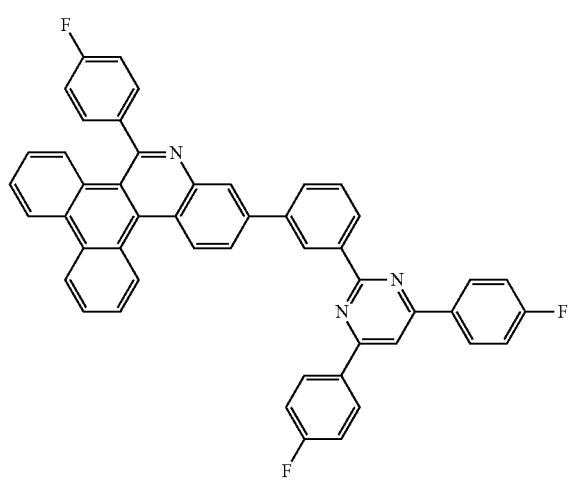
17
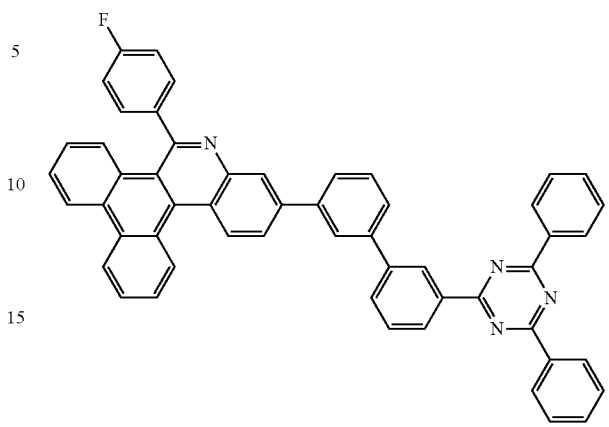
18
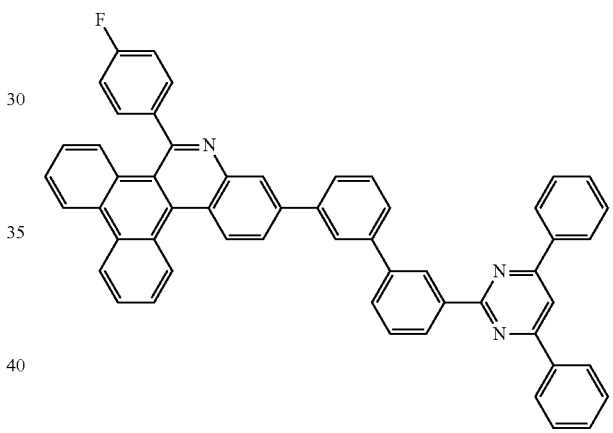
19
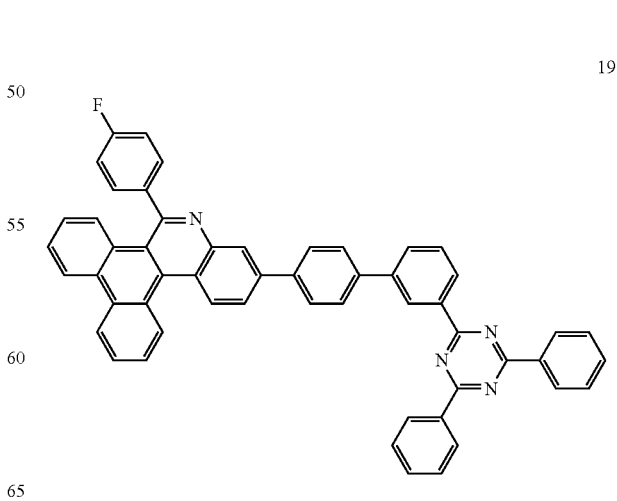

20
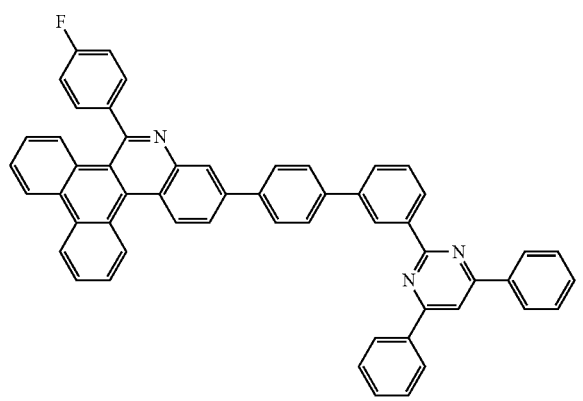
21
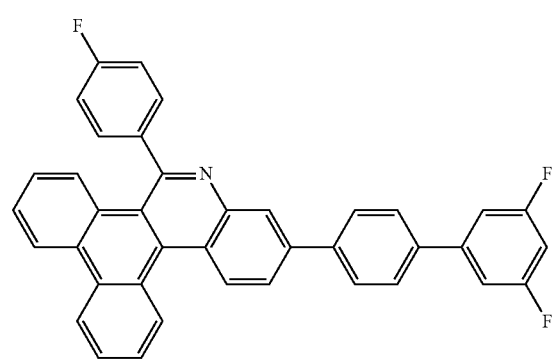
22
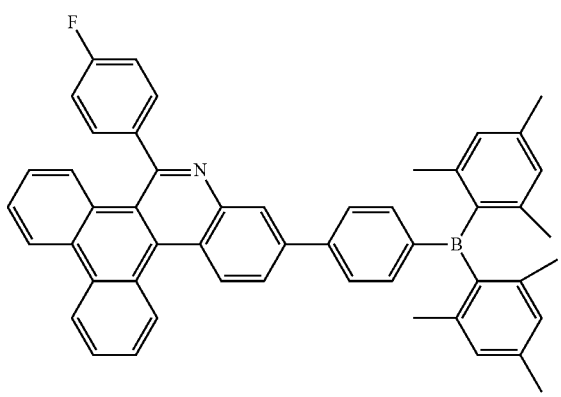
23
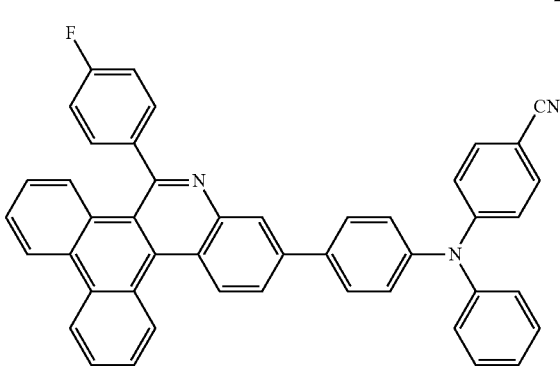
24
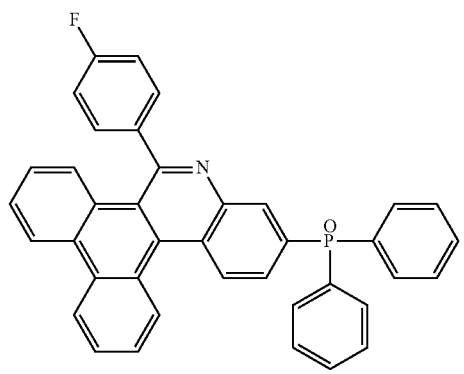
25
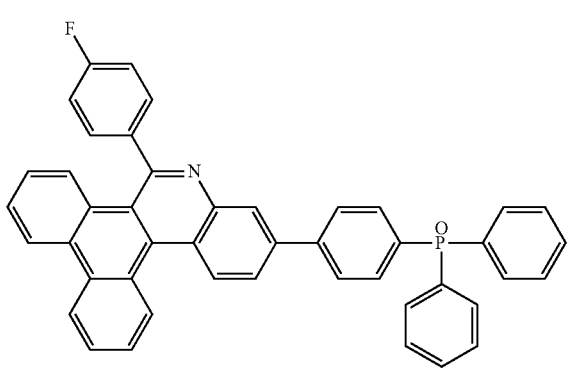
26
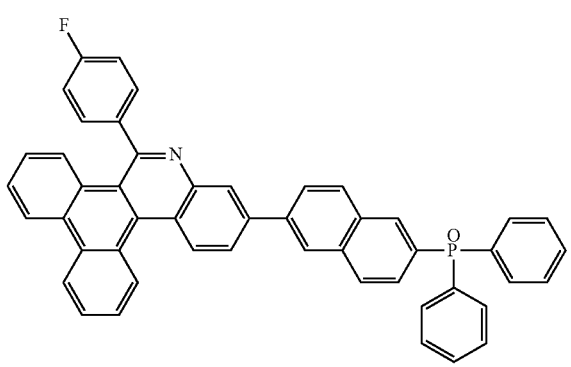
27
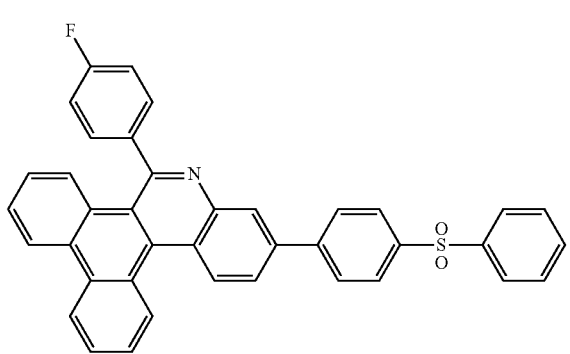

-continued
28
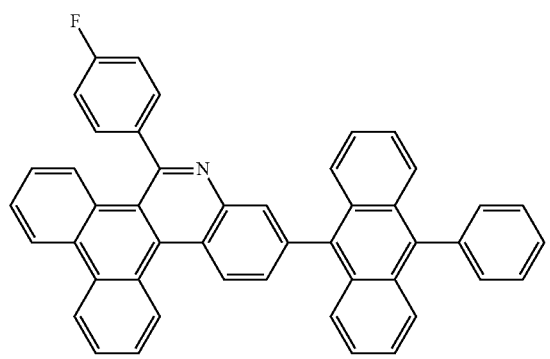
29
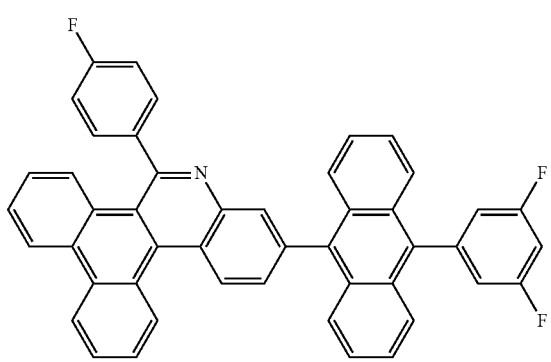
30
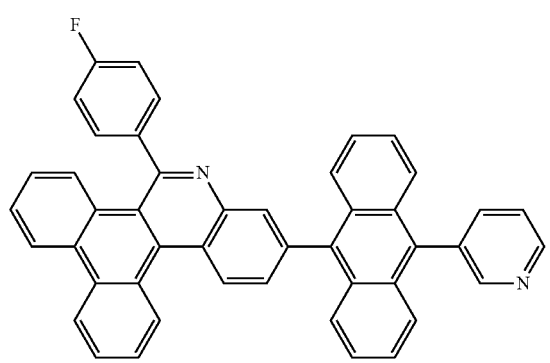
31
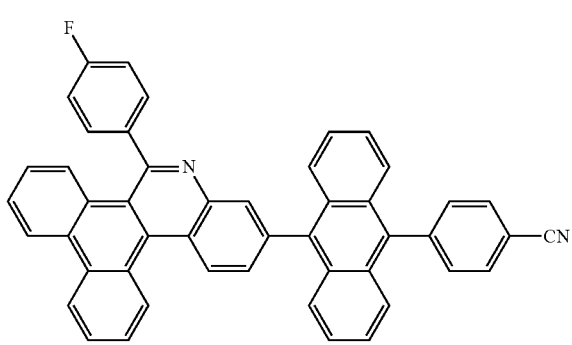
-continued
32
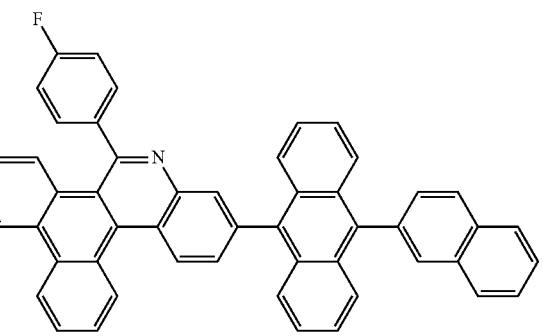
33
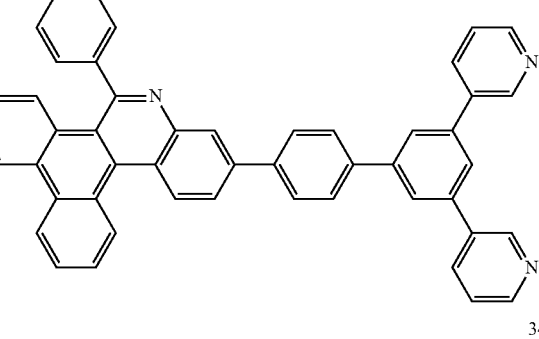
34
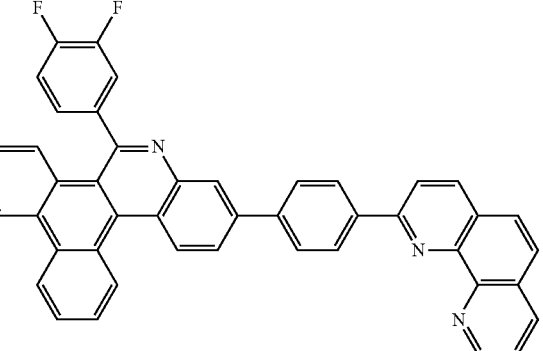
35
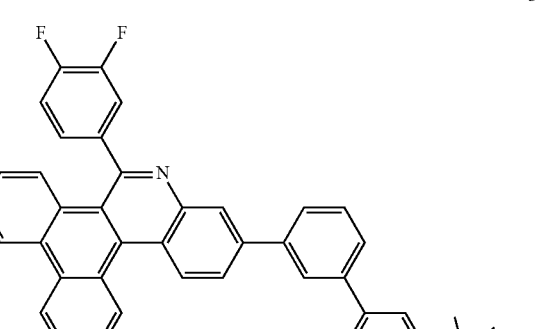
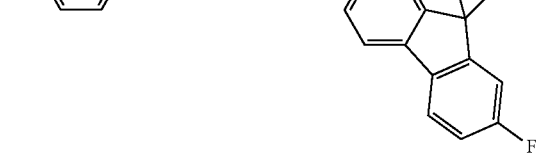

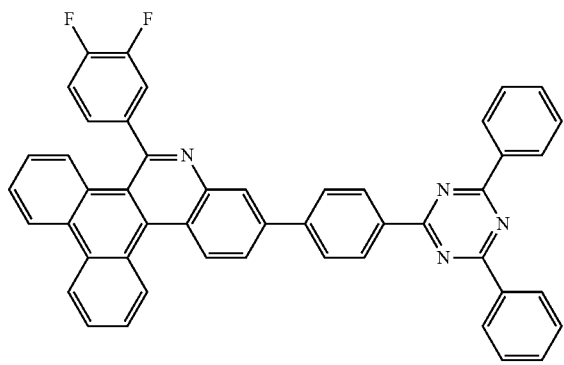
36
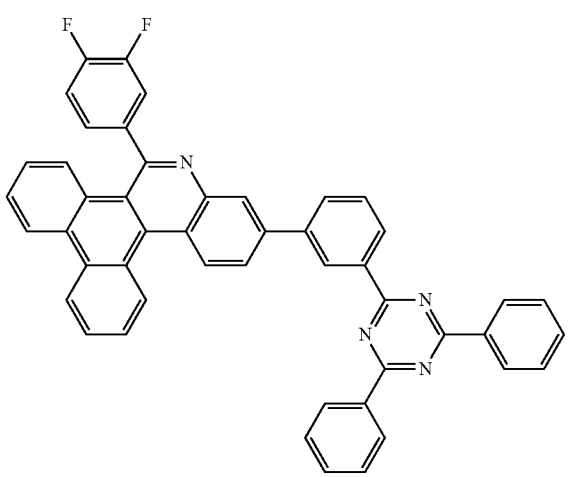
37
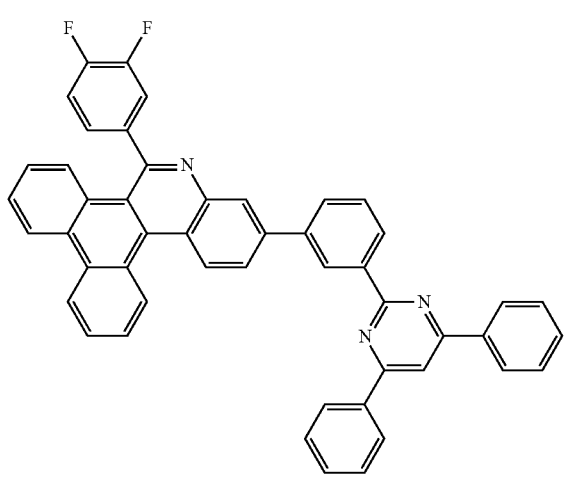
38
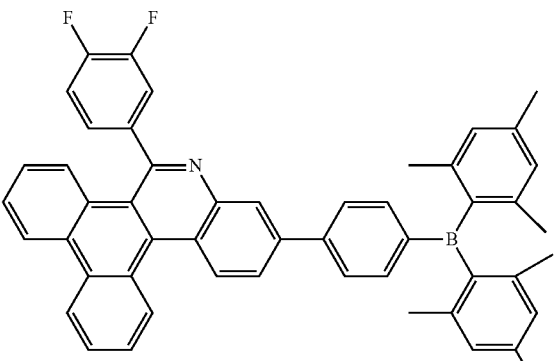
39

43
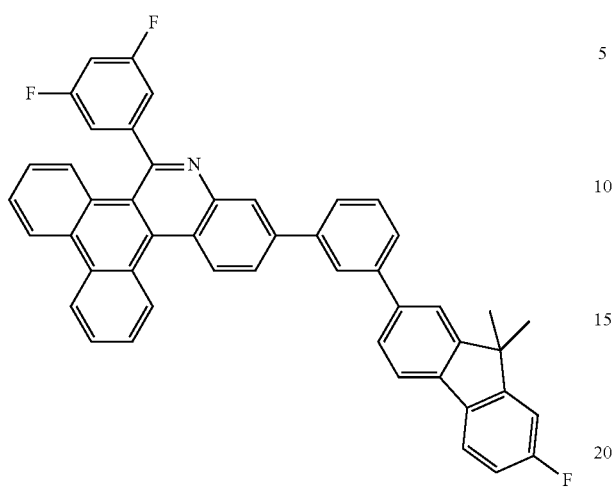
44
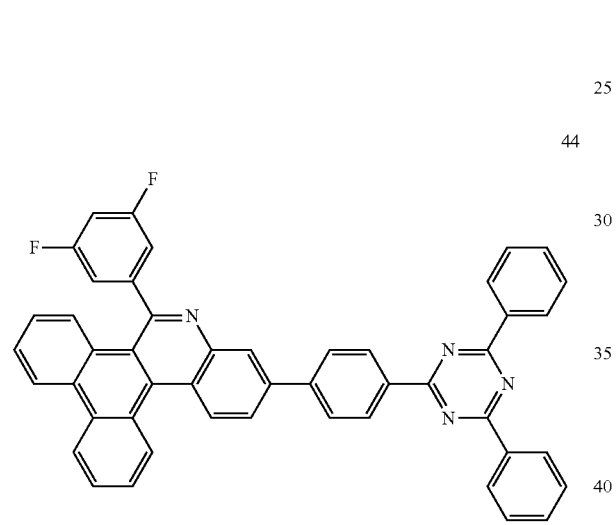
45
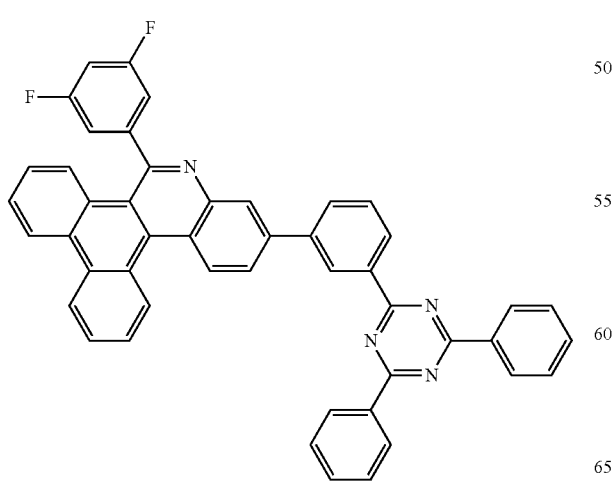
46
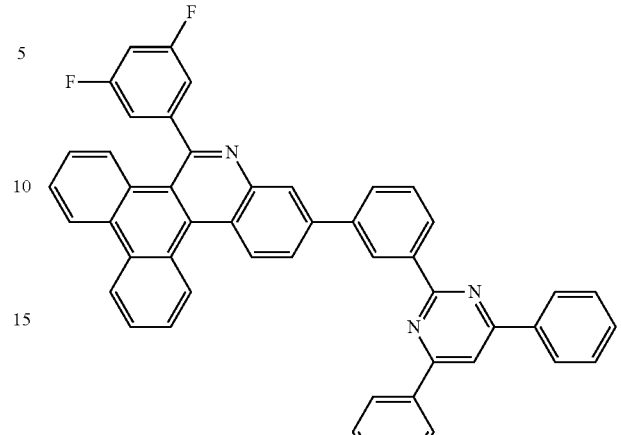
47
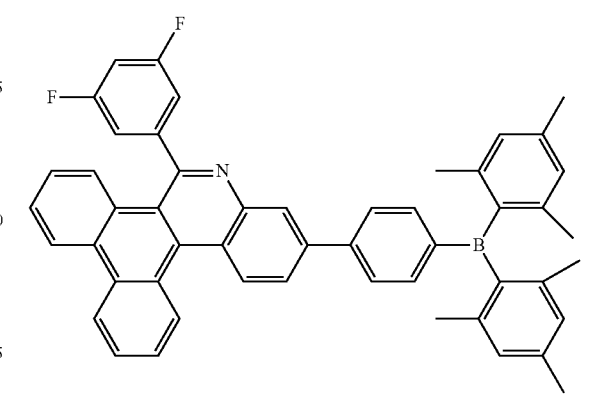
48
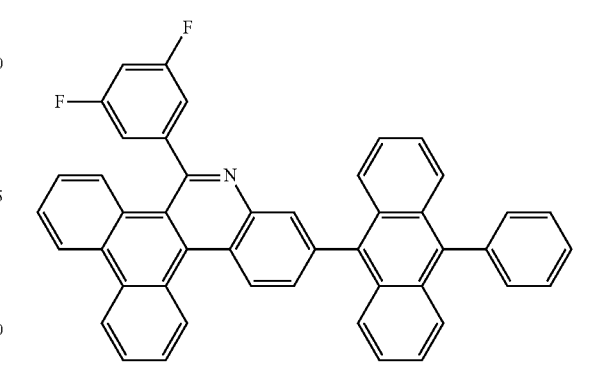
49
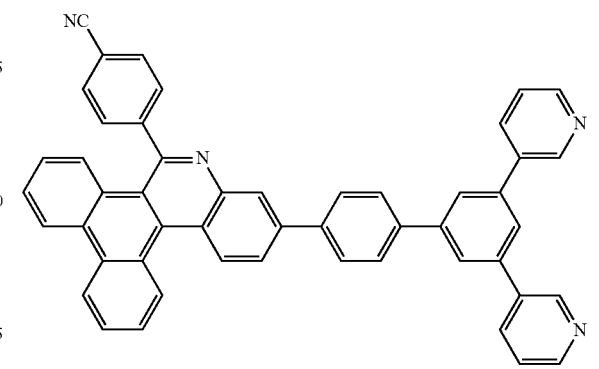

50
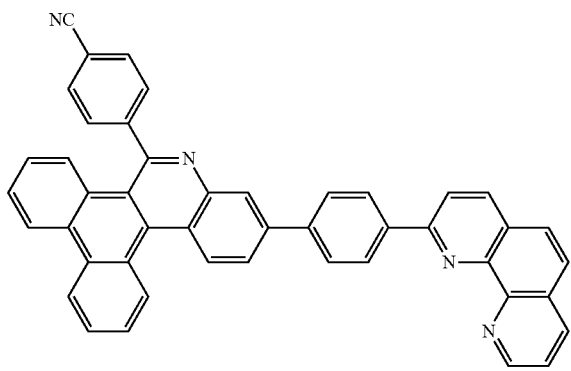
51
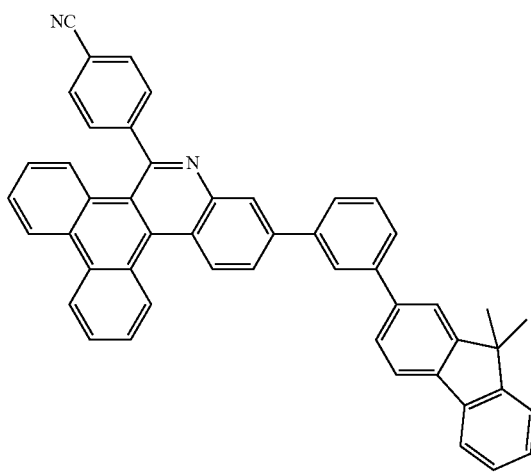
52
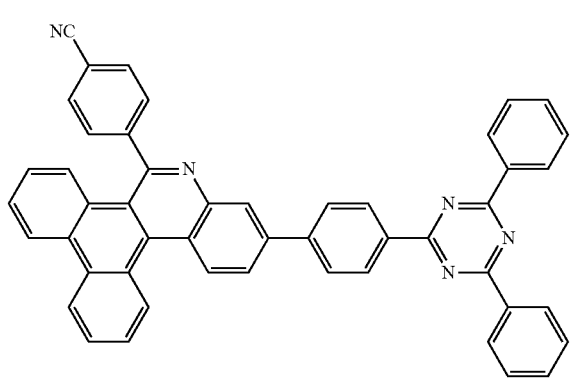
53
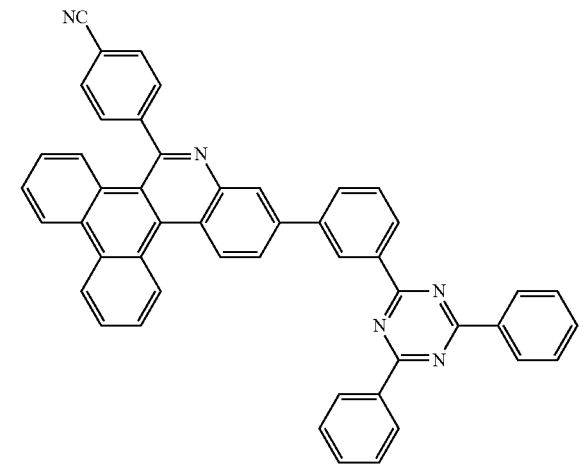
54
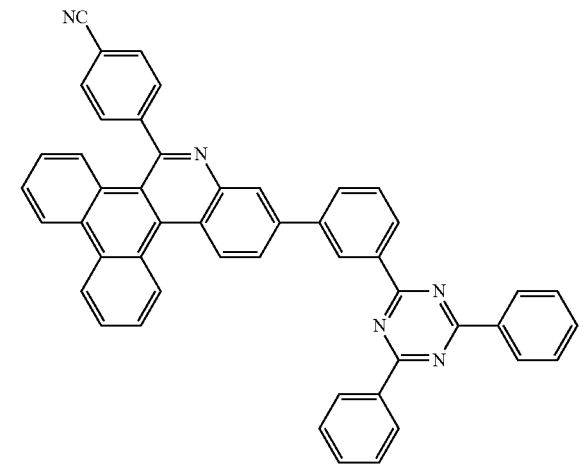
55
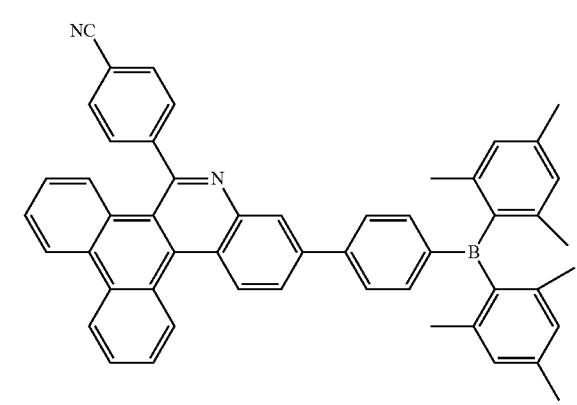

56
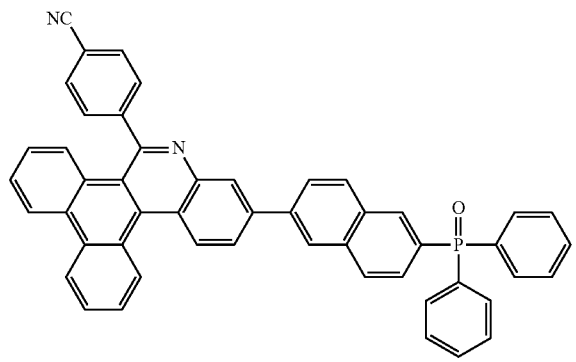
57
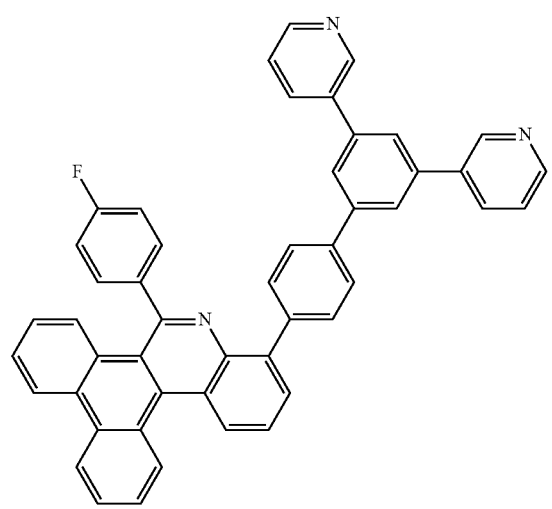
58
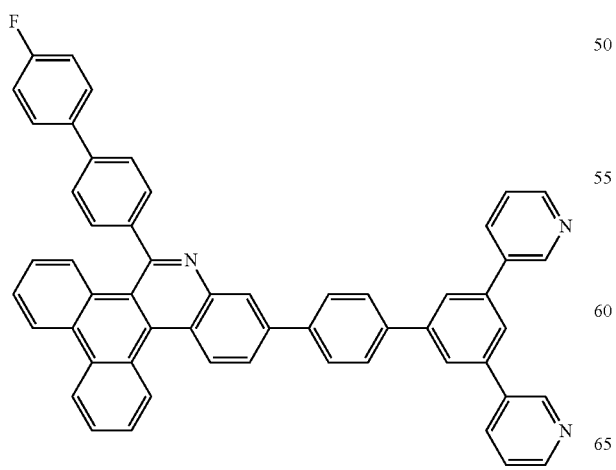
59
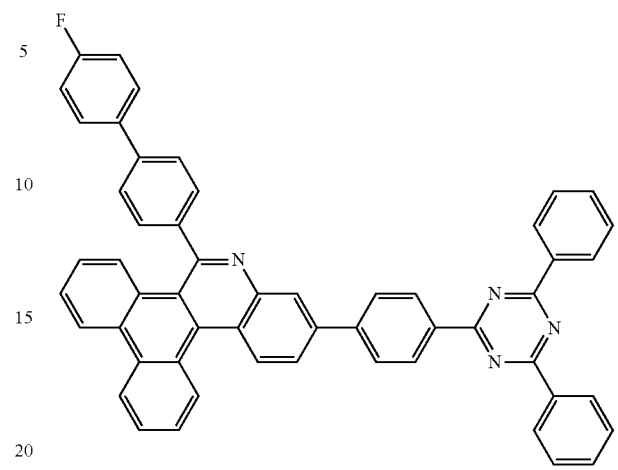
60
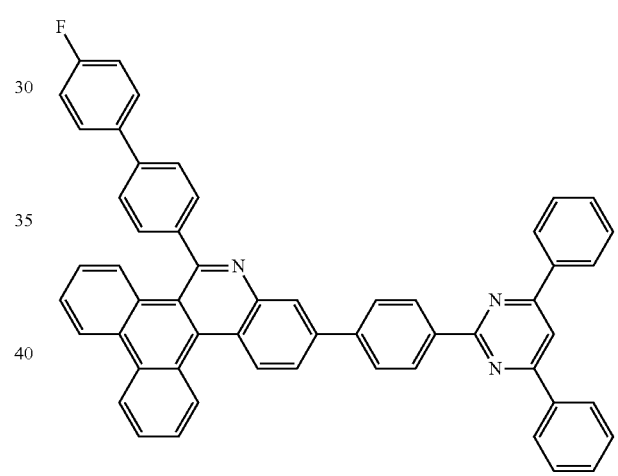
61
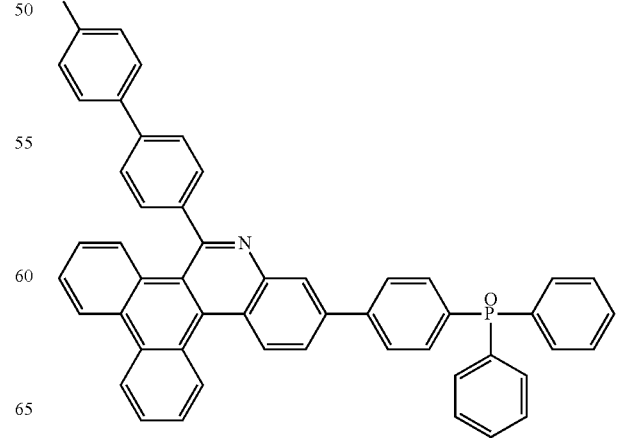

62
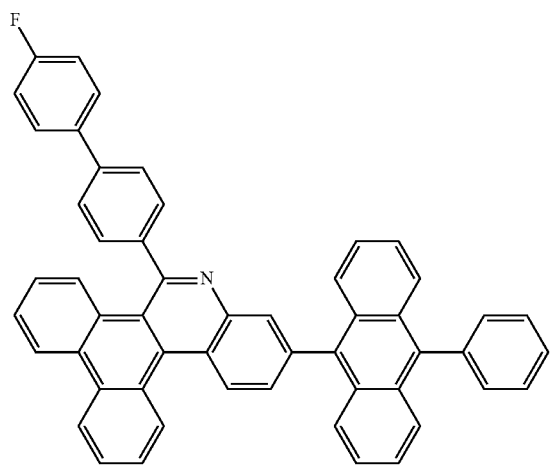
63
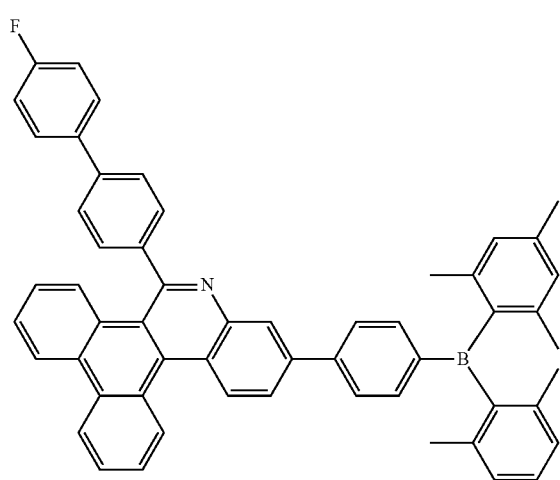
64
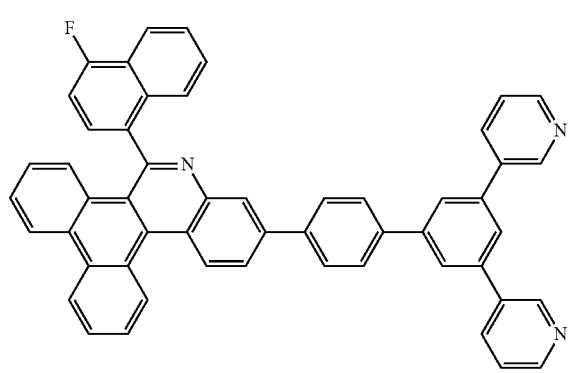
65
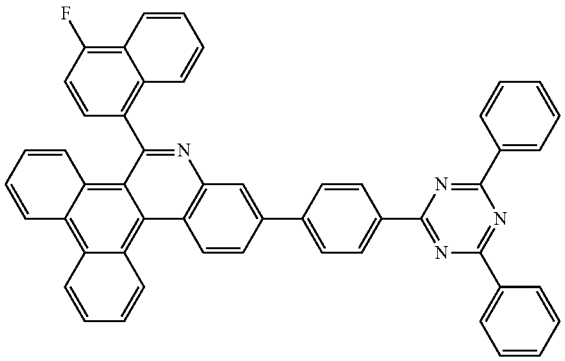
66
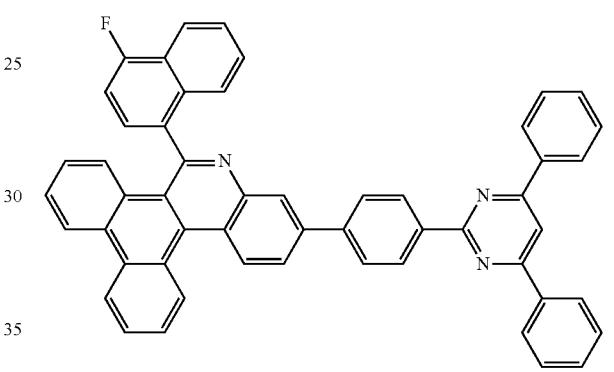
67
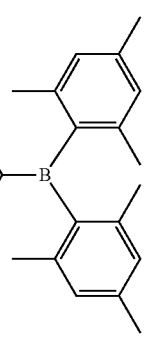
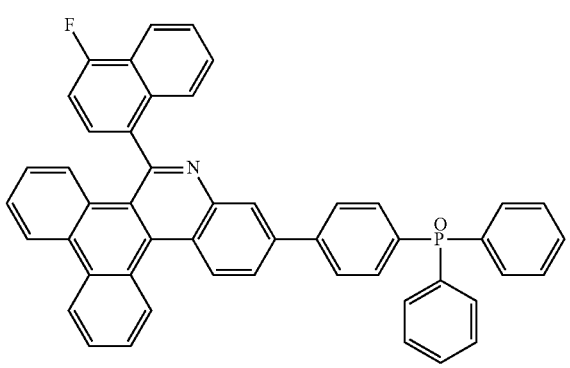
68
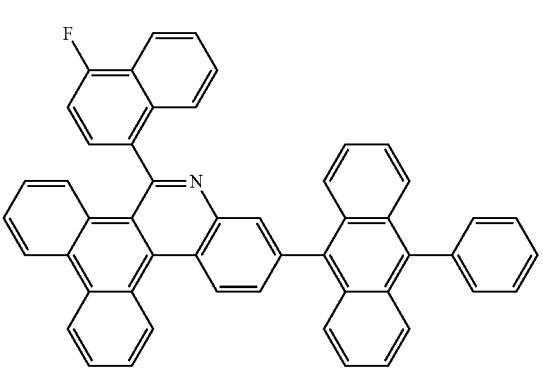

69
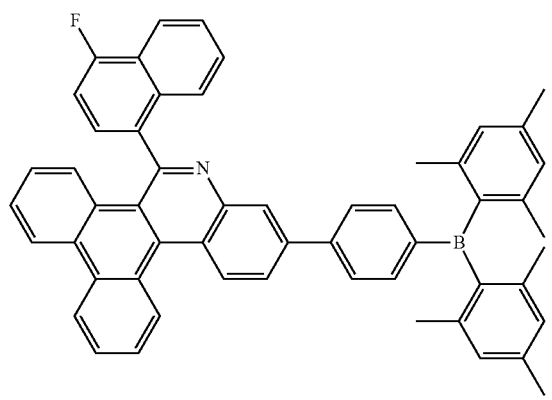
70
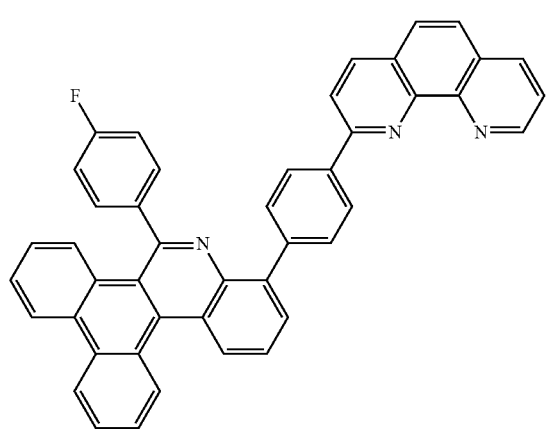
71
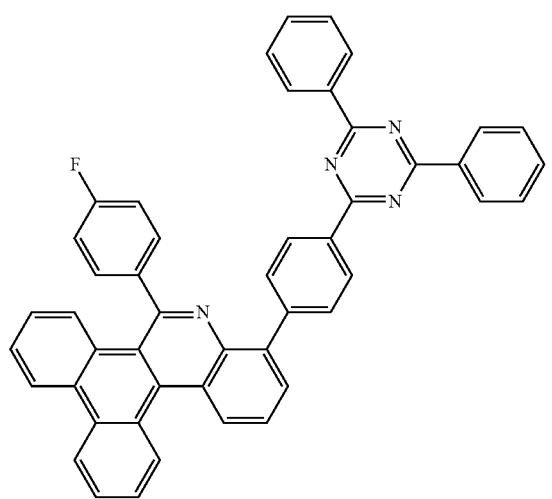
72
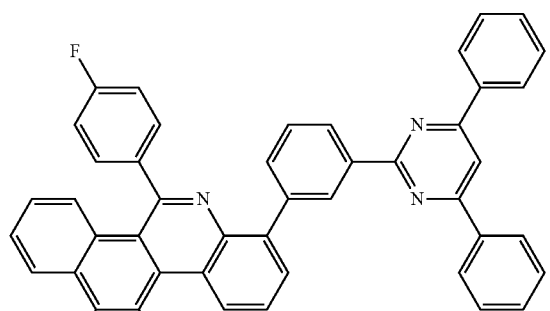
73
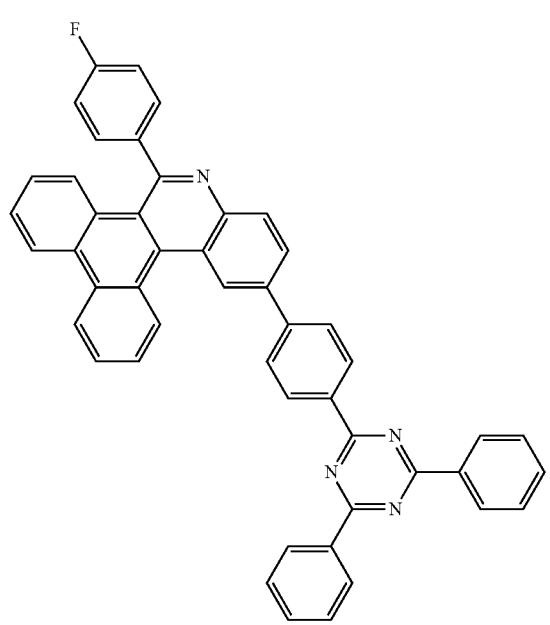
74
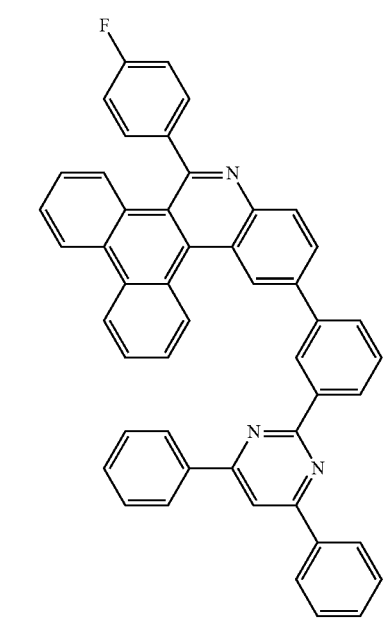

-continued

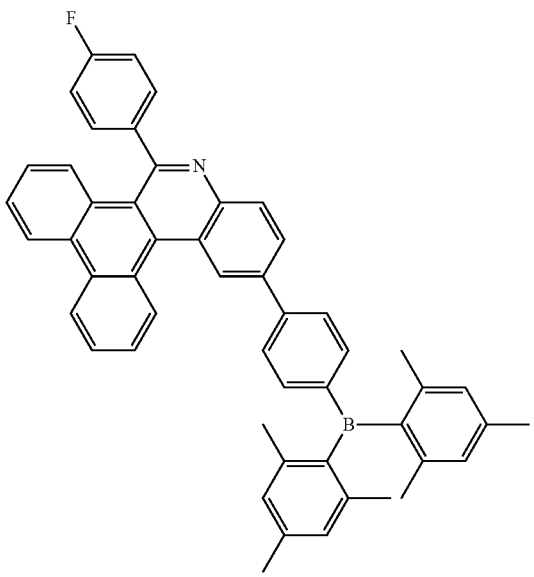

75

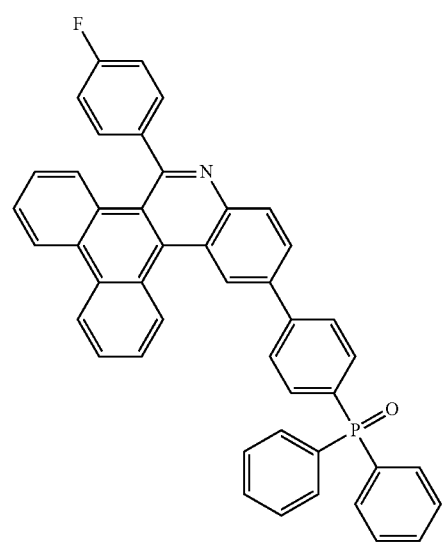

76

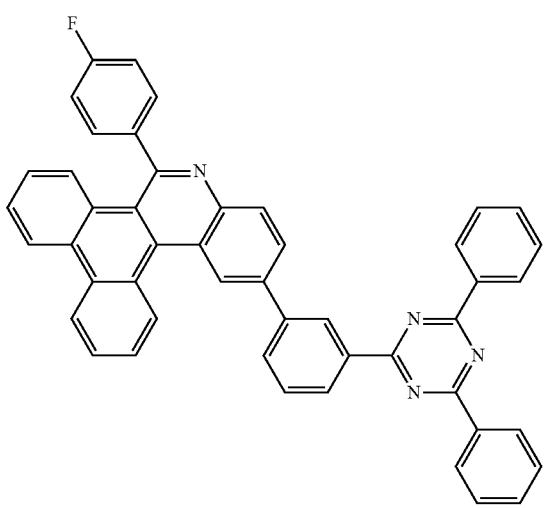

77

The condensed cyclic compound includes the structure of Formula 1, which includes the structure of Formula 2. In particular, due to at least one electron-withdrawing group (EWG) substituent in the carbon adjacent to nitrogen in the core of the condensed cyclic compound, electron-injection and transport effects may be obtained according to the principle of dipole-dipole interaction.

A synthesis method for the condensed cyclic compound represented by Formula 1 will be apparent to one of ordinary skill in the art by referring to the following examples.

At least one condensed cyclic compound represented by Formula 1 may be used between a pair of electrodes constituting an organic light-emitting device. For example, the condensed cyclic compound may be included in at least one layer selected from a hole transport region, an electron transport region, and an emission layer. In one or more embodiments, the condensed cyclic compound of Formula 1 may be used as a material for a capping layer located outside a pair of electrodes of an organic light-emitting device.

Accordingly, provided is an organic light-emitting device including: a first electrode; a second electrode facing the first electrode; and an organic layer between the first electrode and the second electrode, the organic layer including an emission layer, wherein the organic layer includes at least one condensed cyclic compound.

The expression "(an organic layer) includes at least one condensed cyclic compound" used herein may include a case in which "(an organic layer) includes identical compounds represented by Formula 1" and a case in which "(an organic layer) includes two or more different condensed cyclic compounds."

In one embodiment, the first electrode is an anode, and the second electrode is a cathode, and the organic layer further a hole transport region between the first electrode and the emission layer and an electron transport region between the emission layer and the second electrode, and the hole transport region includes a hole injection layer, a hole transport layer, an emission auxiliary layer, an electron blocking layer, or any combination thereof, and the electron transport region includes a buffer layer, a hole blocking layer, an electron control layer, an electron transport layer, an electron injection layer, or any combination thereof.

In one embodiment, the electron transport region may include at least one of the condensed cyclic compounds.

In one or more embodiments, the electron transport region may include an electron transport layer, and the electron transport layer may be included in the condensed cyclic compound.

For example, the electron transport region may include an emission auxiliary layer, the condensed cyclic compound may be included in the emission auxiliary layer.

In one or more embodiments, the hole transport region may include a p-dopant, and a lowest unoccupied molecular orbital (LUMO) of the p-dopant may be −3.5 eV or less.

For example, the p-dopant may contain a cyano group-containing compound.

The emission layer may include a host, and the host of the emission layer may include at least one selected from an anthracene-based compound, a pyrene-based compound, and a spiro-bifluorene-based compound, but embodiments are not limited thereto.

The emission layer may include a dopant, and the dopant of the emission layer may include at least one selected from a styryl-based compound and an amine-based compound, but embodiments are not limited thereto.

The emission layer of the organic light-emitting device may be a first color light-emitting first emission layer, i) at least one second color light-emitting second emission layer is, or ii) at least one second color light-emitting second emission layer and at least one third color light-emitting third emission layer may be additionally included between the first electrode and the second electrode, a maximum emission wavelength of the first color light, a maximum emission wavelength of the second color light, and a maximum emission wavelength of the third color light are identical to or different from each other, and the first color light and the second color light are emitted as mixed light, or the first color light, the second color light, and the third color light are emitted as mixed light.

As used herein, the term maximum emission wavelength indicates a wavelength of maximum emission.

The organic light-emitting device may further include at least one selected from a first capping layer disposed in a pathway along which light generated in an emission layer proceeds toward the outside through the first electrode and a second capping layer disposed in a pathway along which light generated in an emission layer proceeds toward the outside through the second electrode, and the at least one selected from the first capping layer and the second capping layer may include at least one condensed cyclic compound represented by Formula 1.

For example, the organic light-emitting device may have i) a stacked structure including a first electrode, an organic layer, a second electrode, and a second capping layer which are sequentially stacked in this stated order, ii) a stacked structure including a first capping layer, a first electrode, an organic layer, and a second electrode which are sequentially stacked in this stated order, or iii) a stacked structure including a first capping layer, a first electrode, an organic layer, a second electrode, and a second capping layer which are sequentially stacked in this stated order, and at least one selected from the first capping layer and the second capping layer may include the condensed cyclic compound.

The term "organic layer" used herein refers to a single layer and/or a plurality of layers disposed between the first electrode and the second electrode of the organic light-emitting device. A material included in the "organic layer" is not limited to an organic material.

[Description of FIG. 1]

Figure 1:
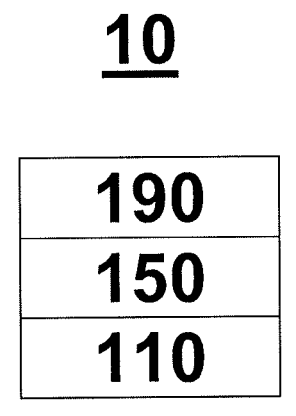

FIG. 1 is a schematic view of an organic light-emitting device 10 according to an embodiment. The organic light-emitting device 10 includes a first electrode 110, an organic layer 150, and a second electrode 190.

Hereinafter, the structure of the organic light-emitting device 10 according to an embodiment and a method of manufacturing the organic light-emitting device 10 will be described in connection with FIG. 1.

[First Electrode 110]

In FIG. 1, a substrate may be additionally disposed under the first electrode 110 or above the second electrode 190. The substrate may be a glass substrate or a plastic substrate, each having excellent mechanical strength, thermal stability, transparency, surface smoothness, ease of handling, and water resistance.

The first electrode 110 may be formed by depositing or sputtering a material for forming the first electrode 110 on the substrate. When the first electrode 110 is an anode, the material for a first electrode may be selected from materials with a high work function to facilitate hole injection.

The first electrode 110 may be a reflective electrode, a semi-transmissive electrode, or a transmissive electrode. When the first electrode 110 is a transmissive electrode, a material for forming a first electrode may be selected from indium tin oxide (ITO), indium zinc oxide (IZO), tin oxide ($SnO_2$), zinc oxide (ZnO), and any combinations thereof, but embodiments are not limited thereto. In one or more embodiments, when the first electrode 110 is a semi-transmissive electrode or a reflectable electrode, a material for forming a first electrode may be selected from magnesium (Mg), silver (Ag), aluminum (Al), aluminum-lithium (Al—Li), calcium (Ca), magnesium-indium (Mg—In), magnesium-silver (Mg—Ag), and any combinations thereof, but embodiments are not limited thereto.

The first electrode 110 may have a single-layered structure, or a multi-layered structure including two or more layers. For example, the first electrode 110 may have a three-layered structure of ITO/Ag/ITO, but the structure of the first electrode 110 is not limited thereto.

[Organic Layer 150]

The organic layer 150 is disposed on the first electrode 110. The organic layer 150 may include an emission layer.

The organic layer 150 may further include a hole transport region between the first electrode 110 and the emission layer, and an electron transport region between the emission layer and the second electrode 190.

[Hole Transport Region in Organic Layer 150]

The hole transport region may have i) a single-layered structure including a single layer including a single material, ii) a single-layered structure including a single layer including a plurality of different materials, or iii) a multi-layered structure having a plurality of layers including a plurality of different materials.

The hole transport region may include at least one layer selected from a hole injection layer (HIL), a hole transport layer (HTL), an emission auxiliary layer, and an electron blocking layer (EBL).

For example, the hole transport region may have a single-layered structure including a single layer including a plurality of different materials, or a multi-layered structure having a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein for each structure, constituting layers are sequentially stacked from the first electrode 110 in this stated order, but the structure of the hole transport region is not limited thereto.

The hole transport region may include at least one selected from m-MTDATA, TDATA, 2-TNATA, NPB (NPD), β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), a compound represented by Formula 201, and a compound represented by Formula 202:

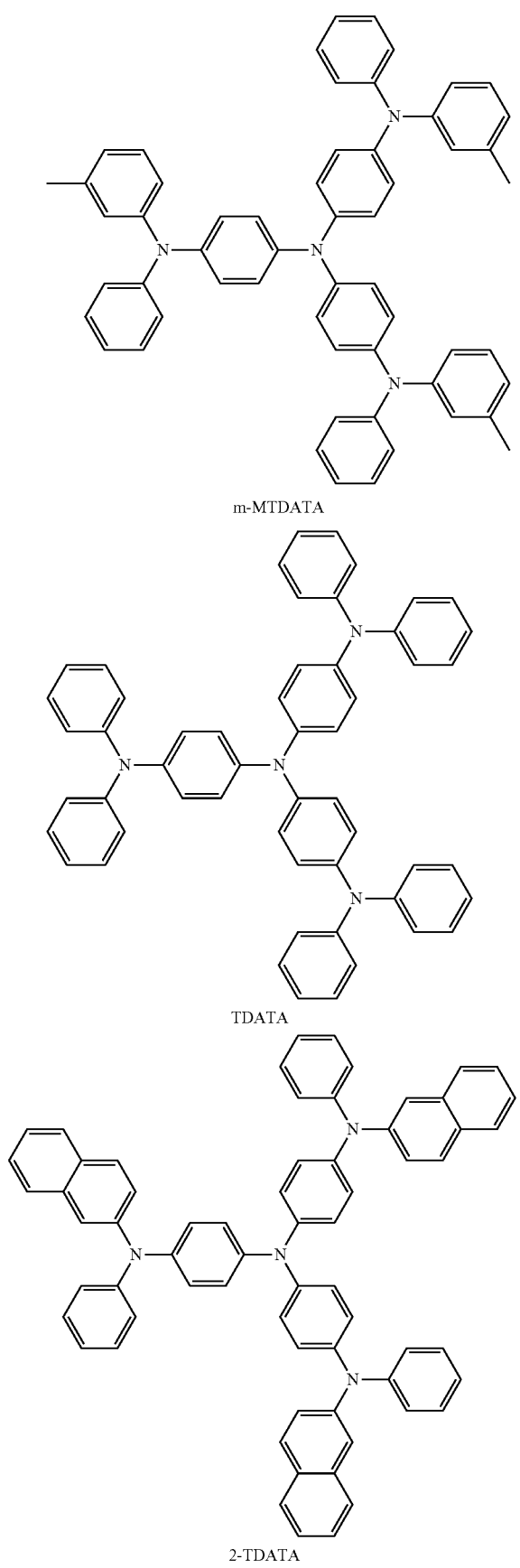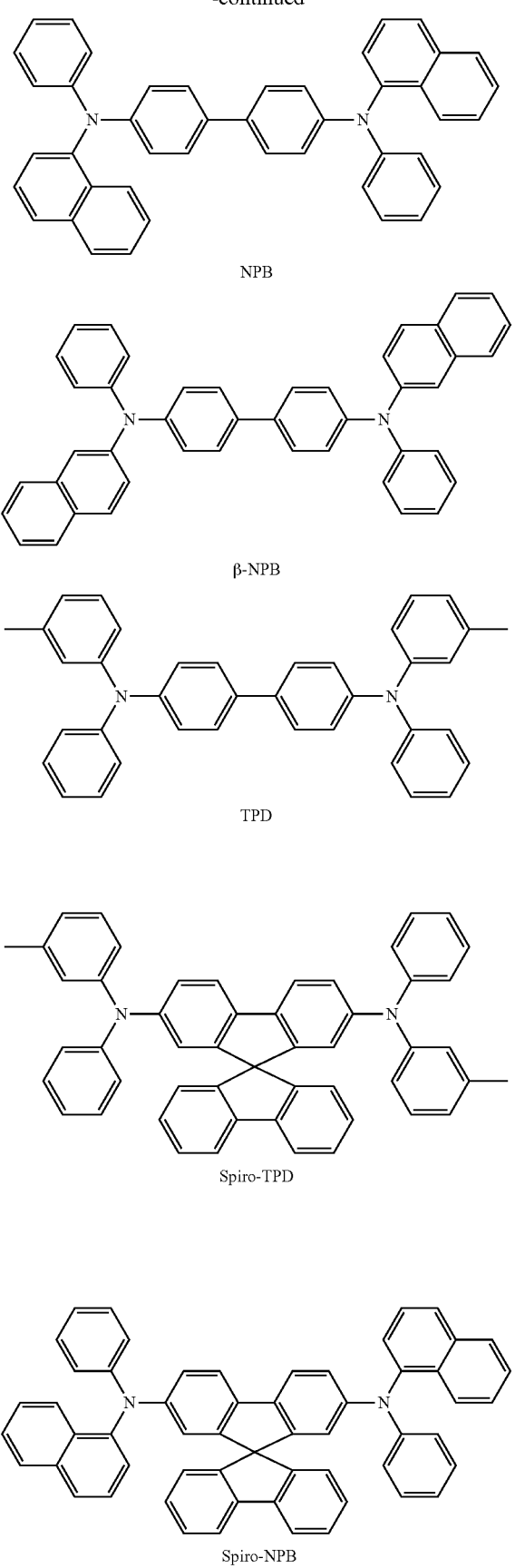

-continued

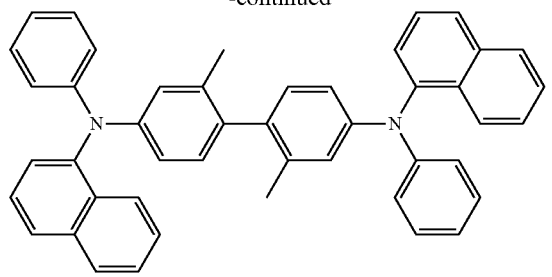

methylated NPB

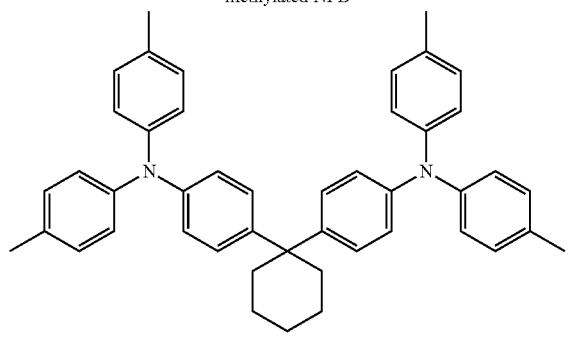

TAPC

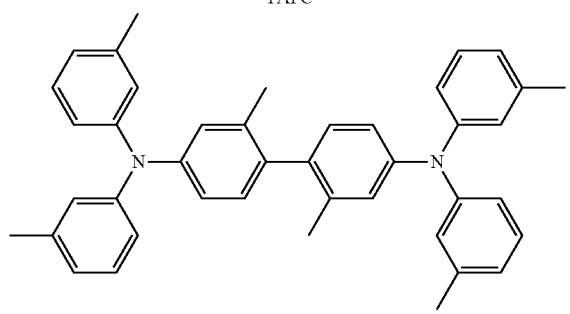

HMTPD

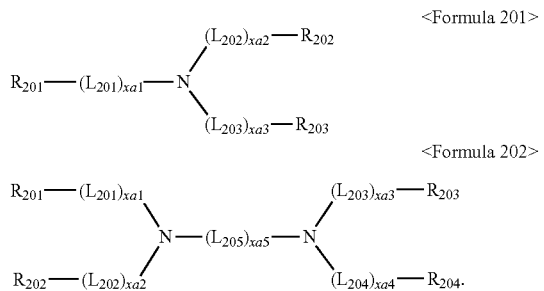

<Formula 201>

<Formula 202>

In Formulae 201 and 202, $L_{201}$ to $L_{204}$ may each independently be selected from a substituted or unsubstituted $C_3$-$C_{10}$ cycloalkylene group, a substituted or unsubstituted heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{205}$ may be selected from *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer from 0 to 3, xa5 may be an integer from 1 to 10, and $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, in Formula 202, $R_{201}$ and $R_{202}$ may optionally be linked via a single bond, a dimethyl-methylene group, or a diphenyl-methylene group, and $R_{203}$ and $R_{204}$ may optionally be linked via a single bond, a dimethyl-methylene group, or a diphenyl-methylene group.

In one embodiment, in Formulae 201 and 202, $L_{201}$ to $L_{205}$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xa1 to xa4 may each independently be 0, 1, or 2.

In one or more embodiments, xa5 may be 1, 2, 3, or 4.

In one or more embodiments, $R_{201}$ to $R_{204}$ and $Q_{201}$ may each independently be selected from a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), $Q_{31}$ to $Q_{33}$ may be the same as described above.

In one or more embodiments, at least one selected from $R_{201}$ to $R_{203}$ in Formula 201 may each independently be selected from:

a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cycloheptyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments are not limited thereto.

In one or more embodiments, in Formula 202, i) $R_{201}$ and $R_{202}$ may be linked via a single bond, and/or ii) $R_{203}$ and $R_{204}$ may be linked via a single bond.

In one or more embodiments, at least one selected from $R_{201}$ to $R_{204}$ in Formula 202 may be selected from, a carbazolyl group; and a carbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments are not limited thereto.

The compound represented by Formula 201 may be represented by Formula 201A:

<Formula 201A>

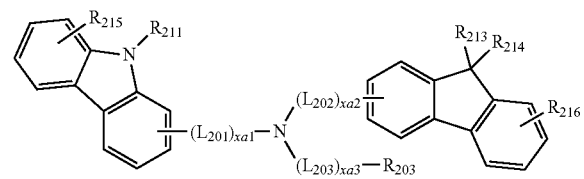

For example, the compound represented by Formula 201 may be represented by Formula 201A(1), but embodiments are not limited thereto:

<Formula 201A(1)>

For example, the compound represented by Formula 201 may be represented by Formula 201A-1, but embodiments are not limited thereto:

<Formula 201A-1>

The compound represented by Formula 202 may be represented by Formula 202A:

<Formula 202A>

In one or more embodiments, the compound represented by Formula 202 may be represented by Formula 202A-1:

<Formula 202A-1>

In Formulae 201A, 201A(1), 201A-1, 202A, and 202A-1, $L_{201}$ to $L_{203}$, xa1 to xa3, xa5, and $R_{202}$ to $R_{204}$ are the same as described above, $R_{211}$ and $R_{212}$ may be the same as described in connection with $R_{203}$, $R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one compound selected from Compounds HT1 to HT39, but embodiments are not limited thereto:

HT1
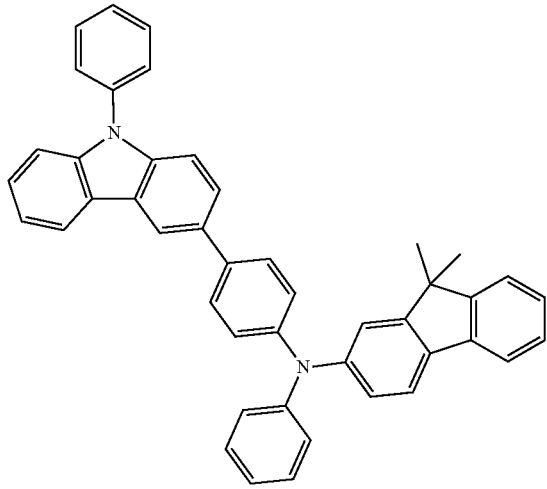

HT2
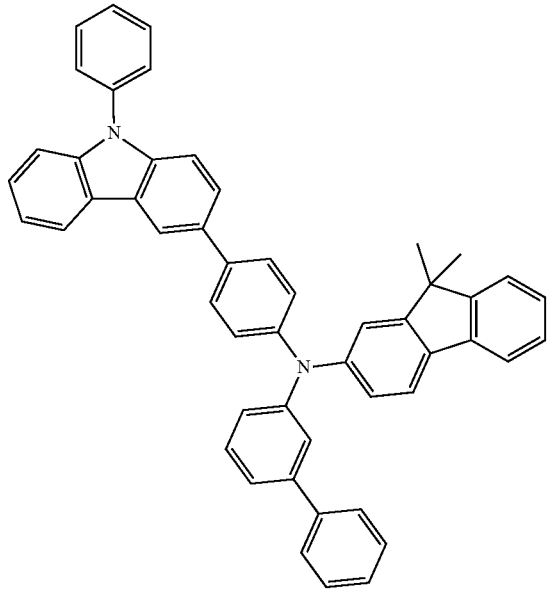

HT3
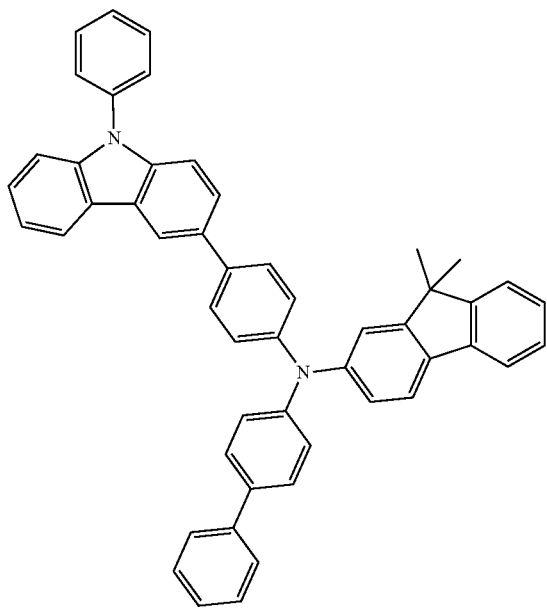

HT4
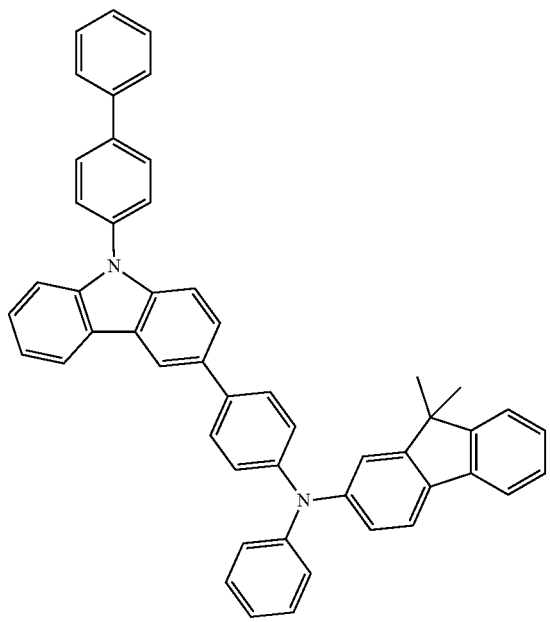

HT5
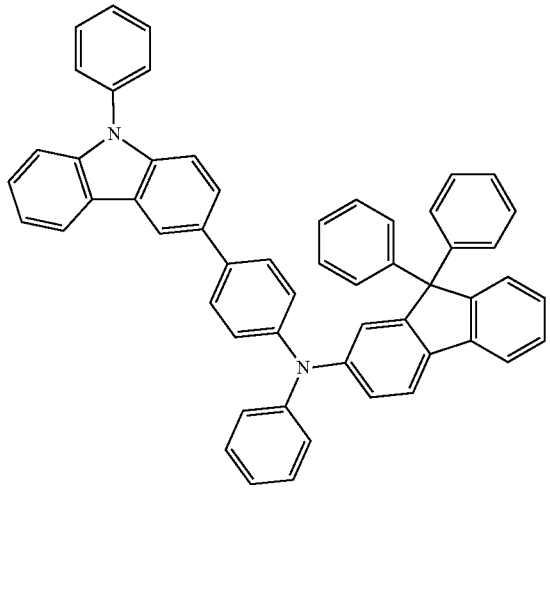
HT6
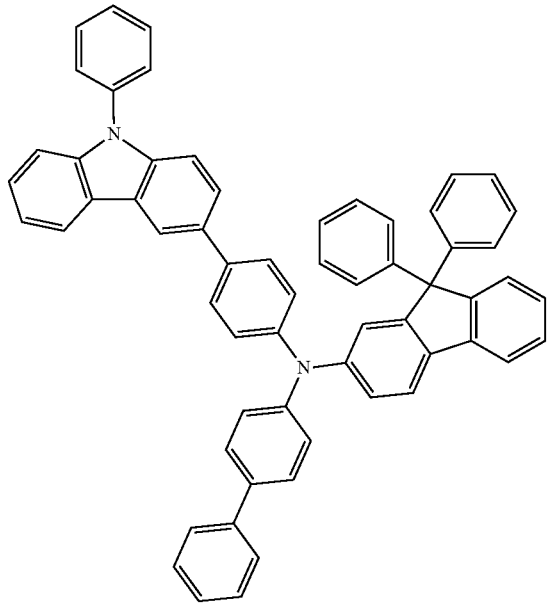
HT7
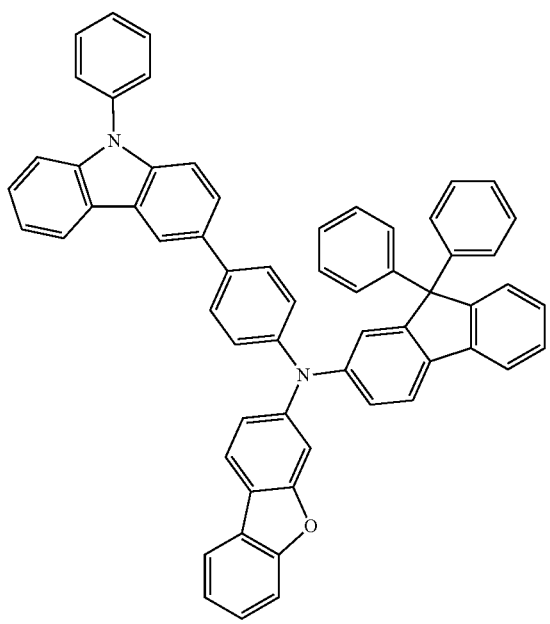
HT8
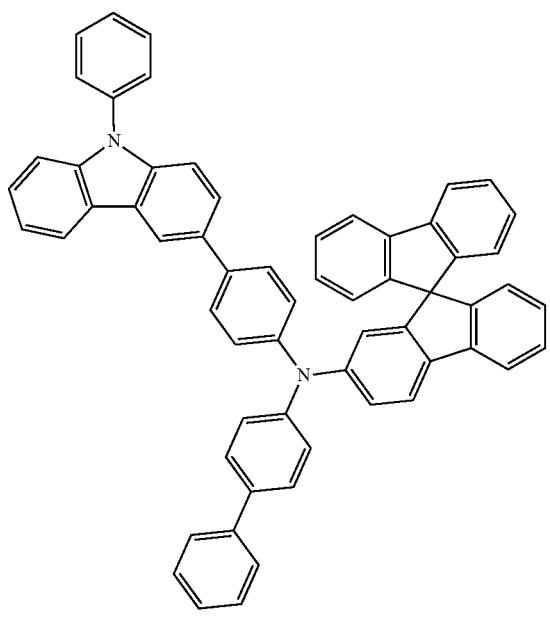

-continued
HT9
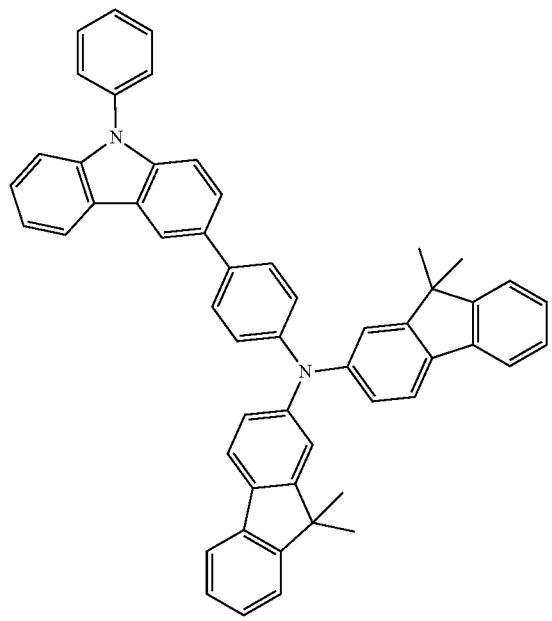
HT10
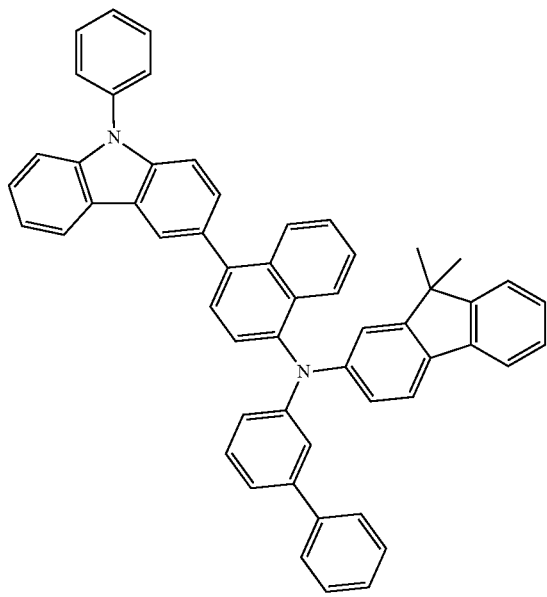
HT11
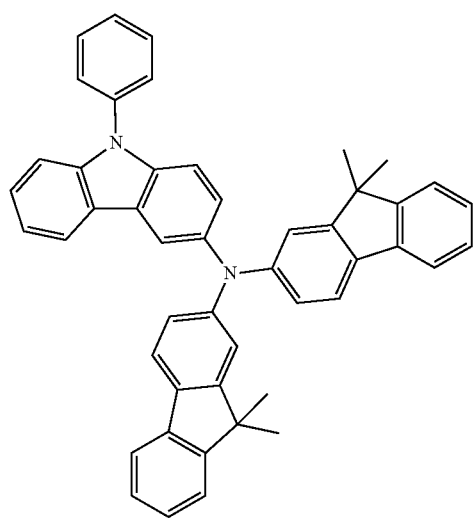
HT12
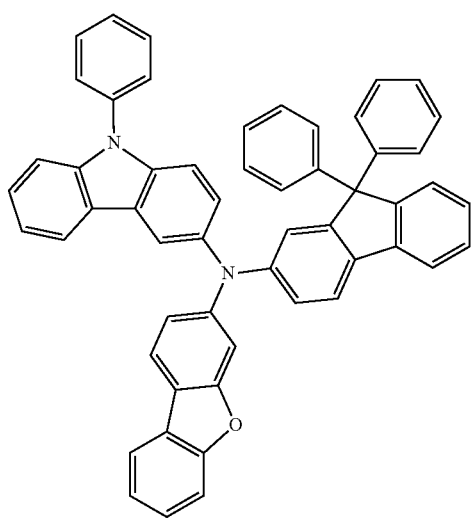

-continued
HT13
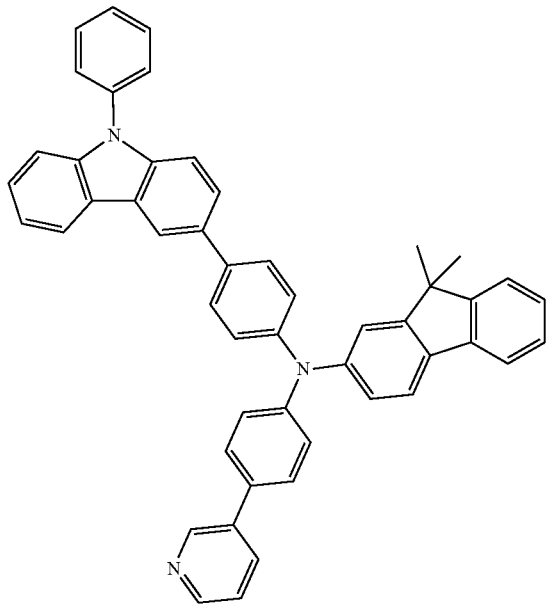
HT14
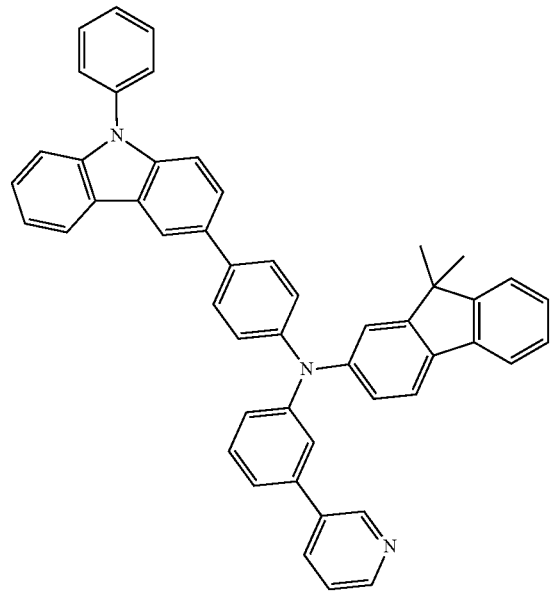
HT15
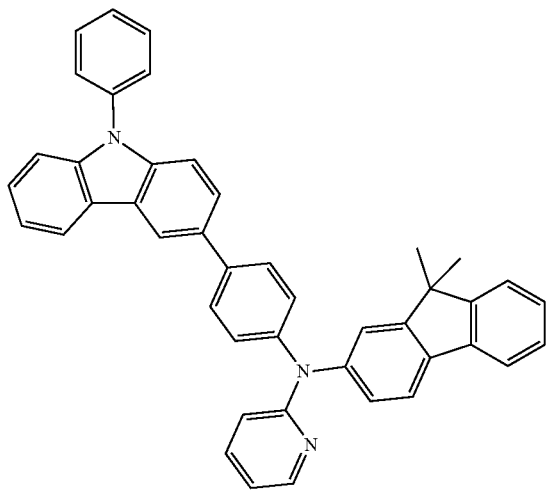
HT16
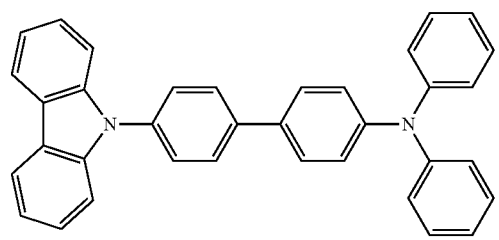
HT17
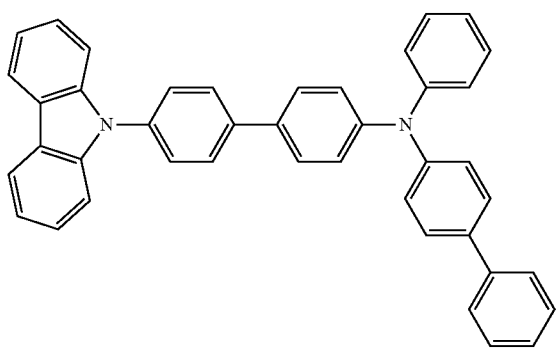
HT18
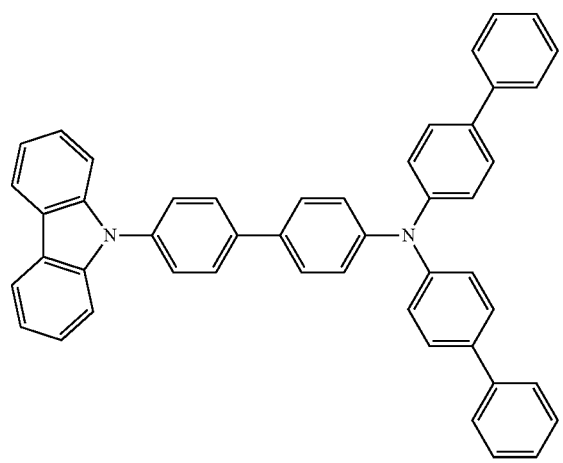

-continued
HT19
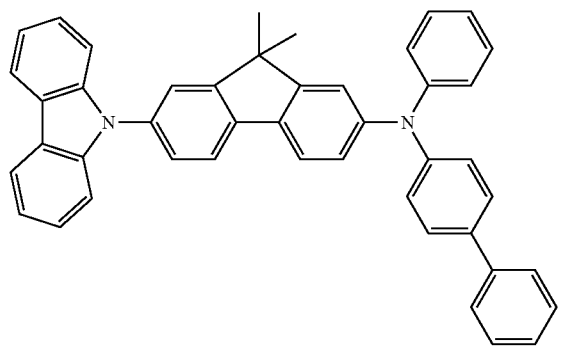
HT20
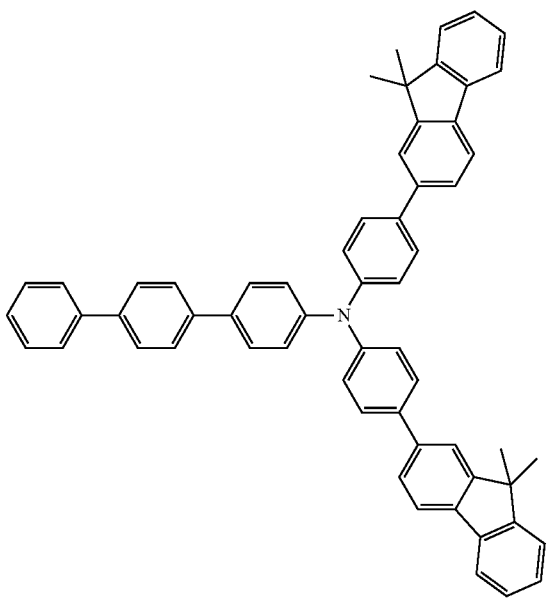
HT21
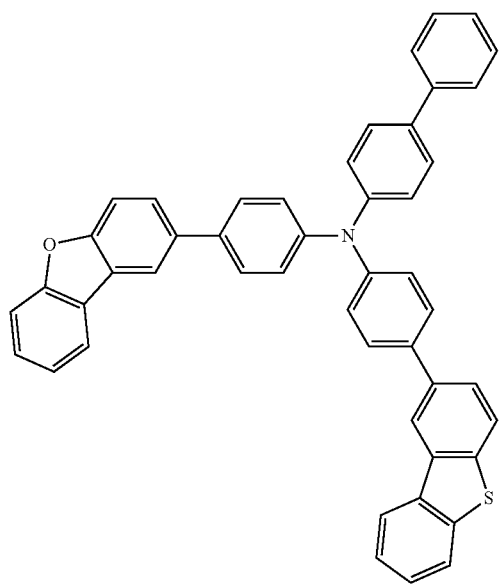
HT22
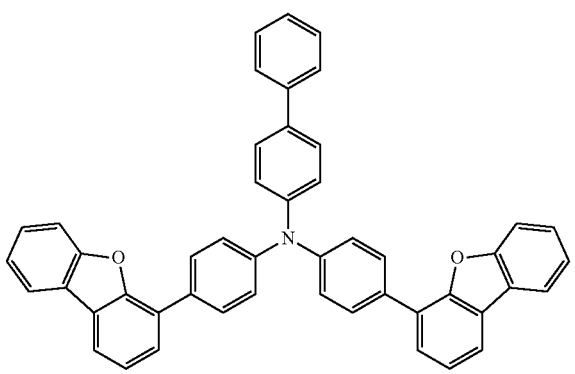

-continued
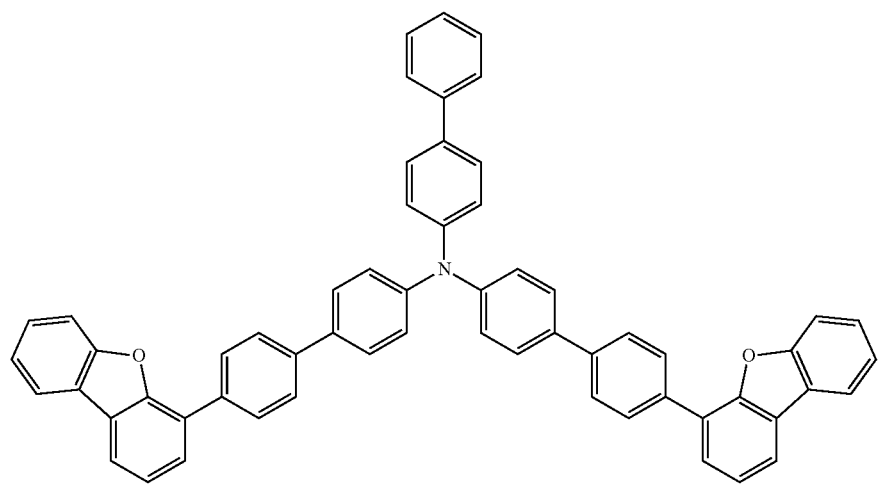
HT23
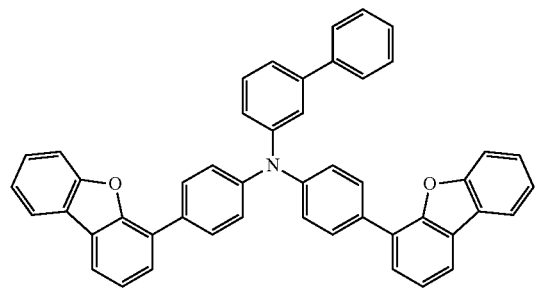
HT24
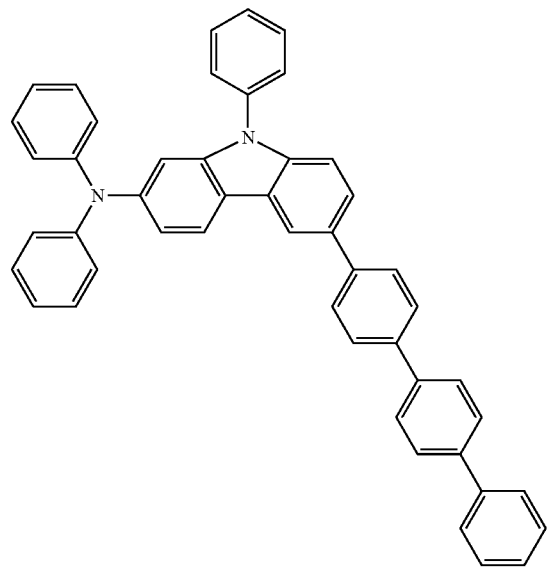
HT25
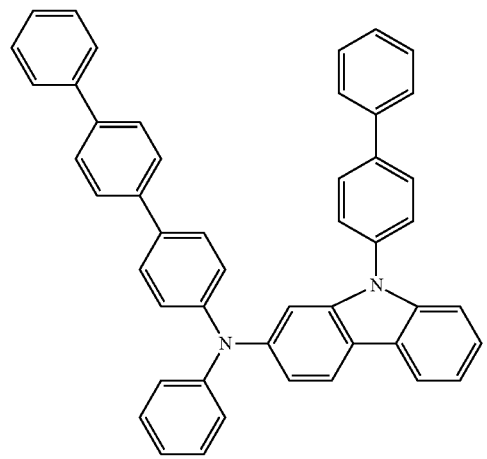
HT26
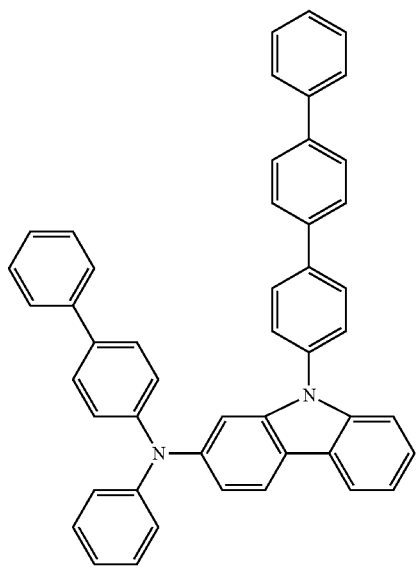
HT27

-continued
HT28
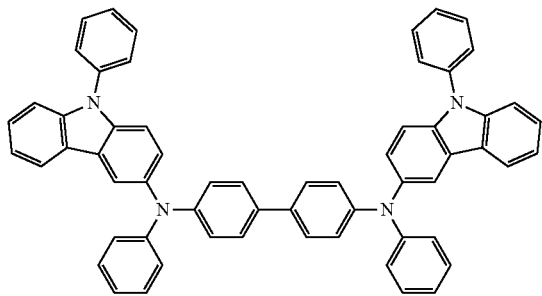
HT29
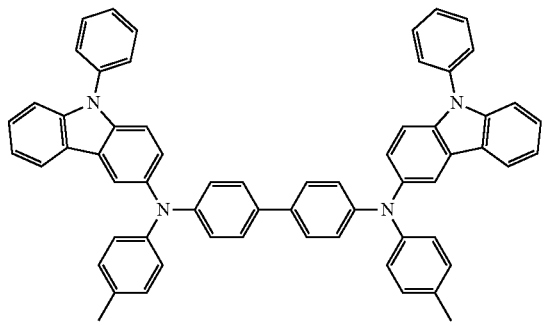
HT30
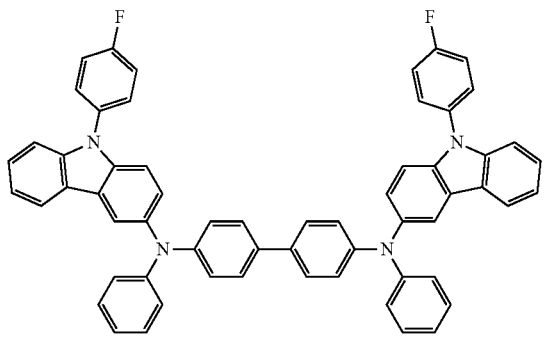
HT31
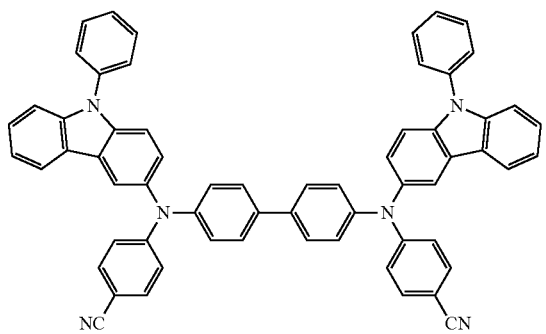
HT32
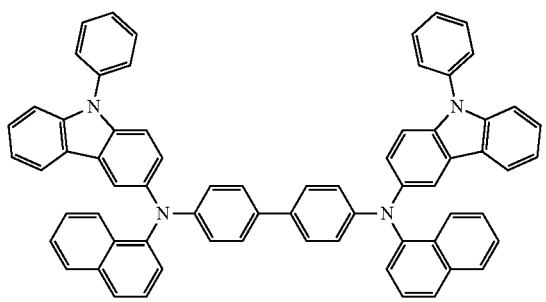
HT33
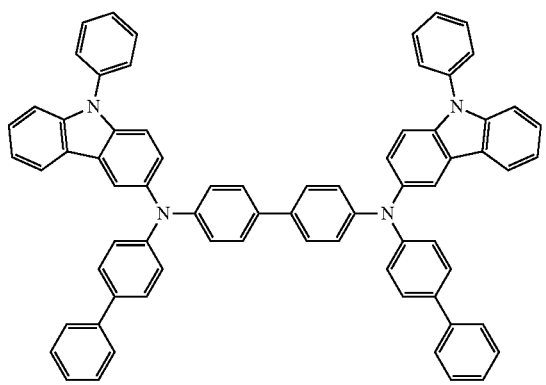
HT34
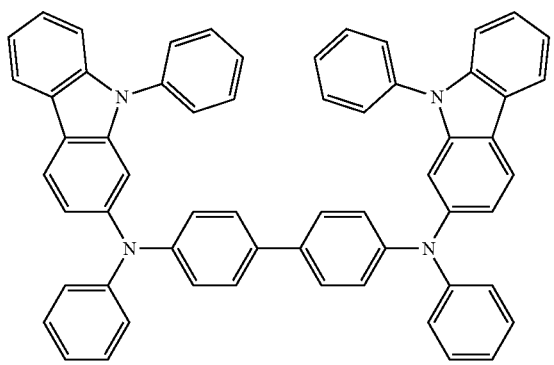
HT35
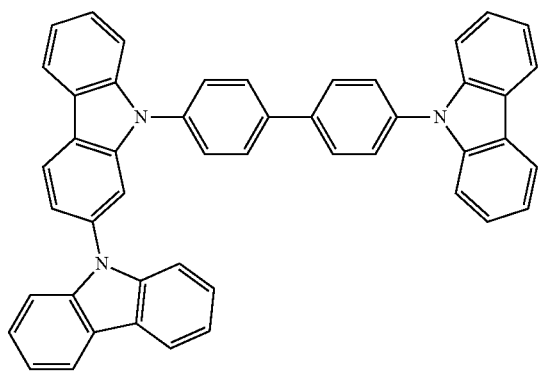

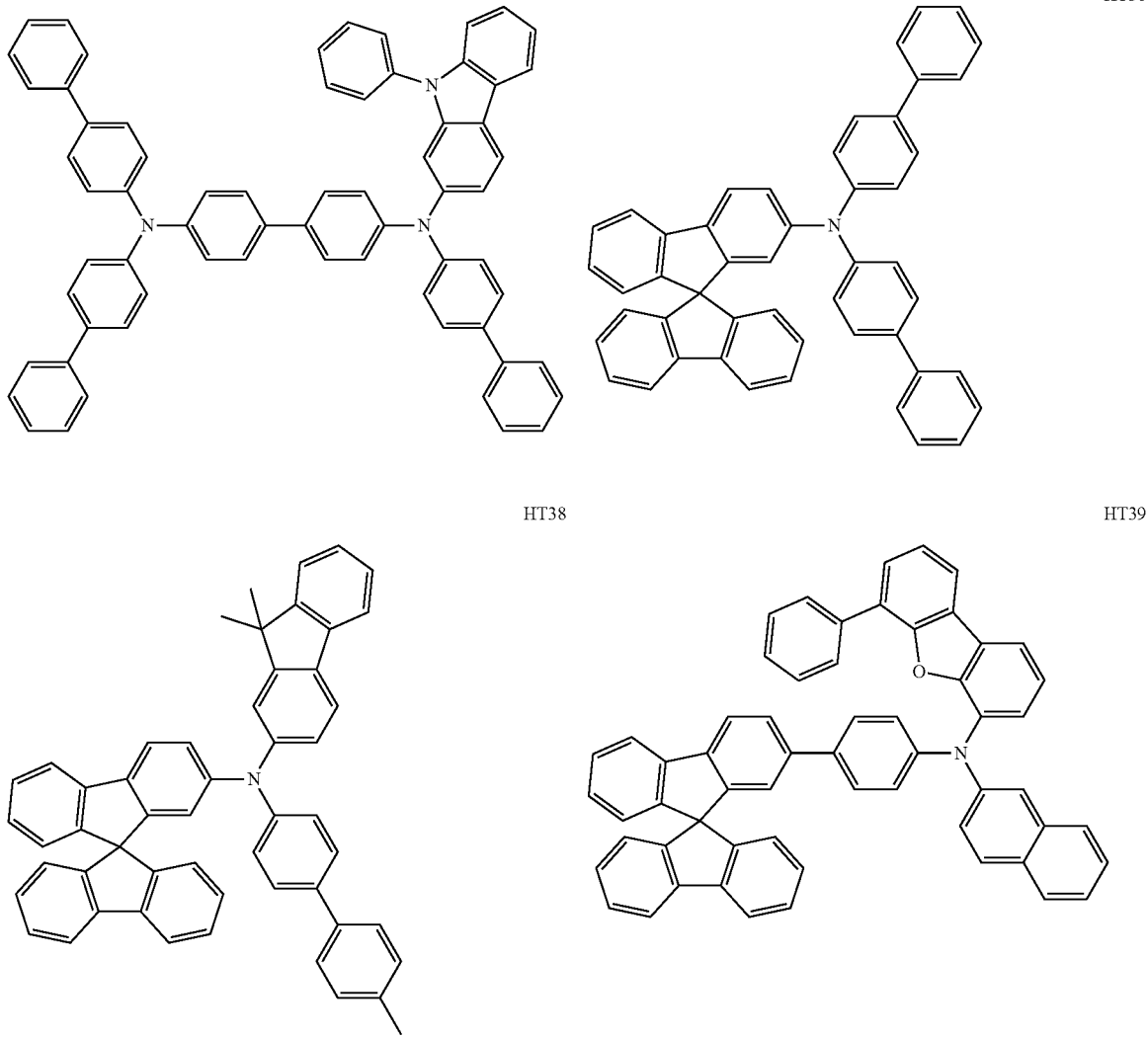

A thickness of the hole transport region may be in a range of about 100 Å to about 10,000 Å, for example, about 100 Å to about 1,000 Å. When the hole transport region includes at least one selected from a hole injection layer and a hole transport layer, the thickness of the hole injection layer may be in a range of about 100 Å to about 9,000 Å, and for example, about 100 Å to about 1,000 Å, and the thickness of the hole transport layer may be in a range of about 50 Å to about 2,000 Å, and for example, about 100 Å to about 1500 Å. When the thicknesses of the hole transport region, the hole injection layer, and the hole transport layer are within these ranges, satisfactory hole transporting characteristics may be obtained without a substantial increase in driving voltage.

The emission auxiliary layer may increase light-emission efficiency by compensating for an optical resonance distance according to the wavelength of light emitted by an emission layer, and the electron blocking layer may block the flow of electrons from an electron transport region. The emission auxiliary layer and the electron blocking layer may include the materials as described above.

[p-Dopant]

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant.

In one embodiment, the LUMO of the p-dopant may be −3.5 eV or less.

The p-dopant may include at least one selected from a quinone derivative, a metal oxide, and a cyano group-containing compound, but embodiments are not limited thereto.

For example, the p-dopant may include at least one selected from a quinone derivative, such as tetracyanoquinodimethane (TCNQ) or 2,3,5,6-tetralluoro-7,7,8,8-tetracyanoquinodimethane (F4-TCNQ);

a metal oxide, such as tungsten oxide or molybdenum oxide;

1,4,5,8,9,12-hexaazatriphenylene-hexacarbonitrile (HAT-CN); and a compound represented by Formula 221 below:

but embodiments are not limited thereto:

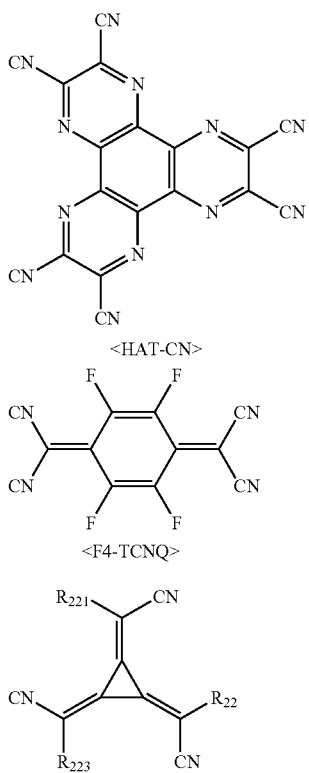

<HAT-CN>

<F4-TCNQ>

<Formula 221>

In Formula 221, $R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, provided that at least one selected from $R_{221}$ to $R_{223}$ has at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

[Emission Layer in Organic Layer 150]

When the organic light-emitting device 10 is a full-color organic light-emitting device, the emission layer may be patterned into a red emission layer, a green emission layer, or a blue emission layer, according to a sub-pixel. In one or more embodiments, the emission layer may have a stacked structure of two or more layers selected from a red emission layer, a green emission layer, and a blue emission layer, in which the two or more layers contact each other or are separated from each other. In one or more embodiments, the emission layer may include two or more materials selected from a red light-emitting material, a green light-emitting material, and a blue light-emitting material, in which the two or more materials are mixed with each other in a single layer to emit white light.

The emission layer may include a host and a dopant. The dopant may include at least one selected from a phosphorescent dopant and a fluorescent dopant.

An amount of the dopant in the emission layer may be, in general, in a range of about 0.01 parts by weight to about 15 parts by weight based on 100 parts by weight of the host, but embodiments are not limited thereto.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

[Host in Emission Layer]

In one or more embodiments, the host may further include a compound represented by Formula 301 below.

$[Ar_{301}]_{xb11}$-$[(L_{301})_{xb1}$-$R_{301}]_{xb21}$   <Formula 301>

In Formula 301, $Ar_{301}$ may be a substituted or unsubstituted $C_5$-$C_{60}$ carbocyclic group or a substituted or unsubstituted $C_1$-$C_{60}$ heterocyclic group, xb11 may be 1, 2, or 3, $L_{301}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

xb1 may be an integer from 0 to 5, $R_{301}$ may be selected from deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$) and —P(=O)($Q_{301}$)($Q_{302}$), xb21 may be an integer from 1 to 5, $Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments are not limited thereto.

In one embodiment, $Ar_{301}$ in Formula 301 may be selected from:

a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group; and a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments are not limited thereto.

When xb11 in Formula 301 is two or more, two or more of $Ar_{301}$ may be linked via a single bond.

In one or more embodiments, the compound represented by Formula 301 may be a group represented by Formula 301-1 or 301-2:

<Formula 301-1>

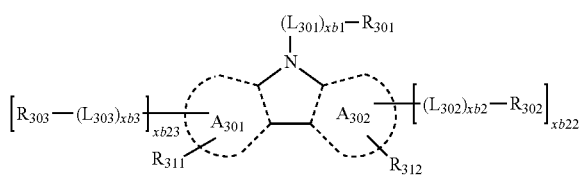

<Formula 301-2>

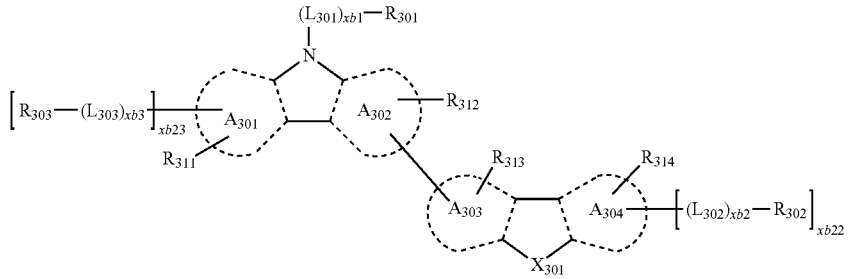

In Formulae 301-1 and 301-2, $A_{301}$ to $A_{304}$ may each independently be selected from a benzene group, a naphthalene group, a phenanthrene group, a fluoranthene group, a triphenylene group, a pyrene group, a chrysene group, a pyridine group, a pyrimidine group, an indene group, a fluorene group, a spiro-bifluorene group, a benzofluorene group, a dibenzofluorene group, an indole group, a carbazole group, benzocarbazole group, dibenzocarbazole group, a furan group, a benzofuran group, a dibenzofuran group, a naphthofuran group, a benzonaphthofuran group, dinaphthofuran group, a thiophene group, a benzothiophene group, a dibenzothiophene group, a naphthothiophene group, a benzonaphthothiophene group, and a dinaphthothiophene group, $X_{301}$ may be O, S, or N-[($L_{304}$)$_{xb4}$-$R_{304}$], $R_{311}$ to $R_{314}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), xb22 and xb23 may each independently be 0, 1, or 2, $L_{301}$, xb1, $R_{301}$ and $Q_{31}$ to $Q_{33}$ are the same as described above, $L_{302}$ to $L_{304}$ may each independently be the same as described in connection with $L_{301}$, xb2 to xb4 may each independently be the same as described in connection with xb1, $R_{302}$ to $R_{304}$ may each independently be the same as described in connection with $R_{301}$.

For example, $L_{301}$ to $L_{304}$ in Formulae 301, 301-1, and 301-2 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), $Q_{31}$ to $Q_{33}$ are the same as described above.

In one embodiment, $R_{301}$ to $R_{304}$ in Formulae 301, 301-1, and 301-2 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$ ($Q_{31}$) and —P(=O)($Q_{31}$)($Q_{32}$), wherein $Q_{31}$ to $Q_{33}$ may be the same as described above.

In one embodiment, the host may include an alkali earth metal complex. For example, the host may be selected from a Be complex (for example, Compound H55), a Mg complex, and a Zn complex.

The host may include at least one selected from 9,10-di (2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), and Compounds H1 to H55, but is not limited thereto:

H1
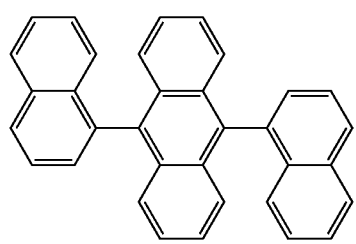

H2
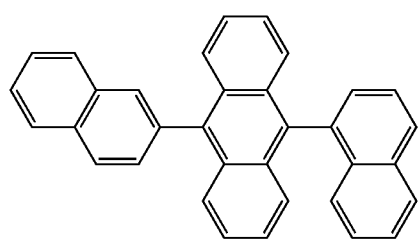

H3
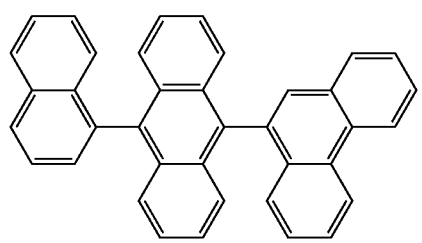

H4
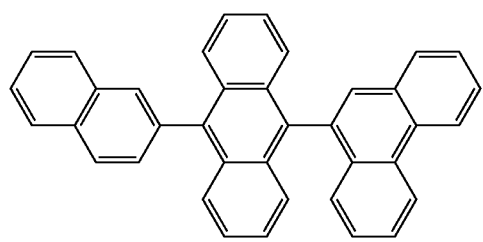

-continued

H5
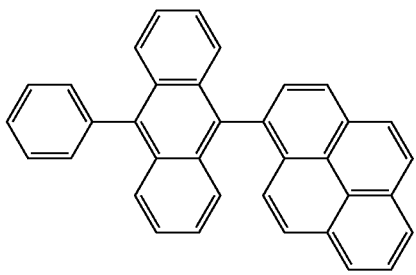

H6
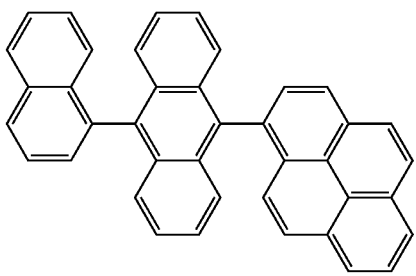

H7
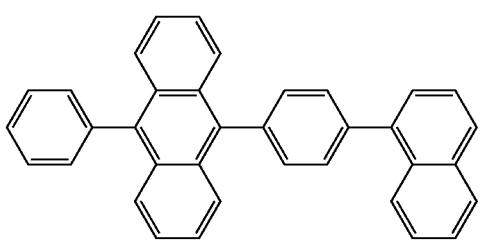

H8
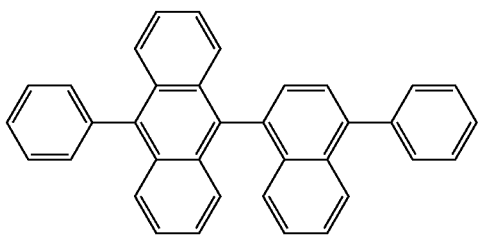

H9
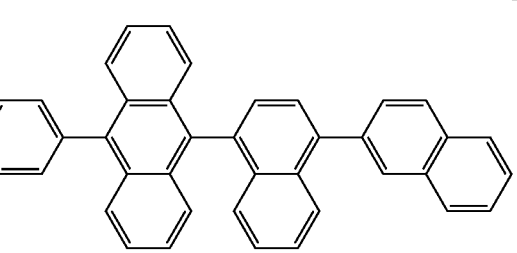

H10
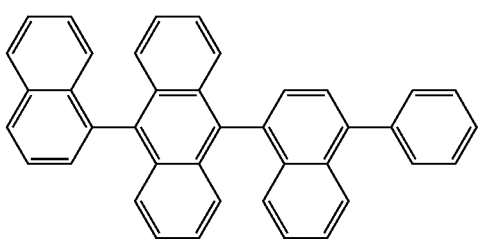

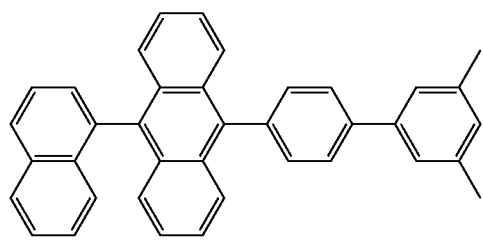 H11
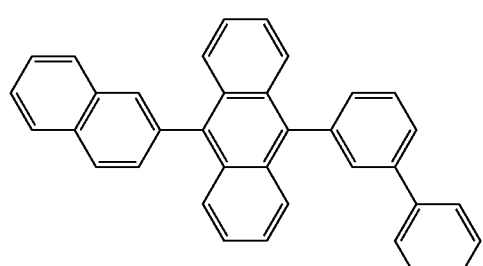 H12
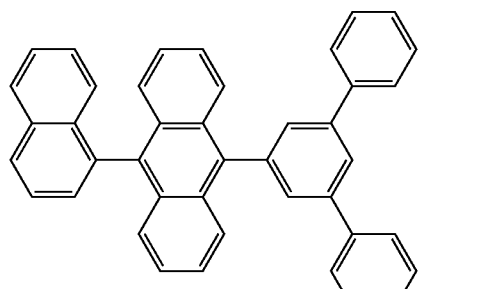 H13
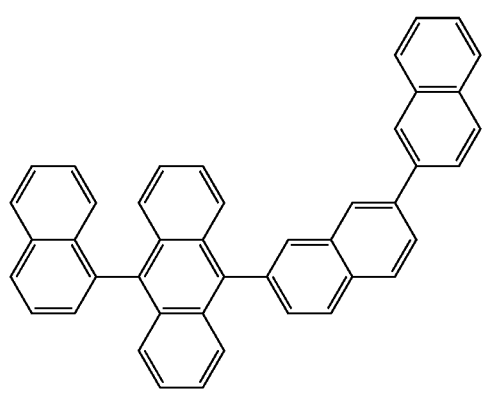 H14
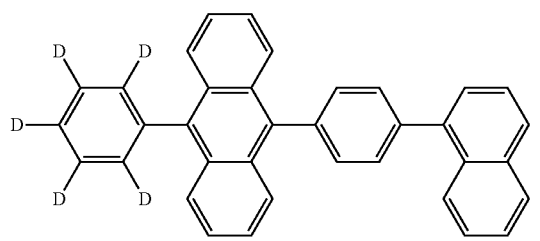 H15
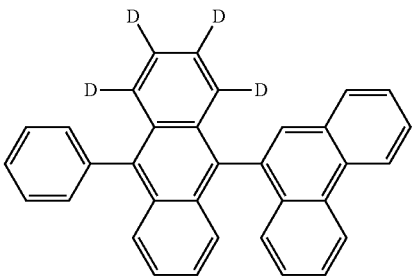 H16
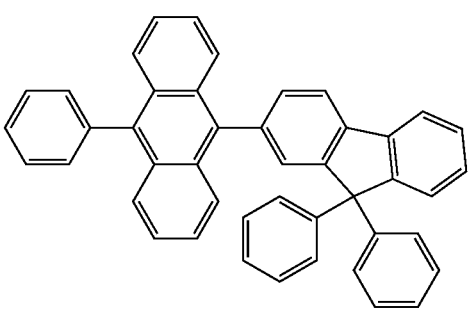 H17
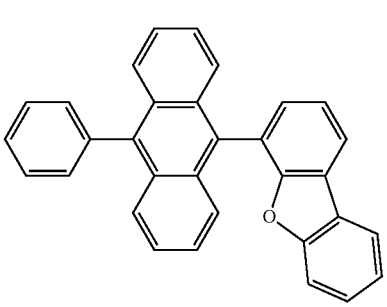 H18
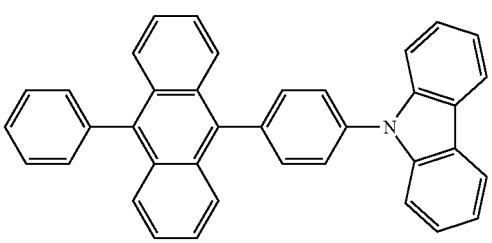 H19
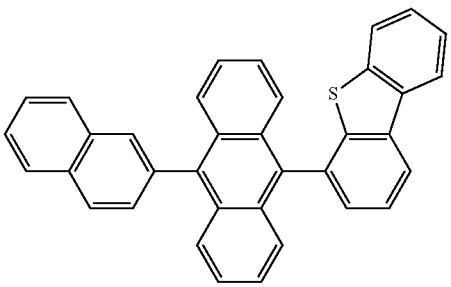 H20

H21
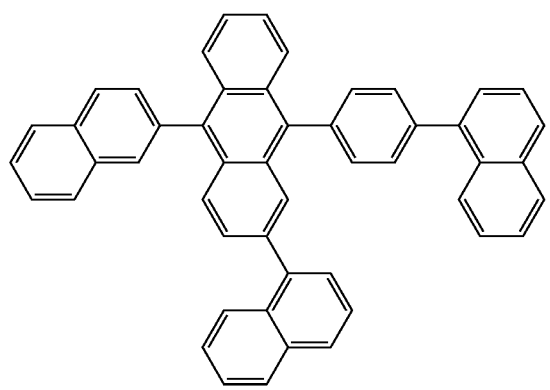
H22
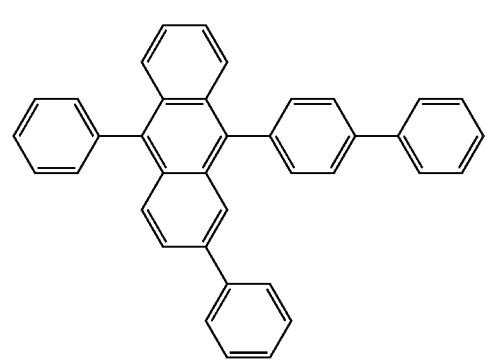
H23
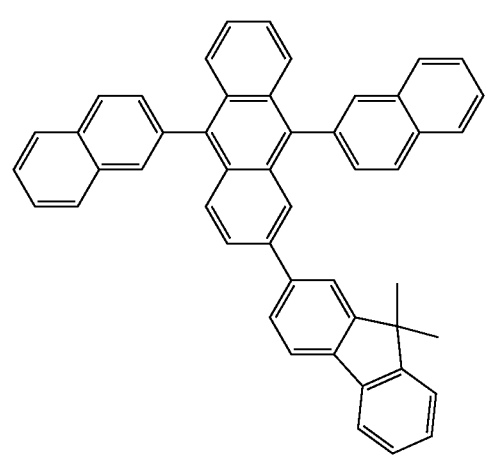
H24
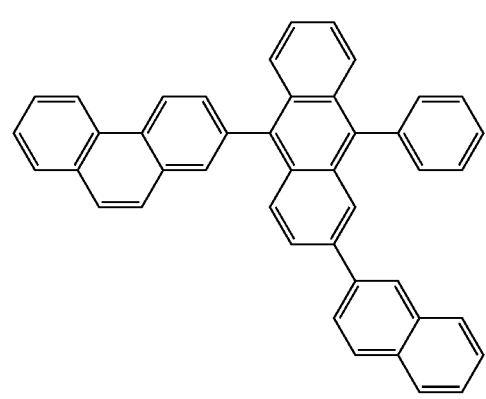
H25
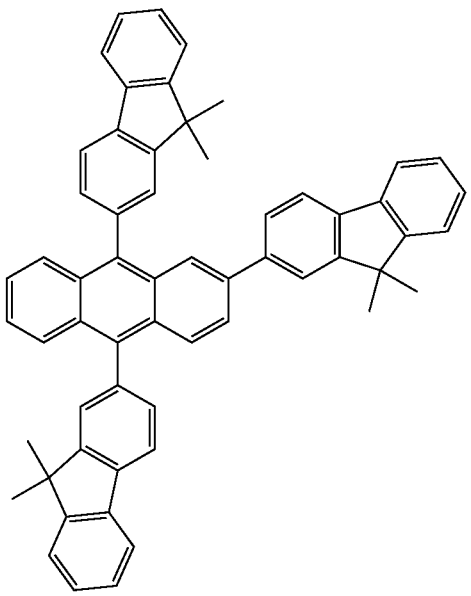
H26

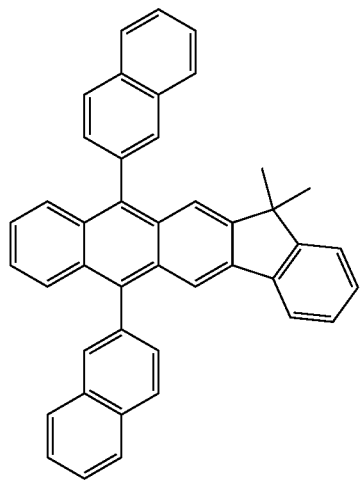
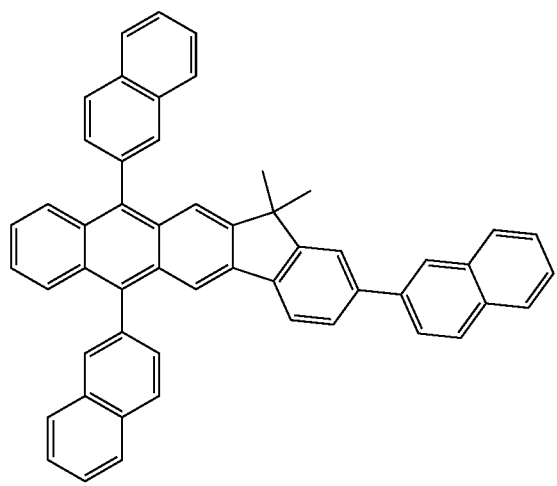
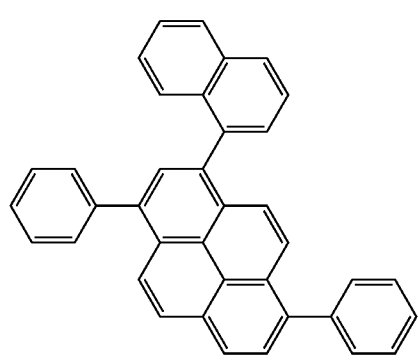
H27
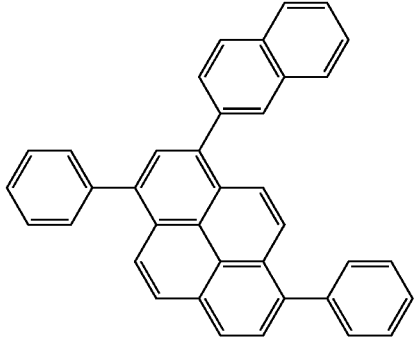
H28
H29
H30
H31
H32
H33
H34

H35
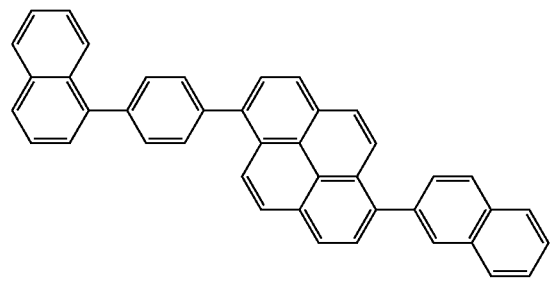
H36
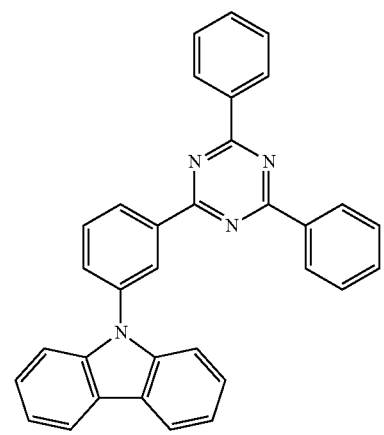
H37
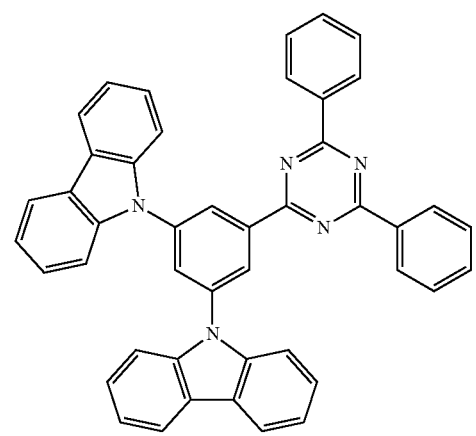
H38
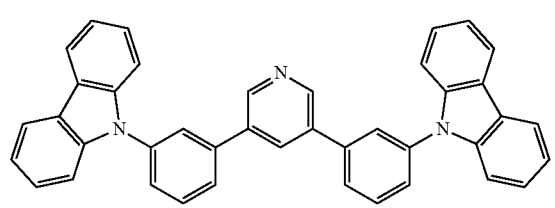
H39
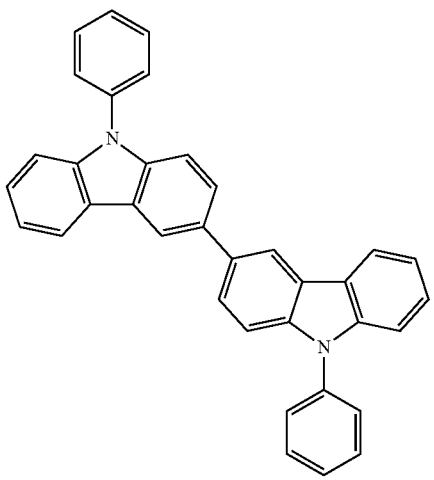
H40
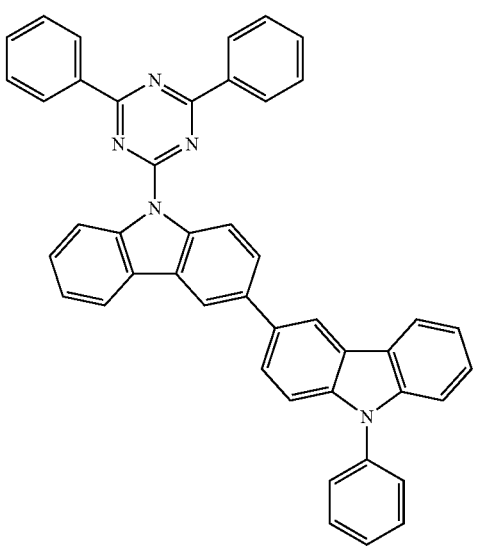
H41
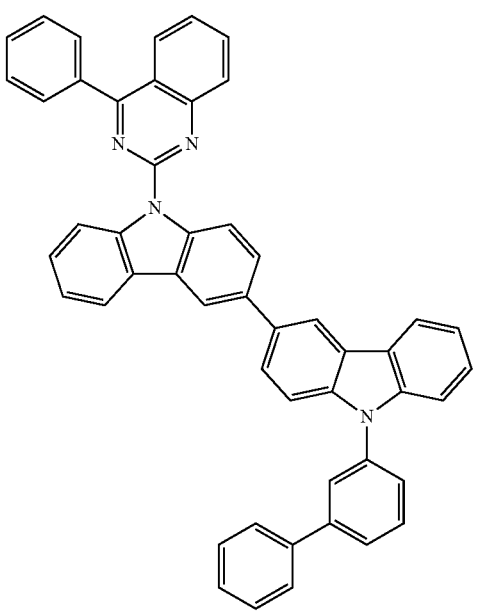

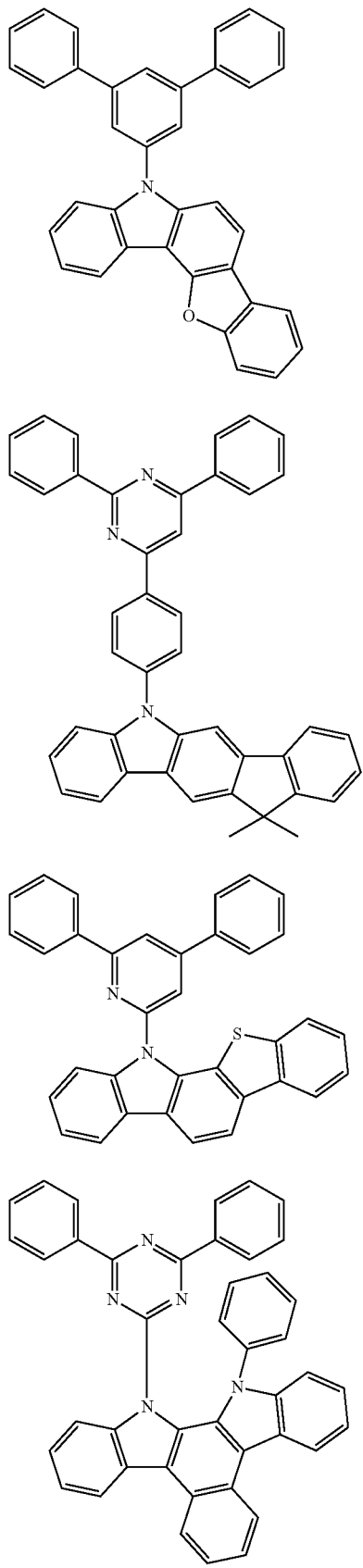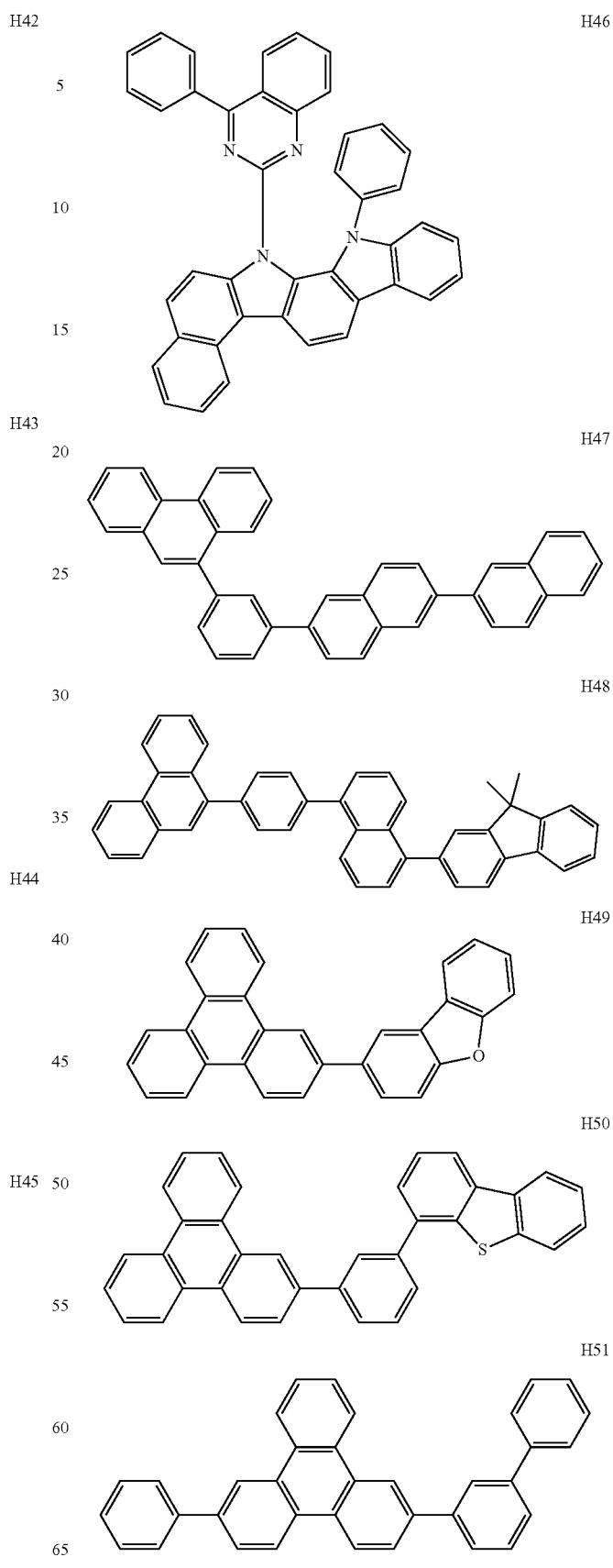

-continued

H52
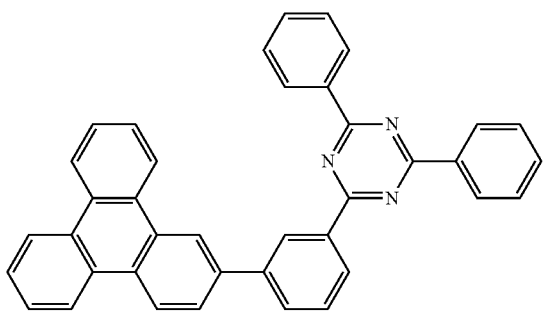

H53
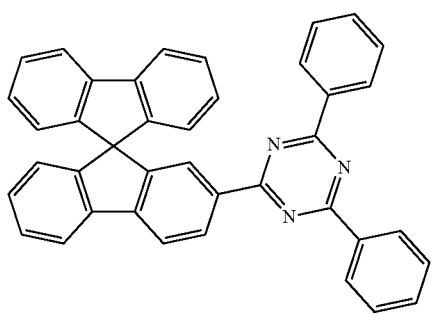

H54
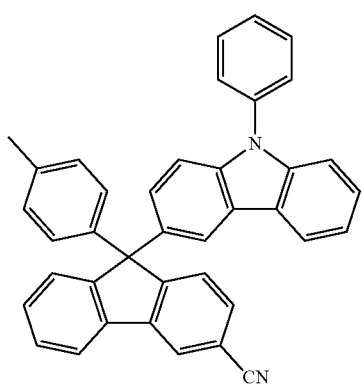

H55
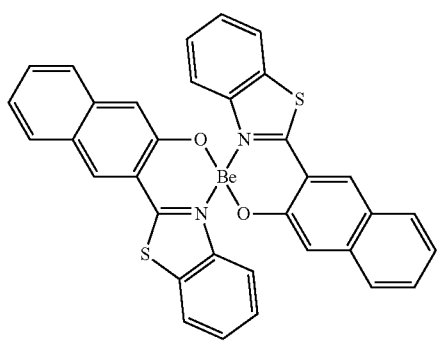

[Phosphorescent Dopant Included in Emission Layer of Organic Layer]

The phosphorescent dopant may include an ogranometallic complex represented by Formula 401:

$$M(L_{401})_{xc1}(L_{402})_{xc2}$$ <Formula 401>

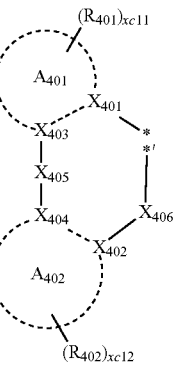

<Formula 402>

In Formulae 401 and 402,

M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ may be a ligand represented by Formula 402, and xc1 may be 1, 2, or 3, wherein, when xc1 is two or more, two or more of $L_{401}$(s) may be identical to or different from each other, $L_{402}$ may be an organic ligand, and xc2 may be an integer from 0 to 4, wherein, when xc2 is two or more, two or more of $L_{402}$(s) may be identical to or different from each other, $X_{401}$ to $X_{404}$ may each independently be nitrogen or carbon, $X_{401}$ and $X_{403}$ may be connected via a single bond or a double bond, and $X_{402}$ and $X_{404}$ may be connected via a single bond or a double bond, $A_{401}$ and $A_{402}$ may each independently be a $C_5$-$C_{60}$ carbocyclic group or a $C_1$-$C_{60}$ heterocyclic group, $X_{405}$ may be a single bond, *—O—*', *—S—*', *—C(=O)—*', *—N($Q_{411}$)-*', *—C($Q_{411}$)($Q_{412}$)-*', *—C($Q_{411}$)=C($Q_{412}$)-*', *—C($Q_{411}$)=*', or *=C=*', $Q_{411}$ and $Q_{412}$ may each be hydrogen, deuterium, a $C_1$-$C_{20}$ alkyl group, a $C_1$-$C_{20}$ alkoxy group, a phenyl group, a biphenyl group, a terphenyl group, or a naphthyl group, $X_{406}$ may be a single bond, O, or S, $R_{401}$ and $R_{402}$ may each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{20}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, and a $C_1$-$C_{20}$ heteroaryl group, xc11 and xc12 may each independently be an integer from 0 to 10, and

* and *' in Formula 402 each indicate a binding site to M in Formula 401.

In one embodiment, $A_{401}$ and $A_{402}$ in Formula 402 may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In one or more embodiments, in Formula 402, i) $X_{401}$ may be nitrogen and $X_{402}$ may be carbon, or ii) $X_{401}$ and $X_{402}$ may each be nitrogen.

In one or more embodiments, in Formula 402, $R_{401}$ and $R_{402}$ may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group, and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantanyl group, a norbornanyl group, and a norbornenyl group;

a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantanyl group, a norbornanyl group, a norbornenyl group a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group, but embodiments are not limited thereto.

In one or more embodiments, in Formula 401, when xc1 is two or more, two $A_{401}$(s) in two or more $L_{401}$(s) may be optionally linked via $X_{407}$, which is a linking group, and two $A_{402}$(s) may be optionally linked via $X_{408}$, which is a linking group (see Compounds PD1 to PD4 and PD7). $X_{407}$ and $X_{408}$ may each independently be a single bond, *—O—*', *—S—*', *—C(=O)—*', *—N($Q_{413}$)-*', *—C($Q_{413}$)($Q_{414}$)-*', or *—C($Q_{413}$)=C($Q_{414}$)-*' (Herein, $Q_{413}$ and $Q_{414}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group), but embodiments are not limited thereto.

$L_{402}$ in Formula 401 may be a monovalent, divalent, or trivalent organic ligand. For example, $L_{402}$ may be selected from halogen, diketone (for example, acetylacetonate), carboxylic acid (for example, picolinate), —C(=O), isonitrile, —CN, and a phosphorus-containing material (for example, phosphine and phosphite), but embodiments are not limited thereto.

In one or more embodiments, the phosphorescent dopant may be, for example, selected from Compounds PD1 to PD25, but embodiments are not limited thereto:

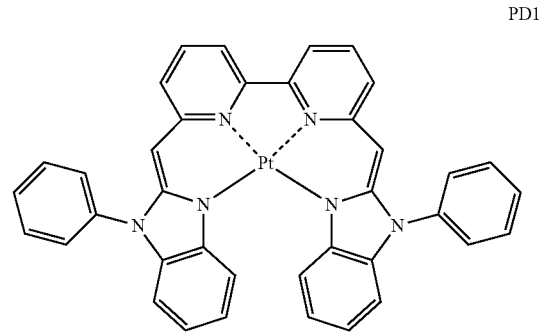

PD1

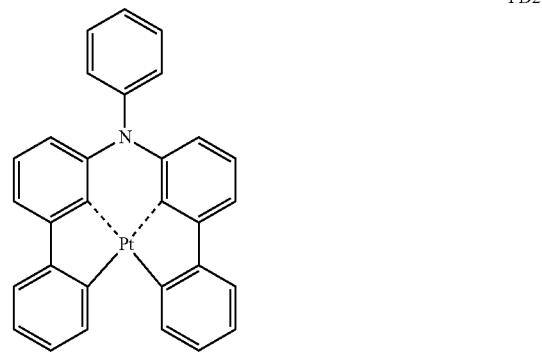

PD2

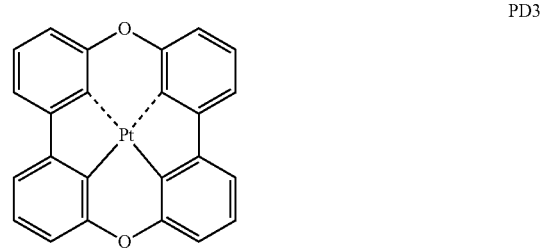

PD3

-continued
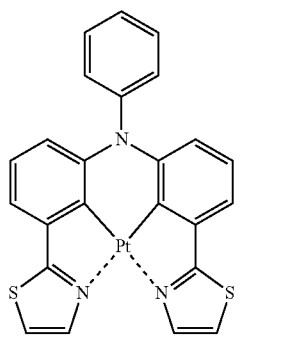
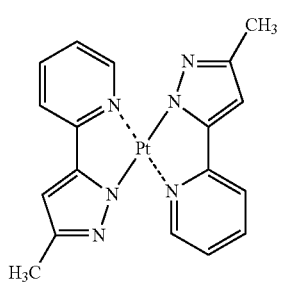
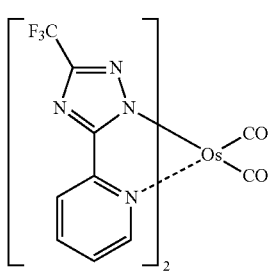
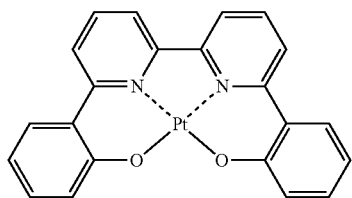
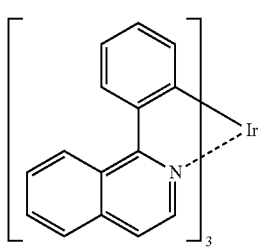
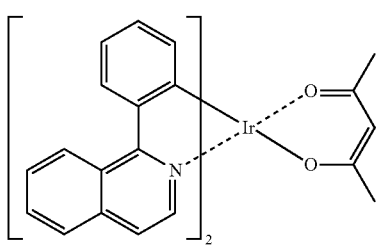
-continued
PD4
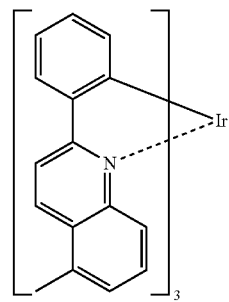
PD5
PD6
PD7
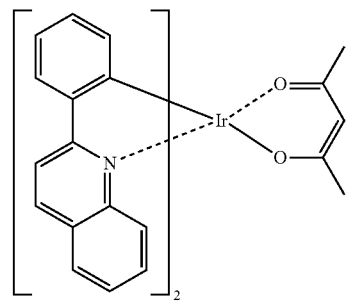
PD8
PD9
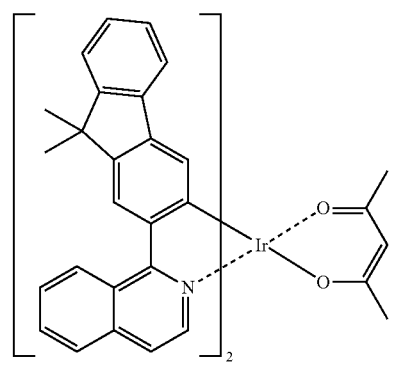
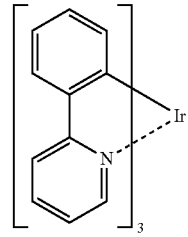
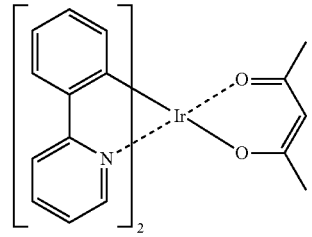
PD10
PD11
PD12
PD13
PD14

PD15 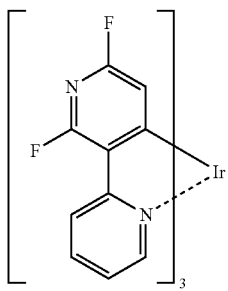
PD16 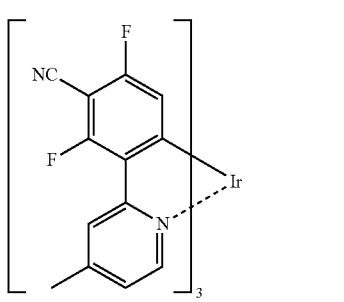
PD17 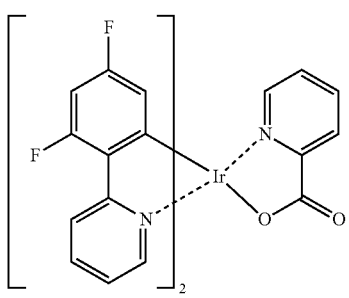
PD18 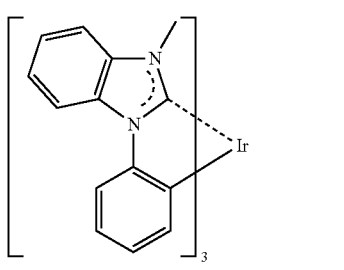
PD19 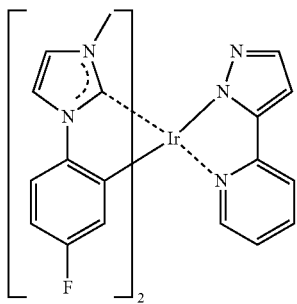
PD20 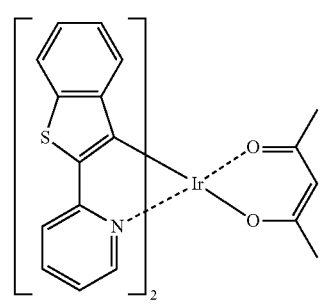
PD21 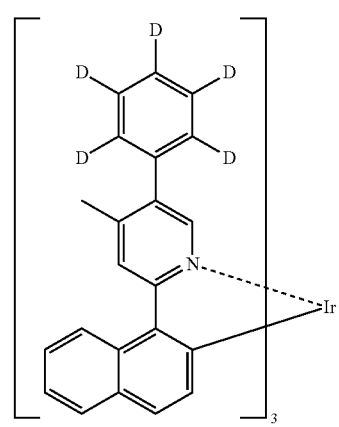
PD22 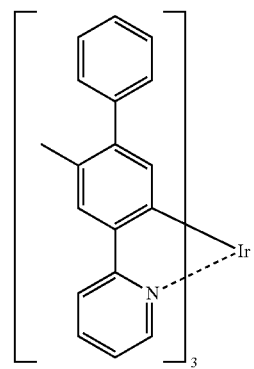
PD23 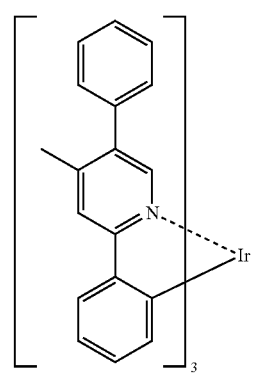

PD24

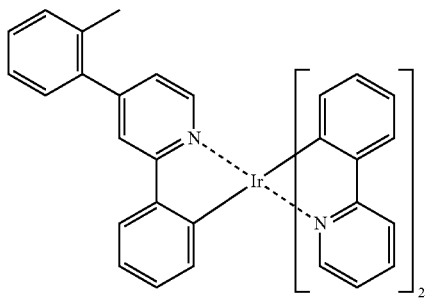

PD25

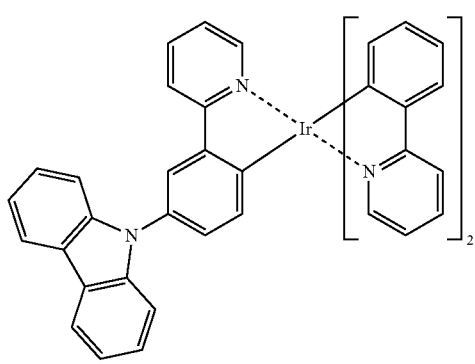

[Fluorescent Dopant in Emission Layer]

The fluorescent dopant may include an arylamine compound or a styrylamine compound.

The fluorescent dopant may include a compound represented by Formula 501 below.

<Formula 501>

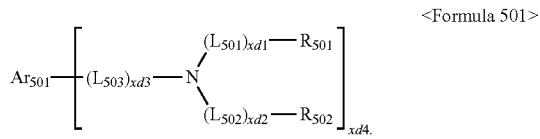

In Formula 501, $Ar_{501}$ may be a substituted or unsubstituted $C_5$-$C_{60}$ carbocyclic group or a substituted or unsubstituted $C_1$-$C_{60}$ heterocyclic group, $L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer of 0 to 3;

$R_{501}$ and $R_{502}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, xd4 may be an integer of 1 to 6.

In one embodiment, $Ar_{501}$ in Formula 501 may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one or more embodiments, $L_{501}$ to $L_{503}$ in Formula 501 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In one or more embodiments, $R_{501}$ and $R_{502}$ in Formula 501 may each independently be selected from a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$);

$Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xd4 in Formula 501 may be 2, but embodiments are not limited thereto.

For example, the fluorescent dopant may be selected from Compounds FD1 to FD22:

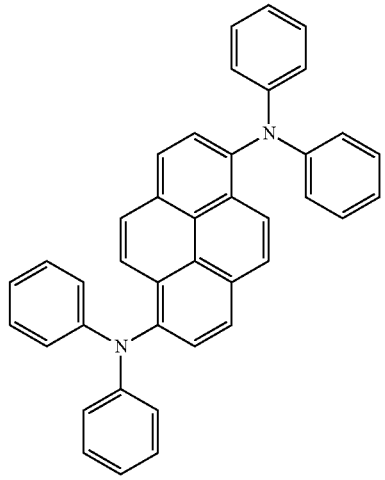
FD1

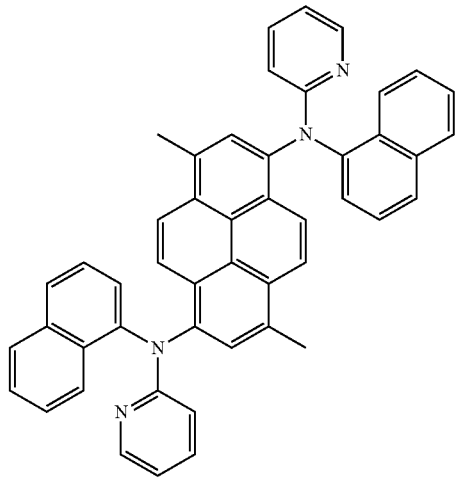
FD2

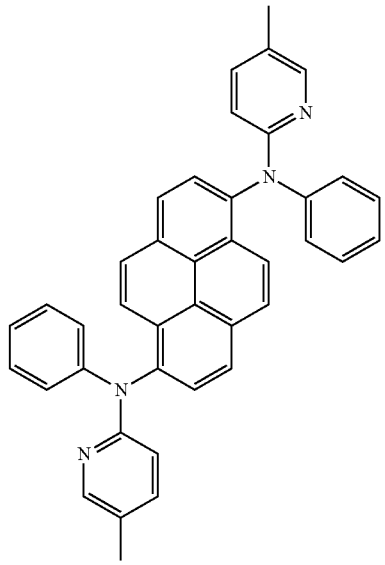
FD3

111
-continued
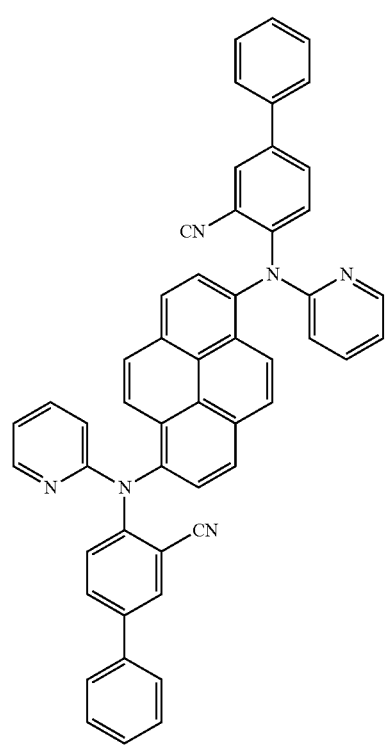
FD4
112
-continued
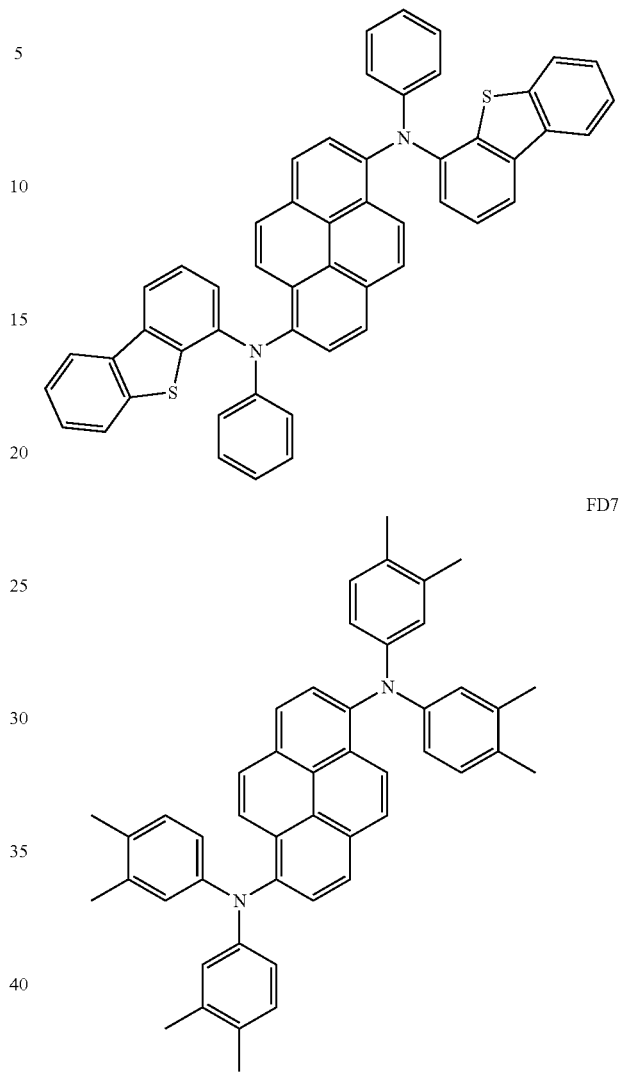
FD6
FD7
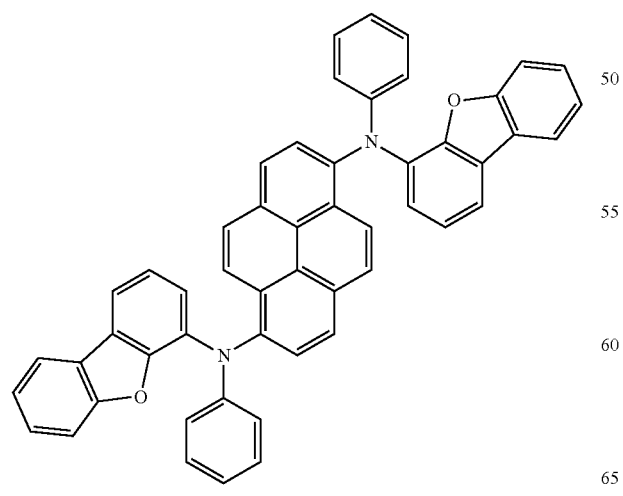
FD5
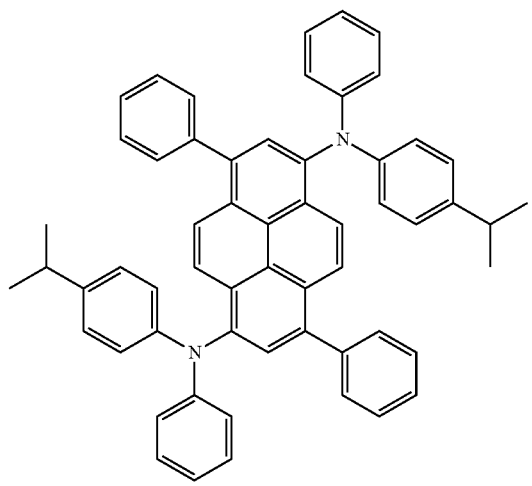
FD8

FD9
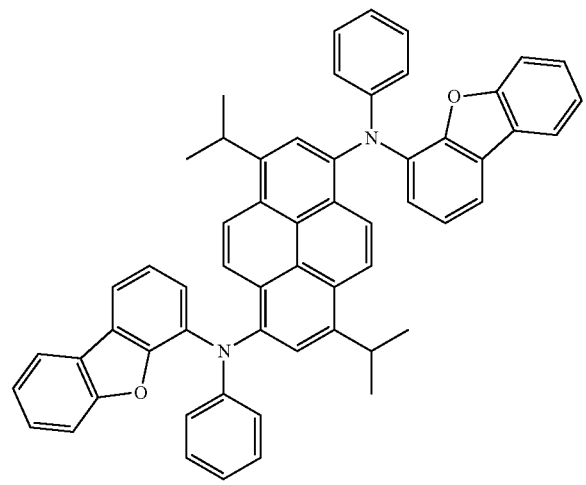
FD10
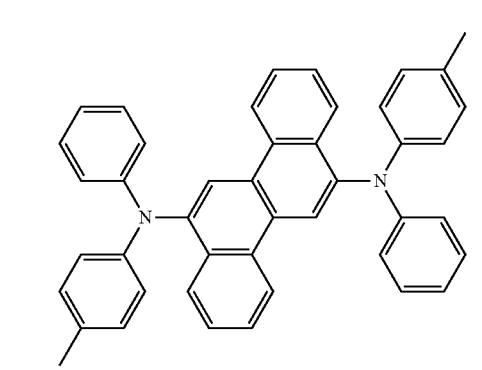
FD11
FD12
FD13
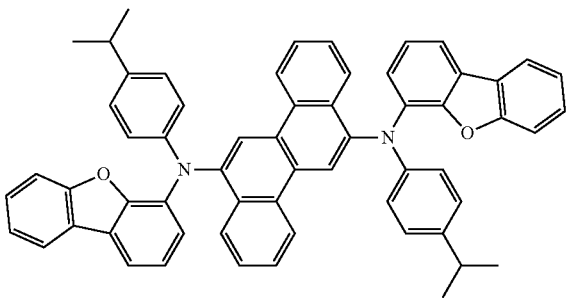
FD14
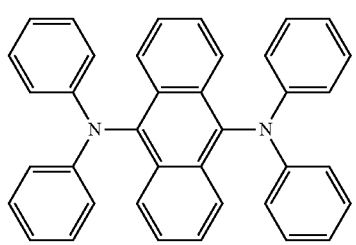
FD15
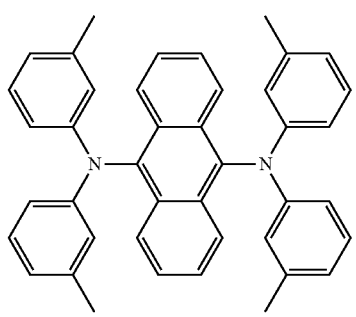
FD16
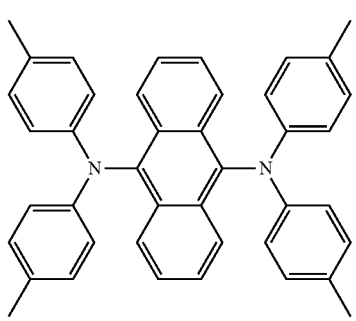
FD17
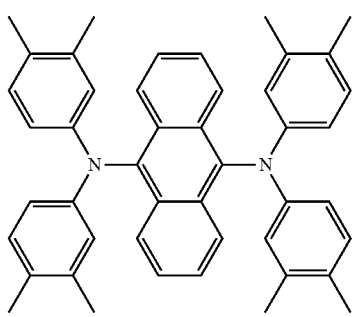

FD18
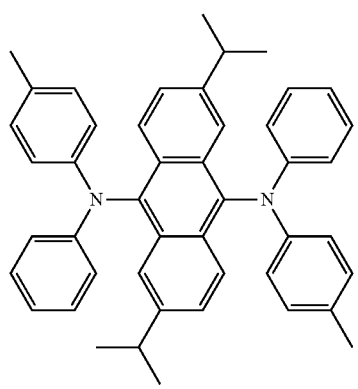
FD20
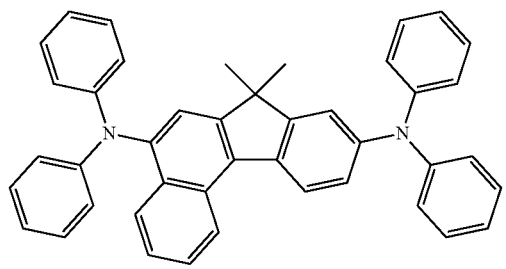
FD21
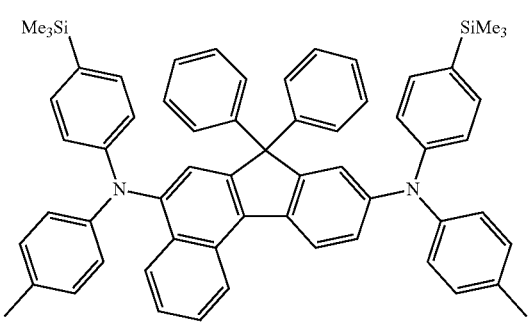
FD19
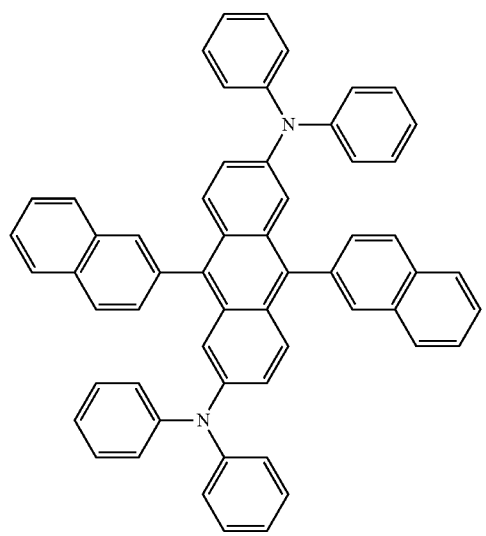
FD22
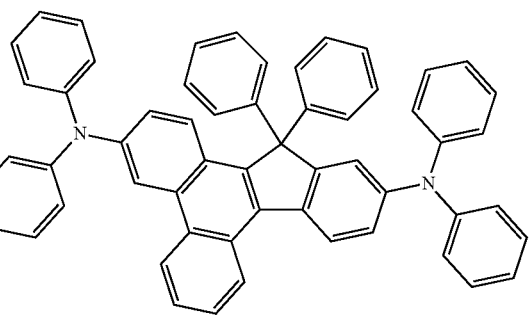
In one or more embodiments, the fluorescent dopant may be selected from the following compounds, but embodiments are not limited thereto.
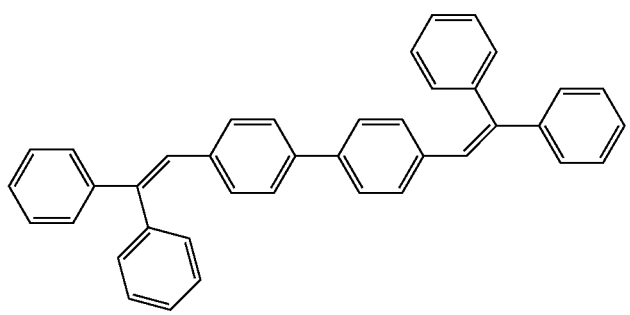
DPVBi

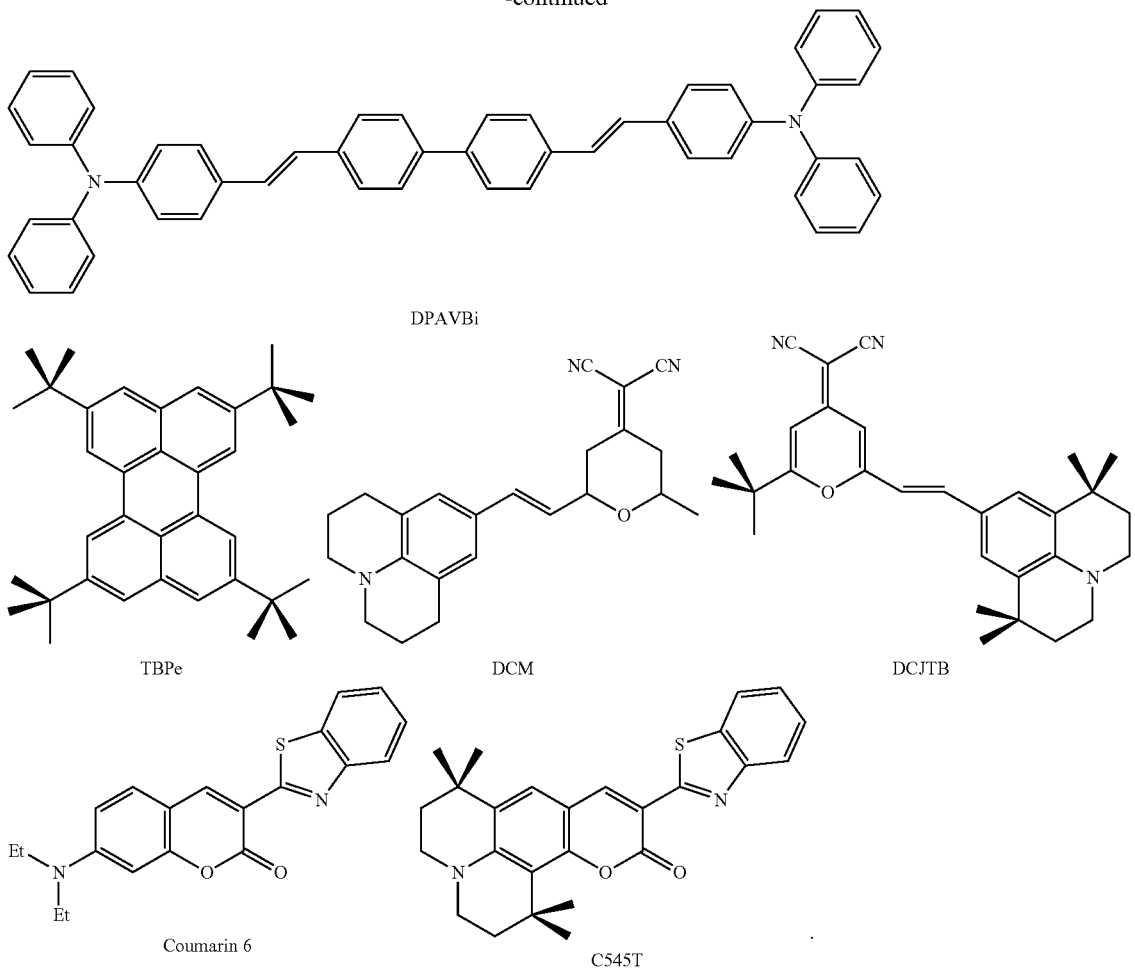

[Electron Transport Region in Organic Layer 150]

The electron transport region may have i) a single-layered structure including a single layer including a single material, ii) a single-layered structure including a single layer including a plurality of different materials, or iii) a multi-layered structure having a plurality of layers including a plurality of different materials.

The electron transport region may include at least one selected from a buffer layer, a hole blocking layer, an electron control layer, an electron transport layer, and an electron injection layer, but embodiments are not limited thereto.

For example, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein for each structure, constituting layers are sequentially stacked from an emission layer. However, embodiments of the structure of the electron transport region are not limited thereto.

The electron transport region may include the condensed cyclic compound represented by Formula 1.

In one embodiment, the electron transport region (for example, a buffer layer, a hole blocking layer, an electron control layer, or an electron transport layer in the electron transport region) may include a metal-free compound containing at least one it electron-depleted nitrogen-containing ring.

The "π electron-depleted nitrogen-containing ring" indicates a $C_1$-$C_{60}$ heterocyclic group having at least one *—N=*' moiety as a ring-forming moiety.

For example, the "it electron-depleted nitrogen-containing ring" may be i) a 60-membered to 7-membered heteromonocyclic group having at least one *—N=*' moiety, ii) a heteropolycyclic group in which two or more 5-membered to 7-membered heteromonocyclic groups each having at least one *—N=*' moiety are condensed with each other, or iii) a heteropolycyclic group in which at least one of 5-membered to 7-membered heteromonocyclic groups, each having at least one *—N=*' moiety, is condensed with at least one $C_5$-$C_{60}$ carbocyclic group.

Examples of the it electron-depleted nitrogen-containing ring include an imidazole, a pyrazole, a thiazole, an isothiazole, an oxazole, an isoxazole, a pyridine, a pyrazine, a pyrimidine, a pyridazine, an indazole, a purine, a quinoline, an isoquinoline, a benzoquinoline, a phthalazine, a naphthyridine, a quinoxaline, a quinazoline, a cinnoline, a phenanthridine, an acridine, a phenanthroline, a phenazine, a benzimidazole, an isobenzothiazole, a benzoxazole, an isobenzoxazole, a triazole, a tetrazole, an oxadiazole, a triazine, thiadiazol, an imidazopyridine, an imidazopyrimidine, and an azacarbazole, but are not limited thereto.

For example, the electron transport region may include a compound represented by Formula 601:

  <Formula 601>

In Formula 601, $Ar_{601}$ may be a substituted or unsubstituted $C_5$-$C_{60}$ carbocyclic group or a substituted or unsubstituted $C_1$-$C_{60}$ heterocyclic group, xe11 may be 1, 2, or 3, $L_{601}$ may each independently be selected from a substituted or unsubstituted $C_3$-$C_{10}$ cycloalkylene group, a substituted or unsubstituted heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

xe1 may be an integer from 0 to 5, $R_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $-Si(Q_{601})(Q_{602})(Q_{603})$, $-C(=O)(Q_{601})$, $-S(=O)_2(Q_{601})$, and $-P(=O)(Q_{601})(Q_{602})$, $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer from 1 to 5.

In one embodiment, at least one of $Ar_{601}(s)$ in the number of xe11 and $R_{601}(s)$ in the number of xe21 may include the π electron-depleted nitrogen-containing ring.

In one embodiment, ring $Ar_{601}$ in Formula 601 may be selected from a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an iso-benzothiazole group, a benzoxazole group, an isobenzoxazole group, a triazole group, a tetrazole group, an oxadiazole group, a triazine group, a thiadiazol group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, phenanthroline group, phenazine group, a benzimidazole group, an iso-benzothiazole group, a benzoxazole group, an isobenzoxazole group, a triazole group, a tetrazole group, an oxadiazole group, a triazine group, a thiadiazol group, an imidazopyridine group, an imidazopyrimidine group, and an azacarbazole group, each substituted with at least one selected from deuterium, $-F$, $-Cl$, $-Br$, $-I$, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, $-Si(Q_{31})(Q_{32})(Q_{33})$, $-S(=O)_2(Q_{31})$, and $-P(=O)(Q_{31})(Q_{32})$, wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is two or more, two or more $Ar_{601}(s)$ may be linked via a single bond.

In one or more embodiments, $Ar_{601}$ in Formula 601 may be an anthracene group.

In one or more embodiments, the compound represented by Formula 601 may be represented by Formula 601-1:

<Formula 601-1>

$$R_{613}-(L_{613})_{xe613}\underset{X_{616}}{\overset{\begin{subarray}{c}(L_{611})_{xe611}-R_{611}\\X_{614}\quad X_{615}\end{subarray}}{\diagdown\diagup}}(L_{612})_{xe612}-R_{612}.$$

In Formula 601-1, $X_{614}$ may be N or $C(R_{614})$, $X_{615}$ may be N or $C(R_{615})$, $X_{616}$ may be N or $C(R_{616})$, and at least one selected from $X_{614}$ to $X_{616}$ may be N, $L_{611}$ to $L_{613}$ may each independently be the same as described in connection with $L_{601}$, xe611 to xe613 may each independently be the same as described in connection with xe1, $R_{611}$ to $R_{613}$ may each independently be the same as described in connection with $R_{601}$, $R_{614}$ to $R_{616}$ may each independently be selected from hydrogen, deuterium, $-F$, $-Cl$, $-Br$, $-I$, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one embodiment, $L_{601}$ and $L_{611}$ to $L_{613}$ in Formulae 601 and 601-1 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, but embodiments are not limited thereto.

In one or more embodiments, xe1 and xe611 to xe613 in Formulae 601 and 601-1 may each independently be 0, 1, or 2.

In one or more embodiments, $R_{601}$ and $R_{611}$ to $R_{613}$ in Formulae 601 and 601-1 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S(=O)$_2$(Q$_{601}$) and —P(=O)(Q$_{601}$)(Q$_{602}$), wherein Q$_{601}$ and Q$_{602}$ are the same as described above.

The electron transport region may include at least one compound selected from Compounds ET1 to ET36, but embodiments are not limited thereto:

ET1

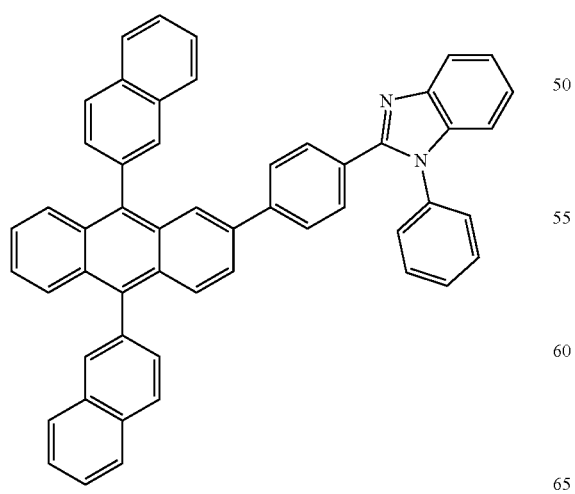

ET2

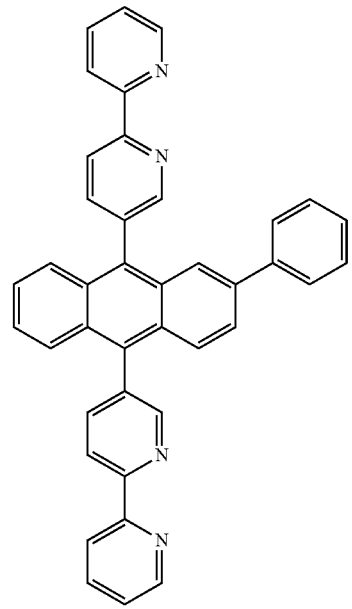

ET3

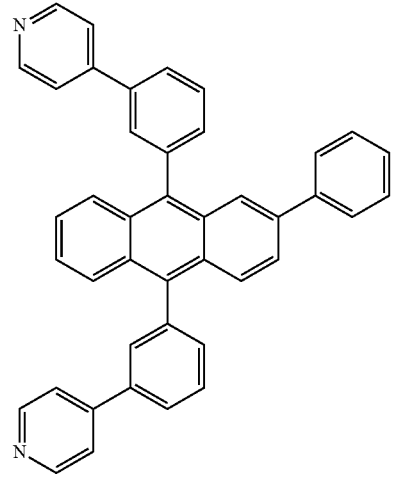

ET4

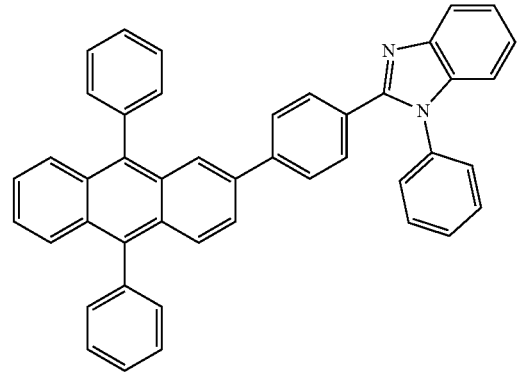

ET5
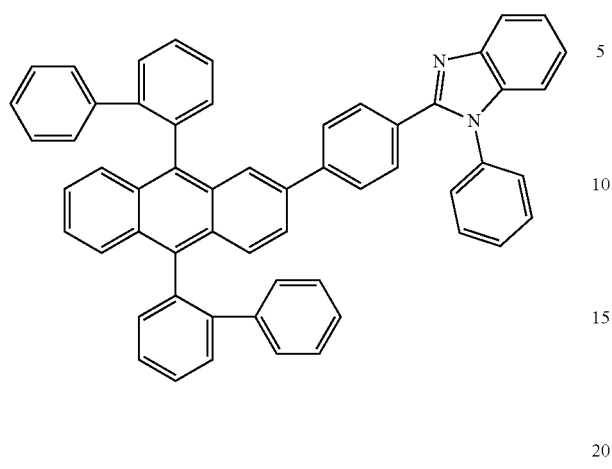
ET6
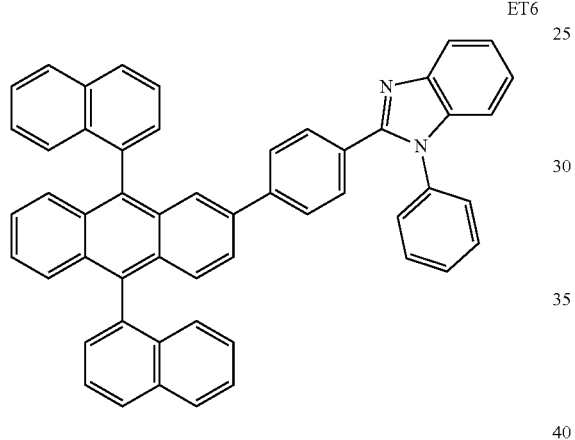
ET7
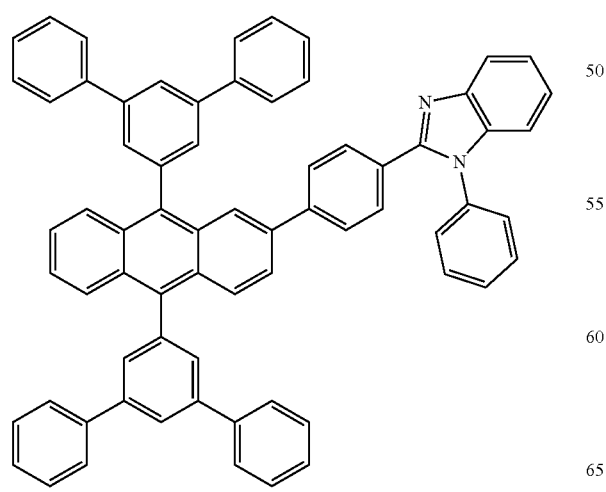
ET8
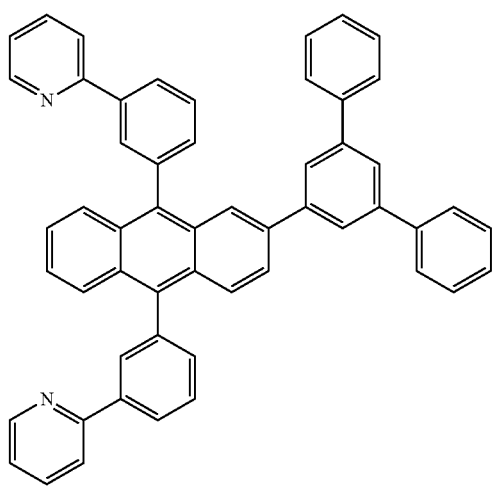
ET9
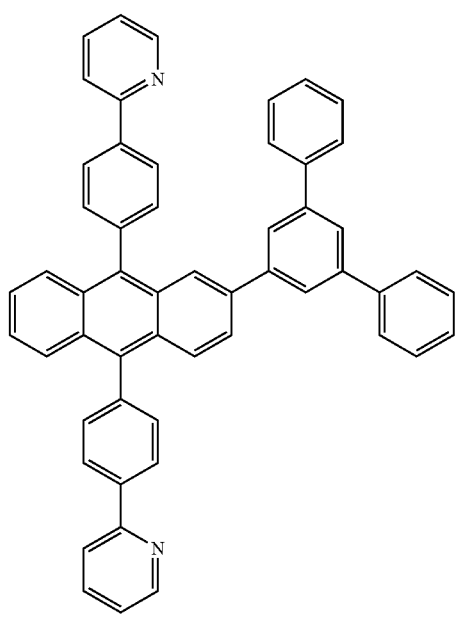

ET10
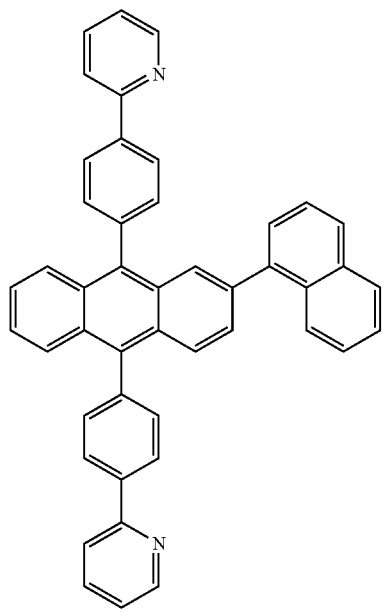
ET11
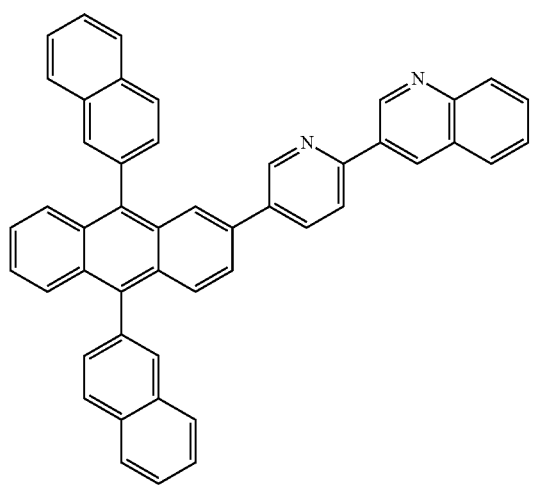
ET12
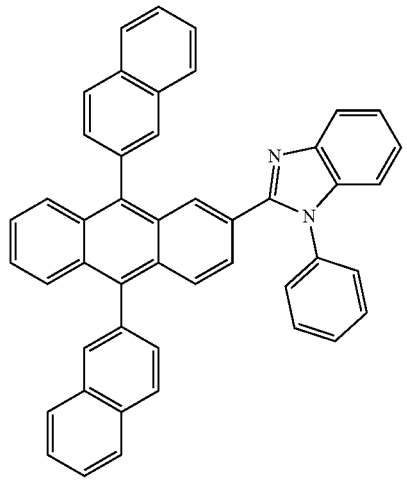
ET13
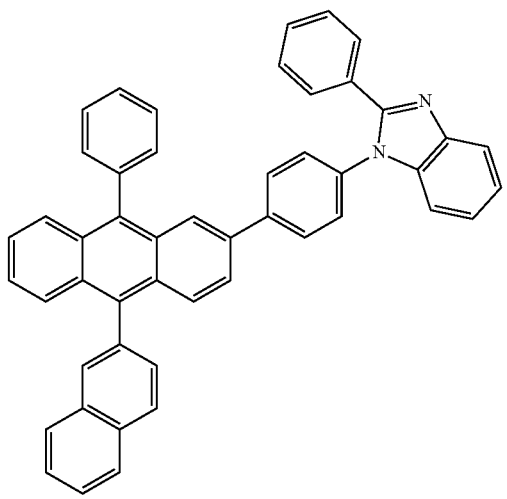
ET14
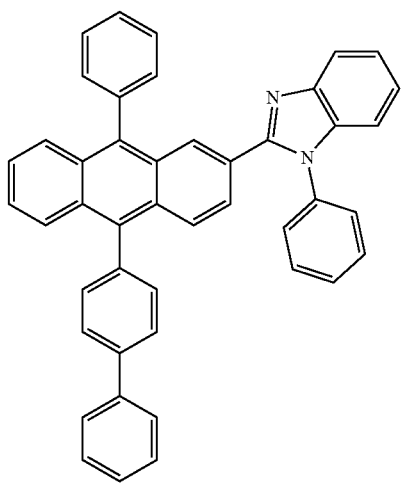
ET15
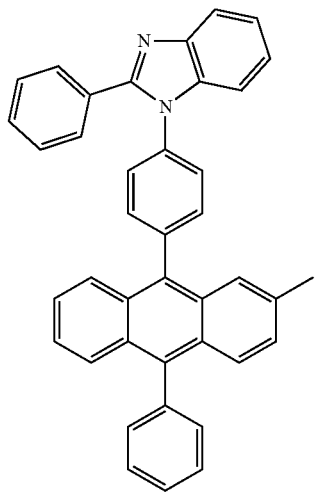

ET16
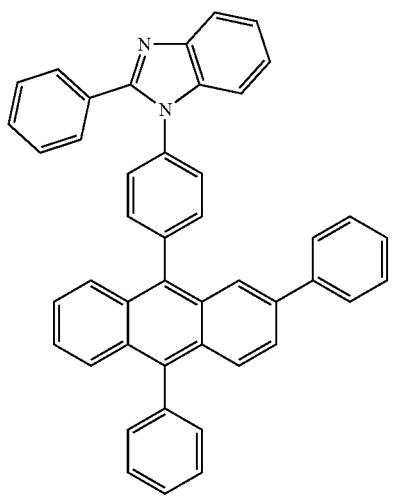
ET17
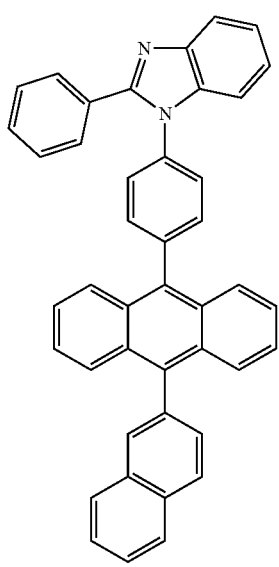
ET18
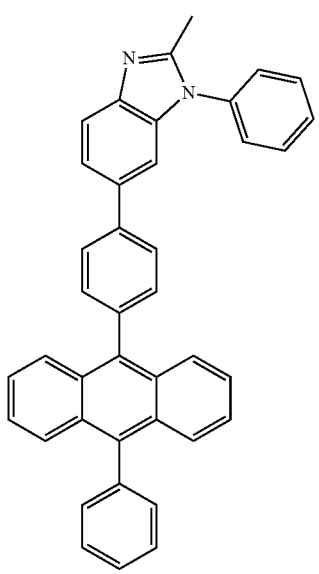
ET19
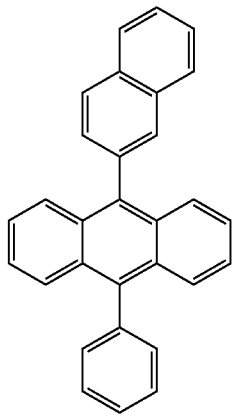
ET20
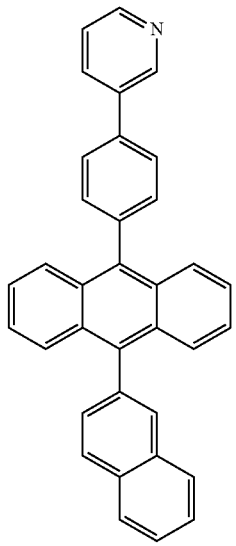
ET21
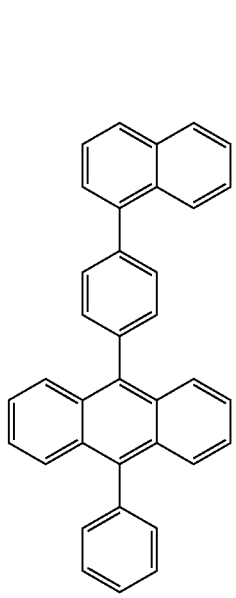

ET22
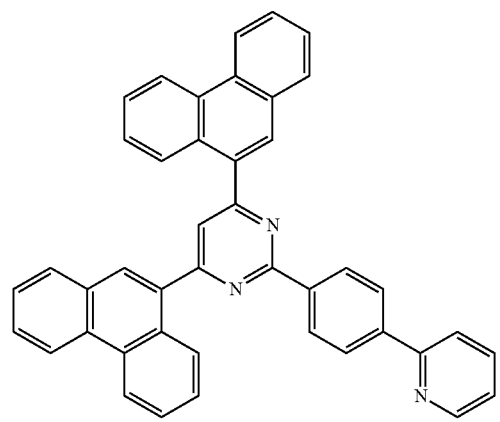
ET23
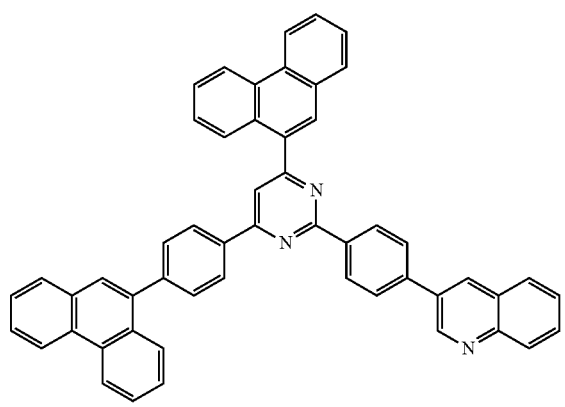
ET24
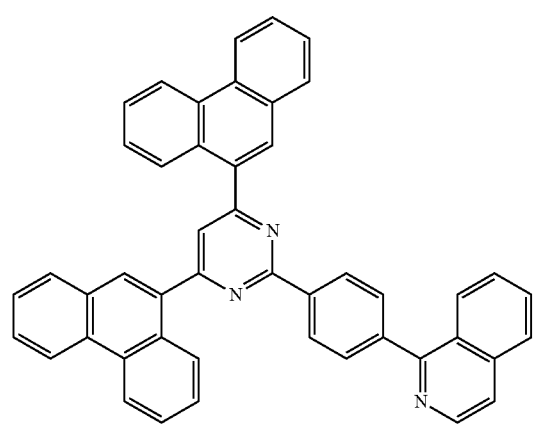
ET25
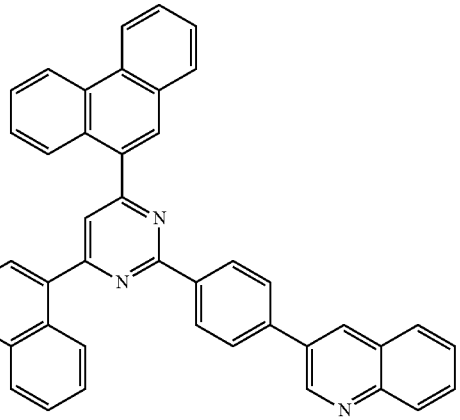
ET26
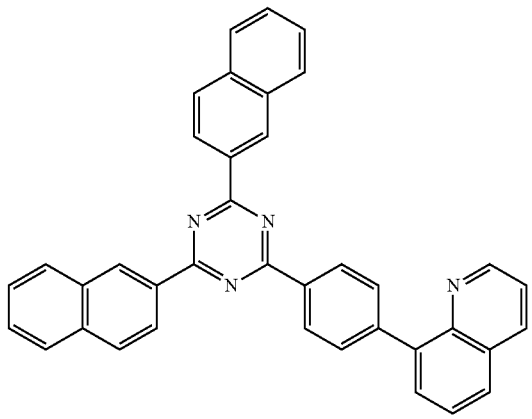
ET27

ET28
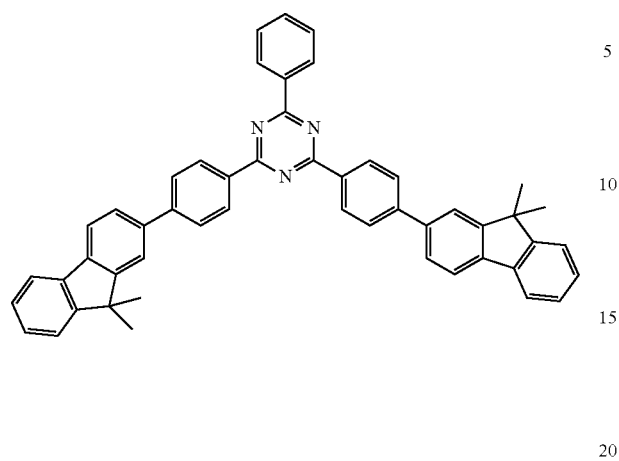
ET31
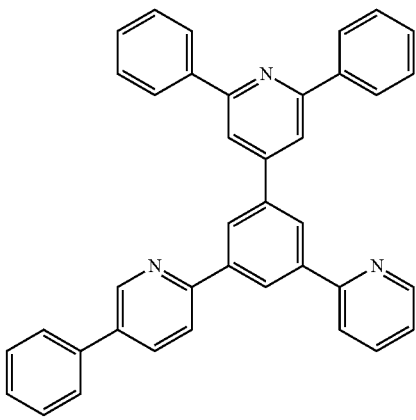
ET29
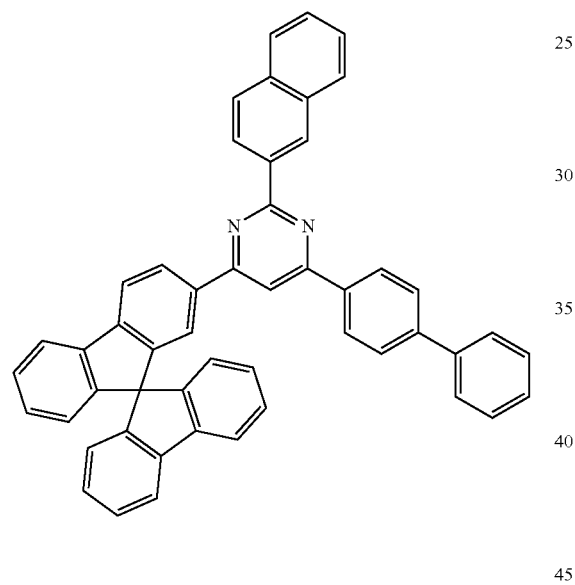
ET32
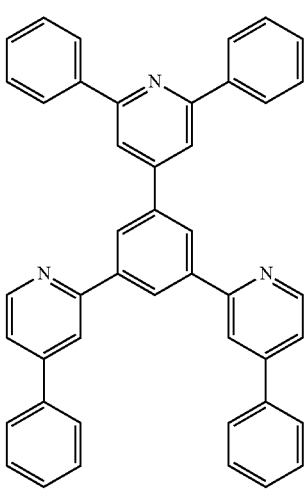
ET30
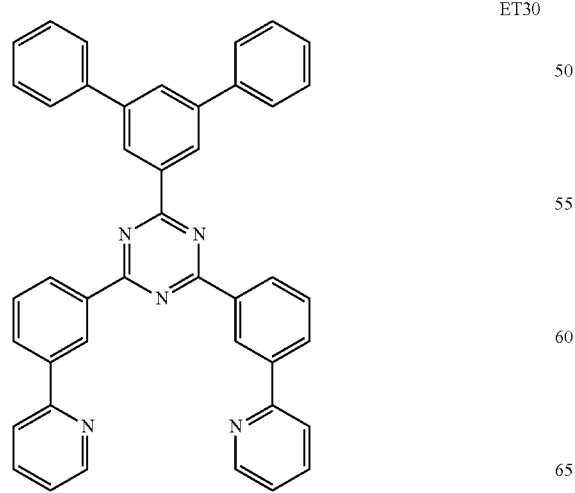
ET33
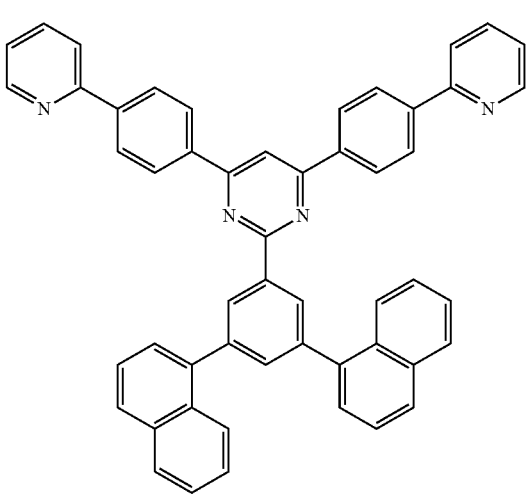

ET34

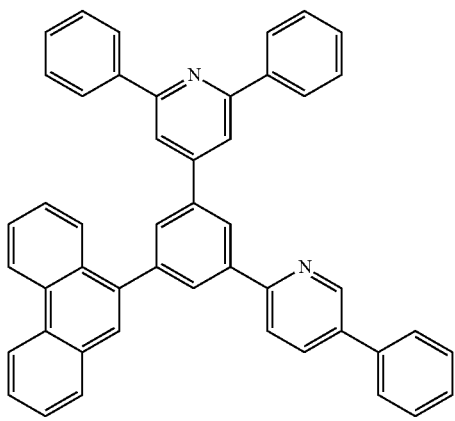

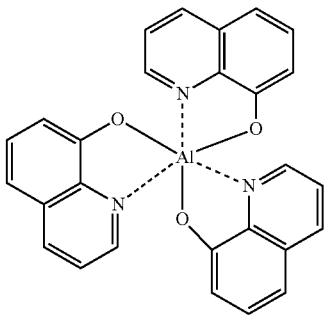

Alq₃

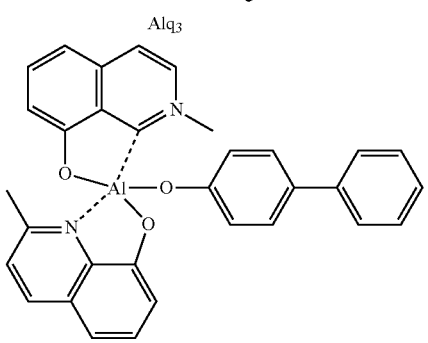

BAlq

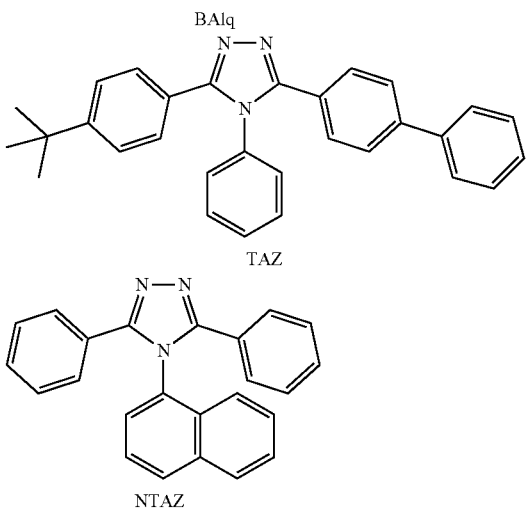

TAZ

NTAZ

ET35

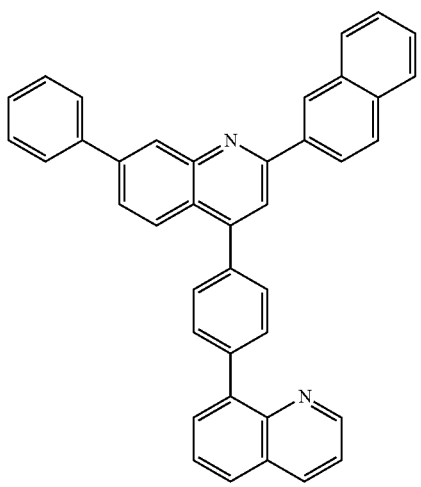

ET36

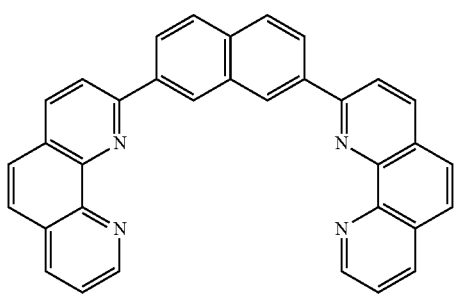

In one or more embodiments, the electron transport region may include at least one selected from 2,9-dimethyl-4,7-diphenyl-1,10-phenanthroline (BCP), 4,7-dphenyl-1,10-phenanthroline (Bphen), Alq₃, BAlq, 3-(biphenyl-4-yl)-5-(4-tert-butylphenyl)-4-phenyl-4H-1,2,4-triazole (TAZ), and NTAZ.

Thicknesses of the buffer layer, the hole blocking layer, and the electron control layer may each be in a range of about 20 Å to about 1,000 Å, for example, about 30 Å to about 300 Å. When the thicknesses of the buffer layer, the hole blocking layer, and the electron control layer are within these ranges, the electron blocking layer may have excellent electron blocking characteristics or electron control characteristics without a substantial increase in driving voltage.

A thickness of the electron transport layer may be in a range of about 100 Å to about 1,000 Å, for example, about 150 Å to about 500 Å. When the thickness of the electron transport layer is within the range described above, the electron transport layer may have satisfactory electron transport characteristics without a substantial increase in driving voltage.

The electron transport region (for example, the electron transport layer in the electron transport region) may further include, in addition to the materials described above, a metal-containing material.

The metal-containing material may include at least one selected from alkali metal complex and alkaline earth-metal complex. The alkali metal complex may include a metal ion selected from a Li ion, a Na ion, a K ion, a Rb ion, and a Cs ion, and the alkaline earth-metal complex may include a metal ion selected from a Be ion, a Mg ion, a Ca ion, a Sr ion, and a Ba ion. A ligand coordinated with the metal ion of the alkali metal complex or the alkaline earth-metal complex may be selected from a hydroxy quinoline, a hydroxy isoquinoline, a hydroxy benzoquinoline, a hydroxy acridine, a hydroxy phenanthridine, a hydroxy phenylan oxazole, a hydroxy phenylthiazole, a hydroxy diphenylan oxadiazole, a hydroxy diphenylthiadiazol, a hydroxy phenylpyridine, a hydroxy phenylbenzimidazole, a hydroxy phenylbenzothiazole, a bipyridine, a phenanthroline, and a cyclopentadiene, but embodiments are not limited thereto.

For example, the metal-containing material may include a Li complex. The Li complex may include, for example, Compound ET-D1 (lithium quinolate, LiQ) or ET-D2.

ET-D1

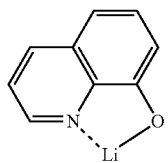

ET-D2

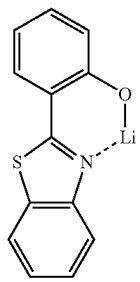

The electron transport region may include an electron injection layer that facilitates injection of electrons from the second electrode 190. The electron injection layer may directly contact the second electrode 190.

The electron injection layer may have i) a single-layered structure including a single layer including a single material, ii) a single-layered structure including a single layer including a plurality of different materials, or iii) a multi-layered structure having a plurality of layers including a plurality of different materials.

The electron injection layer may include an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof.

The alkali metal may be selected from Li, Na, K, Rb, and Cs. In one embodiment, the alkali metal may be Li, Na, or Cs. In one or more embodiments, the alkali metal may be Li or Cs, but embodiments are not limited thereto.

The alkaline earth metal may be selected from Mg, Ca, Sr, and Ba.

The rare earth metal may be selected from Sc, Y, Ce, Tb, Yb, and Gd.

The alkali metal compound, the alkaline earth-metal compound, and the rare earth metal compound may be selected from oxides and halides (for example, fluorides, chlorides, bromides, or iodides) of the alkali metal, the alkaline earth-metal, and the rare earth metal.

The alkali metal compound may be selected from alkali metal oxides, such as $Li_2O$, $Cs_2O$, or $K_2O$, and alkali metal halides, such as LiF, NaF, CsF, KF, LiI, NaI, CsI, or KI. In one embodiment, the alkali metal compound may be selected from LiF, $Li_2O$, NaF, LiI, NaI, CsI, and KI, but embodiments are not limited thereto.

The alkaline earth-metal compound may be selected from alkaline earth-metal oxides, such as BaO, SrO, CaO, $Ba_xSr_{1-x}O$ (0<x<1), or $Ba_xCa_{1-x}O$ (0<x<1). In one embodiment, the alkaline earth-metal compound may be selected from BaO, SrO, and CaO, but embodiments are not limited thereto.

The rare earth metal compound may be selected from $YbF_3$, $ScF_3$, $ScO_3$, $Y_2O_3$, $Ce_2O_3$, $GdF_3$, and $TbF_3$. In one embodiment, the rare earth metal compound may be selected from $YbF_3$, $ScF_3$, $TbF_3$, $YbI_3$, $ScI_3$, and $TbI_3$, but embodiments are not limited thereto.

The alkali metal complex, the alkaline earth-metal complex, and the rare earth metal complex may include an ion of alkali metal, alkaline earth-metal, and rare earth metal as described above, and a ligand coordinated with a metal ion of the alkali metal complex, the alkaline earth-metal complex, or the rare earth metal complex may be selected from hydroxy quinoline, hydroxy isoquinoline, hydroxy benzoquinoline, hydroxy acridine, hydroxy phenanthridine, hydroxy phenylan oxazole, hydroxy phenylthiazole, hydroxy diphenylan oxadiazole, hydroxy diphenylthiadiazol, hydroxy phenylpyridine, hydroxy phenylbenzimidazole, hydroxy phenylbenzothiazole, bipyridine, phenanthroline, and cyclopentadiene, but embodiments are not limited thereto.

The electron injection layer may consist of an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof, as described above. In one or more embodiments, the electron injection layer may further include an organic material. When the electron injection layer further includes an organic material, an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof may be homogeneously or non-homogeneously dispersed in a matrix including the organic material.

A thickness of the electron injection layer may be in a range of about 1 Å to about 100 Å, for example, about 3 Å to about 90 Å. When the thickness of the electron injection layer is within the range described above, the electron injection layer may have satisfactory electron injection characteristics without a substantial increase in driving voltage.

[Second Electrode 190]

The second electrode 190 may be disposed on the organic layer 150 having such a structure. The second electrode 190 may be a cathode which is an electron injection electrode, and in this regard, a material for forming the second electrode 190 may be selected from metal, an alloy, an electrically conductive compound, and a combination thereof, which have a relatively low work function.

The second electrode 190 may include at least one selected from lithium (Li), silver (Ag), magnesium (Mg), aluminum (Al), aluminum-lithium (Al—Li), calcium (Ca), magnesium-indium (Mg—In), magnesium-silver (Mg—

Ag), ITO, and IZO, but embodiments are not limited thereto. The second electrode 190 may be a transmissive electrode, a semi-transmissive electrode, or a reflective electrode.

The second electrode 190 may have a single-layered structure, or a multi-layered structure including two or more layers.

Figure 3:
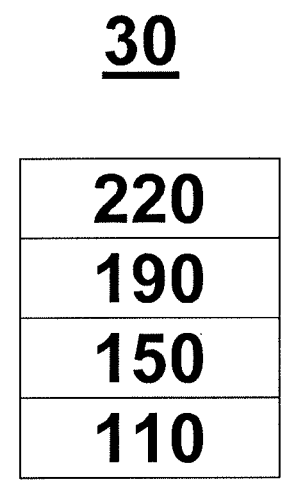
Figure 4:
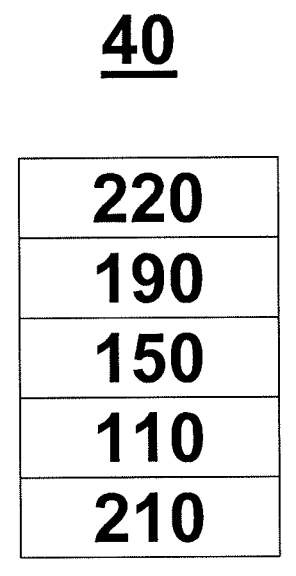

[Description of FIGS. 2 to 4]

Figure 2:
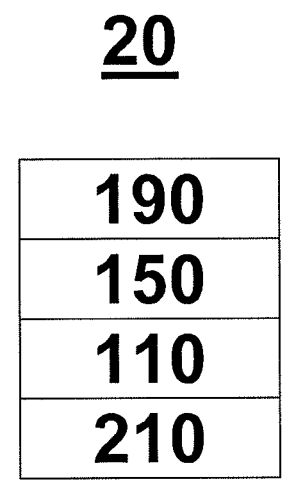

An organic light-emitting device 20 of FIG. 2 includes a first capping layer 210, a first electrode 110, an organic layer 150, and a second electrode 190 which are sequentially stacked in this stated order, an organic light-emitting device 30 of FIG. 3 includes a first electrode 110, an organic layer 150, a second electrode 190, and a second capping layer 220 which are sequentially stacked in this stated order, and an organic light-emitting device 40 of FIG. 4 includes a first capping layer 210, a first electrode 110, an organic layer 150, a second electrode 190, and a second capping layer 220.

Regarding FIGS. 2 to 4, the first electrode 110, the organic layer 150, and the second electrode 190 may be understood by referring to the description presented in connection with FIG. 1.

In the organic layer 150 of each of the organic light-emitting devices 20 and 40, light generated in an emission layer may pass through the first electrode 110, which is a semi-transmissive electrode or a transmissive electrode, and the first capping layer 210 toward the outside, and in the organic layer 150 of each of the organic light-emitting devices 30 and 40, light generated in an emission layer may pass through the second electrode 190, which is a semi-transmissive electrode or a transmissive electrode, and the second capping layer 220 toward the outside.

The first capping layer 210 and the second capping layer 220 may increase external luminescent efficiency according to the principle of constructive interference.

The first capping layer 210 and the second capping layer 220 may each independently be an organic capping layer including an organic material, an inorganic capping layer including an inorganic material, or a composite capping layer including an organic material and an inorganic material.

At least one selected from the first capping layer 210 and the second capping layer 220 may each independently include at least one material selected from carbocyclic compounds, heterocyclic compounds, amine-based compounds, porphyrine derivatives, phthalocyanine derivatives, a naphthalocyanine derivatives, alkali metal complexes, and alkaline earth-based complexes. The carbocyclic compound, the heterocyclic compound, and the amine-based compound may be optionally substituted with a substituent containing at least one element selected from O, N, S, Se, Si, F, Cl, Br, and I. In one embodiment, at least one selected from the first capping layer 210 and the second capping layer 220 may each independently include an amine-based compound.

In one embodiment, at least one selected from the first capping layer 210 and the second capping layer 220 may each independently include the compound represented by Formula 201 or the compound represented by Formula 202.

In one or more embodiments, at least one selected from the first capping layer 210 and the second capping layer 220 may each independently include a compound selected from Compounds HT28 to HT33 and Compounds CP1 to CP5, but embodiments are not limited thereto.

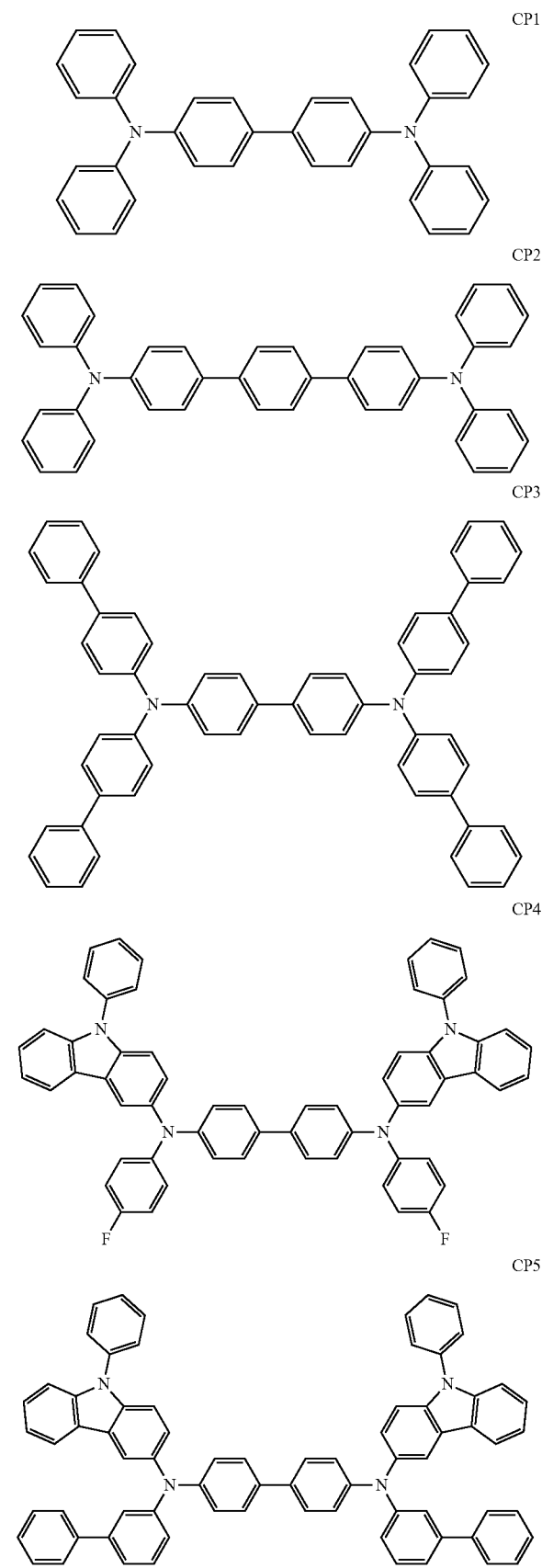

Hereinbefore, the organic light-emitting device according to an embodiment has been described in connection with FIGS. 1-4. However, embodiments are not limited thereto.

Layers constituting the hole transport region, an emission layer, and layers constituting the electron transport region may be formed in a certain region by using one or more suitable methods selected from vacuum deposition, spin coating, casting, Langmuir-Blodgett (LB) deposition, ink-jet printing, laser-printing, and laser-induced thermal imaging.

When layers constituting the hole transport region, an emission layer, and layers constituting the electron transport region are formed by vacuum deposition, for example, the vacuum deposition may be performed at a deposition temperature of about 100 to about 500° C. at a vacuum degree of about $10^{-8}$ to about $10^{-3}$ torr, and at a deposition rate of about 0.01 to about 100 Å/sec by taking into account a material to be included in a layer to be formed, and the structure of a layer to be formed.

When layers constituting the hole transport region, an emission layer, and layers constituting the electron transport region are formed by spin coating, the spin coating may be performed at a coating speed of about 2,000 rpm to about 5,000 rpm and at a heat treatment temperature of about 80° C. to 200° C. by taking into account a material to be included in a layer to be formed, and the structure of a layer to be formed.

[General Definition of Substituents]

The term "$C_1$-$C_{60}$ alkyl group" used herein refers to a linear or branched aliphatic saturated hydrocarbon monovalent group having 1 to 60 carbon atoms, and examples thereof include a methyl group, an ethyl group, a propyl group, an isobutyl group, a sec-butyl group, a tert-butyl group, a pentyl group, an iso-amyl group, and a hexyl group. The term "$C_1$-$C_{60}$ alkylene group" used herein refers to a divalent group having the same structure as the $C_1$-$C_{60}$ alkyl group.

The term "$C_2$-$C_{60}$ alkenyl group" as used herein refers to a hydrocarbon group having at least one carbon-carbon double bond in the middle or at the terminus of the $C_2$-$C_{60}$ alkyl group, and examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group having at least one carbon-carbon triple bond in the middle or at the terminus of the $C_2$-$C_{60}$ alkyl group, and examples thereof include an ethynyl group, and a propynyl group. The term "$C_2$-$C_{60}$ alkynylene group" as used herein refers to a divalent group having the same structure as the $C_2$-$C_{60}$ alkynyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group" as used herein refers to a monovalent saturated hydrocarbon monocyclic group having 3 to 10 carbon atoms, and examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term $C_1$-$C_{10}$ heterocycloalkyl group used herein refers to a monovalent monocyclic group having at least one heteroatom selected from N, O, Si, P, and S as a ring-forming atom and 1 to 10 carbon atoms, and examples thereof include a 1,2,3,4-oxatriazolidinyl group, a tetrahydrofuranyl group, and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term $C_3$-$C_{10}$ cycloalkenyl group used herein refers to a monovalent monocyclic group that has 3 to 10 carbon atoms and at least one carbon-carbon double bond in the ring thereof and no aromaticity, and examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group that has at least one heteroatom selected from N, O, Si, P, and S as a ring-forming atom, 1 to 10 carbon atoms, and at least one double bond in its ring. Non-limiting examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group" as used herein refers to a monovalent group having a carbocyclic aromatic system that has at least one heteroatom selected from N, O, Si, P, and S as a ring-forming atom, in addition to 1 to 60 carbon atoms. The term "$C_1$-$C_{60}$ heteroarylene group" as used herein refers to a divalent group having a carbocyclic aromatic system that has at least one heteroatom selected from N, O, Si, P, and S as a ring-forming atom, in addition to 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be condensed with each other.

The term "$C_6$-$C_{60}$ aryloxy group" as used herein refers to —$OA_{102}$ (wherein $A_{102}$ is the $C_6$-$C_{60}$ aryl group), and a $C_6$-$C_{60}$ arylthio group used herein indicates —$SA_{103}$ (wherein $A_{103}$ is the $C_6$-$C_{60}$ aryl group).

The term "monovalent non-aromatic condensed polycyclic group" as used herein refers to a monovalent group (for example, having 8 to 60 carbon atoms) having two or more rings condensed with each other, only carbon atoms as ring-forming atoms, and no aromaticity in its entire molecular structure. A detailed example of the monovalent non-aromatic condensed polycyclic group is a fluorenyl group. The term "divalent non-aromatic condensed polycyclic group," used herein, refers to a divalent group having the same structure as the monovalent non-aromatic condensed polycyclic group.

The term "monovalent non-aromatic condensed heteropolycyclic group" as used herein refers to a monovalent group (for example, having 1 to 60 carbon atoms) having two or more rings condensed to each other, at least one heteroatom selected from N, O, Si, P, and S, other than carbon atoms, as a ring-forming atom, and no aromaticity in its entire molecular structure. An example of the monovalent non-aromatic condensed heteropolycyclic group is a carbazolyl group. The term "divalent non-aromatic condensed heteropolycyclic group" as used herein refers to a divalent group having the same structure as the monovalent non-aromatic condensed heteropolycyclic group.

The term "$C_5$-$C_{60}$ carbocyclic group" as used herein refers to a monocyclic or polycyclic group having 5 to 60 carbon atoms in which a ring-forming atom is a carbon atom only. The $C_5$-$C_{60}$ carbocyclic group may be an aromatic carbocyclic group or a non-aromatic carbocyclic group. The $C_5$-$C_{60}$ carbocyclic group may be a ring, such as benzene, a monovalent group, such as a phenyl group, or a divalent group, such as a phenylene group. In one or more embodiments, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group" as used herein refers to a group having the same structure as the $C_1$-$C_{60}$ carbocyclic group, except that as a ring-forming atom, at least one heteroatom selected from N, O, Si, P, and S is used in addition to carbon (the number of carbon atoms may be in a range of 1 to 60).

At least one substituent of the substituted $C_5$-$C_{60}$ carbocyclic group, substituted $C_1$-$C_{60}$ heterocyclic group, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group and substituted monovalent non-aromatic condensed heteropolycyclic group may be selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$) and —P(=O)($Q_{31}$)($Q_{32}$), wherein $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

The term "Ph" used herein refers to a phenyl group, the term "Me" used herein refers to a methyl group, the term "Et" used herein refers to an ethyl group, the term "ter-Bu" or "Bu$^t$" used herein refers to a tert-butyl group, and the term "OMe" used herein refers to a methoxy group.

The term "biphenyl group" as used herein refers to "a phenyl group substituted with a phenyl group." In other words, the "biphenyl group" is a substituted phenyl group having a $C_6$-$C_{60}$ aryl group as a substituent.

The term "terphenyl group" as used herein refers to "a phenyl group substituted with a biphenyl group." In other words, the "terphenyl group" is a phenyl group having, as a substituent, a $C_6$-$C_{60}$ aryl group substituted with a $C_6$-$C_{60}$ aryl group.

* and *' used herein, unless defined otherwise, each refer to a binding site to a neighboring atom in a corresponding formula.

Hereinafter, a compound according to embodiments and an organic light-emitting device according to embodiments will be described in detail with reference to Synthesis Examples and Examples. The wording "B was used instead of A" used in describing Synthesis Examples refers to that an identical molar equivalent of B was used in place of A.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

Synthesis Example 1: Synthesis of Compound 2

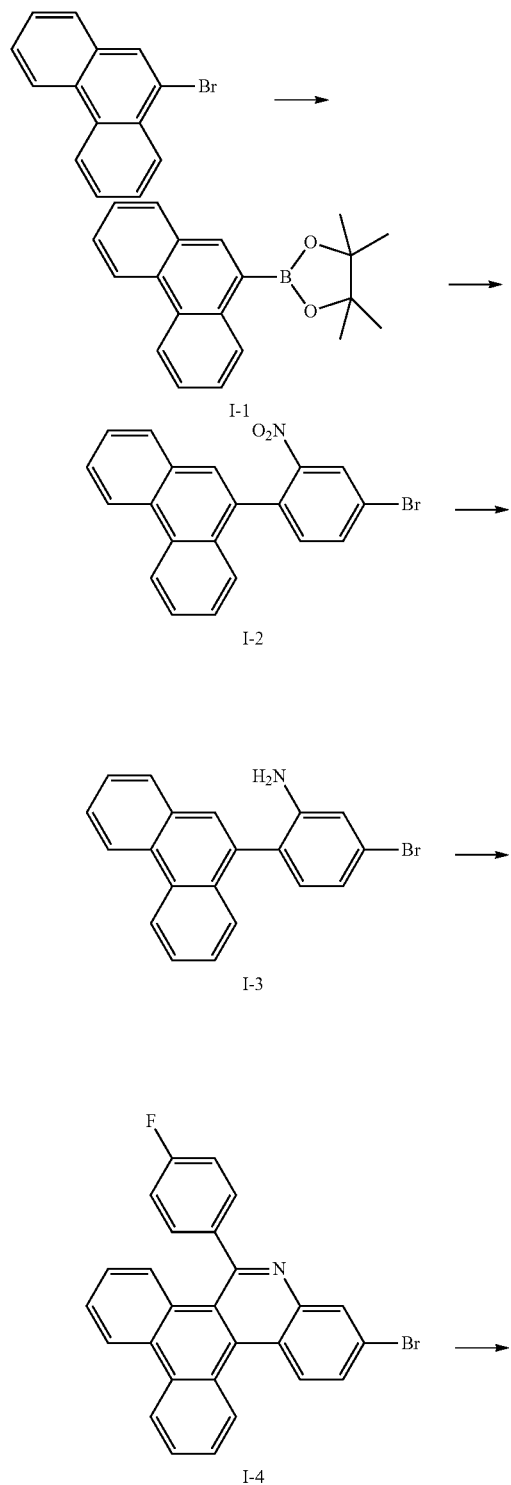

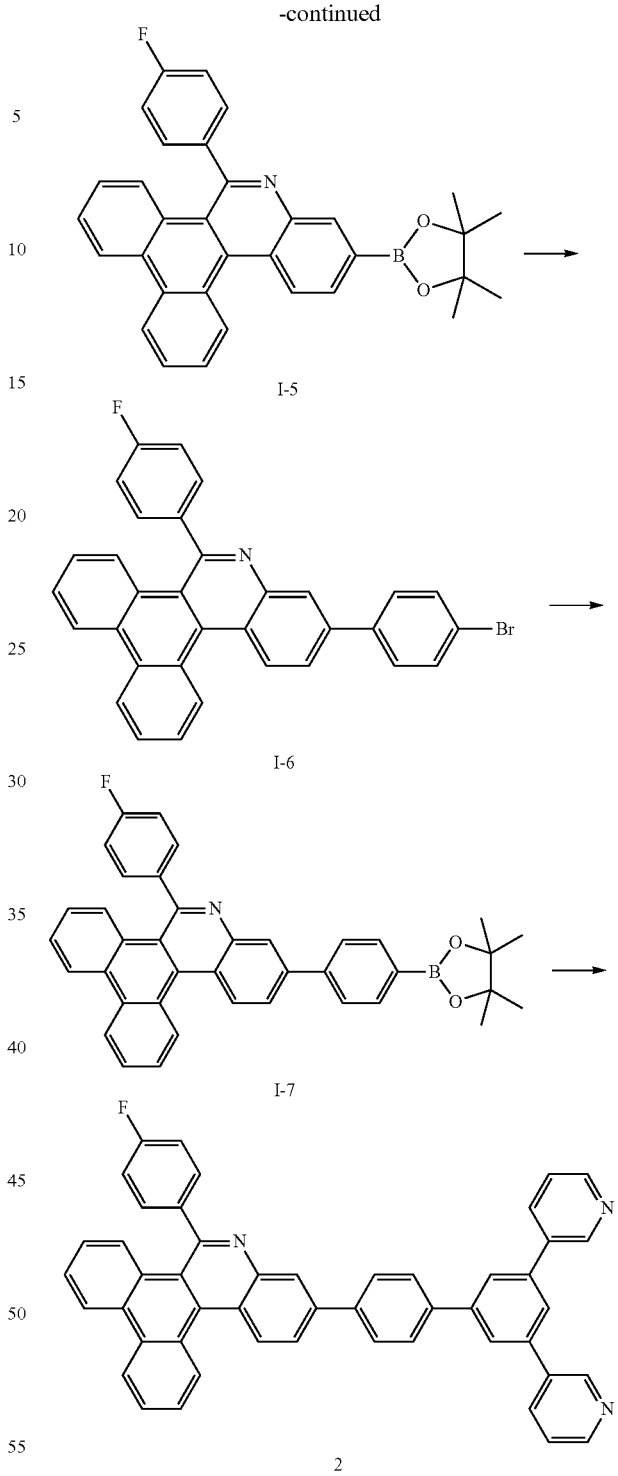

Synthesis of Intermediate I-1

2.60 g (10 mmol) of 9-bromophenanthrene was dissolved in 30 mL of THF, and then, 4 mL (2.5 M in Hexane) of normal butyllithium was added thereto at a temperature of −78° C. After one hour, at the same temperature, 2.0 mL (10 mmol) of 2-isopropoxy-4,4,5,5-tetramethyl-1,3,2-dioxaborolane was added thereto. At room temperature, the result was stirred for 5 hours, and then, water was added thereto and the result solution was washed three times with 30 ml of diethylether. A diethyl ether layer obtained by the washing was dried by using MgSO$_4$ and dried under reduced pressure. The obtained product was separation-purified by silica gel column chromatography to obtain 2.34 g (yield: 77%) of Intermediate I-1. The obtained compound was identified by LC-MS. C$_{20}$H$_{21}$BO$_2$: M+1 304.2

Synthesis of Intermediate I-2

3.04 g (10.0 mmol) of Intermediate I-1, 2.80 g (10.0 mmol) of 1,4-dibromo-2-nitrobenzene, 0.58 g (0.50 mmol) of Pd(PPh$_3$)$_4$, 0.16 g (0.5 mmol) of tetrabutylammonium bromide (TBAB), and 3.18 g (30.0 mmol) of Na$_2$CO$_3$ were dissolved in 60 mL of a mixed solution of toluene/ethanol/H$_2$O (3/3/1), and then, at a temperature of 80° C., the mixture was stirred for 16 hours. The reaction solution was cooled to room temperature, and then subjected to an extraction process three times by using 60 mL of water and 60 mL of diethylether. An organic layer obtained by the extraction process was dried by using magnesium sulfate, and the residual obtained by evaporating a solvent was separation-purified by silica gel column chromatography to obtain 3.03 g (yield of 80%) of Intermediate I-2. The obtained compound was identified by LC-MS. C$_{20}$H$_{12}$BrNO$_2$: M+1 377.0

Synthesis of Intermediate I-3

3.78 g (10.0 mmol) of Intermediate I-2, 3.56 g (30 mmol) of tin, and 5 mL (50 mmol, conc. 36.5%) of HCl were dissolved in 60 mL of ethanol, and then, at a temperature of 100° C., the mixture was stirred for 8 hours. The reaction solution was cooled to room temperature, and then, 3 g of sodium hydroxide dissolved in 10 mL of water was added to a filtrate obtained by reduced-pressure filtration performed thereon. Then, the result was subjected three times to an extraction process by using 60 mL of water and 60 mL of dichloromethane. An organic layer obtained by the extraction process was dried by using magnesium sulfate, and the residual obtained by evaporating a solvent was separation-purified by silica gel column chromatography to obtain 3.17 g (yield of 91%) of Intermediate I-3. The obtained compound was identified by LC-MS. C$_{20}$H$_{14}$BrN: M+1 347.0

Synthesis of Intermediate I-4

3.48 g (10 mmol) of Intermediate I-3 and 2.48 g (20 mmol) of 4-fluorobenzaldehyde were dissolved in 10 mL of trifluoroacetic acid, and then, the mixture was stirred in a seal tube at a temperature of 130° C. for 3 days. The reaction solution was cooled to room temperature, and then subjected to quenching using NaHCO$_3$, and then an extraction process was performed thereon three times by using 60 mL of water and 60 mL of dichloromethane. An organic layer obtained by the extraction process was dried by using magnesium sulfate, and the residual obtained by evaporating a solvent was separation-purified by silica gel column chromatography to obtain 3.17 g (yield of 91%) of Intermediate I-3. The obtained compound was identified by LC-MS. C$_{27}$H$_{15}$BrFN: M+1 451.0

Synthesis of Intermediate I-5

3.80 g (yield of 76%) of Intermediate I-5 was obtained in the same manner as used to synthesize Intermediate I-1, except that Intermediate I-4 was used instead of 9-bromophenanthrene. The obtained compound was identified by LC-MS. C$_{33}$H$_{27}$BFNO$_2$: M+1 499.2

Synthesis of Intermediate I-6

3.80 g (yield 72%) of Intermediate I-6 was obtained in the same manner as used to synthesize Intermediate I-2, except that Intermediate I-5 was used instead of Intermediate I-1 and 1-bromo-4-iodobenzene was used instead of 1,4-dibromo-2-nitrobenzene. The obtained compound was identified by LC-MS. C$_{33}$H$_{19}$BrFN: M+1 527.1

Synthesis of Intermediate I-7

4.03 g (yield 70%) of Intermediate I-7 was obtained in the same manner as used to synthesize Intermediate I-1, except that Intermediate I-6 was used instead of 9-bromophenanthrene. The obtained compound was identified by LC-MS. C$_{39}$H$_{31}$BFNO$_2$: M+1 575.2

Synthesis of Compound 2

5.75 g (10 mmol) of Intermediate I-7, 3.11 g (10 mmol) of 3,3'-(5-bromo-1,3-phenylene)dipyridine, 0.58 g (0.5 mmol) of Pd(PPh$_3$)$_4$ (tetrakis(triphenylphosphine)palladium), and 4.14 g (30 mmol) of K$_2$CO$_3$ were dissolved in 60 mL of a mixed solution of THF/H$_2$O (a volumetric ratio of 2/1), and then, at a temperature of 80° C., the mixture was stirred for 16 hours. The reaction solution was cooled to room temperature, and then, 40 mL of water was added thereto, and then, the resultant reaction solution was subjected to an extraction process three times by using 50 mL of ethylether. The collected organic layer was dried by using magnesium sulfate and the residual obtained by evaporating a solvent therefrom was separation-purified by silica gel column chromatography to obtain 4.21 g of Compound 2 (yield of 62%). The obtained compound was confirmed by MS/FAB and $^1$H NMR. C$_{49}$H$_{30}$FN$_3$ cal. 679.24, found 679.25.

Synthesis Example 2: Synthesis of Compound 12

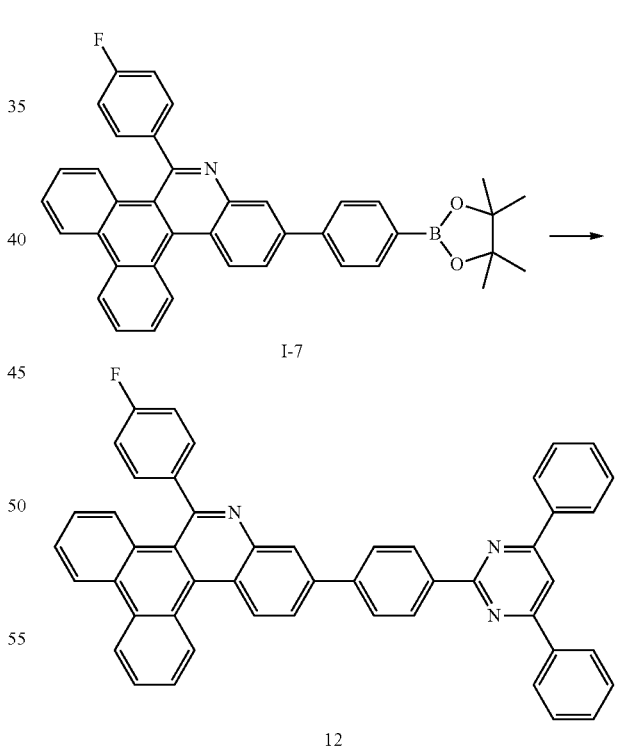

4.21 g (yield of 62%) of Compound 12 was obtained in the same manner as used to synthesize Compound 2, except that 2-chloro-4,6-diphenylpyrimidine was used instead of 3,3'-(5-bromo-1,3-phenylene)dipyridine The obtained compound was confirmed by MS/FAB and $^1$H NMR. C$_{49}$H$_{30}$FN$_3$ cal. 679.24. found 679.25.

Synthesis Example 3: Synthesis of Compound 13

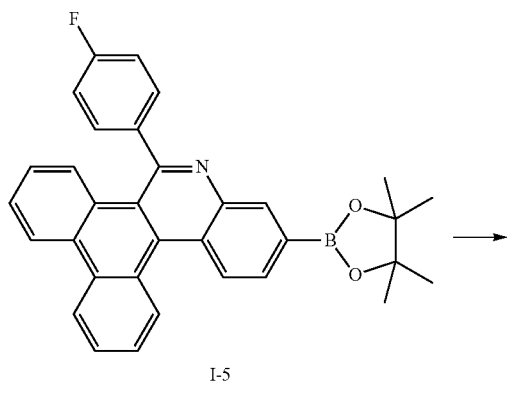

I-5

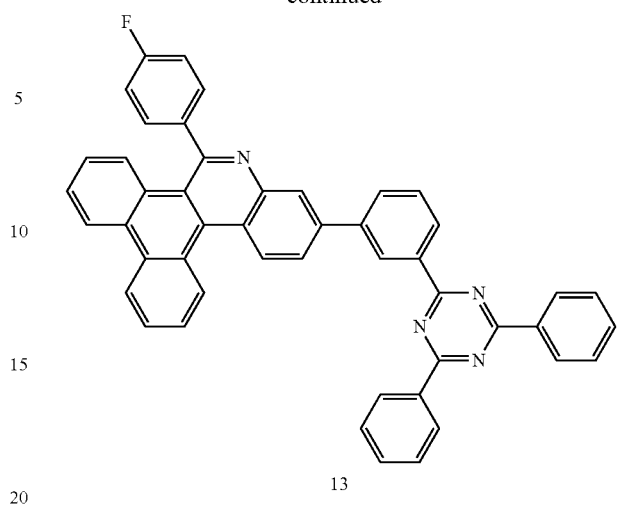

13

Synthesis of Intermediate I-8

3.80 g (yield of 72%) of Intermediate I-8 was obtained in the same manner as used to synthesize Intermediate I-6, except that 1-bromo-3-iodobenzene was used instead of 1-bromo-4-iodobenzene. The obtained compound was identified by LC-MS. $C_{33}H_{19}BrFN$: M+1 527.1

Synthesis of Intermediate I-9

4.55 g (yield of 79%) of Intermediate I-9 was obtained in the same manner as used to synthesize Intermediate I-7, except that Intermediate I-8 was used instead of Intermediate I-6. The obtained compound was identified by LC-MS. $C_{39}H_{31}BFNO_2$: M+1 575.2

Synthesis of Compound 13

4.56 g (yield of 67%) of Compound 13 was obtained in the same manner as used to synthesize Compound 2, except that Intermediate I-9 was used instead of Intermediate I-7, and 2-chloro-4,6-diphenyl-1,3,5-triazine was used instead of 3,3'-(5-bromo-1,3-phenylene)dipyridine. The obtained compound was confirmed by MS/FAB and $^1$H NMR. $C_{48}H_{29}FN_4$ cal. 680.24, found 680.23.

Synthesis Example 4: Synthesis of Compound 15

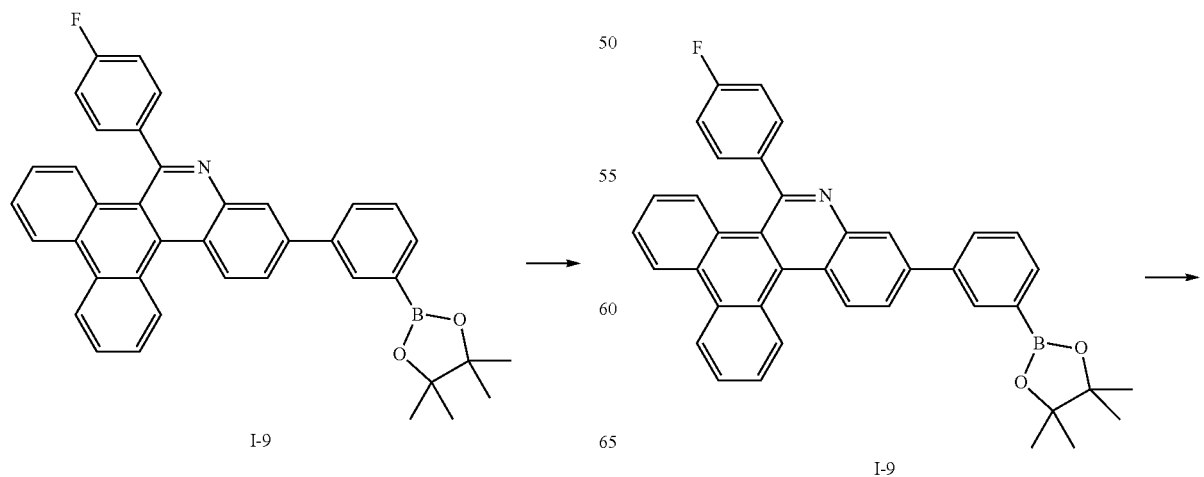

I-9

-continued

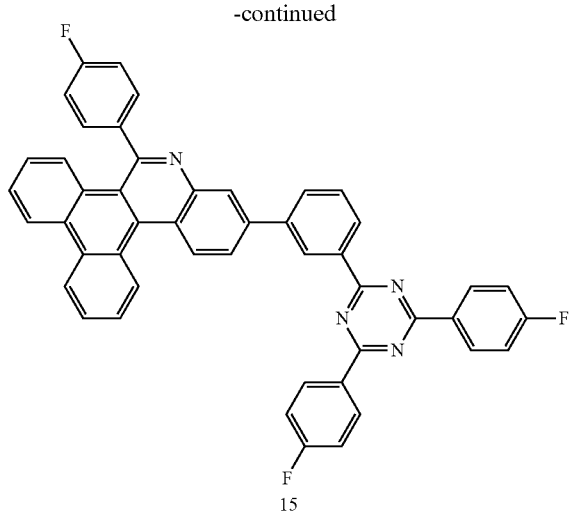
15

5.02 g (yield of 70%) of Compound 15 was obtained in the same manner as used to synthesize Compound 13, except that 2-chloro-4,6-bis(4-fluorophenyl)-1,3,5-triazine was used instead of 3,3'-(5-bromo-1,3-phenylene)dipyridine. The obtained compound was confirmed by MS/FAB and NMR. $C_{48}H_{27}F_3N_4$ cal. 716.22, found 716.21.

Synthesis Example 5: Synthesis of Compound 17

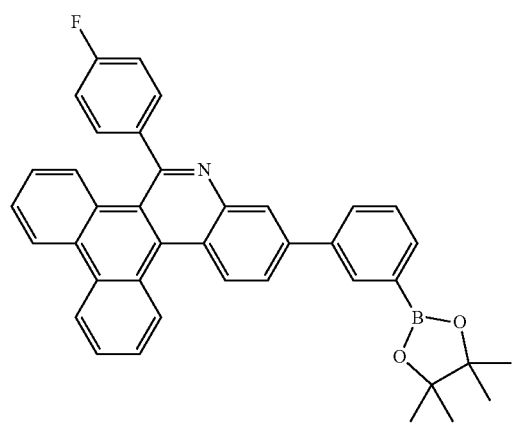

5.22 g (yield of 69%) of Compound 17 was obtained in the same manner as used to synthesize Compound 13, except that 2-(3-bromophenyl)-4,6-diphenyl-1,3,5-triazine was used instead of 3,3'-(5-bromo-1,3-phenylene)dipyridine. The obtained compound was confirmed by MS/FAB and $^1$H NMR. $C_{54}H_{33}FN_4$ cal. 756.27, found 756.28.

Synthesis Example 6: Synthesis of Compound 19

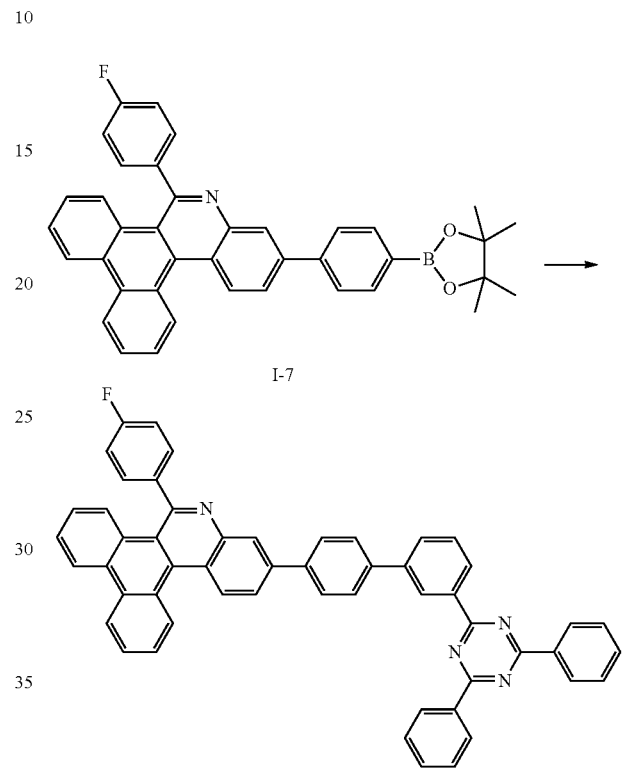

4.92 g (yield of 65%) of Compound 19 was obtained in the same manner as used to synthesize Compound 2, except that 2-(3-bromophenyl)-4,6-diphenyl-1,3,5-triazine was used instead of 3,3'-(5-bromo-1,3-phenylene)dipyridine. The obtained compound was confirmed by MS/FAB and $^1$H NMR. $C_{54}H_{33}FN_4$ cal. 756.27, found 756.26.

Synthesis Example 7: Synthesis of Compound 22

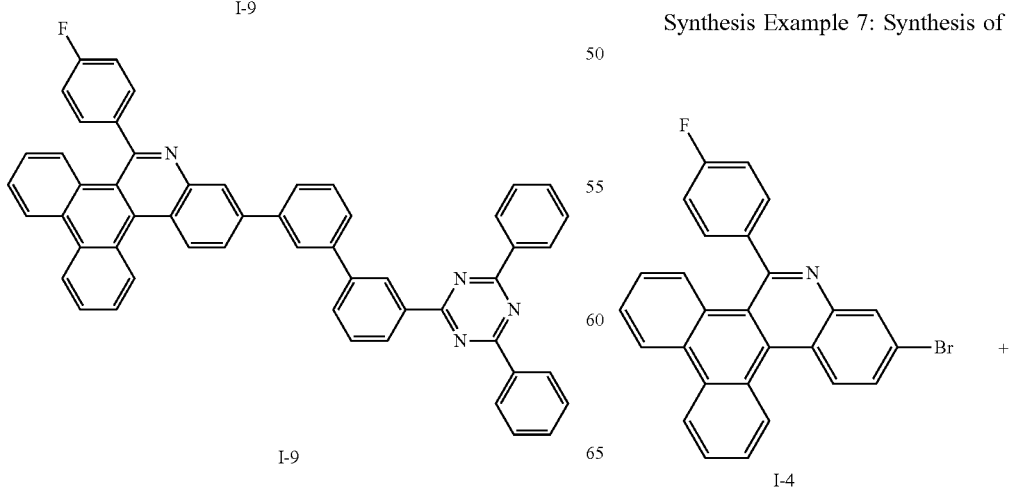

-continued

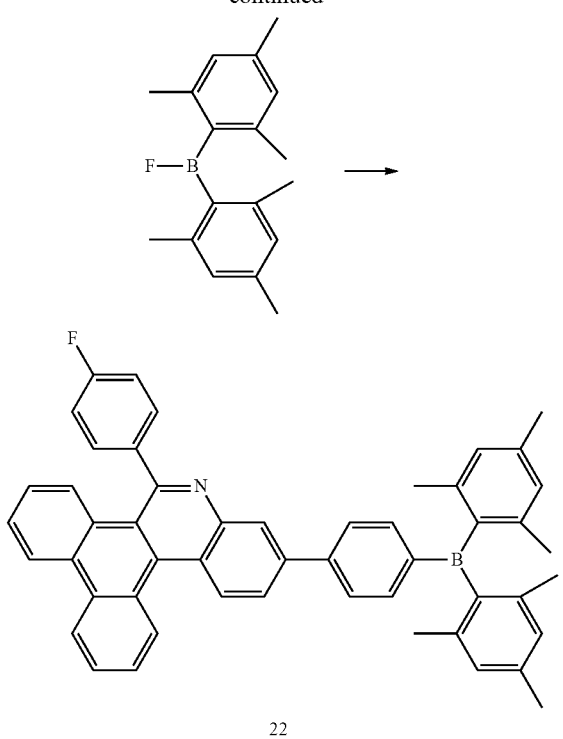

22

4.52 g (10 mmol) of Intermediate I-4 was dissolved in 50 mL of THF, and then, 4 mL (2.5 M in Hexane) of normal butyllithium was added thereto at a temperature of −78° C. After one hour, 2.95 g (10 mmol) of dimesitylboron fluoride was added thereto at the same temperature. At room temperature, the result was stirred for 12 hours, and then, water was added thereto and the result solution was washed three times with 30 ml of ethylacetate. An ethylacetate layer obtained by the washing was dried by using $MgSO_4$ and dried under reduced pressure. The obtained product was separation-purified by silica gel column chromatography to obtain 5.02 g (yield of 72%) of Compound 22. The obtained compound was confirmed by MS/FAB and $^1H$ NMR. $C_{51}H_{41}BFN$ cal. 697.33, found 697.32.

Synthesis Example 8: Synthesis of Compound 24

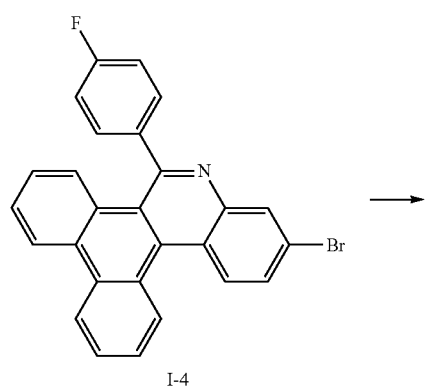

I-4

-continued

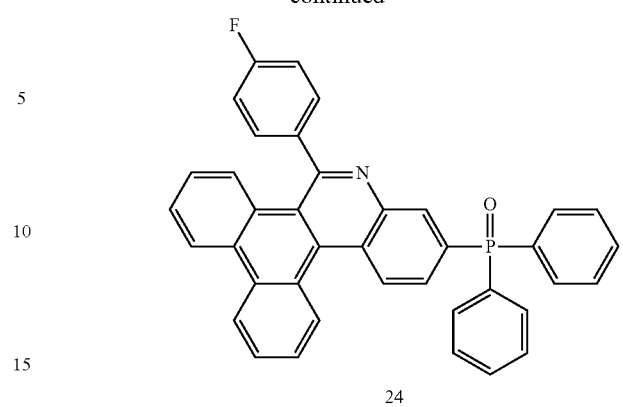

24

4.52 g (10 mmol) of Intermediate I-4 was dissolved in 100 mL of THF, and then, 4 mL (2.5 M in Hexane) of normal butyllithium was added thereto at a temperature of −78° C. After one hour, 2.20 g (10 mmol) of chlorodiphenyl phosphine was slowly added dropwise, and the mixture was stirred for 3 hours and then the temperature thereof was adjusted to room temperature. Then, water was added thereto, and the resultant solution was washed three times with 30 mL of ethylacetate. An ethylacetate layer obtained by the washing was dried by using $MgSO_4$ and dried under reduced pressure to obtain an intermediate. The intermediate was dissolved in 40 mL of dichloromethane, and then, 4 mL of hydrogen peroxide was added thereto, and the mixture was stirred at room temperature for 20 hours. 20 mL of water was added to the reaction solution and then, extracted three times with 20 mL of dichloromethane. The collected organic layer was dried by using magnesium sulfate and the residual obtained by evaporating a solvent therefrom was separation-purified by silica gel column chromatography to obtain 4.70 g (yield of 82%) of Compound 24. The obtained compound was confirmed by MS/FAB and $^1H$ NMR. $C_{39}H_{25}FNOP$ cal. 573.17, found 573.18.

Synthesis Example 9: Synthesis of Compound 29

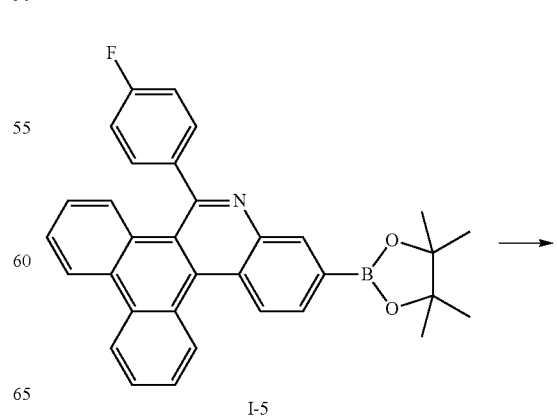

I-5

-continued

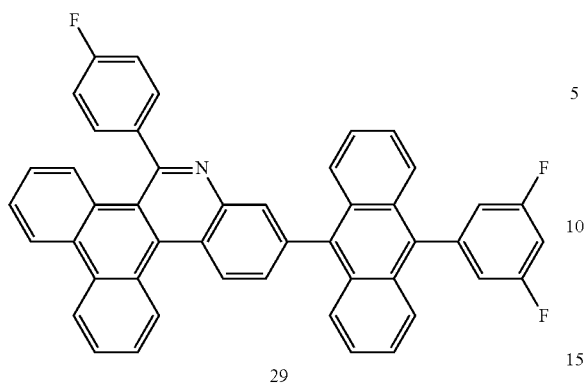

29

4.17 g (yield of 63%) of Compound 29 was obtained in the same manner as used to synthesize Compound 2, except that Intermediate I-5 was used instead of Intermediate I-7, and 9-bromo-10-(3,5-difluorophenyl)anthracene was used instead of 3,3'-(5-bromo-1,3-phenylene)dipyridine. The obtained compound was confirmed by MS/FAB and $^1$H NMR. $C_{47}H_{26}F_3N$ cal. 661.20, found 661.21.

Synthesis Example 10: Synthesis of Compound 32

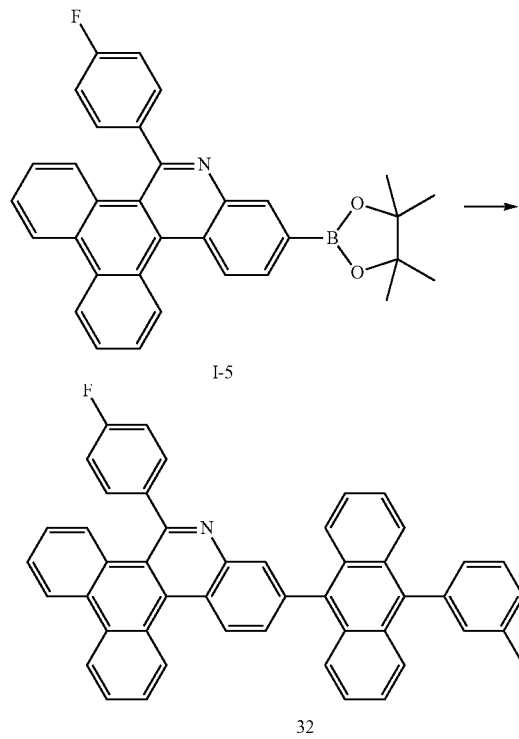

4.53 g (yield of 67%) of Compound 32 was obtained in the same manner as used to synthesize Compound 2, except that Intermediate I-5 was used instead of Intermediate I-7, and 9-bromo-10-(naphthalen-2-yl)anthracene was used instead of 3,3'-(5-bromo-1,3-phenylene)dipyridine. The obtained compound was confirmed by MS/FAB and $^1$H NMR. $C_{51}H_{30}FN$ cal. 675.24, found 675.25.

Synthesis Example 11: Synthesis of Compound 48

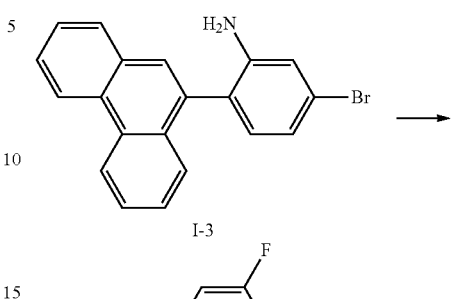

I-3

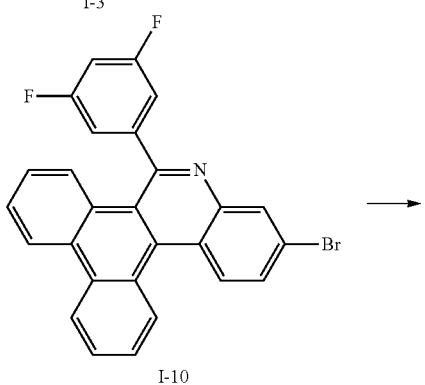

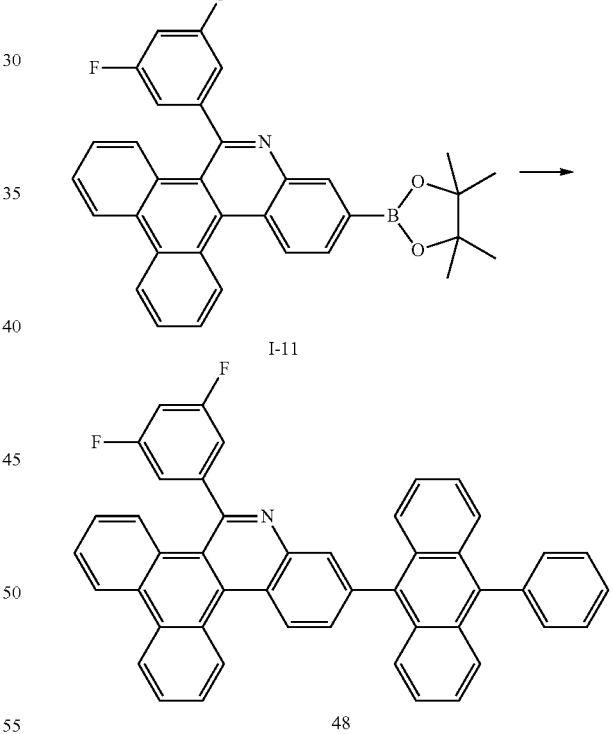

Synthesis of Intermediate I-10

3.81 g (yield of 81%) of Intermediate I-10 was obtained in the same manner as used to synthesize Intermediate I-4, except that 3,5-difluorobenzaldehyde was used instead of 4-fluorobenzaldehyde. The obtained compound was identified by LC-MS. $C_{27}H_{14}BrF_2N$: M+1 469.1

Synthesis of Intermediate I-11

4.45 g (yield of 86%) of Intermediate I-11 was obtained in the same manner as used to synthesize Intermediate I-5, except that Intermediate I-10 was used instead of Intermediate I-4. The obtained compound was identified by LC-MS. $C_{33}H_{26}BF_2NO_2$: M+1 517.2

Synthesis of Compound 48

4.70 g (yield of 73%) of Compound 48 was obtained in the same manner as used to synthesize Compound 2, except that Intermediate I-11 was used instead of Intermediate I-5, and 9-bromo-10-(naphthalen-2-yl)anthracene was used instead of 3,3'-(5-bromo-1,3-phenylene)dipyridine. The obtained compound was confirmed by MS/FAB and $^1$H NMR. $C_{47}H_{27}F_2N$ cal. 643.21, found 643.22.

Synthesis Example 12: Synthesis of Compound 60

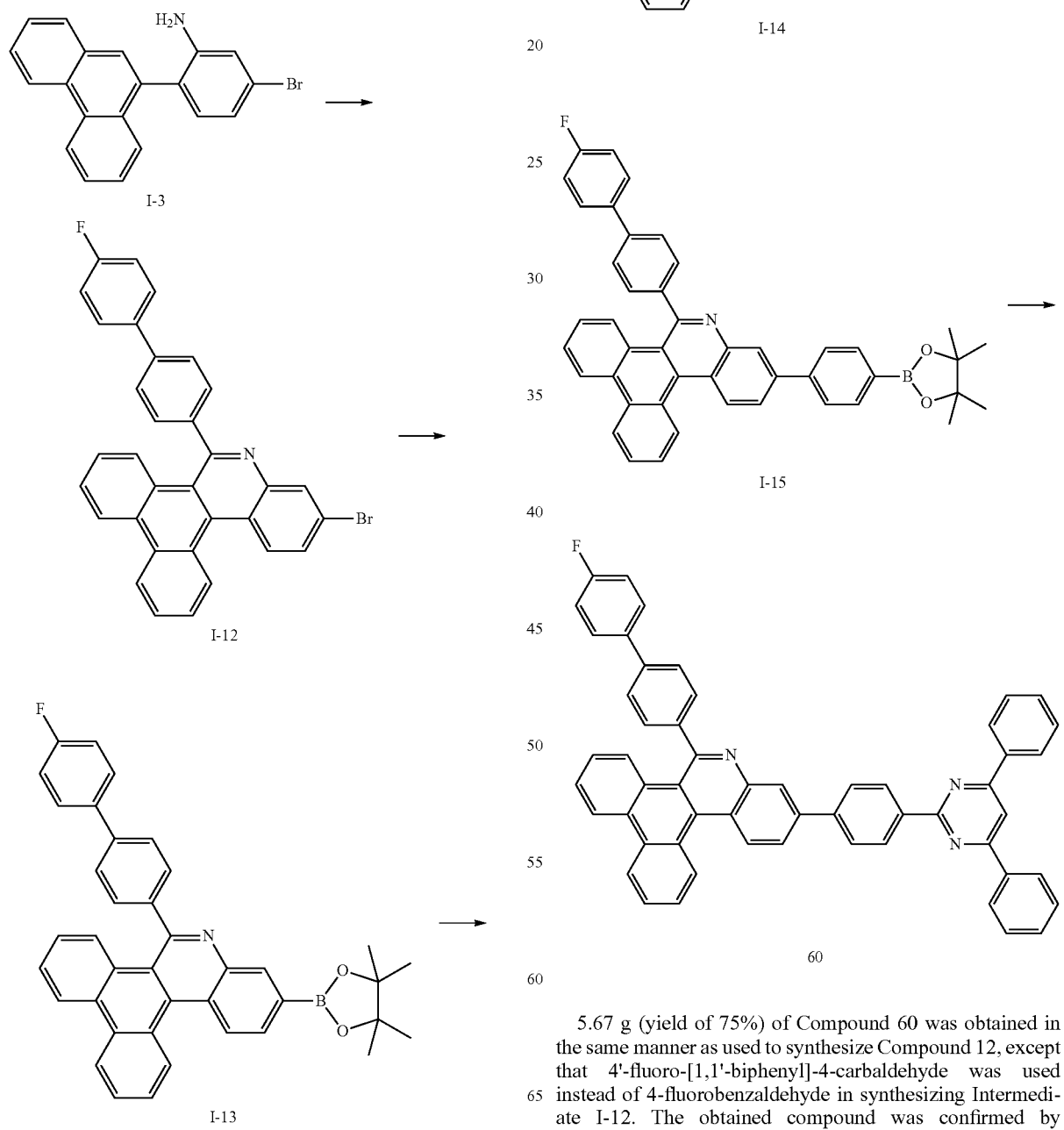

5.67 g (yield of 75%) of Compound 60 was obtained in the same manner as used to synthesize Compound 12, except that 4'-fluoro-[1,1'-biphenyl]-4-carbaldehyde was used instead of 4-fluorobenzaldehyde in synthesizing Intermediate I-12. The obtained compound was confirmed by MS/FAB and NMR. $C_{55}H_{34}FN_3$ cal. 755.27, found 755.26.

Synthesis Example 13: Synthesis of Compound 72

Synthesis Example 14: Synthesis of Compound 77

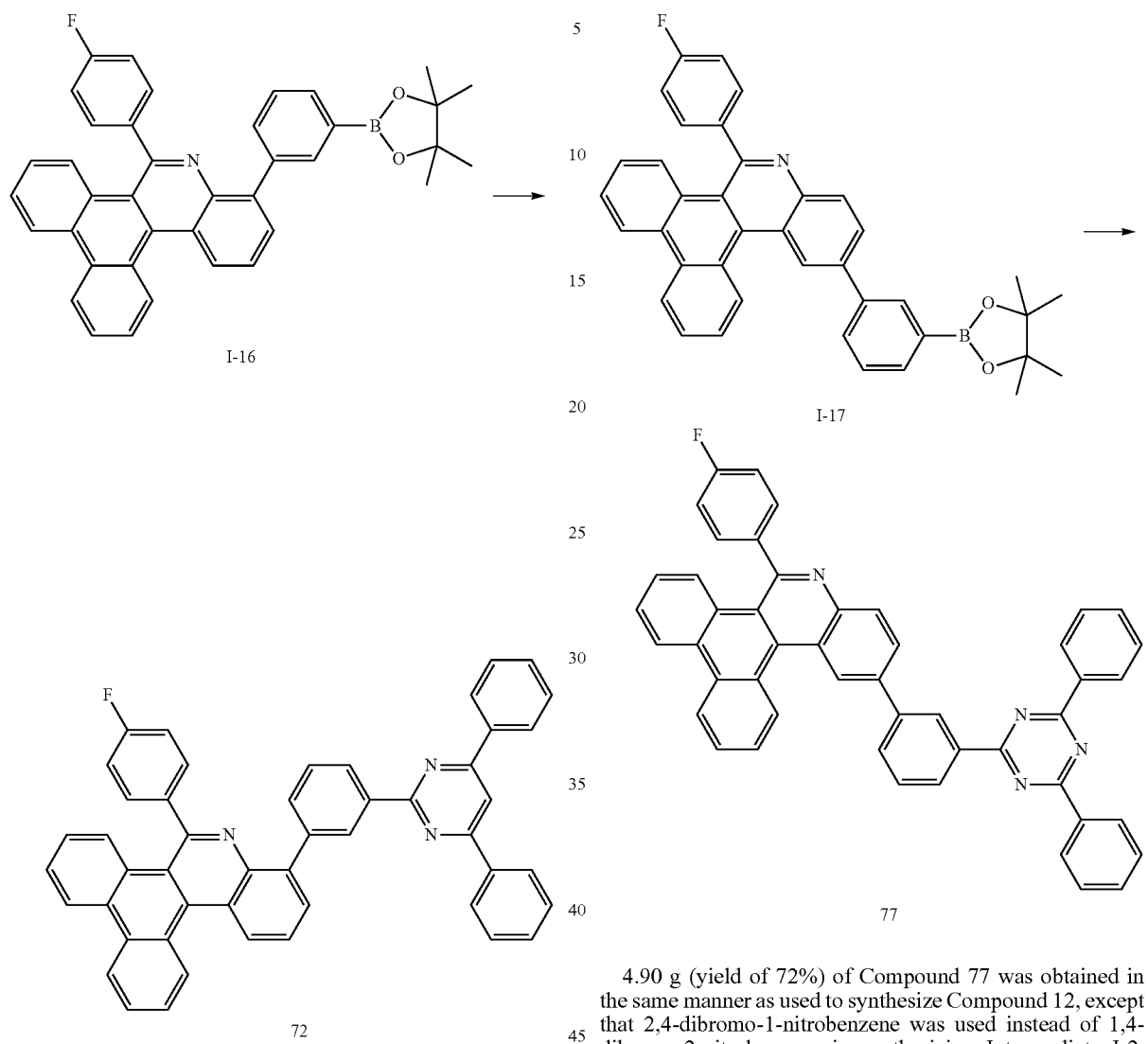

4.96 g (yield of 73%) of Compound 72 was obtained in the same manner as used to synthesize Compound 12, except that 1,3-dibromo-2-nitrobenzene was used instead of 1,4-dibromo-2-nitrobenzene in synthesizing Intermediate I-2, and 1,3-dibromobenzene was used instead of 1,4-dibromobenzene in synthesizing Intermediate I-7. The obtained compound was confirmed by MS/FAB and $^1$H NMR. $C_{49}H_{30}FN_3$ cal. 679.24, found 679.23.

4.90 g (yield of 72%) of Compound 77 was obtained in the same manner as used to synthesize Compound 12, except that 2,4-dibromo-1-nitrobenzene was used instead of 1,4-dibromo-2-nitrobenzene in synthesizing Intermediate I-2, and 1,3-dibromobenzene was used instead of 1,4-dibromobenzene in synthesizing Intermediate I-7. The obtained compound was confirmed by MS/FAB and $^1$H NMR. $C_{48}H_{29}FN_4$ cal. 680.24, found 680.25.

Table 1 shows $^1$H NMR and MS/FAB of the synthesized compounds. Compounds other than the compounds shown in Table 1 may be easily recognized by those skilled in the art with reference to the above synthetic routes and raw materials.

TABLE 1

| Compound | $^1$H NMR (CDCl$_3$, 400 MHz) | MS/FAB found | calc. |
|---|---|---|---|
| 2 | 8.96-8.92 (m, 2H), 8.87-8.82 (m, 2H), 8.74-8.70 (m, 2H), 8.67-8.62 (m, 3H), 8.60-8.57 (m, 1H), 8.20 (dd, 1H), 8.10-8.00 (m, 5H), 7.94-7.85 (m, 7H), 7.80-7.62 (m, 4H), 7.49 (d, 1H), 7.47 (d, 1H), 7.23-7.17 (m, 2H) | 679.25 | 679.24 |
| 12 | 8.86-8.82 (m, 2H), 8.73-8.70 (m, 1H), 8.66-8.62 (m, 1H), 8.60-8.53 (m, 3H), 8.30-8.26 (m, 4H), 8.20 (dd, 1H), 8.10-8.02 (m, 4H), 7.96 (s, 1H), 7.80-7.63 (m, 4H), | 679.25 | 679.24 |

TABLE 1-continued

| Compound | $^1$H NMR (CDCl$_3$, 400 MHz) | MS/FAB found | MS/FAB calc. |
|---|---|---|---|
| | 7.53-7.48 (m, 4H), 7.30 (t, 1H), 7.29 (dd, 1H), 7.27 (t, 1H), 7.25-7.20 (m, 2H) | | |
| 13 | 8.85-8.78 (m, 6H), 8.73-8.70 (m, 2H), 8.66-8.55 (m, 3H), 8.40 (dd, 1H), 8.11-8.05 (m, 3H), 7.98-7.96 (m, 1H), 7.80-7.59 (m, 9H), 7.42-7.38 (m, 2H), 7.23-7.19 (m, 2H) | 680.23 | 680.24 |
| 15 | 8.86-8.82 (m, 2H), 8.73-8.70 (m, 2H), 8.66-8.58 (m, 3H), 8.40 (dd, 1H), 8.35-8.30 (m, 4H), 8.11-8.06 (m, 3H), 7.99-7.96 (m, 1H), 7.80-7.62 (m, 5H), 7.30-7.18 (m, 6H) | 716.21 | 716.22 |
| 17 | 8.85-8.78 (m, 6H), 8.72-8.70 (m, 1H), 8.65-8.56 (m, 4H), 8.24-8.18 (m, 2H), 8.10-8.06 (m, 3H), 7.94-7.74 (m, 3H), 7.70-7.49 (m, 9H), 7.42-7.30 (m, 3H), 7.23-7.17 (m, 2H) | 756.28 | 756.27 |
| 19 | 8.85-8.80 (m, 6H), 8.73-8.57 (m, 5H), 8.20-8.18 (m, 1H), 8.10-7.96 (m, 5H), 7.86-7.82 (m, 3H), 7.80-7.54 (m, 9H), 7.42-7.38 (m, 2H), 7.23-7.20 (m, 2H) | 756.26 | 756.27 |
| 22 | 8.85-8.83 (m, 2H), 8.72-8.57 (m, 3H), 8.27-8.25 (m, 1H), 8.10-8.01 (m, 3H), 7.80-7.51 (m, 8H), 7.23-7.17 (m, 2H), 6.79-6.77 (m, 4H), 2.19 (s, 18H) | 697.32 | 697.33 |
| 24 | 8.89-8.85 (m, 2H), 8.73-8.62 (m, 4H), 8.12-8.07 (m, 2H), 7.86-7.60 (m, 9H), 7.52-7.39 (m, 6H), 7.23-7.20 (m, 2H) | 573.18 | 573.17 |
| 29 | 8.85-8.81 (m, 2H), 8.75-8.63 (m, 3H), 8.45-8.43 (m, 1H), 8.26-8.23 (m, 2H), 8.15-8.13 (m, 1H), 8.10-7.97 (m, 2H), 7.80-7.54 (m, 6H) 7.40-7.32 (m, 4H), 7.23-7.17 (m, 2H), 7.05-6.98 (m, 2H), 6.66-6.60 (m, 1H) | 661.21 | 661.20 |
| 32 | 8.87-8.82 (m, 2H), 8.73-8.62 (m, 3H), 8.45-8.43 (m, 1H), 8.15-8.07 (m, 3H), 8.00-7.89 (m, 7H), 7.80-7.54 (m, 8H), 7.38-7.32 (m, 4H), 7.25-7.19 (m, 2H) | 675.25 | 675.24 |
| 48 | 8.91-8.88 (m, 1H), 8.85-8.82 (m, 1H), 8.73-8.61 (m, 3H), 8.51-8.50 (m, 1H), 8.15-8.13 (m, 1H), 7.83-7.62 (m, 10H), 7.56-7.45 (m, 4H), 7.41-7.28 (m, 5H), 6.98-6.92 (m, 1H) | 643.22 | 643.21 |
| 60 | 8.86-8.83 (m, 2H), 8.73-8.70 (m, 1H), 8.66-8.53 (m, 4H), 8.30-8.26 (m, 6H), 8.20 (dd, 1H), 8.05-8.00 (m, 3H), 7.96 (s, 1H), 7.88-7.85 (m, 2H), 7.80-7.62 (m, 4H), 7.53-7.48 (m, 4H), 7.31-7.26 (m, 2H), 7.18-7.13 (m, 2H), 6.71-6.65 (m, 2H) | 755.26 | 755.27 |
| 72 | 8.93-8.86 (m, 3H), 8.72-8.70 (m, 1H), 8.58-8.56 (m, 1H), 8.50-8.47 (m, 1H), 8.37-8.35 (m, 1H), 8.29-8.21 (m, 5H), 8.13-8.09 (m, 2H), 7.99 (s, 1H), 7.87-7.61 (m, 7H), 7.53-7.48 (m, 4H), 7.31-7.17 (m, 4H) | 679.23 | 679.24 |
| 77 | 8.93-8.86 (m, 2H), 8.81-8.70 (m, 7H), 8.59-8.55 (m, 2H), 8.36-8.34 (m, 1H), 8.15 (dd, 1H), 8.07-8.02 (m, 2H), 7.91-7.88 (m, 1H), 7.80-7.69 (m, 3H), 7.65-7.55 (m, 6H), 7.42-7.38 (m, 2H), 7.23-7.16 (m, 2H) | 680.25 | 680.24 |

Other compounds than the compounds synthesized according to Synthesis Examples 1 to 14 can be easily recognized by those skilled in the art by referring to the above synthetic methods and raw materials.

Example 1 le;3qAs an anode, a Corning 15 Ω/cm2 (1,200 Å) ITO glass substrate was cut to a size of 50 mm×50 mm×0.7 mm, and then, sonicated by using isopropyl alcohol and pure water, each for 5 minutes, and cleaned by exposure to ultraviolet rays for 30 minutes and then to ozone. The resultant glass substrate was mounted on a vacuum deposition apparatus.

On the glass substrate, 2-TNATA, which is a known material, was vacuum-deposited to form a hole injection layer having a thickness of 600 Å, and then, 4,4'-bis[N-(1-naphthyl)-N-phenylamino]biphenyl(hereinafter, referred to as NPB), which is a known hole transport compound, was vacuum-deposited thereon to form a hole transport layer having a thickness of 300 Å.

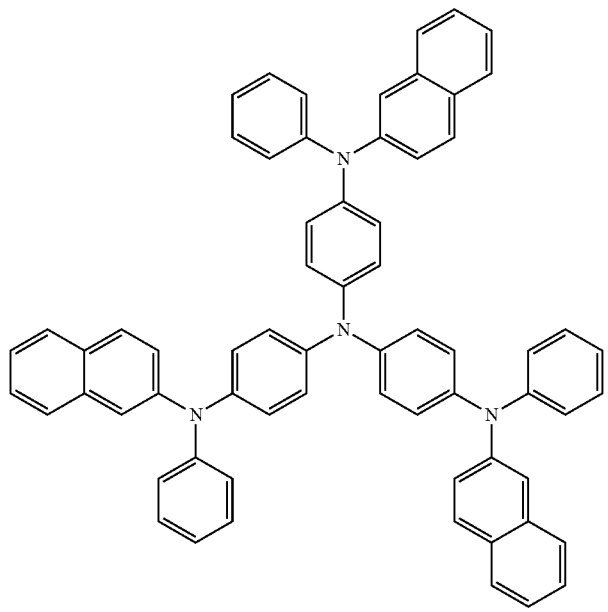

2-TNATA

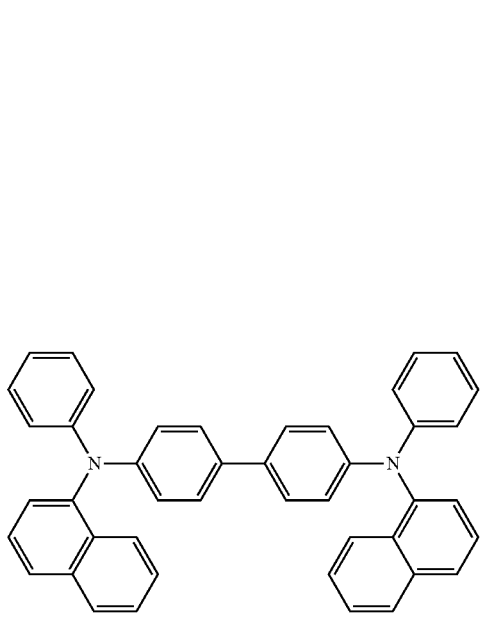

NPB

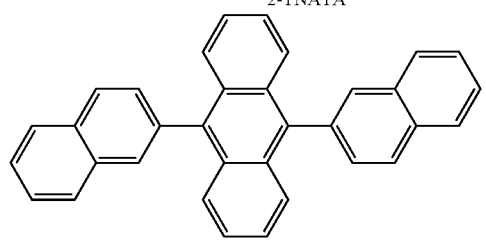

ADN

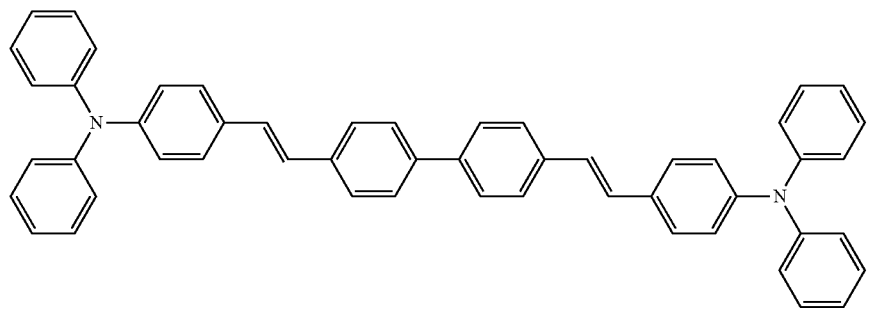

DPAVBi 9,10-di-naphthalene-2-yl-anthracene (hereinafter referred to as ADN), which is a known blue fluorescent host compound, and 4,4'-bis[2-(4-(N,N-diphenylamino)phenyl)vinyl] biphenyl (hereinafter referred to as DPAVBi), which is a known blue fluorescent dopant, were co-deposited on the hole transport layer at a weight ratio of 98:2 to form an emission layer having a thickness of 300 Å.

Then, Compound 2 was deposited on the emission layer to form an electron transport layer having a thickness of 300 Å, and then, LiF, which is a halogenated alkali metal, was deposited on the electron transport layer to form an electron injection layer having a thickness of 10 Å, and Al was vacuum-deposited thereon to a thickness of 3,000 Å (cathode), thereby completing the formation of a LiF/Al electrode and thus, the manufacture of an organic light-emitting device.

Example 2

An organic light-emitting device was manufactured in the same manner as used in Example 1, except that, in forming the electron transport layer, Compound 12 was used instead of Compound 2.

Example 3

An organic light-emitting device was manufactured in the same manner as used in Example 1, except that, in forming the electron transport layer, Compound 13 was used instead of Compound 2.

Example 4

An organic light-emitting device was manufactured in the same manner as used in Example 1, except that, in forming the electron transport layer, Compound 15 was used instead of Compound 2.

Example 5

An organic light-emitting device was manufactured in the same manner as used in Example 1, except that, in forming the electron transport layer, Compound 17 was used instead of Compound 2.

Example 6

An organic light-emitting device was manufactured in the same manner as used in Example 1, except that, in forming the electron transport layer, Compound 19 was used instead of Compound 2.

Example 7

An organic light-emitting device was manufactured in the same manner as used in Example 1, except that, in forming the electron transport layer, Compound 22 was used instead of Compound 2.

Example 8

An organic light-emitting device was manufactured in the same manner as used in Example 1, except that, in forming the electron transport layer, Compound 24 was used instead of Compound 2.

Example 9

An organic light-emitting device was manufactured in the same manner as used in Example 1, except that, in forming the electron transport layer, Compound 29 was used instead of Compound 2.

Example 10

An organic light-emitting device was manufactured in the same manner as used in Example 1, except that, in forming the electron transport layer, Compound 32 was used instead of Compound 2.

Example 11

An organic light-emitting device was manufactured in the same manner as used in Example 1, except that, in forming the electron transport layer, Compound 48 was used instead of Compound 2.

Example 12

An organic light-emitting device was manufactured in the same manner as used in Example 1, except that, in forming the electron transport layer, Compound 60 was used instead of Compound 2.

Example 13

An organic light-emitting device was manufactured in the same manner as used in Example 1, except that, in forming the electron transport layer, Compound 72 was used instead of Compound 2.

Example 14

An organic light-emitting device was manufactured in the same manner as used in Example 1, except that, in forming the electron transport layer, Compound 77 was used instead of Compound 2.

Comparative Example 1

An organic light-emitting device was manufactured in the same manner as used in Example 1, except that, in forming the electron transport layer, Compound 200, which is a known material, was used instead of Compound 2.

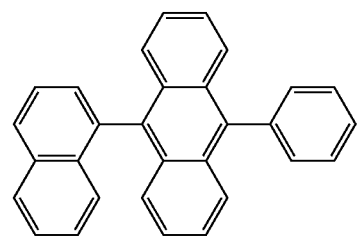

200

Comparative Example 2

An organic light-emitting device was manufactured in the same manner as used in Example 1, except that, in forming the electron transport layer, Compound 201 was used instead of Compound 2.

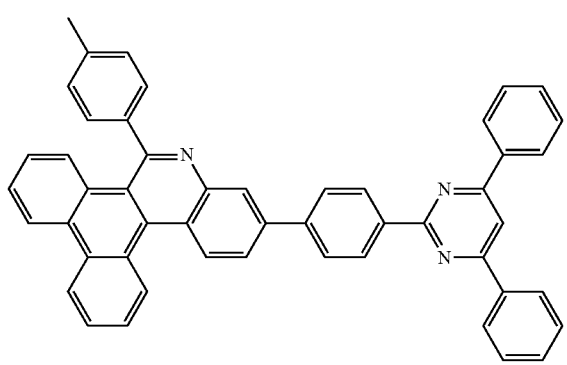

201

The driving voltage, luminance, efficiency (cd/A) and half-life of the organic light-emitting devices manufactured according to Examples 1 to 14 and Comparative Examples 1 and 2 were measured at a current density of 50 mA/cm$^2$. Results thereof are shown in Table 2 below.

TABLE 2

| | Material | Driving voltage (V) | Current density (mA/cm$^2$) | Luminance (cd/m$^2$) | Efficiency (cd/A) | Emission color | Half lifespan (hr @ 100 mA/cm$^2$) |
|---|---|---|---|---|---|---|---|
| Example1 | Compound 2 | 3.65 | 50 | 3,550 | 7.10 | blue | 700 hr |
| Example2 | Compound 12 | 3.25 | 50 | 3,790 | 7.58 | blue | 705 hr |
| Example3 | Compound 13 | 3.28 | 50 | 3,805 | 7.61 | blue | 717 hr |
| Example 4 | Compound 15 | 3.20 | 50 | 3,810 | 7.62 | blue | 753 hr |
| Example5 | Compound 17 | 3.21 | 50 | 3,830 | 7.66 | blue | 723 hr |
| Example6 | Compound 19 | 3.20 | 50 | 3,825 | 7.65 | blue | 735 hr |
| Example7 | Compound 22 | 3.36 | 50 | 3,760 | 7.52 | blue | 727 hr |
| Example8 | Compound 24 | 3.70 | 50 | 3,700 | 7.40 | blue | 712 hr |
| Example9 | Compound 29 | 3.29 | 50 | 3,800 | 7.60 | blue | 728 hr |
| Example10 | Compound 32 | 3.27 | 50 | 3,795 | 7.59 | blue | 720 hr |
| Example11 | Compound 48 | 3.25 | 50 | 3,810 | 7.62 | blue | 713 hr |
| Example12 | Compound 60 | 3.30 | 50 | 3,785 | 7.57 | blue | 709 hr |
| Example13 | Compound 72 | 3.35 | 50 | 3,780 | 7.56 | blue | 725 hr |
| Example14 | Compound 77 | 3.32 | 50 | 3,775 | 7.55 | blue | 716 hr |
| Comparative Example 1 | Compound 200 | 4.28 | 50 | 3,050 | 6.10 | blue | 485 hr |
| Comparative Example 2 | Compound 201 | 3.85 | 50 | 3,515 | 7.03 | blue | 572 hr |

Table 1 shows that, when used as an electron transport material, the compound according to embodiments shows a lower driving voltage, better I-V-L characteristics having higher efficiency and luminance, and better lifetime improvement effects than Compound 200 and Compound 201, which are known materials.

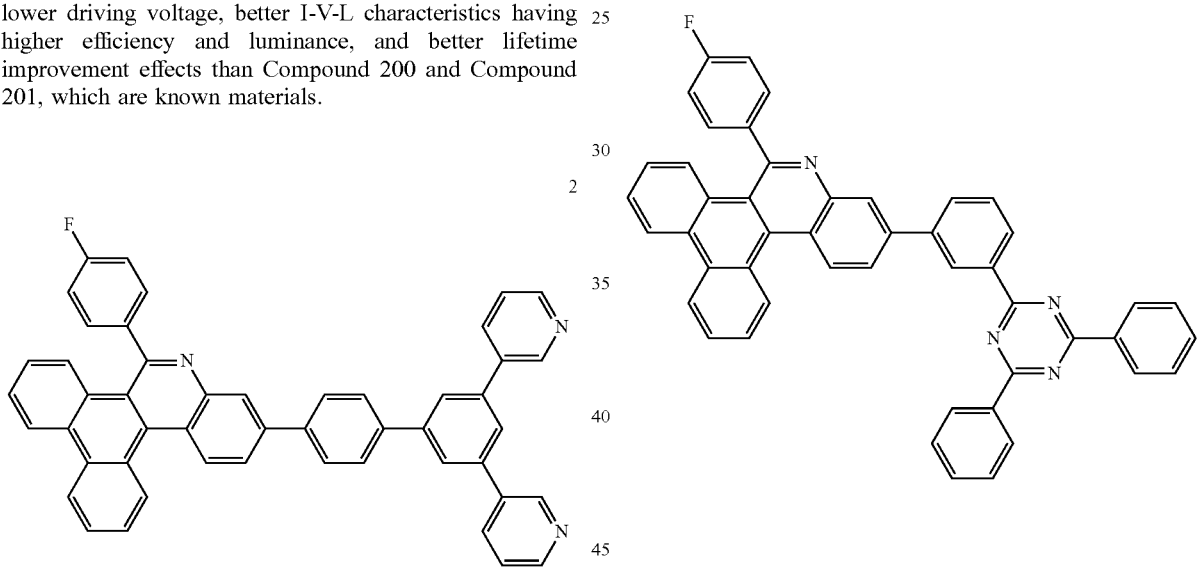

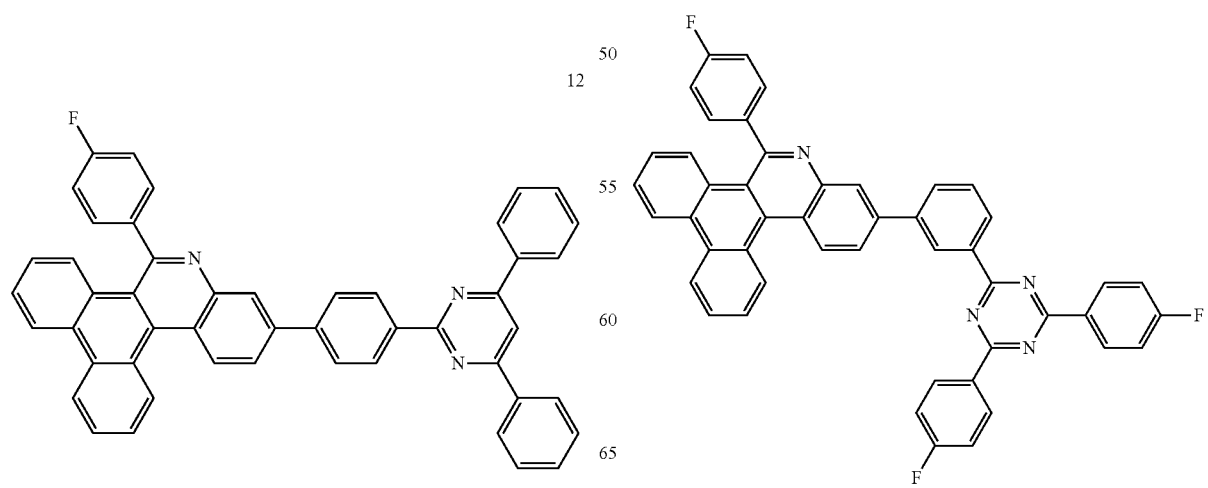

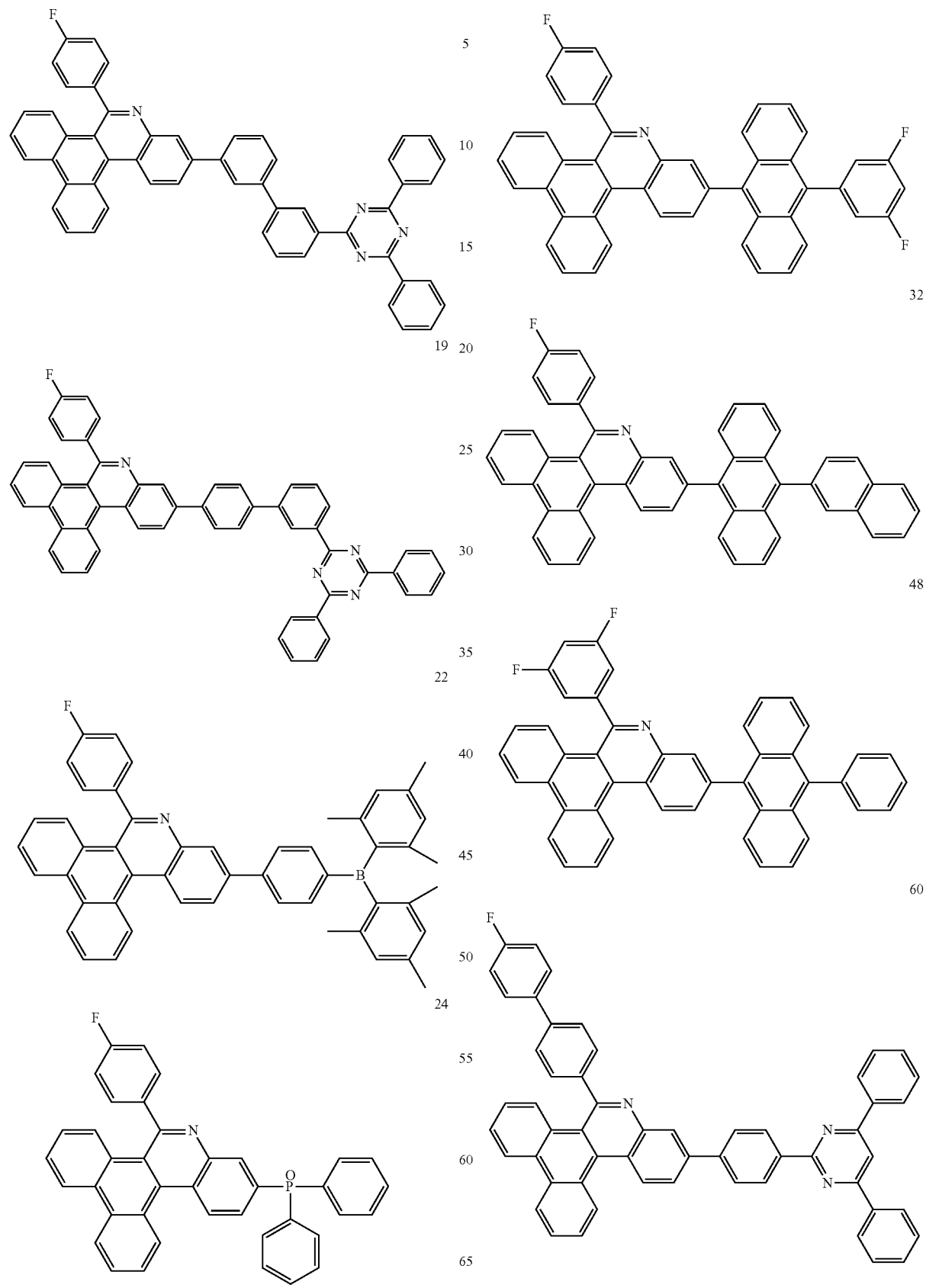

-continued

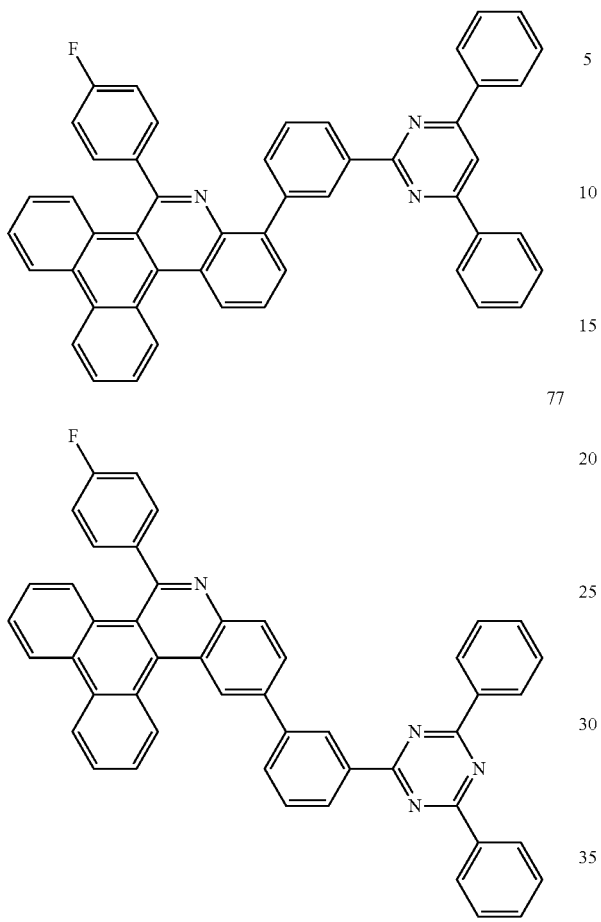

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:
1. An organic light-emitting device, comprising:
a first electrode;
a second electrode facing the first electrode; and
an organic layer between the first electrode and the second electrode, the organic layer including an emission layer, wherein
the first electrode is an anode,
the second electrode is a cathode,
the organic layer includes a hole transport region between the first electrode and the emission layer and an electron transport region between the emission layer and the second electrode, wherein
the hole transport region includes a hole injection layer, a hole transport layer, an emission auxiliary layer, an electron blocking layer, or any combination thereof, and
the electron transport region includes a buffer layer, a hole blocking layer, an electron control layer, an electron transport layer, an electron injection layer, or any combination thereof,
wherein the electron transport region includes an electron transport layer, and the electron transport layer includes at least one condensed cyclic compound, and
wherein the electron transport region includes an emission auxiliary layer, and the at least one condensed cyclic compound is included in the emission auxiliary layer, and
wherein the at least one condensed cyclic compound is represented by Formula 1:

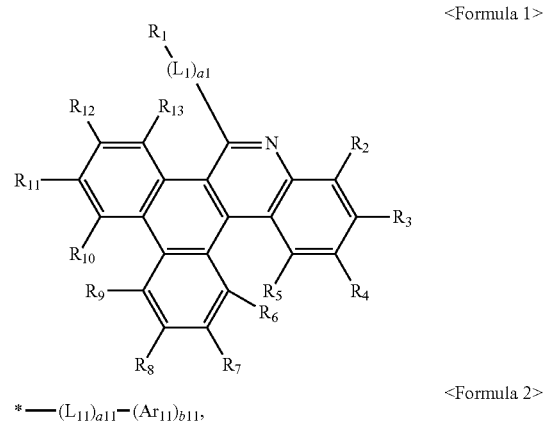

$$*-(L_{11})_{a11}-(Ar_{11})_{b11},$$ <Formula 2> wherein, in Formulae 1 and 2,
$L_1$ and $L_{11}$ are each independently a substituted or unsubstituted $C_3$-$C_{60}$ carbocyclic group or a substituted or unsubstituted $C_1$-$C_{60}$ heterocyclic group,
a1 and a11 are each independently an integer from 0 to 3,
$Ar_{11}$ is selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group(substituted or unsubstituted monovalent non-aromatic condensed polycyclic group), a substituted or unsubstituted monovalent non-aromatic condensed heteropolycyclic group(substituted or unsubstituted monovalent non-aromatic condensed heteropolycyclic group), $-Si(Q_1)(Q_2)(Q_3)$, $-N(Q_1)(Q_2)$, $-B(Q_1)(Q_2)$, $-C(=O)(Q_1)$, $-S(=O)_2(Q_1)$, and $-P(=O)(Q_1)(Q_2)$,
b11 is an integer from 1 to 4,
$R_1$ is selected from a $C_6$-$C_{60}$ aryl group, a $C_1$-$C_{60}$ heteroaryl group, a monovalent non-aromatic condensed polycyclic group, and a monovalent non-aromatic condensed heteropolycyclic group, each substituted with at least one selected from —F, —Cl, —Br, —I, a cyano group, and a nitro group, $R_2$ to $R_{13}$ are each independently selected from a group represented by Formula 2, hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, and a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —S(=O)$_2$($Q_1$), and —P(=O)($Q_1$)($Q_2$), wherein at least one selected from $R_2$ to $R_{13}$ is a group represented by Formula 2, at least one substituent of the substituted $C_3$-$C_{60}$ carbocyclic group, substituted $C_1$-$C_{60}$ heterocyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_2$-$C_{60}$ heteroaryl group, substituted monovalent non-aromatic condensed polycyclic group, and substituted monovalent non-aromatic condensed heteropolycyclic group is selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$) and —P(=O)($Q_{31}$)($Q_{32}$), $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_6$-$C_{60}$ aryl group substituted with at least one selected from —F, —Cl, —Br, —I, and a cyano group, and indicates a binding site to a neighboring atom.

2. The organic light-emitting device as claimed in claim 1, wherein $L_1$ and $L_{11}$ are each independently selected from:

a benzene group, a pentalene group, an indene group, a naphthalene group, an azulene group, a heptalene group, an indacene group, an acenaphthalene group, a fluorene group, a spiro-bifluorene group, a spiro-benzofluorene-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pyrrole group, a thiophene group, a furan group, a silole group, an imidazole group, a pyrazole group, a thiazole group, an isothiazole group, an oxazole group, an isoxazole group, a pyridine group, a pyrazine group, a pyrimidine group, a pyridazine group, a triazine group, a benzofuran group, a benzothiophene group, a benzosilole group, a dibenzofuran group, a dibenzothiophene group, a dibenzosilole group, a carbazole group, a quinoline group, an isoquinoline group, a benzocarbazole group, a dibenzocarbazole group, a benzimidazole group, an imidazopyridine group, and an imidazopyrimidine group; and a benzene group, a pentalene group, an indene group, a naphthalene group, an azulene group, a heptalene group, an indacene group, an acenaphthalene group, a fluorene group, a spiro-bifluorene group, a spiro-benzofluorene-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pyrrole group, a thiophene group, a furan group, a silole group, an imidazole group, a pyrazole group, a thiazole group, an isothiazole group, an oxazole group, an isoxazole group, a pyridine group, a pyrazine group, a pyrimidine group, a pyridazine group, a triazine group, a benzofuran group, a benzothiophene group, a benzosilole group, a dibenzofuran group, a dibenzothiophene group, a dibenzosilole group, a carbazole group, a quinoline group, an isoquinoline group, a benzocarbazole group, a dibenzocarbazole group, a benzimidazole group, an imidazopyridine group, and an imidazopyrimidine group, each substituted with at least one selected from deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, a carbazolyl group, a pyridinyl group, a pyrazinyl group, a pyrimidinyl group, a pyridazinyl group, a quinolinyl group, an isoquinolinyl group, a benzofuranyl group, a benzothiophenyl group, a dibenzofuranyl group, a dibenzothiophenyl group, a benzocarbazolyl group, a dibenzocarbazolyl group, —Si($Q_{31}$)($Q_{32}$)($Q_{33}$), —N($Q_{31}$)($Q_{32}$), and —B($Q_{31}$)($Q_{32}$), wherein $Q_1$ and $Q_{31}$ to $Q_{33}$ are each independently selected from a $C_1$-$C_{20}$ alkyl group, a $C_1$-$C_{20}$ alkoxy group, a phenyl group, a biphenyl group, a terphenyl group, a naphthyl group, and a pyridinyl group.

3. The organic light-emitting device as claimed in claim 1, wherein $L_1$ and $L_{11}$ are each independently a group represented by one of Formulae 3-1 to 3-33:

3-1
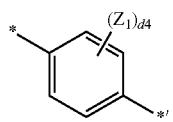

3-2
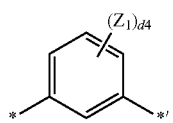

3-3
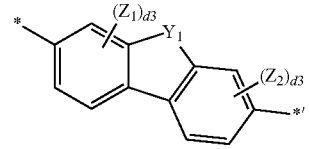

3-4
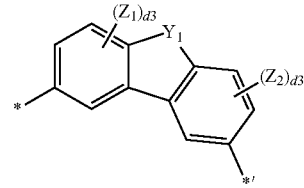

3-5
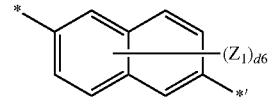

3-6
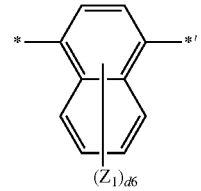

3-7
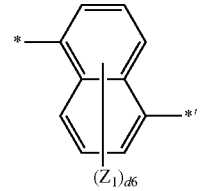

3-8
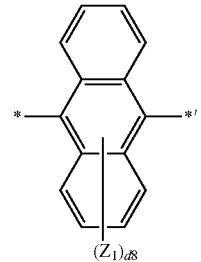

3-9
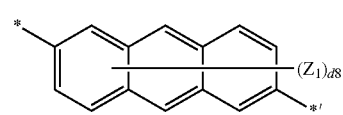

3-10
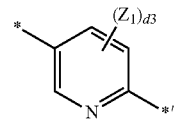

3-11
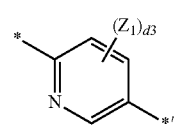

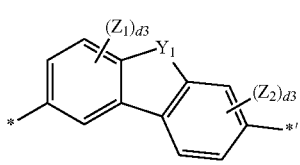

3-31

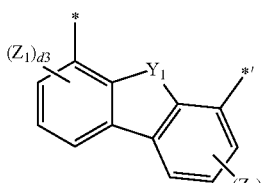

3-32

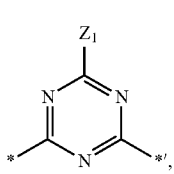

3-33 wherein, in Formulae 3-1 to 3-33, $Y_1$ is O, S, $C(Z_3)(Z_4)$, $N(Z_5)$, or $Si(Z_6)(Z_7)$, $Z_1$ to $Z_7$ are each independently selected from hydrogen, deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a benzofuranyl group, a benzothiophenyl group, a benzosilolyl group, a dibenzofuranyl group, a dibenzothiophenyl group, a dibenzosilolyl group, a benzocarbazolyl group, a dibenzocarbazolyl group, and —$Si(Q_{31})(Q_{32})(Q_{33})$; and a phenyl group substituted with at least one selected from —F, —Cl, —Br, —I, and a cyano group, wherein $Q_{31}$ to $Q_{33}$ are each independently selected from a $C_1$-$C_{20}$ alkyl group, a $C_1$-$C_{20}$ alkoxy group, a phenyl group, a biphenyl group, a terphenyl group, a naphthyl group, and a pyridinyl group, d2 is an integer from 0 to 2, d3 is an integer from 0 to 3, d4 is an integer from 0 to 4, d6 is an integer from 0 to 6, d8 is an integer from 0 to 8, and and *' each indicate a binding site to a neighboring atom.

4. The organic light-emitting device as claimed in claim 1, wherein $Ar_{11}$ is selected from:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyridinyl group, a pyrazinyl group, a pyrimidinyl group, a pyridazinyl group, a triazinyl group, a thiophenyl group, a furanyl group, a quinolinyl group, an isoquinolinyl group, a carbazolyl group, a benzofuranyl group, a benzothiophenyl group, a dibenzofuranyl group, a dibenzothiophenyl group, a benzonaphthofuranyl group, a dinaphthofuranyl group, a benzocarbazolyl group, a dibenzocarbazolyl group, a dibenzosilolyl group, a benzonaphtho silolyl group, a dinaphtho silolyl group, a benzimidazolyl group, a phenanthrolinyl group, and an imidazopyridinyl group;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyridinyl group, a pyrazinyl group, a pyrimidinyl group, a pyridazinyl group, a triazinyl group, a thiophenyl group, a furanyl group, a quinolinyl group, an isoquinolinyl group, a carbazolyl group, a benzofuranyl group, a benzothiophenyl group, a dibenzofuranyl group, a dibenzothiophenyl group, a benzonaphthofuranyl group, a dinaphthofuranyl group, a benzocarbazolyl group, a dibenzocarbazolyl group, a dibenzosilolyl group, a benzonaphtho silolyl group, a dinaphtho silolyl group, a benzimidazolyl group, a phenanthrolinyl group, and an imidazopyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyridinyl group, a pyrazinyl group, a pyrimidinyl group, a pyridazinyl group, a triazinyl group, a thiophenyl group, a furanyl group, a quinolinyl group, an isoquinolinyl group, a carbazolyl group, a benzofuranyl group, a benzothiophenyl group, a dibenzofuranyl group, a dibenzothiophenyl group, a benzocarbazolyl group, a dibenzocarbazolyl group, and a dibenzosilolyl group, —$N(Q_{31})(Q_{32})$ and —$Si(Q_{31})(Q_{32})(Q_{33})$; and —$N(Q_1)(Q_2)$, —$B(Q_1)(Q_2)$, —$S(=O)_2(Q_1)$, and —$P(=O)(Q_1)(Q_2)$, Q₁, Q₂ and Q₃₁ to Q₃₃ are each independently selected from a $C_1$-$C_{20}$ alkyl group, a $C_1$-$C_{20}$ alkoxy group, a phenyl group, a biphenyl group, a terphenyl group, a naphthyl group, and a pyridinyl group; and a phenyl group substituted with at least one selected from —F, —Cl, —Br, —I, a cyano group, and a $C_1$-$C_{20}$ alkyl group.

5. The organic light-emitting device as claimed in claim 4, wherein $Ar_{11}$ is selected from:

a phenyl group, a biphenyl group, a naphthyl group, a fluorenyl group, a pyridinyl group, a pyrimidinyl group, a triazinyl group, a quinolinyl group, a carbazolyl group, and a phenanthrolinyl group;

a phenyl group, a biphenyl group, a naphthyl group, a fluorenyl group, a pyridinyl group, a pyrimidinyl group, a triazinyl group, a quinolinyl group, a carbazolyl group, and a phenanthrolinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a naphthyl group, a fluorenyl group, a pyridinyl group, a pyrimidinyl group, a triazinyl group, a quinolinyl group, a carbazolyl group, a phenanthrolinyl group, —N(Q₃₁)(Q₃₂), and —Si(Q₃₁)(Q₃₂)(Q₃₃); and —N(Q₁)(Q₂), —B(Q₁)(Q₂), —S(=O)₂(Q₁), and —P(=O)(Q₁)(Q₂);

Q₁, Q₂, and Q₃₁ to Q₃₃ are each independently selected from a $C_1$-$C_{20}$ alkyl group, a $C_1$-$C_{20}$ alkoxy group, a phenyl group, a biphenyl group, a terphenyl group, a naphthyl group, and a pyridinyl group, and a phenyl group substituted with at least one selected from —F, —Cl, —Br, —I, a cyano group, and a $C_1$-$C_{20}$ alkyl group.

6. The organic light-emitting device as claimed in claim 1, wherein $Ar_{11}$ is selected from a group represented by one of Formulae 5-1 to 5-47, —N(Q₁)(Q₂), —B(Q₁)(Q₂), —S(=O)₂(Q₁), and —P(=O)(Q₁)(Q₂):

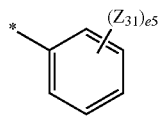

5-1

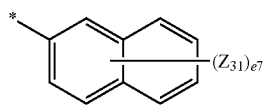

5-2

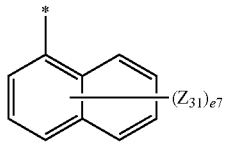

5-3

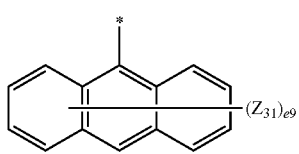

5-4

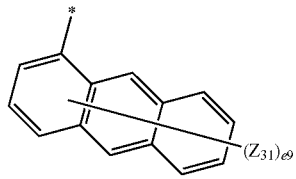

5-5

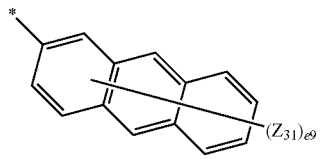

5-6

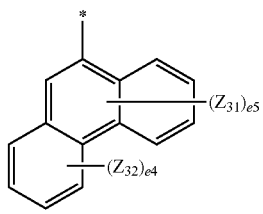

5-7

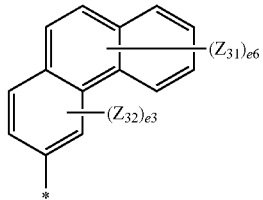

5-8

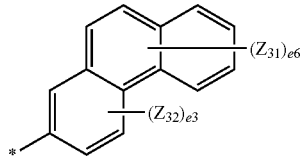

5-9

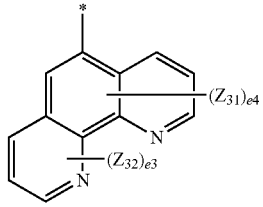

5-10

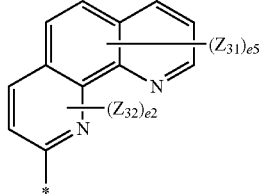

5-11

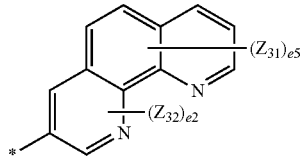

5-12

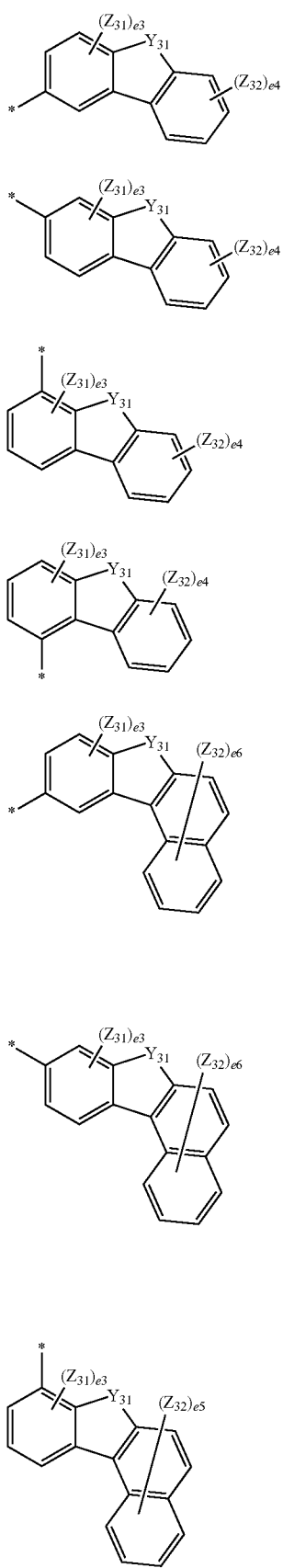

-continued 5-28 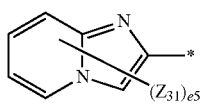

5-29 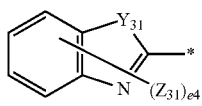

5-30 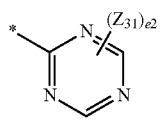

5-31 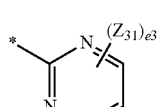

5-32 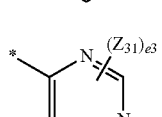

5-33 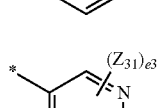

5-34 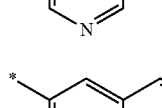

5-35 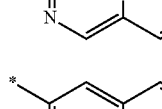

5-36 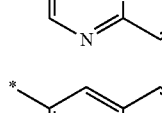

5-37 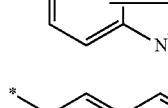

5-38 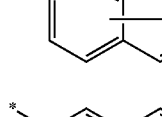

5-39 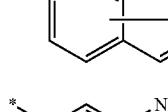

5-40 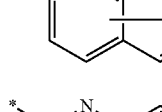

5-41 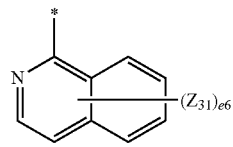

5-42 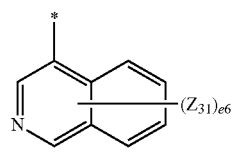

5-43 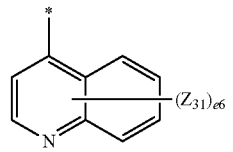

5-44 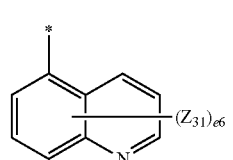

5-45 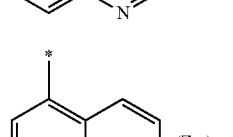

5-46 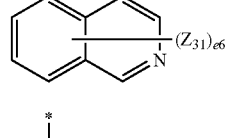

5-47 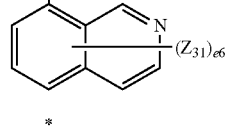

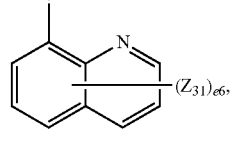

wherein, in Formulae 5-1 to 5-47, $Y_{31}$ is O, S, $C(Z_{33})(Z_{34})$, $N(Z_{35})$, or $Si(Z_{36})(Z_{37})$, $Z_{31}$ to $Z_{37}$ are each independently selected from hydrogen, deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, a silolyl group, a pyridinyl group, an indolyl group, an isoindolyl group, a benzofuranyl group, a benzothiophenyl group, a benzosilolyl group, a dibenzofuranyl group, a dibenzothiophenyl group, a dibenzosilolyl group, a carbazolyl group, a benzocarbazolyl group, a dibenzocarbazolyl group, and —Si($Q_{31}$)($Q_{32}$)($Q_{33}$); and a phenyl group substituted with at least one selected from —F, —Cl, —Br, —I, and a cyano group, $Q_1$, $Q_2$ and $Q_{31}$ to $Q_{33}$ are each independently selected from a $C_1$-$C_{20}$ alkyl group, a $C_1$-$C_{20}$ alkoxy group, a phenyl group, a biphenyl group, a terphenyl group, a naphthyl group, and a pyridinyl group, and a phenyl group substituted with at least one selected from —F, —Cl, —Br, —I, a cyano group, and a $C_1$-$C_{20}$ alkyl group, e2 is an integer from 0 to 2, e3 is an integer from 0 to 3, e4 is an integer from 0 to 4, e5 is an integer from 0 to 5, e6 is an integer from 0 to 6, e7 is an integer from 0 to 7, e9 is an integer from 0 to 9, and \* indicates a binding site to a neighboring atom.

7. The organic light-emitting device as claimed in claim 1, wherein $Ar_{11}$ is selected from a group represented by one of Formulae 6-1 to 6-62 and a group represented by one of Formulae 10-1 to 10-20:

6-1
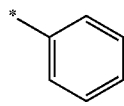

6-2
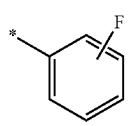

6-3
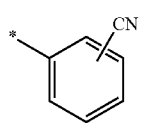

6-4
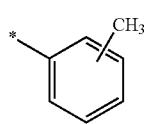

6-5
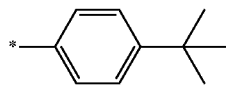

6-6
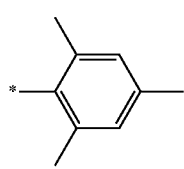

6-7
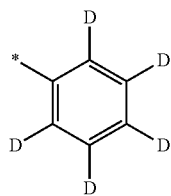

6-8

6-9

6-10
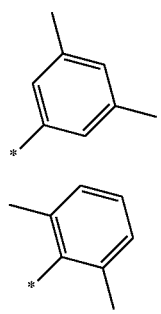

6-11
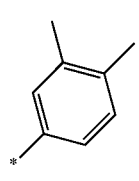

6-12
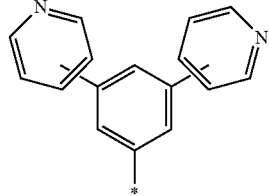

6-13
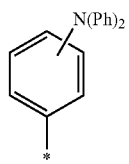

6-14
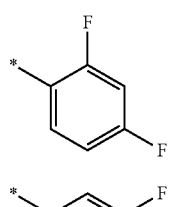

6-15
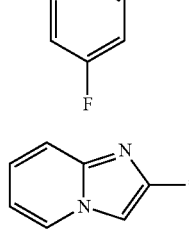

6-16
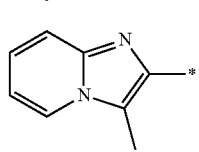

6-17 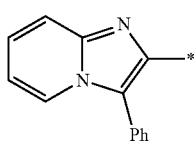
6-18 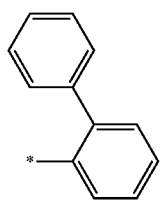
6-19 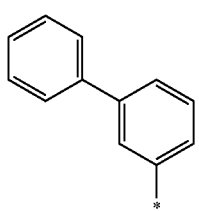
6-20 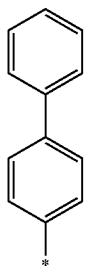
6-21 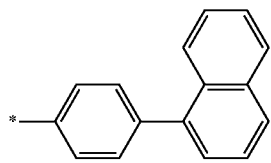
6-22 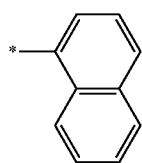
6-23 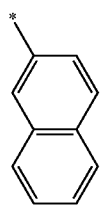
6-24 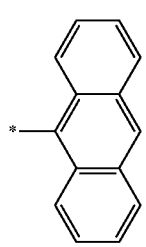
6-25 
6-26 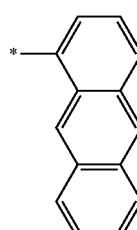
6-27 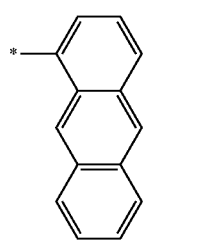
6-28 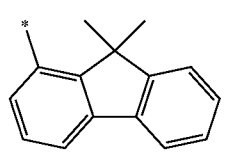
6-29 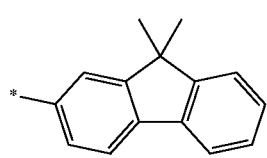
6-30 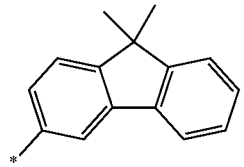
6-31 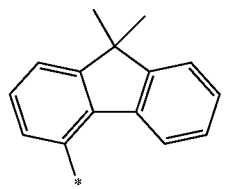
6-32 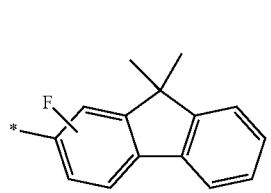

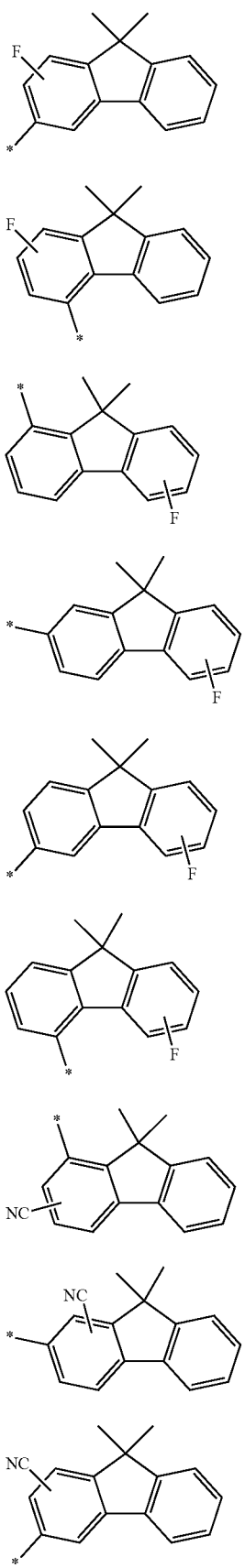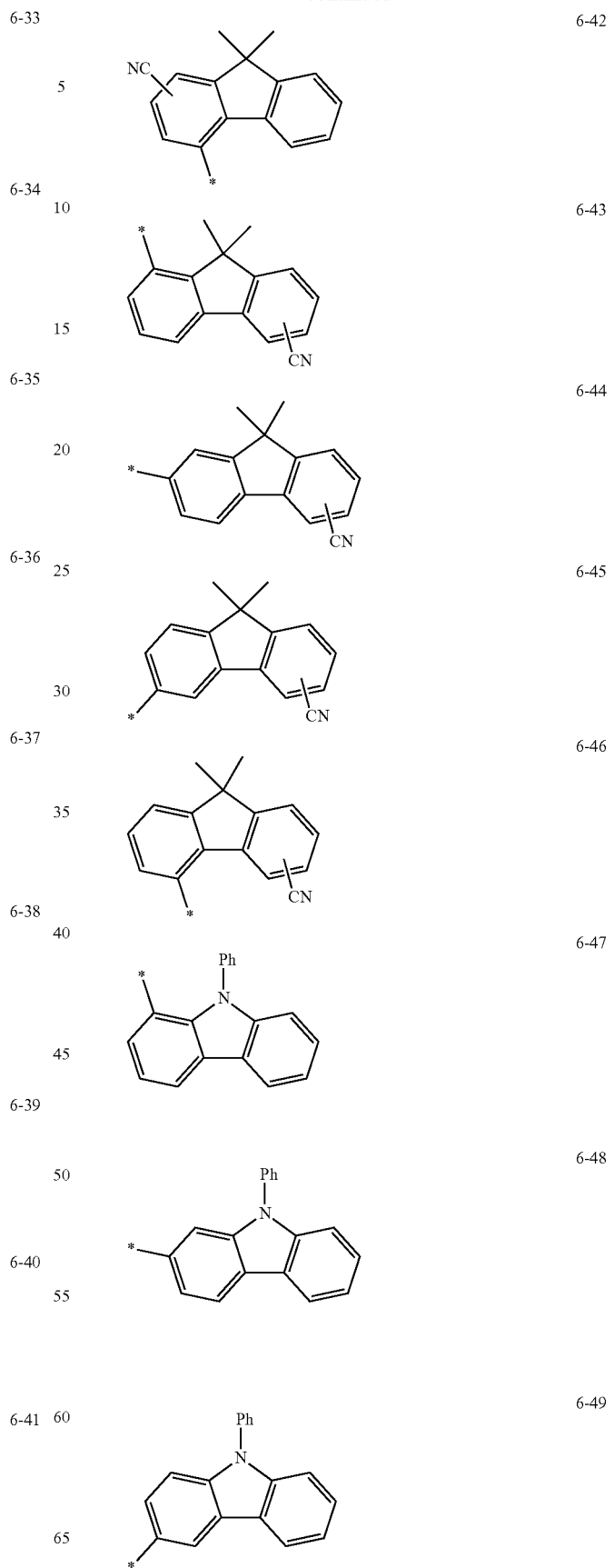

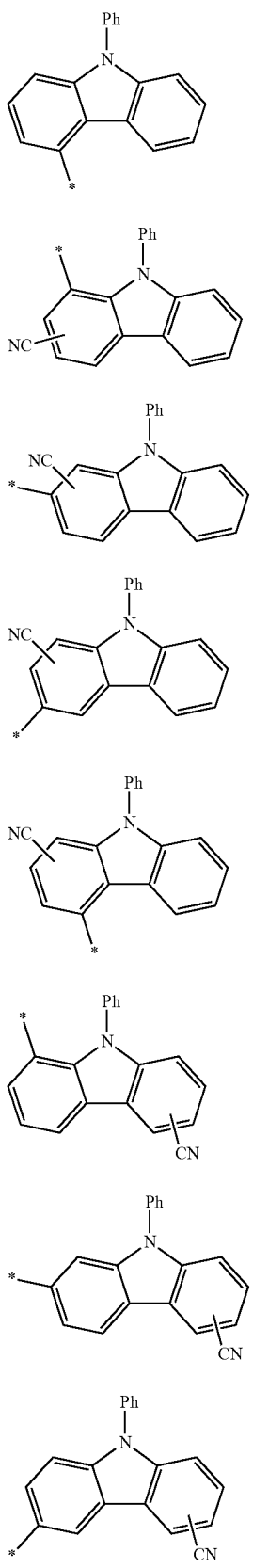
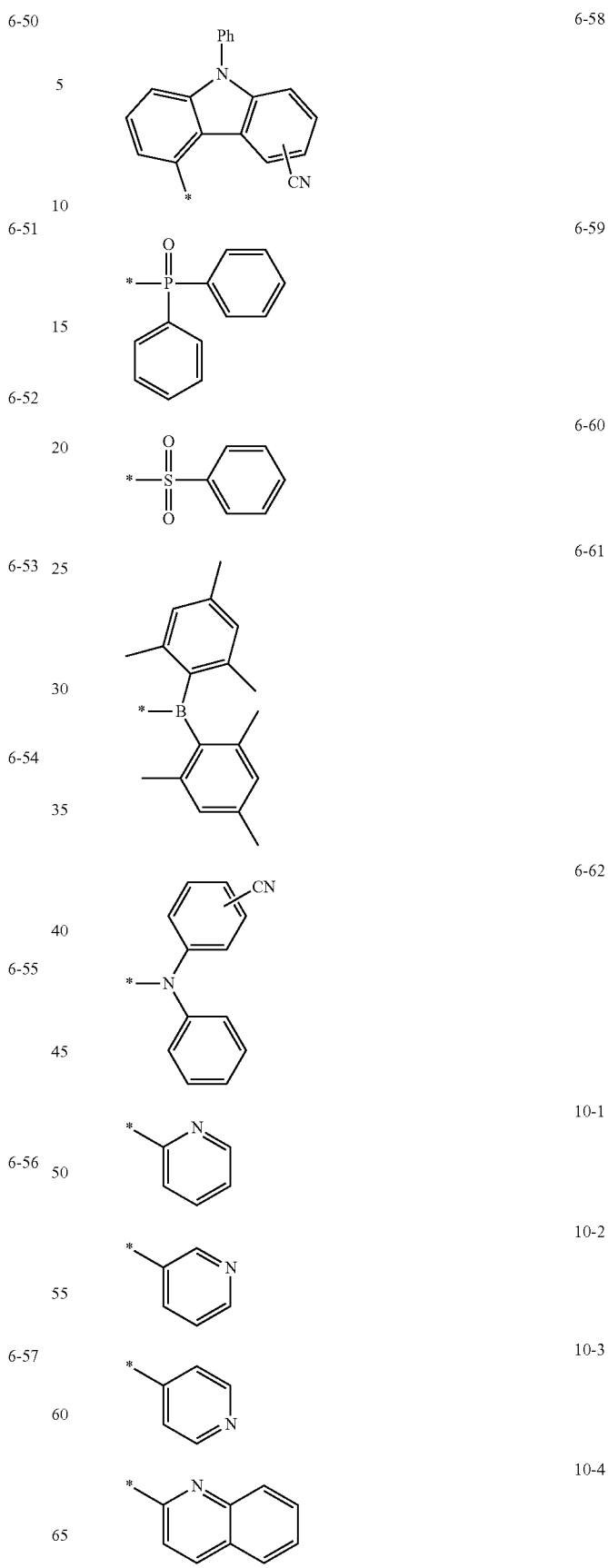

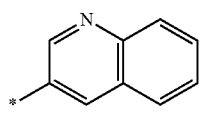
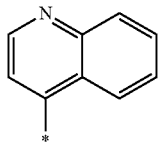
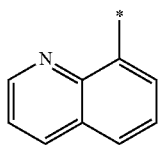
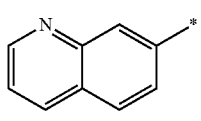
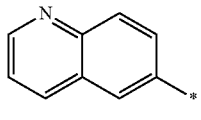
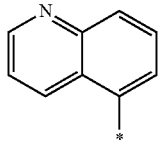
10-11
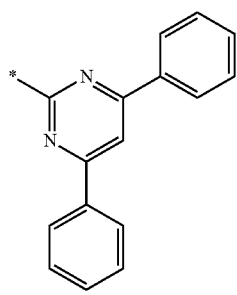
10-12
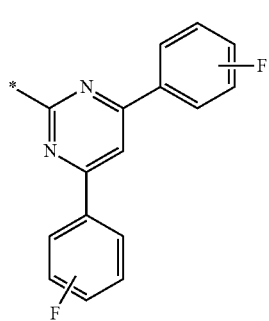
10-5
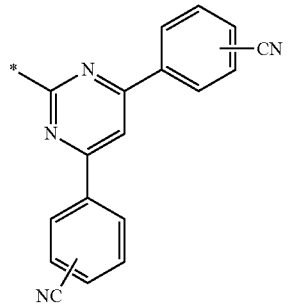
10-6
10-7
10-8
10-9
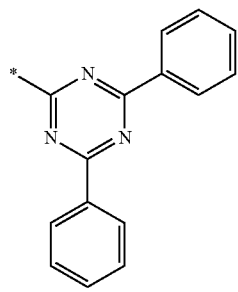
10-10
10-13
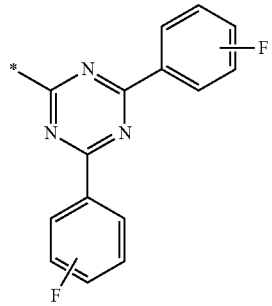
10-14
10-15
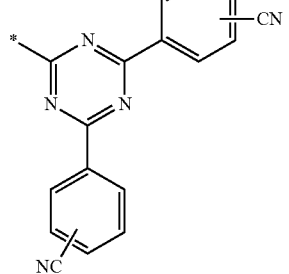
10-16
10-17
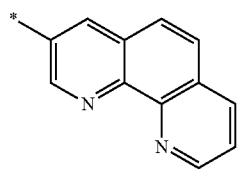
10-18
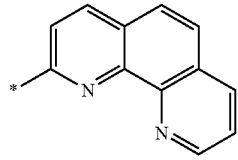

-continued
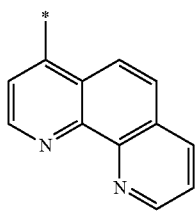
10-19
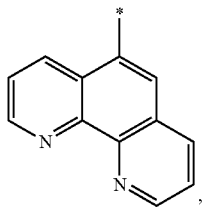
10-20
wherein, in Formulae 6-1 to 6-62 and 10-1 to 10-20, Ph indicates a phenyl group and * indicates a binding site to a neighboring atom.
8. The organic light-emitting device as claimed in claim 1, wherein $R_1$ is a group represented by one of Formulae 4-1 to 4-6 and 4-10 to 4-23:
4-1
4-2
4-3
4-4
4-5
4-6
-continued
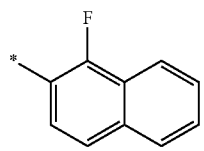
4-10
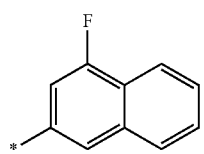
4-11
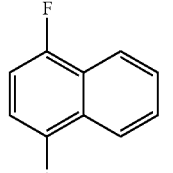
4-12
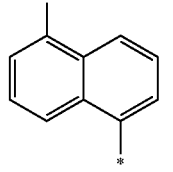
4-13
4-14
4-15
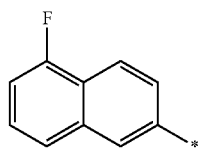
4-16
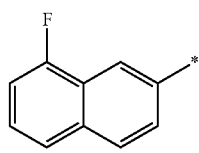
4-17
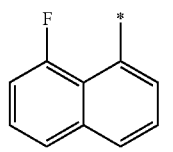
4-18
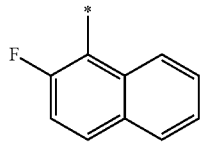
4-19
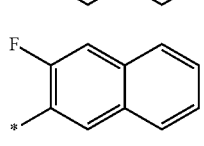
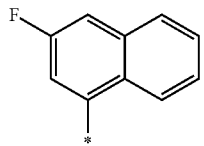

-continued 4-20
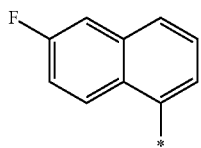

4-21
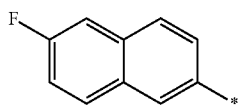

4-22
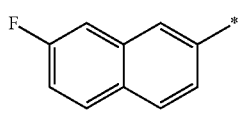

4-23
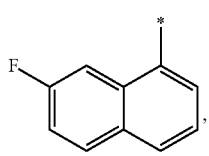

wherein, * in Formulae 4-1 to 4-6 and 4-10 to 4-23 indicates a binding site to a neighboring atom.

9. The organic light-emitting device as claimed in claim 1, wherein at least one selected from $R_2$ to $R_5$ is a group represented by Formula 2.

10. The organic light-emitting device as claimed in claim 1, wherein $R_6$ to $R_{13}$ are each hydrogen.

11. The organic light-emitting device as claimed in claim 1, wherein:
   i) $R_2$ is a group represented by Formula 2, and $R_3$ to $R_{13}$ are each hydrogen; or
   ii) $R_3$ is a group represented by Formula 2, and $R_2$ and $R_4$ to $R_{13}$ are each hydrogen; or
   iii) $R_4$ is a group represented by Formula 2, and $R_2$, $R_3$, and $R_5$ to $R_{13}$ are each hydrogen.

12. The organic light-emitting device as claimed in claim 1, wherein the condensed cyclic compound is selected from Compounds 1 to 48 and 57 to 77:

1
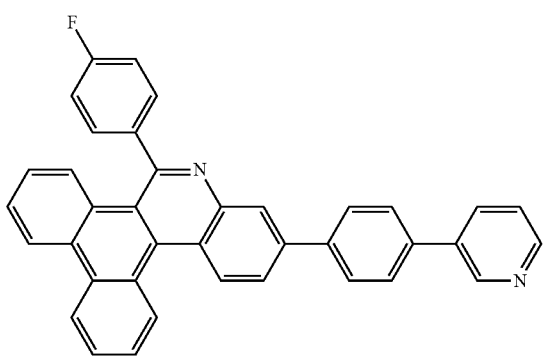

2
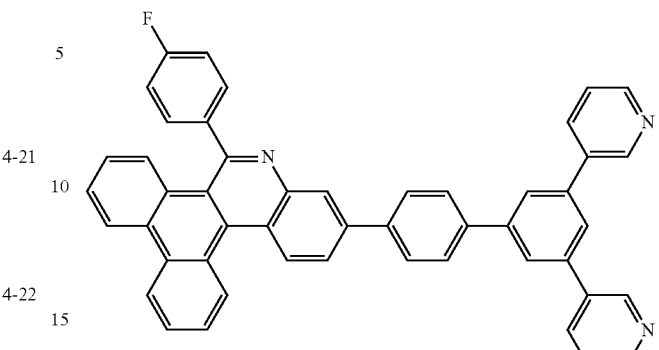

3
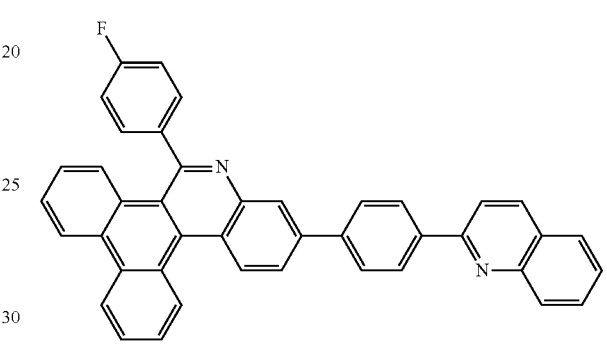

4
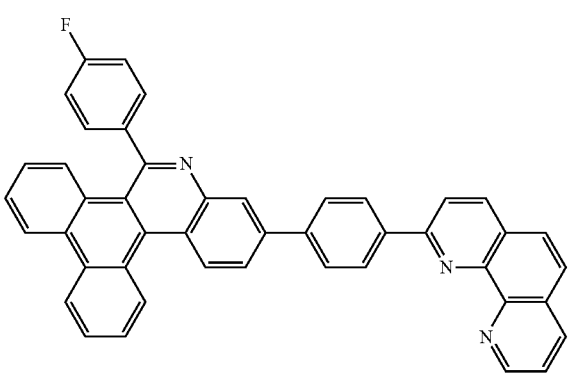

5
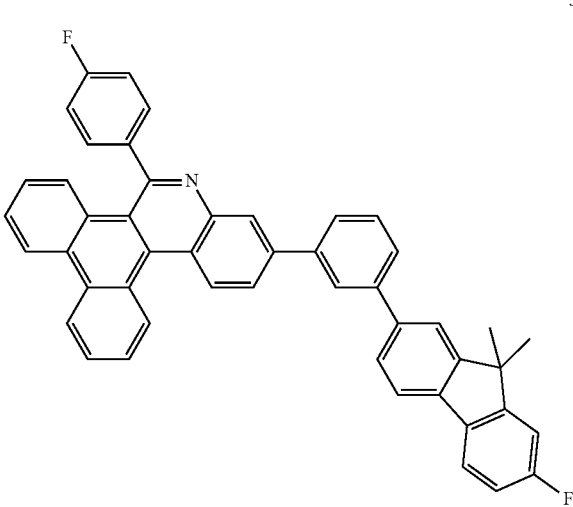

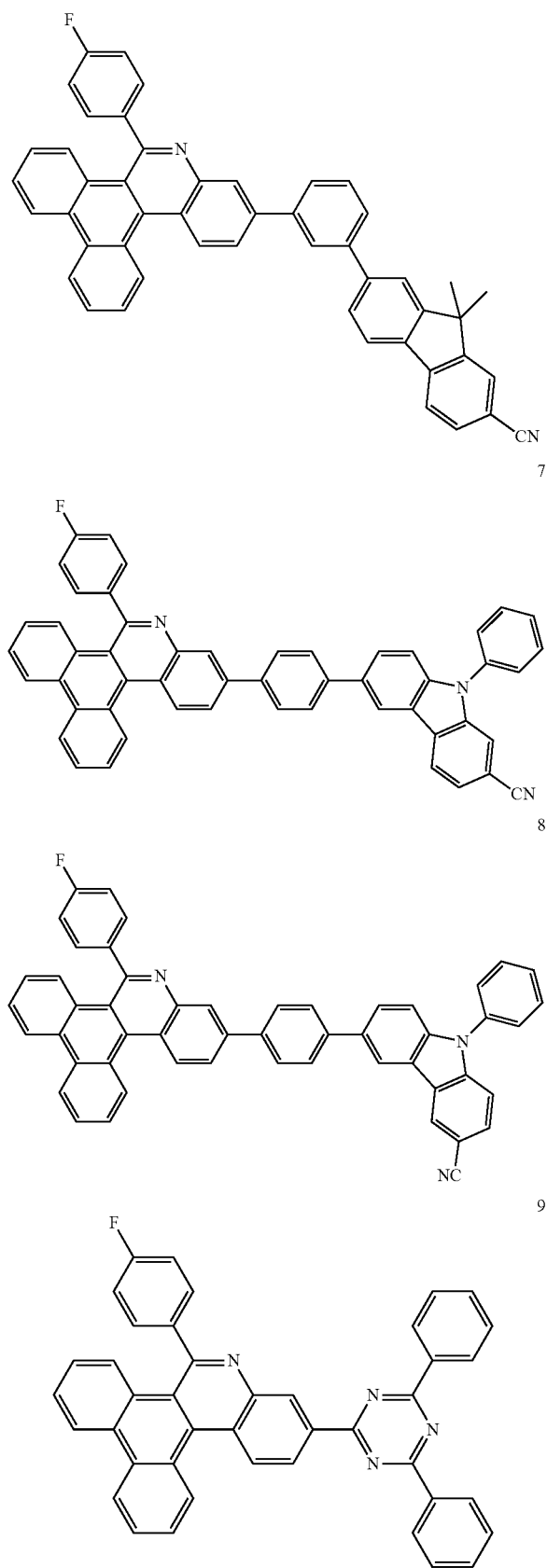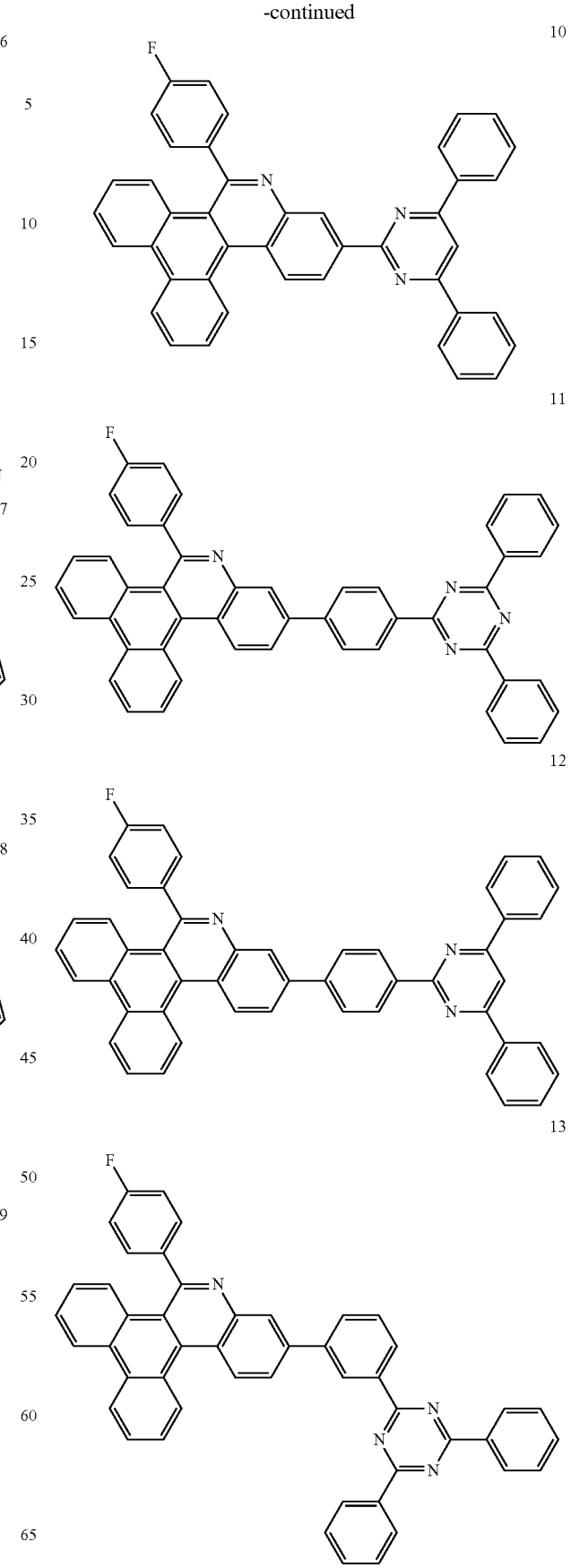

14
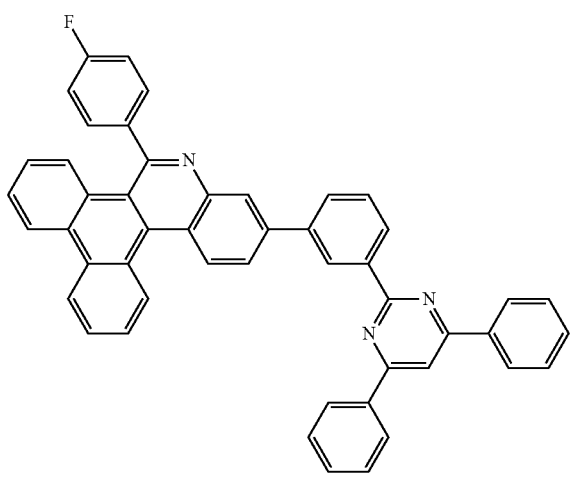
15
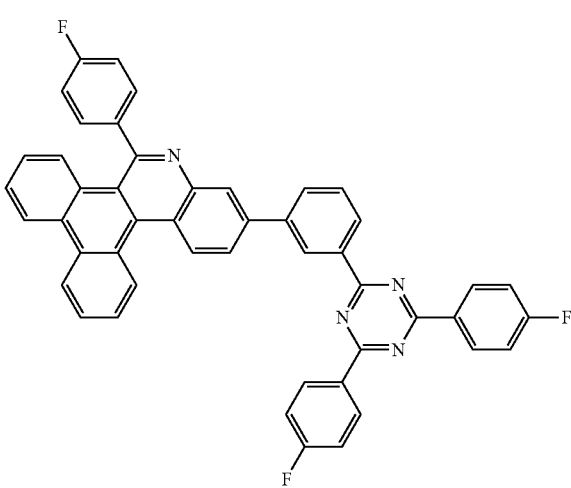
16
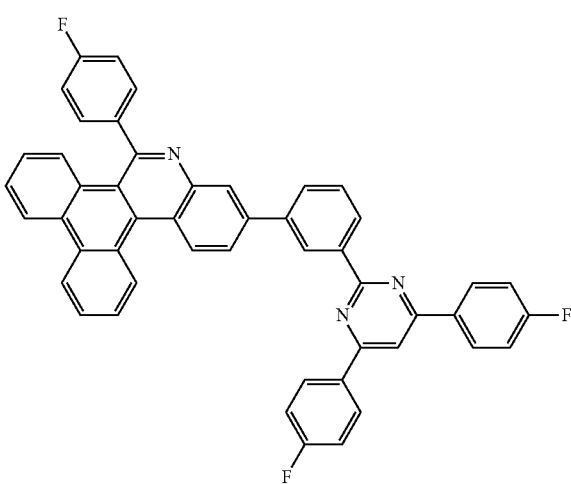
17
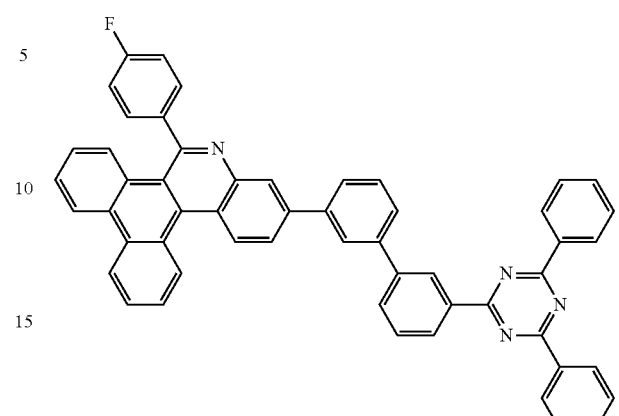
18
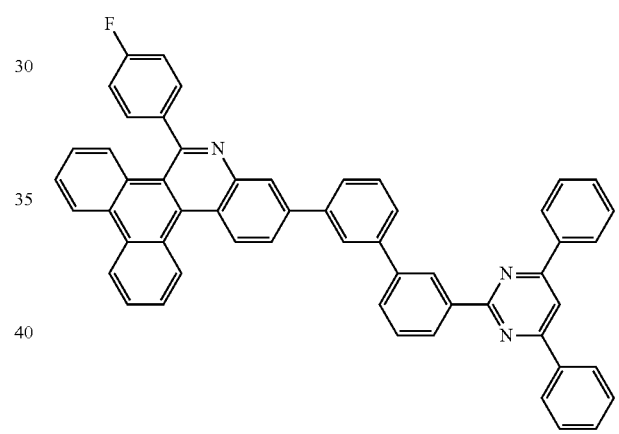
19
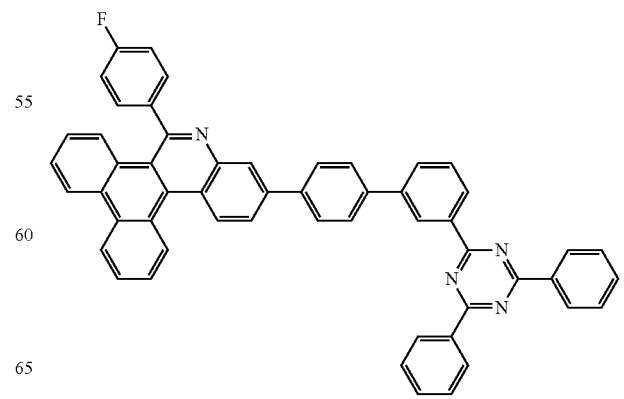

205
-continued
20
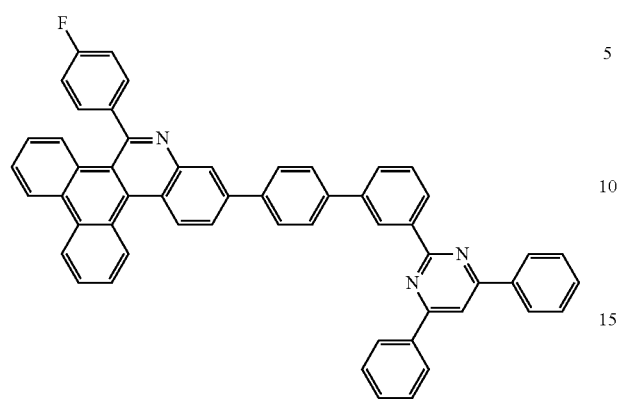
21
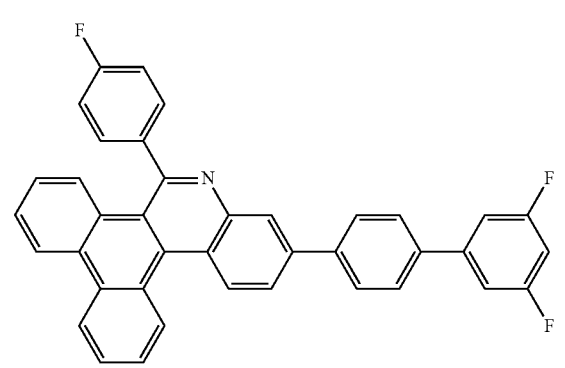
22
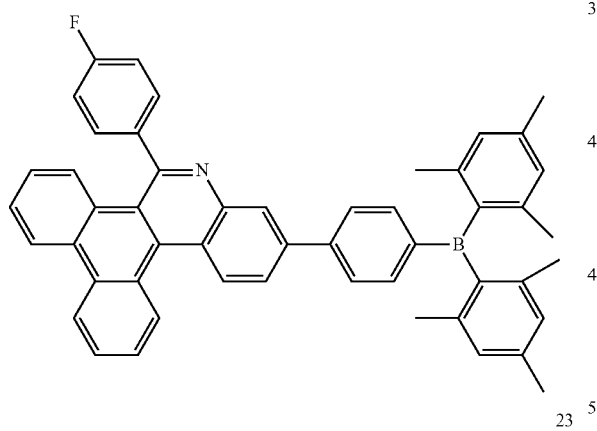
23
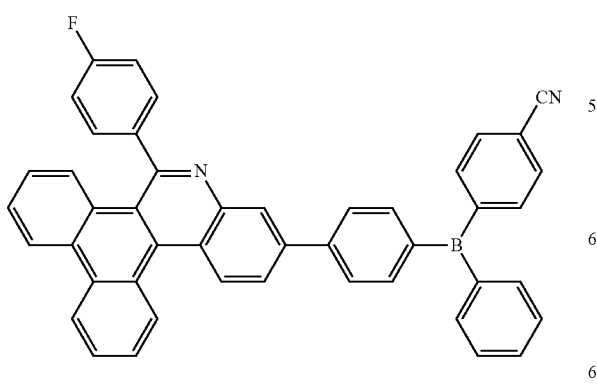
206
-continued
24
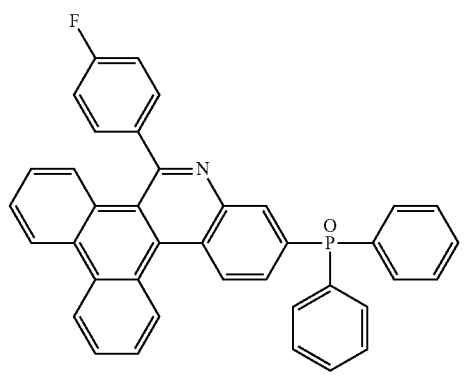
25
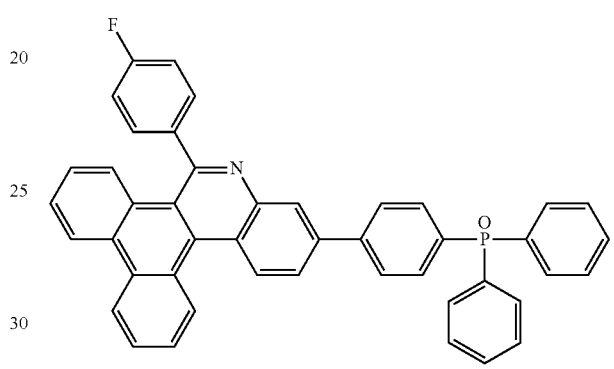
26
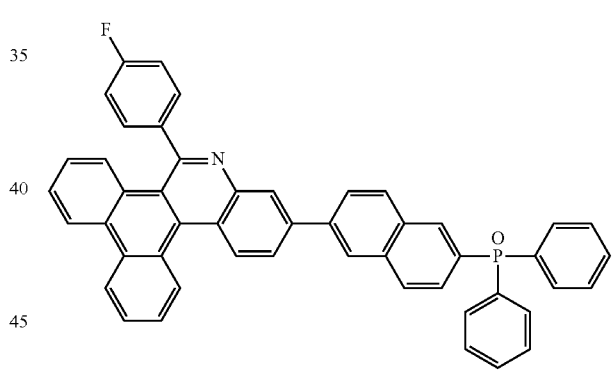
27
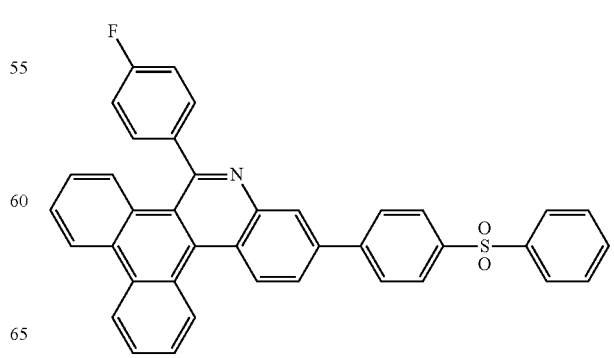

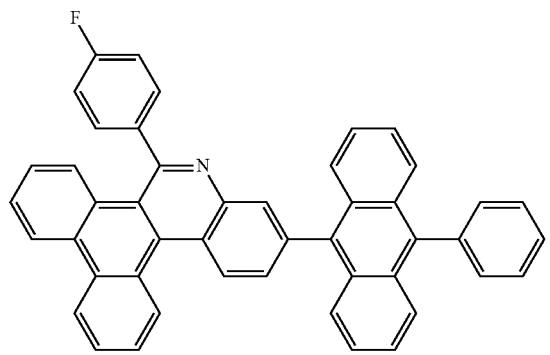
28
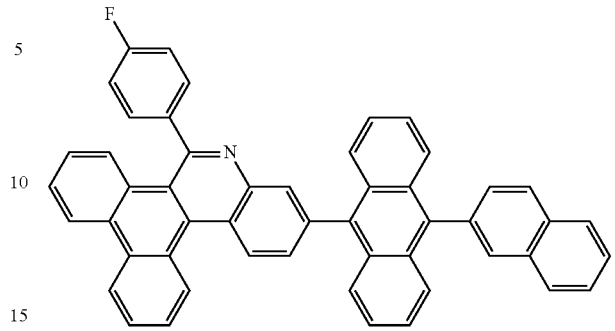
32
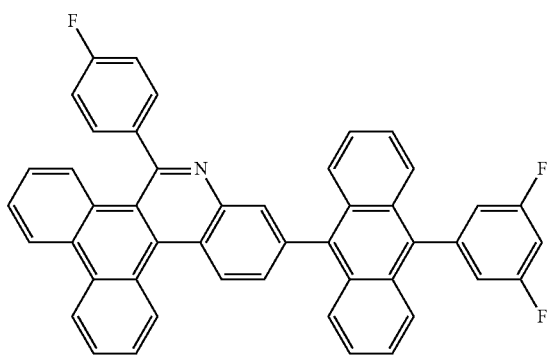
29
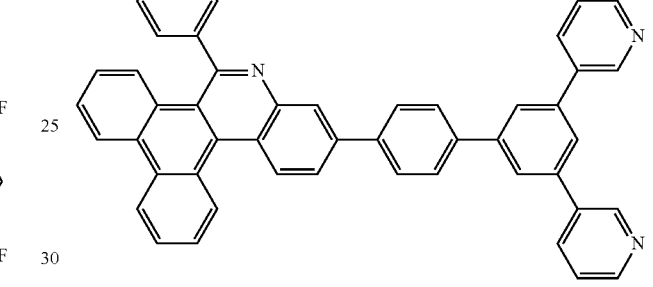
33
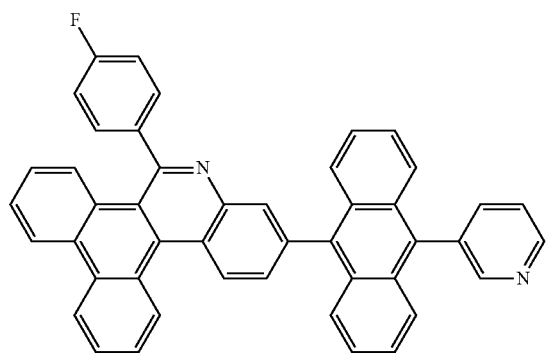
30
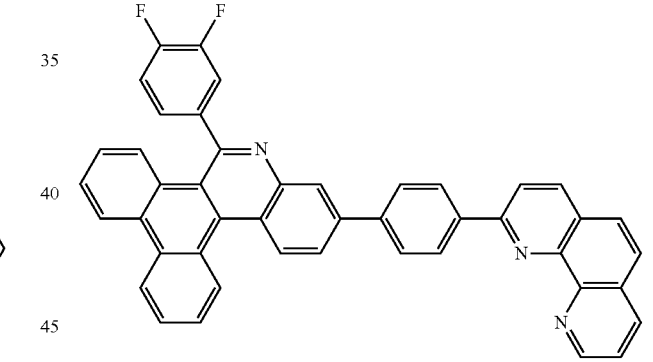
34
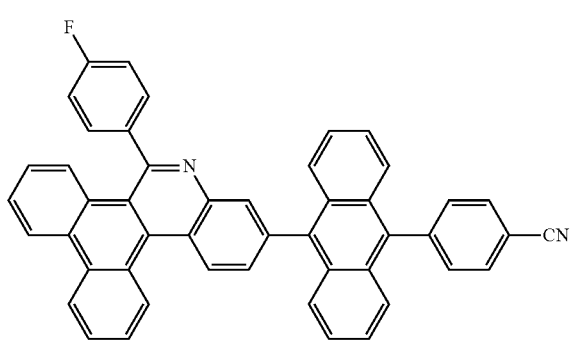
31
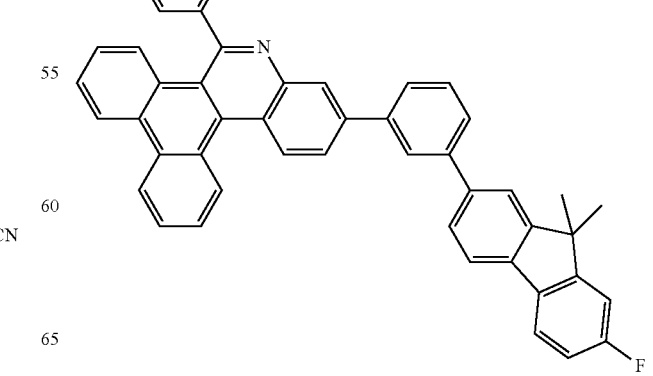
35

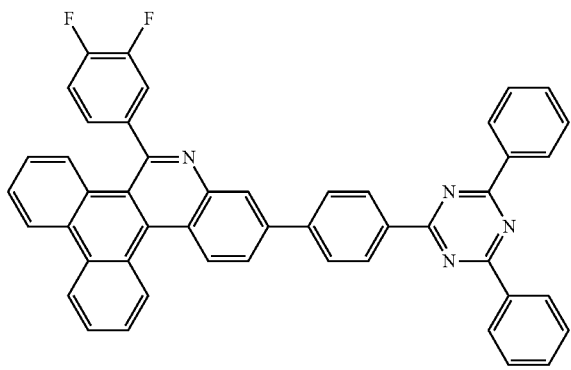
36
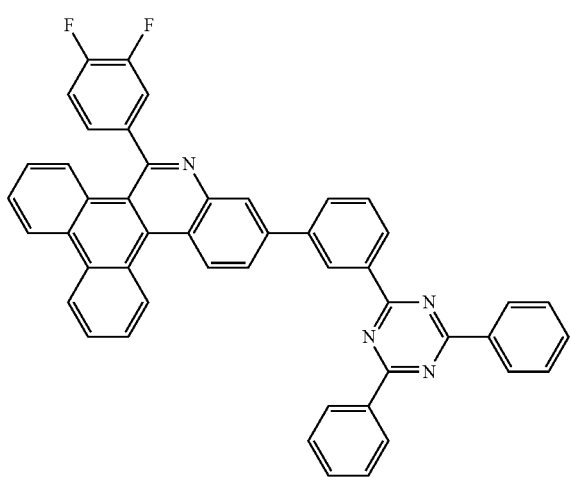
37
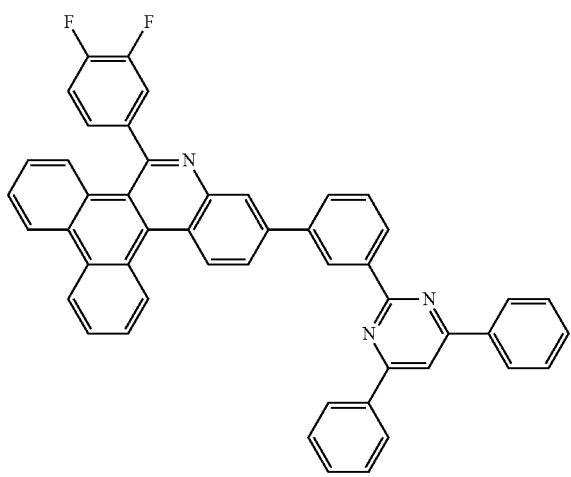
38
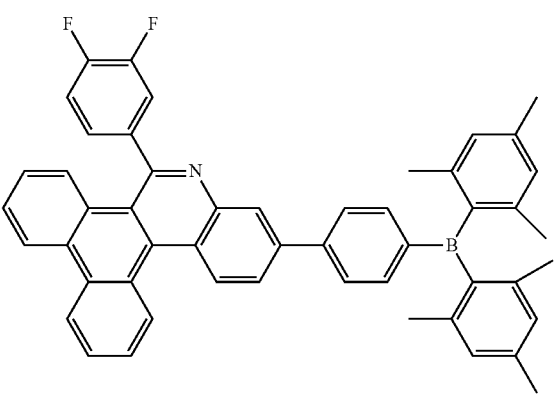
39
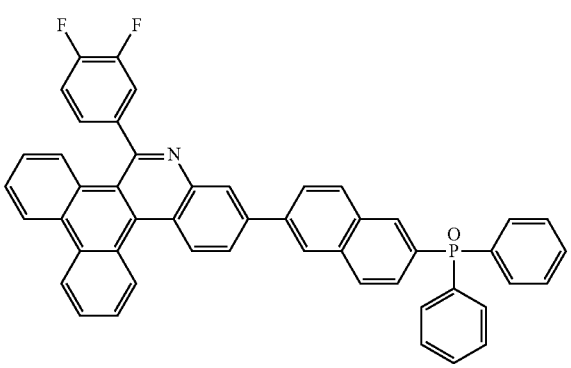
40
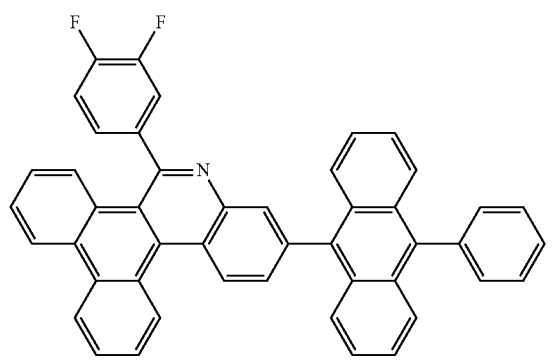
41
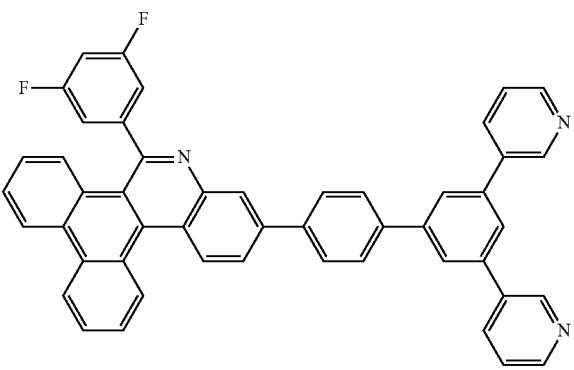
42

211
-continued
43
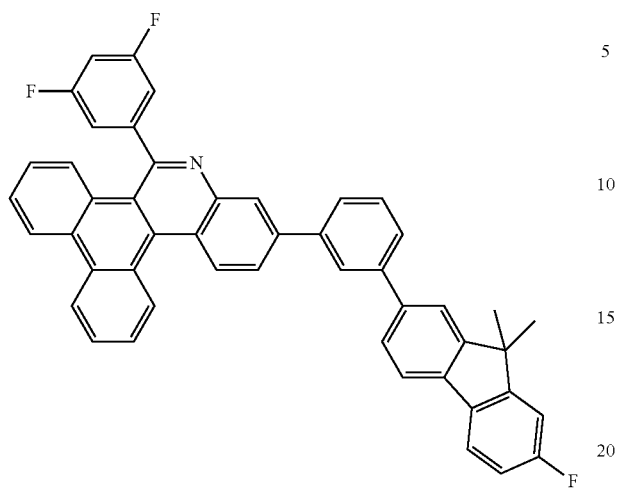
44
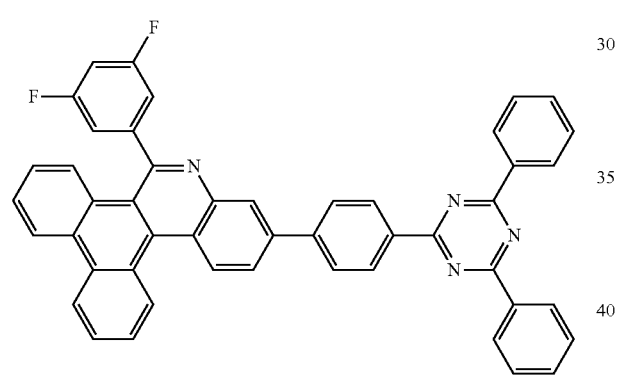
45
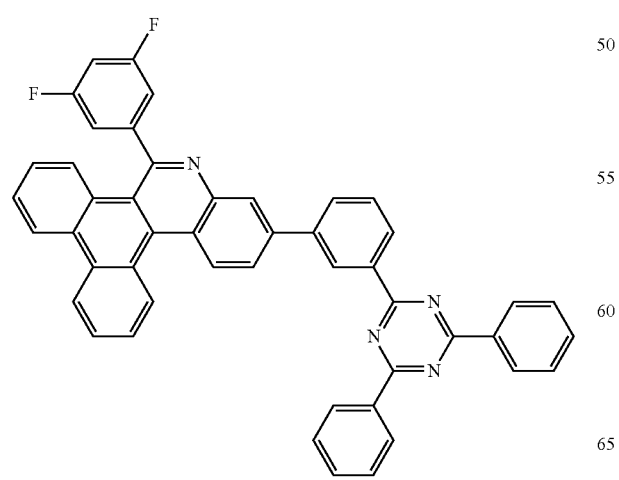
212
-continued
46
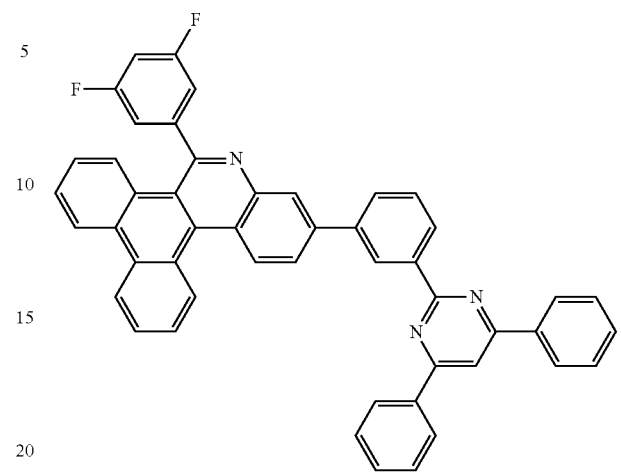
47
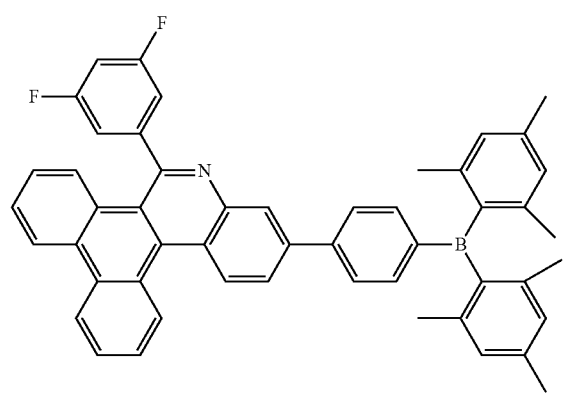
48
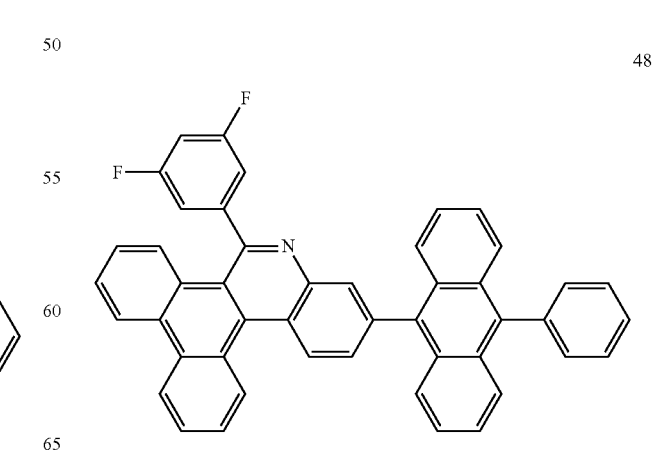

57
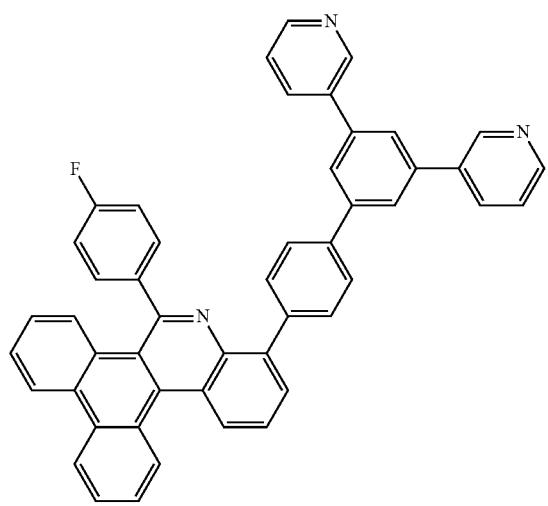
58
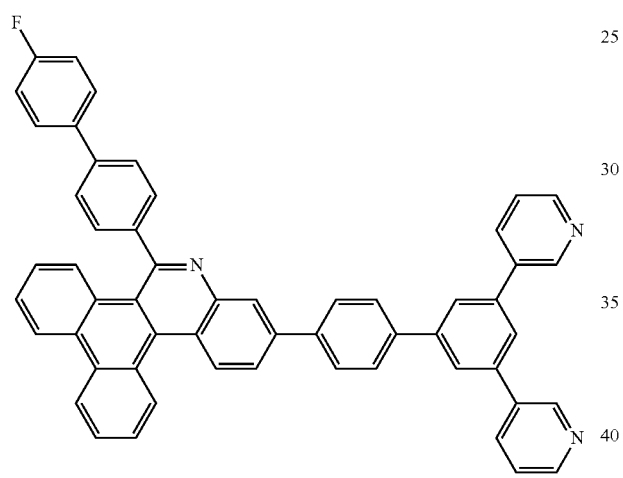
59
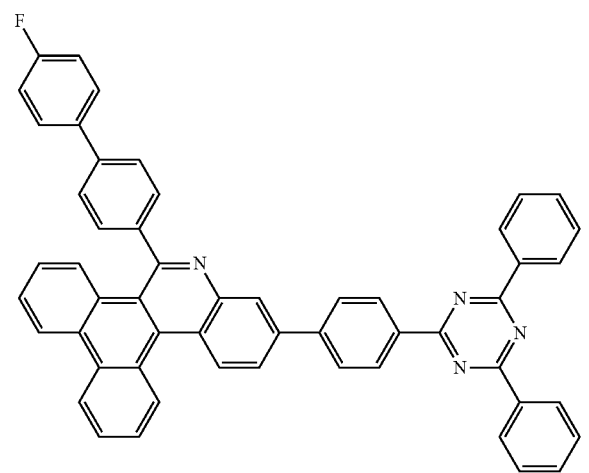
60
61
62
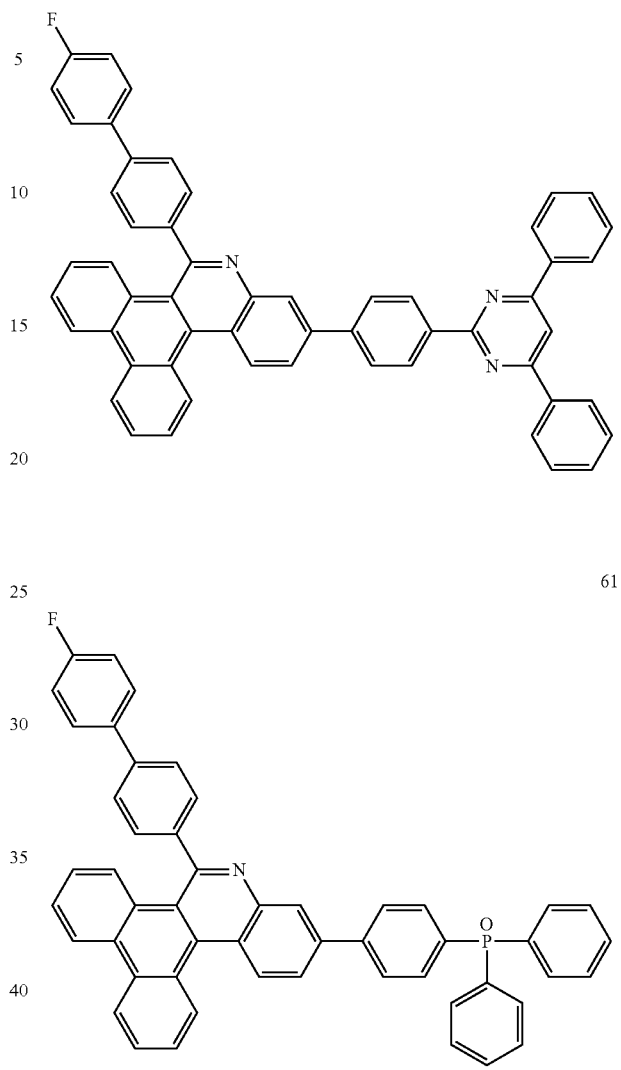

215
-continued
63
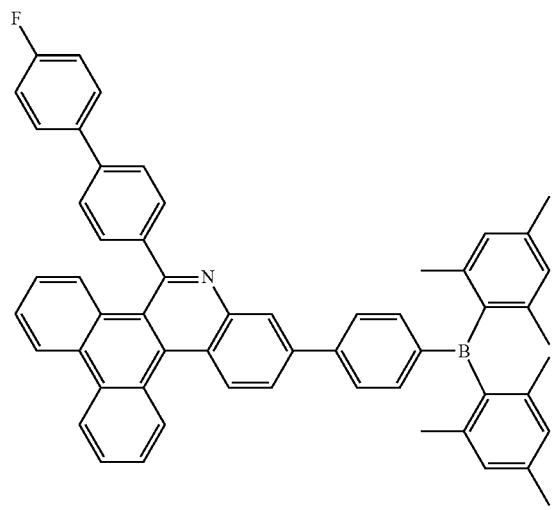
64
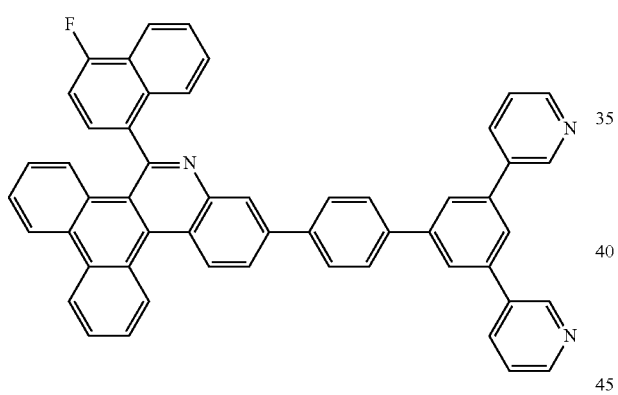
65
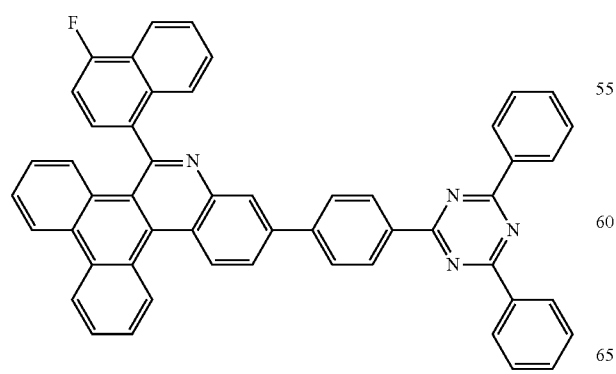
216
-continued
66
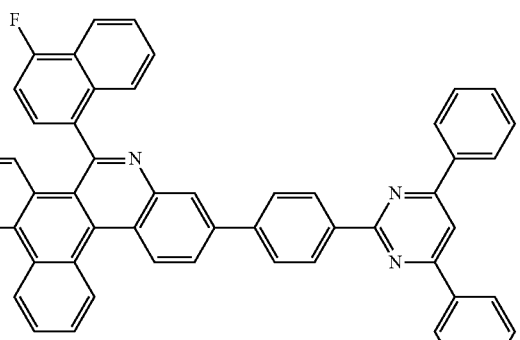
67
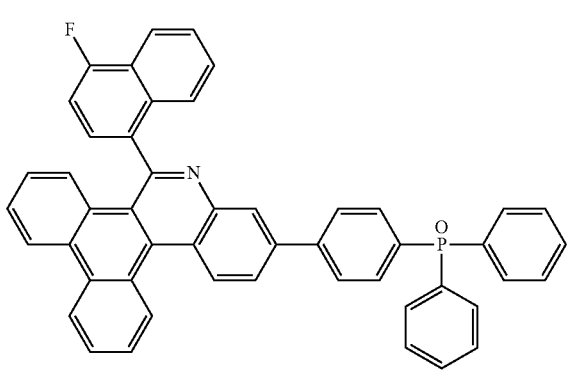
68
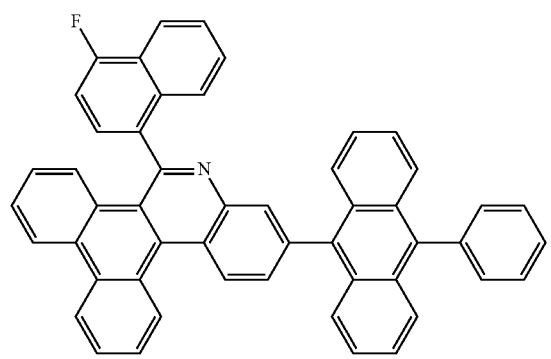
69
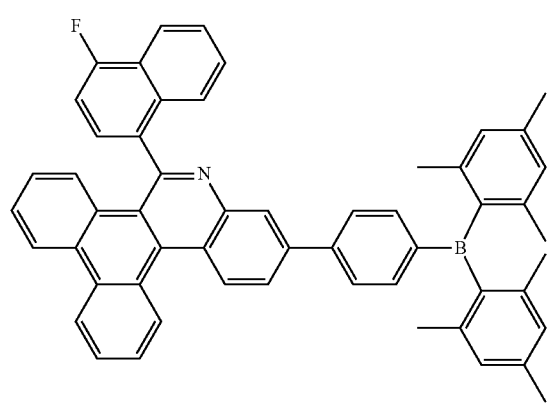

217
-continued
70
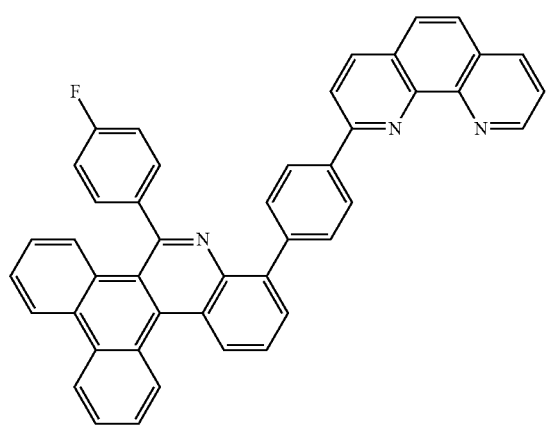
71
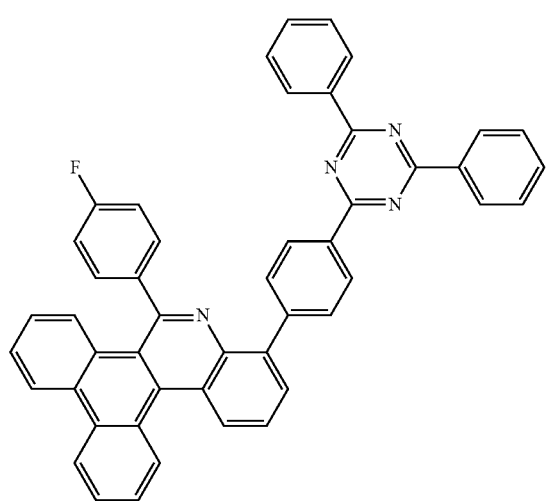
72
218
-continued
73
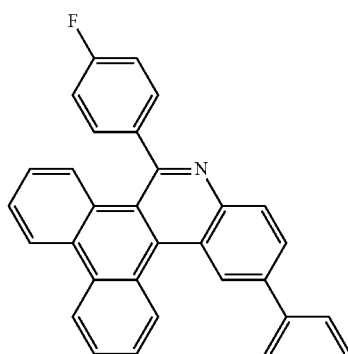
74
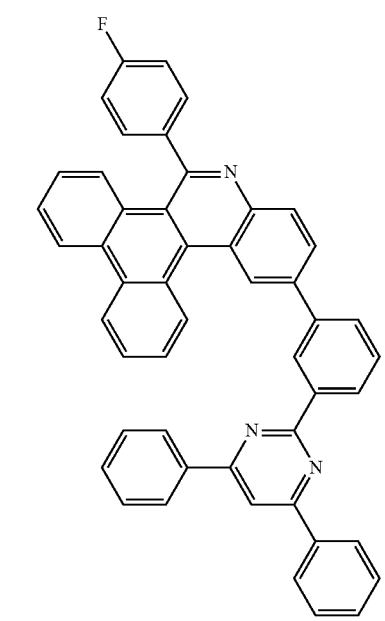

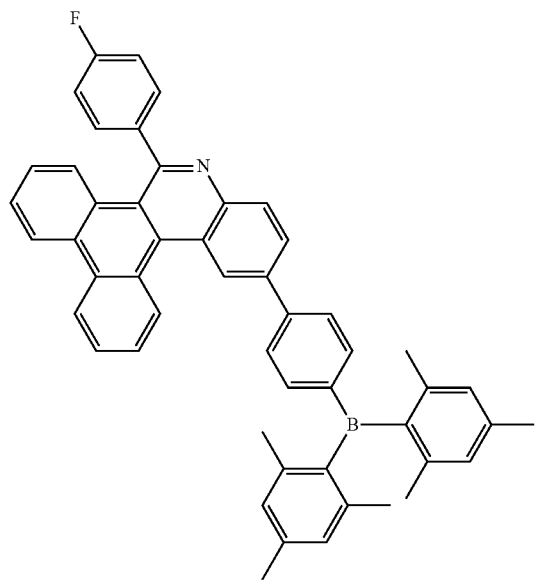

75

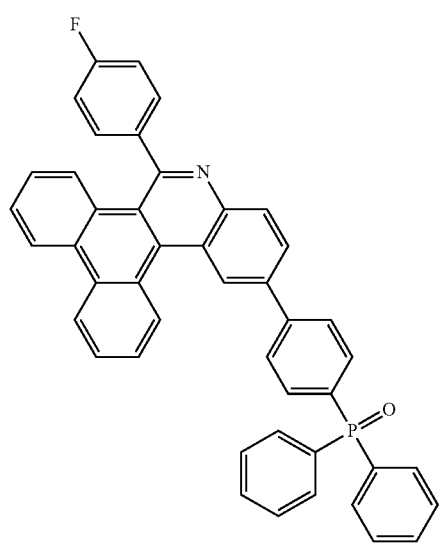

76

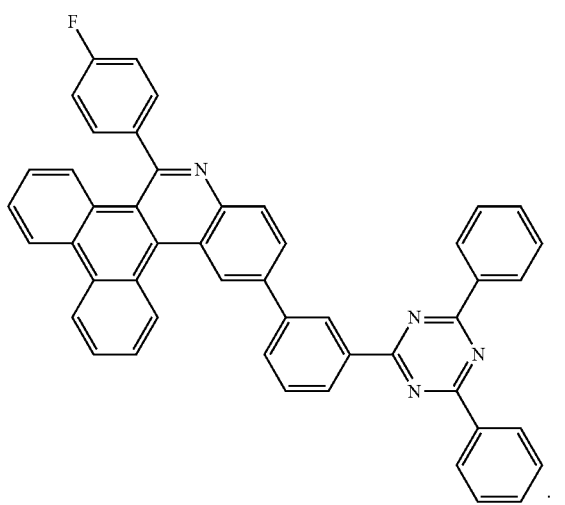

77

13. The organic light-emitting device as claimed in claim 1, wherein the electron transport region includes the at least one condensed cyclic compound.

14. The organic light-emitting device as claimed in claim 1, wherein the electron transport region includes an electron transport layer, and the electron transport layer includes the at least one condensed cyclic compound.

15. The organic light-emitting device as claimed in claim 1, wherein:
the hole transport region includes a p-dopant, and
the p-dopant has a lowest unoccupied molecular orbital (LUMO) level of −3.5 eV or less.

16. The organic light-emitting device as claimed in claim 15, wherein the p-dopant includes a cyano group-containing compound.

17. An organic light-emitting device, comprising:
a first electrode;
a second electrode facing the first electrode; and
an organic layer between the first electrode and the second electrode, the organic layer including an emission layer,
wherein:
the emission layer is a first color light-emitting first emission layer,
included between the first electrode and the second electrode is: i) at least one second color light-emitting second emission layer, or ii) at least one second color light-emitting second emission layer and at least one third color light-emitting third emission layer,
a maximum emission wavelength of the first color light, a maximum emission wavelength of the second color light, and a maximum emission wavelength of the third color light are identical to or different from each other, and
the first color light and the second color light are emitted as mixed light, or the first color light, the second color light, and the third color light are emitted as mixed light, and
wherein the organic layer includes at least one condensed cyclic compound represented by Formula 1:

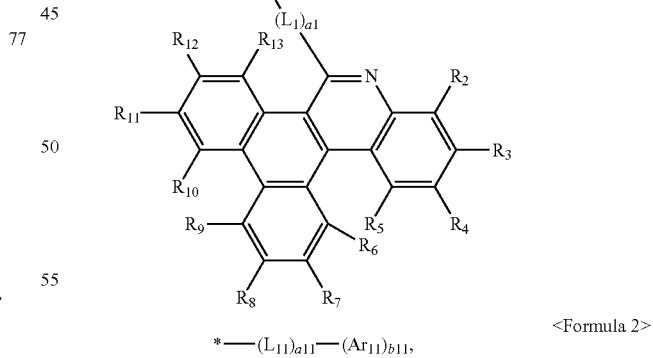

wherein, in Formulae 1 and 2,
$L_1$ and $L_{11}$ are each independently a substituted or unsubstituted $C_3$-$C_{60}$ carbocyclic group or a substituted or unsubstituted $C_1$-$C_{60}$ heterocyclic group,
a1 and a11 are each independently an integer from 0 to 3,
$Ar_{11}$ is selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group(substituted or unsubstituted monovalent non-aromatic condensed polycyclic group), a substituted or unsubstituted monovalent non-aromatic condensed heteropolycyclic group(substituted or unsubstituted monovalent non-aromatic condensed heteropolycyclic group), —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), b11 is an integer from 1 to 4, $R_1$ is selected from a $C_6$-$C_{60}$ aryl group, a $C_1$-$C_{60}$ heteroaryl group, a monovalent non-aromatic condensed polycyclic group, and a monovalent non-aromatic condensed heteropolycyclic group, each substituted with at least one selected from —F, —Cl, —Br, —I, a cyano group, and a nitro group, $R_2$ to $R_{13}$ are each independently selected from a group represented by Formula 2, hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, and a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —S(=O)$_2$($Q_1$), and —P(=O)($Q_1$)($Q_2$), wherein at least one selected from $R_2$ to $R_{13}$ is a group represented by Formula 2, at least one substituent of the substituted $C_3$-$C_{60}$ carbocyclic group, substituted $C_1$-$C_{60}$ heterocyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_2$-$C_{60}$ heteroaryl group, substituted monovalent non-aromatic condensed polycyclic group, and substituted monovalent non-aromatic condensed heteropolycyclic group is selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$) and —P(=O)($Q_{31}$)($Q_{32}$), $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_6$-$C_{60}$ aryl group substituted with at least one selected from —F, —Cl, —Br, —I, and a cyano group, and indicates a binding site to a neighboring atom.

* * * * *